United States Patent
Punnonen et al.

(10) Patent No.: US 10,544,222 B2
(45) Date of Patent: Jan. 28, 2020

(54) PD1/CTLA4 BINDERS

(71) Applicant: Merck Sharp & Dohme Corp., Rahway, NJ (US)

(72) Inventors: Juha Punnonen, Belmont, CA (US); Edward Bowman, Redwood City, CA (US); Maribel Beaumont, San Mateo, CA (US); Marie-Ange Buyse, Merelbeke (BE); Carlo Boutton, Wielsbeke (BE); Bruno Dombrecht, Heusden (BE); Bjorn Victor, Zwijndrecht (BE); David Vlerick, Gentbrugge (BE); Robert A. Kastelein, Portola Valley, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 325 days.

(21) Appl. No.: 15/353,867

(22) Filed: Nov. 17, 2016

(65) Prior Publication Data

US 2017/0137520 A1    May 18, 2017

Related U.S. Application Data

(60) Provisional application No. 62/256,985, filed on Nov. 18, 2015.

(51) Int. Cl.
| | | |
|---|---|---|
| *C07K 16/28* | (2006.01) | |
| *A61K 39/395* | (2006.01) | |
| *A61K 39/00* | (2006.01) | |

(52) U.S. Cl.
CPC ...... *C07K 16/2818* (2013.01); *A61K 39/3955* (2013.01); *A61K 39/39558* (2013.01); *A61K 2039/507* (2013.01); *C07K 2317/31* (2013.01); *C07K 2317/34* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,665,862 A | 9/1997 | Fischbach et al. | |
| 5,869,050 A | 2/1999 | de Boer et al. | |
| 6,632,927 B2 | 10/2003 | Adair et al. | |
| 6,824,779 B1 | 11/2004 | Freeman et al. | |
| 7,807,162 B2 * | 10/2010 | Silence | A61K 38/36 424/133.1 |
| 8,907,065 B2 * | 12/2014 | Hermans | C07K 16/2818 530/387.1 |
| 2002/0006403 A1 | 1/2002 | Yu et al. | |
| 2015/0266958 A1 | 9/2015 | Hermans et al. | |

FOREIGN PATENT DOCUMENTS

| | | |
|---|---|---|
| CN | 104987421 A | 10/2015 |
| WO | WO2002051871 | 7/2002 |
| WO | WO2003042402 | 5/2003 |
| WO | WO2006040153 A2 | 4/2006 |
| WO | 2008071447 | 6/2008 |
| WO | 2013024059 | 2/2013 |
| WO | 2014043509 | 3/2014 |
| WO | 2015044386 | 2/2015 |
| WO | 2015173325 | 11/2015 |
| WO | 2016180034 A1 | 11/2016 |

OTHER PUBLICATIONS

Conrath et al., Camel Single-domain Antibodies as Modular Building Units in Bispecific and Bivalent Antibody Constructs, The Journal of Biological Chemistry, 2001, pp. 7346-7350, vol. 276(10).
Cordy et al., Specificity of human anti variable heavy VH chain autoantibodies and impact on a VH domain antibody antagonist of tumour necrosis factor-alpha receptor 1, Clinical and Experimental Immunology, 2015, No. 2, pp. 139-148, vol. 182.
Curran et al., PD-1 and CTLA-4 combination blockade expands infiltrating T cells and reduces regulatory T adn myeloid cells within B16 melanoma tumors, PNAS, 2010, pp. 4275-4280, vol. 107.
Database WPI/Thomson XP002766907, Oct. 21, 2015—Abstract.
Duraiswamy et al., Dual Blockade of PD-1 and CTLA-4 Combined with Tumor Vaccine Effective Restores T-Cell Rejection Function in Tumors, Cancer Research, 2013, pp. 3591-3603, vol. 73(12).
Larkin et al., Combined Nivolumab and Ipilmumab or Monotherapy in Untreated Melanoma, The New England of Journal of Medicine, Jul. 2, 2015, pp. 23-34, vol. 373.
S. Muyldermans, Single domain camel antibodies: current status, Molecular Biology, 2001, pp. 277-302, vol. 74.
Shin et al., The evolution of checkpoint blockade as a cancer therapy: what's here, what's next?, Current Opinion in Immunology, 2015, pp. 23-35, vol. 33.
Vincke et al., General Strategy to Humanize a Camelid Single-domain antibody and Identification of a universal humanized nanobody scaffold, Journal of Biological Chemistry, 2008, No. 5, pp. 3273-3284, vol. 284.
Wolchok et al., Nivolumab plus Ipilimumab in Advanced Melanoma, The New England Journal of Medicine, 2013, pp. 122-133, vol. 369(2).
Abrams et al., Blockade of T Lymphocyte Costimulation with Cytotoxic T Lymphocyte—associated Antigen 4—Immunoglobulin (CTLA4Ig) Reverses the Cellular Pathology of Psoriatic Plaques, Including the Activation of Keratinocytes, Dendritic Cells, and Endothelial Cells, J. Exp. Med., 2000, pp. 681-693, vol. 192.
Adorini et al., Therapeutic Aspects of Apoptosis, Idrugs, 2000, pp. 496-498, vol. 3.
Alegre et al., T-Cell Regulation by CD28 and CTLA-4, Nat. Rev. Immunol., 2001, pp. 220-228, vol. 1.

(Continued)

*Primary Examiner* — Agnieszka Boesen
(74) *Attorney, Agent, or Firm* — Nichole M. Valeyko; Laura M. Ginkel

(57) ABSTRACT

The present invention provides multispecific molecules, e.g., comprising more than one ISVD or Nanobody, that bind to PD1 and CTLA4. These molecules have been engineered so as to reduce the incidence of binding by pre-existing antibodies in the bodies of a subject administered such a molecule. Methods for increasing immune response, treating cancer and/or treating an infectious disease with such molecules are provided.

15 Claims, 45 Drawing Sheets

Specification includes a Sequence Listing.

(56) References Cited

OTHER PUBLICATIONS

Butte et al., Programmed Death-1 Ligand 1 Interacts Specifically with the B7-1 Costimulatory Molecule to Inhibit T Cell Responses, Immunity, 2007, pp. 111-122, vol. 27.

Chambers et al., CTLA-4-Mediated Inhibition in Regulation of T Cell Responses: Mechanisms and Manipulation in Tumor Immunotherapy, Annu. Rev. Immunol., 2001, pp. 565-594, vol. 19.

Choi et al., Activation of Naive CD4T Cells in Vivo by a Self-Peptide Mimic: Mechanism of Tolerance Maintenance and Preservation of Immunity, J. Immunol., 2004, pp. 7399-7407, vol. 172.

Collins et al., The Interaction Properties of Costimulatory Molecules Revisited, Immunity, 2002, pp. 201-210, vol. 17.

Coyle et al., The Expanding B7 superfamily: Increasing complexity in costimulatory signals regulating T cell function, Nature Immunology, 2001, pp. 203-209, vol. 2/3.

Coyle et al., The role of ICOS and other costimulatory molecules in allergy and asthma, Immune, 2004, pp. 349-359, vol. 25.

Dincq et al., Expression and Purification of Monospecific and Bispecific Recombinant Antibody Fragments Derived from Antibodies That Block the CD80,CD86-CD28 Costimulatory Pathway, Protein Expression and Purification, 2001, pp. 11-24, vol. 22.

Friedberg et al., Updated Results from a Phase II Study of Galiximab (anti-CD80) in Combination with Rituximab for Relapsed or Refractory, Follicular NHL, Blood, 2005, p. 2435, vol. 106.

Furukawa et al., Association of B7-1 Co-Stimulation with the Development of Graft Arterial Disease Studies Using Mice Lacking B7-1, B7-2, or B7-1,B7-2, Am. J. of Pathology, 2000, pp. 473-484, vol. 157.

Gottlieb et al., Abstracts for the 61st Annual Meeting of the Society for Investigative Dermatology, J. Invest. Dermatol., 2001, p. 840, vol. 114.

Howard et al., Therapeutic Blockade of TCR Signal Transduction and Co-Stimulation in Autoimmune Disease, Current Drug Targets, 2005, pp. 85-94, vol. 4.

Hufton et al., Development and application of cytotoxic T lymphocyte-associated antigen 4 as a protein scaffold for the generation of novel binding ligands, Febs Lett., 2000, pp. 225-231, vol. 475.

Kang et al., The Synthetic Peptide Trp-Lys-Tyr-Met-Val-D-Met Inhibits Human Monocyte-Derived Dendritic Cell Maturation via Formyl Peptide Receptor and Formyl Peptide Receptor-Like, J. Immunol., 2005, pp. 685-692, vol. 175.

Karandikar et al., Targeting the B7,CD28:CTLA-4 costimulatory system in CNS autoimmune disease, J. of Neuroimmunology, 1998, pp. 10-18, vol. 89.

Keler et al., Activity and Safety of CTLA-4 Blockade Combined with Vaccines in Cynomolgus Macaques, J. Immunol., 2003, pp. 6251-6259, vol. 171.

Kopf et al., Inducible Costimulator Protein (ICOS) Controls T Helper Cell Subset Polarization after Virus and Parasite Infection, J. Exp. Med., 2000, pp. 53-61, vol. 192.

Larsen et al., Rational Development of LEA29Y (belatacept), a High-Affinity Variant of CTLA4-Ig with Potent Immunosuppressive Properties, Am. J. Transplant, 2005, pp. 443-453, vol. 5.

Oosterwegel et al., CTLA-4 and T cell activation, Current Opinion in Immunology, 1999, pp. 294-300, vol. 11.

Ozkaynak et al., Importance of ICOS-B7RP-1 costimulation in acute and chronic allograft rejection, Nature Immunology, 2001, pp. 591-596, vol. 2.

Panka et al., Variable region framework differences result in decreased or increased affinity of variant anti-digoxin antibodies, Proc. Natl. Acad., 1988, pp. 3080-3084, vol. 85.

Park et al., Targeting and Blocking B7 Costimulatory Molecules on Antigen-Presenting Cells Using CTLA4Ig-Conjugated Liposomes: In Vitro Characterization and in Vivo Factors Affecting Biodistribution, Pharmaceutical Research, 2003, pp. 1239-1248, vol. 20.

Polojil et al., CD4 T Cell Expressed CD80 Regulates Central Nervous System Effector Function and Survival during Experimental Autoimmune Encephalomyelitis, J. of Immunology, 2006, pp. 2948-2958, vol. 177.

Polojil et al., CD86 and beta 2-adrenergic receptor stimulation regulate B-cell activity cooperatively, Trends in Immunology, 2005, pp. 180-185, vol. 26.

Rao et al., Novel cyclic and linear oligopeptides that bind to integrin beta 1 chain and either inhibit or costimulate T lymphocytes, Int. Immunopharmacol., 2003, pp. 435-443, vol. 3.

Rottman et al., The costimulatory molecule ICOS plays an important role in the immunopathogenesis of EAE, Nature Immunology, 2001, pp. 605-611, vol. 2.

Rudikoff, Single amino acid substitution altering antigen-binding specificity, PNAS, 1982, pp. 1979-1983, vol. 79.

Salama et al., Challenges to achieving clinical transplantation tolerance, J. of Clinical Investigation, 2001, pp. 943-948, vol. 108.

Stuart et al., Targeting T Cell Costimulation in Autoimmune Disease, Anti-inflammatory, 2002, Issue No. 3, pp. 275-289, vol. 6.

Van Den Beucken et al., Building Novel Binding Ligands to B7.1 and B7.2 Based on Human Antibody Single Variable Light Chain Domains, J. Mol. Biology, 2001, pp. 591-601, vol. 310.

Waldmann et al., Effective Cancer Therapy Through Immunomodulation, Annu. Rev. Med., 2006, pp. 65-81, vol. 57(1).

Webb et al., Prevention and amelioration of collagen-inducedarthritis by blockade of the CD28 co-stimulatory pathway: requirement for both B7-1 and B7-2, Eur. J. Immunol., 1996, pp. 2320-2328, vol. 26.

Yamada et al., The Role of Novel T Cell Costimulatory Pathways in Autoimmunity and Transplantation, J. Am. Soc. Nephrol., 2002, pp. 559-575, vol. 13.

Zhang et al., Crystal structure of the receptor-binding domain of human B7-2: Insights into organization and signaling, PNAS, 2003, pp. 2586-2591, vol. 100.

Google English Translation of CN104987421.
Google English Translation of WO2016180034.

\* cited by examiner

| Numbering according to Kabat (VH) | Numbering according to Chotia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | --- |
| 110 | 110 | 146 | --- |
| 112 | 112 | 148 | --- |

Source: http://www.bioc.uzh.ch/plueckthun/antibody/Numbering/NumFrame.html

FIG.1

| SEQ ID NO | Description | Sequence |
|---|---|---|
| 1 | WO 2008/071447, SEQ ID NO: 348 (102C12) | EVQLVESGGGLVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTQVTVSS |
| 2 | reference A | EVQLVESGGGLVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVTVSS |
| 3 | CDR1 (Kabat) | IHAMG |
| 4 | CDR2 (kabat) | VITWSGGITYYADSVKG |
| 5 | CDR3 (kabat/Abm) | DKHQSSWYDY |
| 6 | CDR1 (Abm) | GSIASIHAMG |
| 7 | CDR2 (Abm) | VITWSGGITY |
| 8 | CDR3 (Kabat/Abm) | DKHQSSWYDY |
| 9 | reference A: (11F01) | EVQLVESGGGLVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVTVSS |
| 10 | CDR1 (kabat) | FYGMG |
| 11 | CDR2 (kabat) | DIRTSAGRTYYADSVKG |
| 12 | CDR3 (kabat/Abm) | EMSGISGWDY |
| 13 | CDR1 (Abm) | GGTFSFYGMG |
| 14 | CDR2 (Abm) | DIRTSAGRTY |
| 15 | CDR3 (Kabat/Abm) | EMSGISGWDY |

FIG.2

| SEQ ID NO | Description | Sequence |
|---|---|---|
| 16 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTATYYCAGDKHQSSWYDYWGQGTLVTVSS |
| 17 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVKVSS |
| 18 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVQVSS |
| 19 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVTVKS |
| 20 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVTVQS |
| 21 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVKVSS |
| 22 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVQVSS |
| 23 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVKS |
| 24 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVQS |
| 25 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVSS |

FIG.3A-1

| SEQ ID NO | Description | Sequence |
|---|---|---|
| 26 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVKVSS |
| 27 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVQVSS |
| 28 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVKS |
| 29 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVQS |
| 30 | PD1 binding moiety | EVQLVESGGGVVQPGGSLRLSCAASGSIASIHAMGWFRQAPGKEREFVAVITWSGGITYYADSVKGRFTISRDNSKNTVYLQMNSLRPEDTALYYCAGDKHQSSWYDYWGQGTLVTVSS |
| 31 | PD1 binding moiety | DVQLVESGGGVVQPGGSLRLSCAASGSIASIHAMGWFRQAPGKEREFVAVITWSGGITYYADSVKGRFTISRDNSKNTVYLQMNSLRPEDTALYYCAGDKHQSSWYDYWGQGTLVTVSS |
| 32 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTATYYCAGDKHQSSWYDYWGQGTLVTVSSA |
| 33 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVKVSSA |
| 34 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVQVSSA |
| 35 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVTVKSA |

FIG.3A-2

| SEQ ID NO | Description | Sequence |
|---|---|---|
| 36 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTAIYYCAGDKHQSSWYDYWGQGTLVTVQSA |
| 37 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVKVSSA |
| 38 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVQVSSA |
| 39 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVKSA |
| 40 | PD1 binding moiety | EVQLVESGGGLVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVQSA |
| 41 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVSSA |
| 42 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVKVSSA |
| 43 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVQVSSA |
| 44 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVKSA |

FIG.3A-3

| SEQ ID NO | Description | Sequence |
|---|---|---|
| 45 | PD1 binding moiety | EVQLVESGGGVVQAGGSLRLSCAASGSIASIHAMGWFRQAPGKEREFVAVITWSGGITYYADSVKGRFTISRDNAKNTVYLQMNSLKPEDTALYYCAGDKHQSSWYDYWGQGTLVTVQSA |
| 46 | PD1 binding moiety | EVQLVESGGGVVQPGGSLRLSCAASGSIASIHAMGWFRQAPGKEREFVAVITWSGGITYYADSVKGRFTISRDNSKNTVYLQMNSLRPEDTALYYCAGDKHQSSWYDYWGQGTLVTVSSA |
| 47 | PD1 binding moiety | DVQLVESGGGVVQPGGSLRLSCAASGSIASIHAMGWFRQAPGKEREFVAVITWSGGITYYADSVKGRFTISRDNSKNTVYLQMNSLRPEDTALYYCAGDKHQSS

```
                          20              40              60
                          |               |               |
SEQIDNO:1  EVQLVESGGG LVQAGGSLRL SCAASGSIAS IHAMGWFRQA PGKEREFVAV ITWSGGITYY 60
SEQIDNO:2  .......... .......... .......... .......... .......... .......... 60
SEQIDNO:16 .......... .......... .......... .......... .......... .......... 60
SEQIDNO:17 .......... V......... .......... .......... .......... .......... 60
SEQIDNO:18 .......... V......... .......... .......... .......... .......... 60
SEQIDNO:19 .......... V......... .......... .......... .......... .......... 60
SEQIDNO:20 .......... .......... .......... .......... .......... .......... 60
SEQIDNO:21 .......... .......... .......... .......... .......... .......... 60
SEQIDNO:22 .......... .......... .......... .......... .......... .......... 60
SEQIDNO:23 .......... .......... .......... .......... .......... .......... 60
SEQIDNO:24 .......... .......... .......... .......... .......... .......... 60
SEQIDNO:25 .......... V......... .......... .......... .......... .......... 60
SEQIDNO:26 .......... V......... .......... .......... .......... .......... 60
SEQIDNO:27 .......... V......... .......... .......... .......... .......... 60
SEQIDNO:28 .......... V......... .......... .......... .......... .......... 60
SEQIDNO:29 .......... V......... .......... .......... .......... .......... 60
SEQIDNO:30 .......... V..P...... .......... .......... .......... .......... 60
SEQIDNO:31 D......... V..P...... .......... .......... .......... .......... 60
SEQIDNO:32 .......... .......... .......... .......... .......... .......... 60
SEQIDNO:33 .......... V......... .......... .......... .......... .......... 60
SEQIDNO:34 .......... V......... .......... .......... .......... .......... 60
SEQIDNO:35 .......... V......... .......... .......... .......... .......... 60
SEQIDNO:36 .......... V......... .......... .......... .......... .......... 60
SEQIDNO:37 .......... .......... .......... .......... .......... .......... 60
SEQIDNO:38 .......... .......... .......... .......... .......... .......... 60
SEQIDNO:39 .......... .......... .......... .......... .......... .......... 60
SEQIDNO:40 .......... .......... .......... .......... .......... .......... 60
SEQIDNO:41 .......... V......... .......... .......... .......... .......... 60
SEQIDNO:42 .......... V......... .......... .......... .......... .......... 60
SEQIDNO:43 .......... V......... .......... .......... .......... .......... 60
SEQIDNO:44 .......... V......... .......... .......... .......... .......... 60
SEQIDNO:45 .......... V......... .......... .......... .......... .......... 60
SEQIDNO:46 .......... V..P...... .......... .......... .......... .......... 60
SEQIDNO:47 D......... V..P...... .......... .......... .......... .......... 60
```

FIG.3B-1

|            |            | 80         |            | 100        |            | 120        |     |
|------------|------------|------------|------------|------------|------------|------------|-----|
| SEQIDNO:1  | ADSVKGRFTI | SRDNAKNTVY | LQMNSLKPED | TAIYYCAGDK | HQSSWYDYWG | QGTQVTVSS- | 119 |
| SEQIDNO:2  | .......... | .......... | .......... | .......... | .......... | ...L.....- | 119 |
| SEQIDNO:16 | .......... | .......... | .......... | ..T....... | .......... | ...L.....- | 119 |
| SEQIDNO:17 | .......... | .......... | .......... | .......... | .......... | ...L.K...- | 119 |
| SEQIDNO:18 | .......... | .......... | .......... | .......... | .......... | ...L.Q...- | 119 |
| SEQIDNO:19 | .......... | .......... | .......... | .......... | .......... | ...L...K.- | 119 |
| SEQIDNO:20 | .......... | .......... | .......... | .......... | .......... | ...L...Q.- | 119 |
| SEQIDNO:21 | .......... | .......... | .......... | ..L....... | .......... | ...L.K...- | 119 |
| SEQIDNO:22 | .......... | .......... | .......... | ..L....... | .......... | ...L.Q...- | 119 |
| SEQIDNO:23 | .......... | .......... | .......... | ..L....... | .......... | ...L...K.- | 119 |
| SEQIDNO:24 | .......... | .......... | .......... | ..L....... | .......... | ...L...Q.- | 119 |
| SEQIDNO:25 | .......... | .......... | .......... | ..L....... | .......... | ...L.....- | 119 |
| SEQIDNO:26 | .......... | .......... | .......... | ..L....... | .......... | ...L.K...- | 119 |
| SEQIDNO:27 | .......... | .......... | .......... | ..L....... | .......... | ...L.Q...- | 119 |
| SEQIDNO:28 | .......... | .......... | .......... | ..L....... | .......... | ...L...K.- | 119 |
| SEQIDNO:29 | .......... | .......... | .......... | ..L....... | .......... | ...L...Q.- | 119 |
| SEQIDNO:30 | .......... | ....S..... | ......R... | ..L....... | .......... | ...L.....- | 119 |
| SEQIDNO:31 | .......... | ....S..... | ......R... | ..L....... | .......... | ...L.....- | 119 |
| SEQIDNO:32 | .......... | .......... | .......... | ..T....... | .......... | ...L.....A | 120 |
| SEQIDNO:33 | .......... | .......... | .......... | .......... | .......... | ...L.K...A | 120 |
| SEQIDNO:34 | .......... | .......... | .......... | .......... | .......... | ...L.Q...A | 120 |
| SEQIDNO:35 | .......... | .......... | .......... | .......... | .......... | ...L...K.A | 120 |
| SEQIDNO:36 | .......... | .......... | .......... | .......... | .......... | ...L...Q.A | 120 |
| SEQIDNO:37 | .......... | .......... | .......... | ..L....... | .......... | ...L.K...A | 120 |
| SEQIDNO:38 | .......... | .......... | .......... | ..L....... | .......... | ...L.Q...A | 120 |
| SEQIDNO:39 | .......... | .......... | .......... | ..L....... | .......... | ...L...K.A | 120 |
| SEQIDNO:40 | .......... | .......... | .......... | ..L....... | .......... | ...L...Q.A | 120 |
| SEQIDNO:41 | .......... | .......... | .......... | ..L....... | .......... | ...L.....A | 120 |
| SEQIDNO:42 | .......... | .......... | .......... | ..L....... | .......... | ...L.K...A | 120 |
| SEQIDNO:43 | .......... | .......... | .......... | ..L....... | .......... | ...L.Q...A | 120 |
| SEQIDNO:44 | .......... | .......... | .......... | ..L....... | .......... | ...L...K.A | 120 |
| SEQIDNO:45 | .......... | .......... | .......... | ..L....... | .......... | ...L...Q.A | 120 |
| SEQIDNO:46 | .......... | ....S..... | ......R... | ..L....... | .......... | ...L.....A | 120 |
| SEQIDNO:47 | .......... | ....S..... | ......R... | ..L....... | .......... | ...L.....A | 120 |

FIG.3B-2

| SEQ ID NO | Description | Sequence |
|---|---|---|
| 48 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTATYYCAAEMSGISGWDYWGQGTQVTVSS |
| 49 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVKVSS |
| 50 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVQVSS |
| 51 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVTVKS |
| 52 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVTVQS |
| 53 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVKVSS |
| 54 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVQVSS |
| 55 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVKS |
| 56 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVQS |

FIG.4A-1

| SEQ ID NO | Description | Sequence |
|---|---|---|
| 57 | CTLA4 binding moiety | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVTVSS |
| 58 | CTLA4 binding moiety | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVKVSS |
| 59 | CTLA4 binding moiety | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVQVSS |
| 60 | CTLA4 binding moiety | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVTVKS |
| 61 | CTLA4 binding moiety | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVTVQS |
| 62 | CTLA4 binding moiety | EVQLVESGGGVVQPGGSLRLSCAASGGTFSFYGMGWFRQAP GKEQEFVADIRTSAGRTYYADSVKGRFTISRDNSKNTVYLQM NSLRPEDTALYYCAAEMSGISGWDYWGQGTLVTVSS |
| 63 | CTLA4 binding moiety | EVQLVESGGGVVQPGGSLRLSCAASGGTFSFYGMGWFRQAP GKEREFVADIRTSAGRTYYADSVKGRFTISRDNSKNTVYLQM NSLRPEDTALYYCAAEMSGISGWDYWGQGTLVTVSS |
| 64 | CTLA4 binding moiety | DVQLVESGGGVVQPGGSLRLSCAASGGTFSFYGMGWFRQAP GKEQEFVADIRTSAGRTYYADSVKGRFTISRDNSKNTVYLQM NSLRPEDTALYYCAAEMSGISGWDYWGQGTLVTVSS |
| 65 | CTLA4 binding moiety | DVQLVESGGGVVQPGGSLRLSCAASGGTFSFYGMGWFRQAP GKEREFVADIRTSAGRTYYADSVKGRFTISRDNSKNTVYLQM NSLRPEDTALYYCAAEMSGISGWDYWGQGTLVTVSS |

FIG.4A-2

| SEQ ID NO | Description | Sequence |
|---|---|---|
| 66 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTATYYCAAEMSGISGWDYWGQGTQVTVSSA |
| 67 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVKVSSA |
| 68 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVQVSSA |
| 69 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVTVKSA |
| 70 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVTVQSA |
| 71 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVKVSSA |
| 72 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVQVSSA |
| 73 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVKSA |
| 74 | CTLA4 binding moiety | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVQSA |

FIG.4A-3

| SEQ ID NO | Description | Sequence |
|---|---|---|
| 75 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVSSA |
| 76 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVKVSSA |
| 77 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVQVSSA |
| 78 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVKSA |
| 79 | CTLA4 binding moiety | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVQSA |
| 80 | CTLA4 binding moiety | EVQLVESGGGVVQPGGSLRLSCAASGGTFSFYGMGWFRQAPGKEQEFVADIRTSAGRTYYADSVKGRFTISRDNSKNTVYLQMNSLRPEDTALYYCAAEMSGISGWDYWGQGTLVTVSSA |
| 81 | CTLA4 binding moiety | EVQLVESGGGVVQPGGSLRLSCAASGGTFSFYGMGWFRQAPGKEREFVADIRTSAGRTYYADSVKGRFTISRDNSKNTVYLQMNSLRPEDTALYYCAAEMSGISGWDYWGQGTLVTVSSA |
| 82 | CTLA4 binding moiety | DVQLVESGGGVVQPGGSLRLSCAASGGTFSFYGMGWFRQAPGKEQEFVADIRTSAGRTYYADSVKGRFTISRDNSKNTVYLQMNSLRPEDTALYYCAAEMSGISGWDYWGQGTLVTVSSA |
| 83 | CTLA4 binding moiety | DVQLVESGGGVVQPGGSLRLSCAASGGTFSFYGMGWFRQAPGKEREFVADIRTSAGRTYYADSVKGRFTISRDNSKNTVYLQMNSLRPEDTALYYCAAEMSGISGWDYWGQGTLVTVSSA |

FIG.4A-4

```
                        20              40              60
                         |               |               |
SEQIDNO:9  EVQLVESGGG LVQAGGSLRL SCAASGGTFS FYGMGWFRQA PGKEQEFVAD IRTSAGRTYY 60
SEQIDNO:50 .......... V......... .......... .......... .......... .......... 60
SEQIDNO:51 .......... V......... .......... .......... .......... .......... 60
SEQIDNO:52 .......... V......... .......... .......... .......... .......... 60
SEQIDNO:53 .......... .......... .......... .......... .......... .......... 60
SEQIDNO:54 .......... .......... .......... .......... .......... .......... 60
SEQIDNO:55 .......... .......... .......... .......... .......... .......... 60
SEQIDNO:56 .......... .......... .......... .......... .......... .......... 60
SEQIDNO:57 .......... V......... .......... .......... .......... .......... 60
SEQIDNO:58 .......... V......... .......... .......... .......... .......... 60
SEQIDNO:59 .......... V......... .......... .......... .......... .......... 60
SEQIDNO:60 .......... V......... .......... .......... .......... .......... 60
SEQIDNO:61 .......... V......... .......... .......... .......... .......... 60
SEQIDNO:62 .......... V..P...... .......... .......... .......... .......... 60
SEQIDNO:63 .......... V..P...... .......... .......... ....R..... .......... 60
SEQIDNO:64 D......... V..P...... .......... .......... .......... .......... 60
SEQIDNO:65 D......... V..P...... .......... .......... ....R..... .......... 60
SEQIDNO:66 .......... .......... .......... .......... .......... .......... 60
SEQIDNO:67 .......... V......... .......... .......... .......... .......... 60
SEQIDNO:68 .......... V......... .......... .......... .......... .......... 60
SEQIDNO:69 .......... V......... .......... .......... .......... .......... 60
SEQIDNO:70 .......... V......... .......... .......... .......... .......... 60
SEQIDNO:71 .......... .......... .......... .......... .......... .......... 60
SEQIDNO:72 .......... .......... .......... .......... .......... .......... 60
SEQIDNO:73 .......... .......... .......... .......... .......... .......... 60
SEQIDNO:74 .......... .......... .......... .......... .......... .......... 60
SEQIDNO:75 .......... V......... .......... .......... .......... .......... 60
SEQIDNO:76 .......... V......... .......... .......... .......... .......... 60
SEQIDNO:77 .......... V......... .......... .......... .......... .......... 60
SEQIDNO:78 .......... V......... .......... .......... .......... .......... 60
SEQIDNO:79 .......... V......... .......... .......... .......... .......... 60
SEQIDNO:80 .......... V..P...... .......... .......... .......... .......... 60
SEQIDNO:81 .......... V..P...... .......... .......... ...R...... .......... 60
SEQIDNO:82 D......... V..P...... .......... .......... .......... .......... 60
SEQIDNO:83 D......... V..P...... .......... .......... ....R..... .......... 60
```

FIG.4B-1

```
                          80              100             120
                          |               |               |
SEQIDNO:9  ADSVKGRFTI SRDNAKNTVY LQMNSLKPED TAVYYCAAEM SGISWGDYWG QGTQVTVSS- 119
SEQIDNO:50 .......... .......... .......... .......... .......... .....Q...- 119
SEQIDNO:51 .......... .......... .......... .......... .......... .......K.- 119
SEQIDNO:52 .......... .......... .......... .......... .......... .......Q.- 119
SEQIDNO:53 .......... .......... .......... ..L....... .......... .....K...- 119
SEQIDNO:54 .......... .......... .......... ..L....... .......... .....Q...- 119
SEQIDNO:55 .......... .......... .......... ..L....... .......... .......K.- 119
SEQIDNO:56 .......... .......... .......... ..L....... .......... .......Q.- 119
SEQIDNO:57 .......... .......... .......... ..L....... .......... .........- 119
SEQIDNO:58 .......... .......... .......... ..L....... .......... .....K...- 119
SEQIDNO:59 .......... .......... .......... ..L....... .......... .....Q...- 119
SEQIDNO:60 .......... .......... .......... ..L....... .......... .......K.- 119
SEQIDNO:61 .......... .......... .......... ..L....... .......... .......Q.- 119
SEQIDNO:62 .......... ....S..... ......R... ..L....... .......... ..L......- 119
SEQIDNO:63 .......... ....S..... ......R... ..L....... .......... ..L......- 119
SEQIDNO:64 .......... ....S..... ......R... ..L....... .......... ..L......- 119
SEQIDNO:65 .......... ....S..... ......R... ..L....... .......... ..L......- 119
SEQIDNO:66 .......... .......... .......... ....T..... .......... .........A 120
SEQIDNO:67 .......... .......... .......... .......... .......... .....K...A 120
SEQIDNO:68 .......... .......... .......... .......... .......... .....Q...A 120
SEQIDNO:69 .......... .......... .......... .......... .......... .......K.A 120
SEQIDNO:70 .......... .......... .......... .......... .......... .......Q.A 120
SEQIDNO:71 .......... .......... .......... ..L....... .......... .....K...A 120
SEQIDNO:72 .......... .......... .......... ..L....... .......... .....Q...A 120
SEQIDNO:73 .......... .......... .......... ..L....... .......... .......K.A 120
SEQIDNO:74 .......... .......... .......... ..L....... .......... .......Q.A 120
SEQIDNO:75 .......... .......... .......... ..L....... .......... .........A 120
SEQIDNO:76 .......... .......... .......... ..L....... .......... .....K...A 120
SEQIDNO:77 .......... .......... .......... ..L....... .......... .....Q...A 120
SEQIDNO:78 .......... .......... .......... ..L....... .......... .......K.A 120
SEQIDNO:79 .......... .......... .......... ..L....... .......... .......Q.A 120
SEQIDNO:80 .......... ....S..... ......R... ..L....... .......... ...L.....A 120
SEQIDNO:81 .......... ....S..... ......R... ..L....... .......... ...L.....A 120
SEQIDNO:82 .......... ....S..... ......R... ..L....... .......... ...L.....A 120
SEQIDNO:83 .......... ....S..... ......R... ..L....... .......... ...L.....A 120
```

FIG.4B-2

| SEQ ID NO | Description | Sequence |
|---|---|---|
| 84 | albumin binding Nanobody | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 85 | albumin binding Nanobody | EVQLLESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| 86 | 35GS linker | GGGGSGGGGSGGGGSGGGGSGGGGSGGGGSGGGGS |
| 87 | HIS6-FLAG3 tag | HHHHHHGAADYKDHDGDYKDHDIDYKDDDDKGAA |
| 88 | C-terminal end | VTVKS |
| 89 | C-terminal end | VTVQS |
| 90 | C-terminal end | VKVSS |
| 91 | C-terminal end | VQVSS |
| 92 | C-terminal end | VTVKSX(n) |
| 93 | C-terminal end | VTVQSX(n) |
| 94 | C-terminal end | VKVSSX(n) |
| 95 | C-terminal end | VQVSSX(n) |
| 96 | C-terminal end | VTVKSA |
| 97 | C-terminal end | VTVQSA |
| 98 | C-terminal end | VKVSSA |
| 99 | C-terminal end | VQVSSA |
| 100 | C-terminal end | VTVSS |
| 101 | C-terminal end | VTVSSX(n) |
| 102 | C-terminal end | VTVSSA |

FIG.5

| SEQ ID NO | Sequence |
|---|---|
| 103 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDYWGQGTLVTVSSGGGGSGGGGSGGGGSGGGGSEVQLVESG GGVVQPGGSLRLSCAASGGTFSFYGMGWFRQAPGKEQEFVADIRTSAGRTYYADSVKGRFTISRDNSKNTVYLQMNSLRP EDTALYYCAAEMSGISGWDYWGQGTLVTVSSGGGGSGGGGSGGGGSGGGGSEVQLVESGGGV VQPGGSLRLSCAASGGTFSFYGMGWFRQAPGKEQEFVADIRTSAGRTYYADSVKGRFTISRDNSKNTVYLQMNSLRPEDT ALYYCAAEMSGISGWDYWGQGTLVTVSSGGGGSGGGGSGGGGSGGGGSEVQLVESGGGLVQP GNSLRLSCAASGFTFSSFGMSWRQAPGKGLEWSSISGSGSDTLYADSVKGRFTISRDNAKTTLYLQMNSLRPEDTAVYY CTIGGSLSRSSQGTLVTVSSA |
| 104 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDYWGQGTLVTVSSGGGGSGGGGSGGGGSGGGGSEVQLVESG GGVVQPGGSLRLSCAASGGTFSFYGMGWFRQAPGKEQEFVADIRTSAGRTYYADSVKGRFTISRDNSKNTVYLQMNSLRP EDTALYYCAAEMSGISGWDYWGQGTLVTVSSGGGGSGGGGSGGGGSGGGGSEVQLVESGGGV VQPGGSLRLSCAASGGTFSFYGMGWFRQAPGKEQEFVADIRTSAGRTYYADSVKGRFTISRDNSKNTVYLQMNSLRPEDT ALYYCAAEMSGISGWDYWGQGTLVTVSSGGGGSGGGGSGGGGSGGGGSEVQLVESGGGLVQP GNSLRLSCAASGFTFSSFGMSWRQAPGKGLEWSSISGSGSDTLYADSVKGRFTISRDNAKTTLYLQMNSLRPEDTAVYY CTIGGSLSRSSQGTLVTVSSA |
| 105 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDYWGQGTLVTVSSGGGGSGGGGSGGGGSGGGGSEVQLVESG GGVVQPGGSLRLSCAASGGTFSFYGMGWFRQAPGKEQEFVADIRTSAGRTYYADSVKGRFTISRDNSKNTVYLQMNSLRP EDTALYYCAAEMSGISGWDYWGQGTLVTVSSGGGGSGGGGSGGGGSGGGGSEVQLVESGGGV VQPGGSLRLSCAASGGTFSFYGMGWFRQAPGKEQEFVADIRTSAGRTYYADSVKGRFTISRDNSKNTVYLQMNSLRPEDT ALYYCAAEMSGISGWDYWGQGTLVTVSSGGGGSGGGGSGGGGSGGGGSEVQLLESGGGWQP GGSLRLSCAASGFTFRSFGMSWRQAPGKGPEWVSSISGSGSDTLYADSVKGRFTISRDNSKNTLYLQMNSLRPEDTALYY CTIGGSLSRSSQGTLVTVSSA |

FIG.6-1

| 106 | DVQLVESGGGVVQPGSLRLSCAASGSIASIHAMGWFRQAPGKEREFVAVITWSGGITYYADSVKGRFTISRDNSKNTVYL
QMNSLRPEDTALYYCAGDKHQSSWYDYWGQGTLVTVSSGGGGSGGGGSGGGGSGGGGSGGGGSEVQL
VESGGGVVQPGSLRLSCAASGSIASIHAMGWFRQAPGKEREFVAVITWSGGITYYADSVKGRFTISRDNSKNTVYLQMNS
LRPEDTALYYCAGDKHQSSWYDYWGQGTLVTVSSGGGGSGGGGSGGGGSGGGGSGGGGSEVQLVESG
GGVVQPGSLRLSCAASGGTFSFYGMGWFRQAPGKEREFVADIRTSAGRTYYADSVKGRFTISRDNSKNTVYLQMNSLRP
EDTALYYCAAEMSGISGWDYWGQGTLVTVSSGGGGSGGGGSGGGGSGGGGSGGGGSEVQLVESGGGV
VQPGGSLRLSCAASGGTFSFYGMGWFRQAPGKEREFVADIRTSAGRTYYADSVKGRFTISRDNSKNTVYLQMNSLRPEDT
ALYYCAAEMSGISGWDYWGQGTLVTVSSGGGGSGGGGSGGGGSGGGGSGGGGSEVQLLESGGGVVQP
GGSLRLSCAASGFTFRSFGMSWVRQAPGKGPEWVSSISGSGSDTLYADSVKGRFTISRDNSKNTLYLQMNSLRPEDTALYY
CTIGGSLSRSSQGTLVTVSSA |
| 107 | DVQLVESGGGVVQPGSLRLSCAASGSIASIHAMGWFRQAPGKEREFVAVITWSGGITYYADSVKGRFTISRDNSKNTVY
LQMNSLRPEDTALYYCAAEMSGISGWDYWGQGTFSFYGMGWFRQAPGKEQEFVADIRTSAGRTYYADSVKGRFTISRDNSKNTVY
LQMNSLRPEDTALYYCAAEMSGISGWDYWGQGTFSFYGMGWFRQAPGKEQEFVADIRTSAGRTYYADSVKGRFTISRDNSKNTVYLQMNSLRP
EDTALYYCAGDKHQSSWYDYWGQGTLVTVSSGGGGSGGGGSGGGGSGGGGSGGGGSEVQLVESGGGV
VQPGGSLRLSCAASGSIASIHAMGWFRQAPGKEREFVAVITWSGGITYYADSVKGRFTISRDNSKNTVYLQMNSLRPEDTA
LYYCAGDKHQSSWYDYWGQGTLVTVSSGGGGSGGGGSGGGGSGGGGSGGGGSEVQLVESGGGLVQPG
GSLRLSCAASGFTFSSFGMSWVRQAPGKGLEWVSSISGSGSDTLYADSVKGRFTISRDNAKTTLYLQMNSLRPEDTAVYYC
TIGGSLSRSSQGTLVTVSSA |
| 108 | DVQLVESGGGVVQPGSLRLSCAASGSIASIHAMGWFRQAPGKEREFVAVITWSGGITYYADSVKGRFTISRDNSKNTVY
LQMNSLRPEDTALYYCAAEMSGISGWDYWGQGTFSFYGMGWFRQAPGKEREFVADIRTSAGRTYYADSVKGRFTISRDNSKNTVYLQMN
VESGGGVVQPGSLRLSCAASGGTFSFYGMGWFRQAPGKEREFVADIRTSAGRTYYADSVKGRFTISRDNSKNTVYLQMN
SLRPEDTALYYCAAEMSGISGWDYWGQGTLVTVSSGGGGSGGGGSGGGGSGGGGSGGGGSEVQLVESG
GGVVQPGSLRLSCAASGSIASIHAMGWFRQAPGKEREFVAVITWSGGITYYADSVKGRFTISRDNSKNTVYLQMNSLRPE
DTALYYCAGDKHQSSWYDYWGQGTLVTVSSGGGGSGGGGSGGGGSGGGGSGGGGSEVQLVESGGGVV
QPGGSLRLSCAASGSIASIHAMGWFRQAPGKEREFVAVITWSGGITYYADSVKGRFTISRDNSKNTVYLQMNSLRPEDTAL
YYCAGDKHQSSWYDYWGQGTLVTVSSGGGGSGGGGSGGGGSGGGGSGGGGSEVQLVESGGGLVQPGN
SLRLSCAASGFTFSSFGMSWVRQAPGKGLEWVSSISGSGSDTLYADSVKGRFTISRDNAKTTLYLQMNSLRPEDTAVYYCT
IGGSLSRSSQGTLVTVSSA |

FIG. 6-2

| 109 | DVQLVESGGGVVQPGGSLRLSCAASGGTFSFYGMGWFRQAPGKEQEFVADIRTSAGRTYYADSVKGRFTISRDNSKNTVY
LQMNSLRPEDTALYYCAAEMSGISGWDYWGQGTLVTVSSGGGGSGGGGSGGGGSGGGGSEVQL
VESGGGVVQPGGSLRLSCAASGGTFSFYGMGWFRQAPGKEQEFVADIRTSAGRTYYADSVKGRFTISRDNSKNTVYLQM
NSLRPEDTALYYCAAEMSGISGWDYWGQGTLVTVSSGGGGSGGGGSGGGGSGGGGSEVQLVES
GGGVVQPGGSLRLSCAASGSIASIHAMGWFRQAPGKEREFVAVITWSGGITYYADSVKGRFTISRDNSKNTVYLQMNSLRP
EDTALYYCAGDKHQSSWYDYWGQGTLVTVSSGGGGSGGGGSGGGGSGGGGSEVQLVESGGGV
VQPGGSLRLSCAASGSIASIHAMGWFRQAPGKEREFVAVITWSGGITYYADSVKGRFTISRDNSKNTVYLQMNSLRPEDTA
LYYCAGDKHQSSWYDYWGQGTLVTVSSGGGGSGGGGSGGGGSGGGGSEVQLLESGGGVVQPG
GSLRLSCAASGFTFRSFGMSWVRQAPGKGPEWVSSISGSGSDTLYADSVKGRFTISRDNSKNTLYLQMNSLRPEDTALYYC
TIGGSLSRSSQGTLVTVSSA |
| 110 | DVQLVESGGGVVQPGGSLRLSCAASGGTFSFYGMGWFRQAPGKEQEFVADIRTSAGRTYYADSVKGRFTISRDNSKNTVY
LQMNSLRPEDTALYYCAAEMSGISGWDYWGQGTLVTVSSGGGGSGGGGSGGGGSGGGGSEVQL
VESGGGVVQPGGSLRLSCAASGGTFSFYGMGWFRQAPGKEREFVADIRTSAGRTYYADSVKGRFTISRDNSKNTVYLQMN
SLRPEDTALYYCAAEMSGISGWDYWGQGTLVTVSSGGGGSGGGGSGGGGSGGGGSEVQLVESG
GGVVQPGGSLRLSCAASGSIASIHAMGWFRQAPGKEREFVAVITWSGGITYYADSVKGRFTISRDNSKNTVYLQMNSLRPE
DTALYYCAGDKHQSSWYDYWGQGTLVTVSSGGGGSGGGGSGGGGSGGGGSEVQLVESGGGVV
QPGGSLRLSCAASGSIASIHAMGWFRQAPGKEREFVAVITWSGGITYYADSVKGRFTISRDNSKNTVYLQMNSLRPEDTAL
YYCAGDKHQSSWYDYWGQGTLVTVSSGGGGSGGGGSGGGGSGGGGSEVQLLESGGGVVQPGG
SLRLSCAASGFTFRSFGMSWVRQAPGKGPEWVSSISGSGSDTLYADSVKGRFTISRDNSKNTLYLQMNSLRPEDTALYYCTI
GGSLSRSSQGTLVTVSSA |
| 111 | DVQLVESGGGVVQPGGSLRLSCAASGGTFSFYGMGWFRQAPGKEREFVAVITWSGGITYYADSVKGRFTISRDNSKNTVYL
QMNSLRPEDTALYYCAGDKHQSSWYDYWGQGTLVTVSSGGGGSGGGGSGGGGSGGGGSEVQL
VESGGGVVQPGGSLRLSCAASGGTFSFYGMGWFRQAPGKEQEFVADIRTSAGRTYYADSVKGRFTISRDNSKNTVYLQM
NSLRPEDTALYYCAAEMSGISGWDYWGQGTLVTVSSGGGGSGGGGSGGGGSGGGGSEVQLVES
GGGLVQPGNSLRLSCAASGFTFSSFGMSWRQAPGKGLEWVSSISGSGSDTLYADSVKGRFTISRDNAKTTLYLQMNSLRP
EDTAVYYCTIGGSLSRSSQGTLVTVSSA |

FIG.6-3

| 112 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSMYDYWGQGTLVTVSSGGGGSGGGGSGGGGSGGGGSEVQL VESGGGVVQPGGSLRLSCAASGGTFSFYGMGWFRQAPGKEREFVADIRTSAGRTYYADSVKGRFTISRDNSKNTVYLQMN SLRPEDTALYYCAAEMSGISGWDYWGQGTLVTVSSGGGGSGGGGSGGGGSGGGGSEVQLVESG GGLVQPGNSLRLSCAASGFTFSSFGMSWVRQAPGKGLEWVSSISGSGSDTLYADSVKGRFTISRDNAKTTLYLQMNSLRPE DTAVYYCTIGGSLSRSSQGTLVTVSSA |
| 113 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSMYDYWGQGTLVTVSSGGGGSGGGGSGGGGSGGGGSEVQL VESGGGVVQPGGSLRLSCAASGGTFSFYGMGWFRQAPGKEQEFVADIRTSAGRTYYADSVKGRFTISRDNSKNTVYLQM NSLRPEDTALYYCAAEMSGISGWDYWGQGTLVTVSSGGGGSGGGGSGGGGSGGGGSEVQLLES GGGVVQPGGSLRLSCAASGFTFRSFGMSWVRQAPGKGPEWVSSISGSGSDTLYADSVKGRFTISRDNKNTLYLQMNSLRP EDTALYYCTIGGSLSRSSQGTLVTVSSA |
| 114 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSMYDYWGQGTLVTVSSGGGGSGGGGSGGGGSGGGGSEVQL VESGGGVVQPGGSLRLSCAASGGTFSFYGMGWFRQAPGKEREFVADIRTSAGRTYYADSVKGRFTISRDNSKNTVYLQMN SLRPEDTALYYCAAEMSGISGWDYWGQGTLVTVSSGGGGSGGGGSGGGGSGGGGSEVQLESG GGVVQPGGSLRLSCAASGFTFRSFGMSWVRQAPGKGPEWVSSISGSGSDTLYADSVKGRFTISRDNKNTLYLQMNSLRPE DTALYYCTIGGSLSRSSQGTLVTVSSA |
| 115 | DVQLVESGGGVVQPGGSLRLSCAASGGTFSFYGMGWFRQAPGKEQEFVADIRTSAGRTYYADSVKGRFTISRDNSKNTVY LQMNSLRPEDTALYYCAAEMSGISGWDYWGQGTLVTVSSGGGGSGGGGSGGGGSGGGGSEVQLVESG VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSMYDYWGQGTLVTVSSGGGGSGGGGSGGGGSGGGGSEVQLVESG GGLVQPGNSLRLSCAASGFTFSSFGMSWVRQAPGKGLEWVSSISGSGSDTLYADSVKGRFTISRDNAKTTLYLQMNSLRPE DTAVYYCTIGGSLSRSSQGTLVTVSSA |
| 116 | DVQLVESGGGVVQPGGSLRLSCAASGGTFSFYGMGWFRQAPGKEREFVADIRTSAGRTYYADSVKGRFTISRDNSKNTVY LQMNSLRPEDTALYYCAAEMSGISGWDYWGQGTLVTVSSGGGGSGGGGSGGGGSGGGGSEVQLVESG VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSMYDYWGQGTLVTVSSGGGGSGGGGSGGGGSGGGGSEVQLVESG GGLVQPGNSLRLSCAASGFTFSSFGMSWVRQAPGKGLEWVSSISGSGSDTLYADSVKGRFTISRDNAKTTLYLQMNSLRPE DTAVYYCTIGGSLSRSSQGTLVTVSSA |

FIG.6-4

| | |
|---|---|
| 117 | DVQLVESGGGVVQPGGSLRLSCAASGGTFSFYGMCWFRQAPGKEQEFVADIRTSAGRTYYADSVKGRFTISRDNSKNTVY LQMNSLRPEDTALYYCAAEMSGISGWDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDWGQGTLVTVSSGGGGSGGGGSGGGGSGGGGSEVQLLESG GGVVQPGGSLRLSCAASGFTFRSFGMSWVRQAPGKGPEWVSSISGSGSDTLYADSVKGRFTISRDNSKNTILYLQMNSLRPE DTALYYCTIGGSLSRSSQGTLVTVSSA |
| 118 | DVQLVESGGGVVQPGGSLRLSCAASGGTFSFYGMGWFRQAPGKEREFVADIRTSAGRTYYADSVKGRFTISRDNSKNTVY LQMNSLRPEDTALYYCAAEMSGISGWDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDWGQGTLVTVSSGGGGSGGGGSGGGGSGGGGSEVQLLESG GGVVQPGGSLRLSCAASGFTFRSFGMSWVRQAPGKGPEWVSSISGSGSDTLYADSVKGRFTISRDNSKNTILYLQMNSLRPE DTALYYCTIGGSLSRSSQGTLVTVSSA |
| 119 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDWGQGTLVTVSSGGGGSGGGGSGGGGSGGGGSEVQL VESGGGVVQPGGSLRLSCAASGGTFSFYGMGWFRQAPGKEQEFVADIRTSAGRTYYADSVKGRFTISRDNSKNTVYLQM NSLRPEDTALYYCAAEMSGISGWDYWGQGTLVTVSSGGGGSGGGGSGGGGSGGGGSEVQLVES GGGVVQPGGSLRLSCAASGFTFSFYGMCWFRQAPGKEQEFVADIRTSAGRTYYADSVKGRFTISRDNSKNTVYLQMNSLR PEDTALYYCAAEMSGISGWDYWGQGTLVTVSSGGGGSGGGGSGGGGSGGGGSEVQLVESGGGL VQPGNSLRLSCAASGFTFSSFGMSWVRQAPGKGLEWVSSISGSGSDTLYADSVKGRFTISRDNAKTTLYLQMNSLRPEDTA VYYCTIGGSLSRSSQGTLVTVSSA |
| 120 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDWGQGTLVTVSSGGGGSGGGGSGGGGSGGGGSEVQL VESGGGVVQPGGSLRLSCAASGGTFSFYGMGWFRQAPGKEREFVADIRTSAGRTYYADSVKGRFTISRDNSKNTVYLQMN SLRPEDTALYYCAAEMSGISGWDYWGQGTLVTVSSGGGGSGGGGSGGGGSGGGGSEVQLVESG GGVVQPGGSLRLSCAASGFTFSFYGMCWFRQAPGKEREFVADIRTSAGRTYYADSVKGRFTISRDNSKNTVYLQMNSLRP EDTALYYCAAEMSGISGWDYWGQGTLVTVSSGGGGSGGGGSGGGGSGGGGSEVQLVESGGGL VQPGNSLRLSCAASGFTFSSFGMSWVRQAPGKGLEWVSSISGSGSDTLYADSVKGRFTISRDNAKTTLYLQMNSLRPEDTA VYYCTIGGSLSRSSQGTLVTVSSA |

FIG. 6-5

| | |
|---|---|
| 121 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDYWGQGTLVTVSSGGGGSGGGGSGGGGSGGGGSSEVQL VESGGGVVQPGGSLRLSCAASGFTFSFYGMGWFRQAPGKEQEFVADIRTSAGRTYYADSVKGRFTISRDNSKNTVYLQM NSLRPEDTALYYCAAEMSGISGWDYWGQGTLVTVSSGGGGSGGGGSGGGGSGGGGSEVQLVES GGGVVQPGGSLRLSCAASGFTFSFYGMGWFRQAPGKEQEFVADIRTSAGRTYYADSVKGRFTISRDNSKNTVYLQMNSLR PEDTALYYCAAEMSGISGWDYWGQGTLVTVSSGGGGSGGGGSGGGGSGGGGSEVQLLESGGGV VQPGGSLRLSCAASGFTFSRSFGMSWVRQAPGKGPEWVSSISGSGSDTLYADSVKGRFTISRDNSKNTLYLQMNSLRPEDTA LYYCTIGGSLSRSSQGTLVTVSSA |
| 122 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDYWGQGTLVTVSSGGGGSGGGGSGGGGSGGGGSSEVQL VESGGGVVQPGGSLRLSCAASGFTFSFYGMGWFRQAPGKEREFVADIRTSAGRTYYADSVKGRFTISRDNSKNTVYLQMN SLRPEDTALYYCAAEMSGISGWDYWGQGTLVTVSSGGGGSGGGGSGGGGSGGGGSEVQLVESG GGVVQPGGSLRLSCAASGFTFSFYGMGWFRQAPGKEREFVADIRTSAGRTYYADSVKGRFTISRDNSKNTVYLQMNSLRP EDTALYYCAAEMSGISGWDYWGQGTLVTVSSGGGGSGGGGSGGGGSGGGGSEVQLLESGGGV VQPGNSLRLSCAASGFTFSRSFGMSWVRQAPGKGPEWVSSISGSGSDTLYADSVKGRFTISRDNSKNTLYLQMNSLRPEDTA LYYCTIGGSLSRSSQGTLVTVSSA |
| 123 | DVQLVESGGGVVQPGGSLRLSCAASGGTFSFYGMGWFRQAPGKEQEFVADIRTSAGRTYYADSVKGRFTISRDNSKNTVY LQMNSLRPEDTALYYCAAEMSGISGWDYWGQGTLVTVSSGGGGSGGGGSGGGGSGGGGSEVQL VESGGGVVQPGGSLRLSCAASGFTFSFYGMGWFRQAPGKEQEFVADIRTSAGRTYYADSVKGRFTISRDNSKNTVYLQM NSLRPEDTALYYCAAEMSGISGWDYWGQGTLVTVSSGGGGSGGGGSGGGGSGGGGSEVQLVES GGGVVQPGGSLRLSCAASGSIASIHAMGWFRQAPGKEREFVAVITWSGGITYYADSVKGRFTISRDNSKNTVYLQMNSLRP EDTALYYCAGDKHQSSWYDYWGQGTLVTVSSGGGGSGGGGSGGGGSGGGGSEVQLVESGGGL VQPGNSLRLSCAASGFTFSSFGMSWVRQAPGKGLEWVSSISGSGSDTLYADSVKGRFTISRDNAKTTLYLQMNSLRPEDTA VYYCTIGGSLSRSSQGTLVTVSSA |
| 124 | DVQLVESGGGVVQPGGSLRLSCAASGGTFSFYGMGWFRQAPGKEREFVADIRTSAGRTYYADSVKGRFTISRDNSKNTVY LQMNSLRPEDTALYYCAAEMSGISGWDYMCQGTLVTVSSGGGGSGGGGSGGGGSGGGGSEVQL VESGGGVVQPGGSLRLSCAASGFTFSFYGMGWFRQAPGKEREFVADIRTSAGRTYYADSVKGRFTISRDNSKNTVYLQMN SLRPEDTALYYCAAEMSGISGWDYWGQGTLVTVSSGGGGSGGGGSGGGGSGGGGSEVQLVESG GGVVQPGGSLRLSCAASGSIASIHAMGWFRQAPGKEREFVAVITWSGGITYYADSVKGRFTISRDNSKNTVYLQMNSLRPE DTALYYCAGDKHQSSWYDYWGQGTLVTVSSGGGGSGGGGSGGGGSGGGGSEVQLVESGGGLV QPGNSLRLSCAASGFTFSSFGMSWVRQAPGKGLEWVSSISGSGSDTLYADSVKGRFTISRDNAKTTLYLQMNSLRPEDTAV YYCTIGGSLSRSSQGTLVTVSSA |

FIG. 6-6

| 125 | DVQLVESGGGVVQPGGSLRLSCAASGGTFSFYGMCWFRQAPCKEQEFVADIRTSAGRTYYADSVKGRFTISRDNSKNTVY
LQMNSLRPEDTALYYCAAEMSGISGMDYWGQGTLVTVSSGGGGSGGGGSGGGGSGGGGSEVQL
VESGGGVVQPGGSLRLSCAASGGTFSFYGMGWFRQAPGKEQEFVADIRTSAGRTYYADSVKGRFTISRDNSKNTVYLQM
NSLRPEDTALYYCAAEMSGISGMDYWCQGTLVTVSSGGGGSGGGGSGGGGSGGGGSEVQLVES
GGGVVQPGGSLRLSCAASGSIASIHAMGWFRQAPGKEREFVAVITWSGGITYYADSVKGRFTISRDNSKNTVYLQMNSLRP
EDTALYYCAGDKHQSSWYDYWGQGTLVTVSSGGGGSGGGGSGGGGSGGGGSEVQLLESGGGV
VQPGGSLRLSCAASGFTFRSFGMSWVRQAPGKGPEWSSISGSGSDTLYADSVKGRFTISRDNSKNTLYLQMNSLRPEDTA
LYYCTIGGSLSRSSQGTLVTVSSA |
| 126 | DVQLVESGGGVVQPGGSLRLSCAASGGTFSFYGMGWFRQAPGKEREFVADIRTSAGRTYYADSVKGRFTISRDNSKNTVY
LQMNSLRPEDTALYYCAAEMSGISGMDYWCQGTLVTVSSGGGGSGGGGSGGGGSGGGGSEVQL
VESGGGVVQPGGSLRLSCAASGGTFSFYGMGWFRQAPGKEREFVADIRTSAGRTYYADSVKGRFTISRDNSKNTVYLQMN
SLRPEDTALYYCAAEMSGISGMDYWCQGTLVTVSSGGGGSGGGGSGGGGSGGGGSEVQLVESG
GGVVQPGGSLRLSCAASGSIASIHAMGWFRQAPGKEREFVAVITWSGGITYYADSVKGRFTISRDNSKNTVYLQMNSLRPE
DTALYYCAGDKHQSSWYDYWGQGTLVTVSSGGGGSGGGGSGGGGSGGGGSEVQLLESGGGVV
QPGGSLRLSCAASGFTFRSFGMSWVRQAPGKGPEWSSISGSGSDTLYADSVKGRFTISRDNSKNTLYLQMNSLRPEDTAL
YYCTIGGSLSRSSQGTLVTVSSA |
| 127 | DVQLVESGGGVVQPGGSLRLSCAASGSIASIHAMGWFRQAPGKEREFVAVITWSGGITYYADSVKGRFTISRDNSKNTVYL
QMNSLRPEDTALYYCAGDKHQSSWYDYWGQGTLVTVSSGGGGSGGGGSGGGGSGGGGSEVQL
VESGGGVVQPGGSLRLSCAASGSIASIHAMGWFRQAPGKEREFVAVITWSGGITYYADSVKGRFTISRDNSKNTVYLQMNS
LRPEDTALYYCAGDKHQSSWYDYWGQGTLVTVSSGGGGSGGGGSGGGGSGGGGSEVQLVESG
GGVVQPGGSLRLSCAASGGTFSFYGMGWFRQAPGKEREFVADIRTSAGRTYYADSVKGRFTISRDNSKNTVYLQMNSLRP
EDTALYYCAAEMSGISGMDYWCQGTLVTVSSGGGGSGGGGSGGGGSGGGGSEVQLVESGGGL
VQPGNSLRLSCAASGFTFSSFGMSWVRQAPGKGLEWVSSISGSGSDTLYADSVKGRFTISRDNAKTLYLQMNSLRPEDTA
VYYCTIGGSLSRSSQGTLVTVSSA |
| 128 | DVQLVESGGGVVQPGGSLRLSCAASGSIASIHAMGWFRQAPGKEREFVAVITWSGGITYYADSVKGRFTISRDNSKNTVYL
QMNSLRPEDTALYYCAGDKHQSSWYDYWGQGTLVTVSSGGGGSGGGGSGGGGSGGGGSEVQL
VESGGGVVQPGGSLRLSCAASGSIASIHAMGWFRQAPGKEREFVAVITWSGGITYYADSVKGRFTISRDNSKNTVYLQMNS
LRPEDTALYYCAGDKHQSSWYDYWGQGTLVTVSSGGGGSGGGGSGGGGSGGGGSEVQLVESG
GGVVQPGGSLRLSCAASGGTFSFYGMGWFRQAPGKEQEFVADIRTSAGRTYYADSVKGRFTISRDNSKNTVYLQMNSLRP
EDTALYYCAAEMSGISGMDYWCQGTLVTVSSGGGGSGGGGSGGGGSGGGGSEVQLVESGGGL
VQPGNSLRLSCAASGFTFSSFGMSWVRQAPGKGLEWVSSISGSGSDTLYADSVKGRFTISRDNAKTLYLQMNSLRPEDTA
VYYCTIGGSLSRSSQGTLVTVSSA |

FIG.6-7

| | |
|---|---|
| 129 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDYWGQGTLVTVSSGGGGSGGGGSGGGGSGGGGSEVQLVESG GGVVQPGGSLRLSCAASGGTFSFYGMGWFRQAPGCWFRQAPGKEREFVAVITWSGGITYYADSVKGRFTISRDNSKNTVYLQMNSLRP EDTALYYCAAEMSGISGWDYWGQGTLVTVSSGGGGSGGGGSGGGGSGGGGSEVQLLESGGGV VQPGGSLRLSCAASGFTFRSFGMSWVRQAPGKGPEWVSSISGSGSDTLYADSVKGRFTISRDNSKNTLYLQMNSLRPEDTA LYYCTIGGSLSRSSQGTLVTVSSA |
| 130 | DVQLVESGGGVVQPGGSLRLSCAASGSIASIHAMGWFRQAPGKEREFVAVITWSGGITYYADSVKGRFTISRDNSKNTVYL QMNSLRPEDTALYYCAGDKHQSSWYDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDYWGQGTLVTVSSGGGGSGGGGSGGGGSGGGGSEVQLVESG GGVVQPGGSLRLSCAASGGTFSFYGMGWFRQAPGKEQEFVADIRTSAGRTYYADSVKGRFTISRDNSKNTVYLQMNSLRP EDTALYYCAAEMSGISGWDYWGQGTLVTVSSGGGGSGGGGSGGGGSGGGGSEVQLLESGGGV VQPGGSLRLSCAASGFTFRSFGMSWVRQAPGKGPEWVSSISGSGSDTLYADSVKGRFTISRDNSKNTLYLQMNSLRPEDTA LYYCTIGGSLSRSSQGTLVTVSSA |
| 131 | DVQLVESGGGVVQPGGSLRLSCAASGGTFSFYGMGWFRQAPGKEQEFVADIRTSAGRTYYADSVKGRFTISRDNSKNTVY LQMNSLRPEDTALYYCAAEMSGISGWDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDYWGQGTLVTVSSGGGGSGGGGSGGGGSGGGGSEVQLVESG GGVVQPGGSLRLSCAASGSIASIHAMGWFRQAPGKEREFVAVITWSGGITYYADSVKGRFTISRDNAKTTLYLQMNSLRPE DTALYYCAGDKHQSSWYDYWGQGTLVTVSSGGGGSGGGGSGGGGSGGGGSEVQLVESGGGLV QPGNSLRLSCAASGFTFSSFGMSWVRQAPGKGLEWVSSISGSGSDTLYADSVKGRFTISRDNAKTTLYLQMNSLRPEDTAV YYCTIGGSLSRSSQGTLVTVSSA |
| 132 | DVQLVESGGGVVQPGGSLRLSCAASGGTFSFYGMGWFRQAPGKEQEFVADIRTSAGRTYYADSVKGRFTISRDNSKNTVY LQMNSLRPEDTALYYCAAEMSGISGWDYWGQGTLVTVSSGGGGSGGGGSGGGGSGGGGSEVQL VESGGGVVQPGGSLRLSCAASGSIASIHAMGWFRQAPGKEREFVAVITWSGGITYYADSVKGRFTISRDNSKNTVYLQMNS LRPEDTALYYCAGDKHQSSWYDYWGQGTLVTVSSGGGGSGGGGSGGGGSGGGGSEVQLVESG GGVVQPGGSLRLSCAASGSIASIHAMGWFRQAPGKEREFVAVITWSGGITYYADSVKGRFTISRDNAKTTLYLQMNSLRPE DTALYYCAGDKHQSSWYDYWGQGTLVTVSSGGGGSGGGGSGGGGSGGGGSEVQLVESGGGLV QPGNSLRLSCAASGFTFSSFGMSWVRQAPGKGLEWVSSISGSGSDTLYADSVKGRFTISRDNAKTTLYLQMNSLRPEDTAV YYCTIGGSLSRSSQGTLVTVSSA |

FIG. 6-8

| 133 | DVQLVESGGGVVQPGGSLRLSCAASGGTFSFYGMGWFRQAPGKEQEFVADIRTSAGRTYYADSVKGRFTISRDNSKNTVY
LQMNSLRPEDTALYYCAAEMSGISGWDYWGQGTLVTVSSGGGGSGGGGSGGGGSGGGGSEVQL
VESGGGVVQPGGSLRLSCAASGSIASIHAMGWFRQAPGKEREFVAVITWSGGITYYADSVKGRFTISRDNSKNTVYLQMNS
LRPEDTALYYCAGDKHQSSWYDYWGQGTLVTVSSGGGGSGGGGSGGGGSGGGGSEVQLVESG
GGVVQPGGSLRLSCAASGSIASIHAMGWFRQAPGKEREFVAVITWSGGITYYADSVKGRFTISRDNSKNTVYLQMNSLRPE
DTALYYCAGDKHQSSWYDYWGQGTLVTVSSGGGGSGGGGSGGGGSGGGGSEVQLLESGGGVV
QPGGSLRLSCAASGFTFRSFGMSWVRQAPGKGPEWVSSISGSGSDTLYADSVKGRFTISRDNSKNTLYLQMNSLRPEDTAL
YYCTIGGSLSRSSQGTLVTVSSA |
| 134 | DVQLVESGGGVVQPGGSLRLSCAASGGTFSFYGMGWFRQAPGKEQEFVADIRTSAGRTYYADSVKGRFTISRDNSKNTVY
LQMNSLRPEDTALYYCAAEMSGISGWDYWGQGTLVTVSSGGGGSGGGGSGGGGSGGGGSEVQL
VESGGGVVQPGGSLRLSCAASGSIASIHAMGWFRQAPGKEREFVAVITWSGGITYYADSVKGRFTISRDNSKNTVYLQMNS
LRPEDTALYYCAGDKHQSSWYDYWGQGTLVTVSSGGGGSGGGGSGGGGSGGGGSEVQLVESG
GGVVQPGGSLRLSCAASGSIASIHAMGWFRQAPGKEREFVAVITWSGGITYYADSVKGRFTISRDNSKNTVYLQMNSLRPE
DTALYYCAGDKHQSSWYDYWGQGTLVTVSSGGGGSGGGGSGGGGSGGGGSEVQLLESGGGVV
QPGGSLRLSCAASGFTFRSFGMSWVRQAPGKGPEWVSSISGSGSDTLYADSVKGRFTISRDNSKNTLYLQMNSLRPEDTAL
YYCTIGGSLSRSSQGTLVTVSSA |

FIG. 6-9

>F023700906.1 4CTLA011F01(L11V,A14P,Q45R,A74S,K83R,V89L,M96P,Q108L)-FLAG3-
HIS6
EVQLVESGGGVVQPGGSLRLSCAASGGTFSFYGMGWFRQAPGKEREFVADIRTSAGRTYYADSVKGRFTISRDNS
KNTVYLQMNSLRPEDTALYYCAAEPSGISGWDYWGQGTLVTVSSAAADYKDHDGDYKDHDIDYKDDDDKGAAHHH
HHH
(SEQ ID NO: 176)

>F023700910.1 1PD102C12(E1D,L11V,A14P,A74S,K83R,I89L)-35GS-
4CTLA011F01(L11V,A14P,Q45R,A74S,K83R,V89L,M96P,Q108L)-35GS-ALB11002-A
DVQLVESGGGVVQPGGSLRLSCAASGSIASIHAMGWFRQAPGKEREFVAVITWSGGITYYADSVKGRFTISRDNS
KNTVYLQMNSLRPEDTALYYCAGDKHQSSWYDYWGQGTLVTVSSGGGGSGGGGSGGGGSGGGGSGGGGSGGGGSG
GGGSEVQLVESGGGVVQPGGSLRLSCAASGGTFSFYGMGWFRQAPGKEREFVADIRTSAGRTYYADSVKGRFTIS
RDNSKNTVYLQMNSLRPEDTALYYCAAEPSGISGWDYWGQGTLVTVSSGGGGSGGGGSGGGGSGGGGSGGGGSGG
GGSGGGGSEVQLVESGGGVVQPGNSLRLSCAASGFTFSSFGMSWVRQAPGKGLEWVSSISGSGSDTLYADSVKGR
FTISRDNAKTTLYLQMNSLRPEDTALYYCTIGGSLSRSSQGTLVTVSSA
(SEQ ID NO: 146)

>F023700918.1 1PD102C12(E1D,L11V,A14P,A74S,K83R,I89L)-35GS-
1PD102C12(L11V,A14P,A74S,K83R,I89L)-35GS-
4CTLA011F01(L11V,A14P,Q45R,A74S,K83R,V89L,M96P,Q108L)-35GS-ALB11002-A
DVQLVESGGGVVQPGGSLRLSCAASGSIASIHAMGWFRQAPGKEREFVAVITWSGGITYYADSVKGRFTISRDNS
KNTVYLQMNSLRPEDTALYYCAGDKHQSSWYDYWGQGTLVTVSSGGGGSGGGGSGGGGSGGGGSGGGGSGGGGSG
GGGSEVQLVESGGGVVQPGGSLRLSCAASGSIASIHAMGWFRQAPGKEREFVAVITWSGGITYYADSVKGRFTIS
RDNSKNTVYLQMNSLRPEDTALYYCAGDKHQSSWYDYWGQGTLVTVSSGGGGSGGGGSGGGGSGGGGSGGGGSGG
GGSGGGGSEVQLVESGGGVVQPGGSLRLSCAASGGTFSFYGMGWFRQAPGKEREFVADIRTSAGRTYYADSVKGR
FTISRDNSKNTVYLQMNSLRPEDTALYYCAAEPSGISGWDYWGQGTLVTVSSGGGGSGGGGSGGGGSGGGGSGGG
GSGGGGSGGGGSEVQLVESGGGVVQPGNSLRLSCAASGFTFSSFGMSWVRQAPGKGLEWVSSISGSGSDTLYADS
VKGRFTISRDNAKTTLYLQMNSLRPEDTALYYCTIGGSLSRSSQGTLVTVSSA
(SEQ ID NO: 149)

>F023700925.1 1PD102C12(E1D,L11V,A14P,A74S,K83R,I89L)-35GS-
1PD102C12(L11V,A14P,A74S,K83R,I89L)-35GS-
4CTLA011F01(L11V,A14P,Q45R,A74S,K83R,V89L,M96P,Q108L)-35GS-
4CTLA011F01(L11V,A14P,Q45R,A74S,K83R,V89L,M96P,Q108L)-35GS-ALB11002-A
DVQLVESGGGVVQPGGSLRLSCAASGSIASIHAMGWFRQAPGKEREFVAVITWSGGITYYADSVKGRFTISRDNS
KNTVYLQMNSLRPEDTALYYCAGDKHQSSWYDYWGQGTLVTVSSGGGGSGGGGSGGGGSGGGGSGGGGSGGGGSG
GGGSEVQLVESGGGVVQPGGSLRLSCAASGSIASIHAMGWFRQAPGKEREFVAVITWSGGITYYADSVKGRFTIS
RDNSKNTVYLQMNSLRPEDTALYYCAGDKHQSSWYDYWGQGTLVTVSSGGGGSGGGGSGGGGSGGGGSGGGGSGG
GGSGGGGSEVQLVESGGGVVQPGGSLRLSCAASGGTFSFYGMGWFRQAPGKEREFVADIRTSAGRTYYADSVKGR
FTISRDNSKNTVYLQMNSLRPEDTALYYCAAEPSGISGWDYWGQGTLVTVSSGGGGSGGGGSGGGGSGGGGSGGG
GSGGGGSEVQLVESGGGVVQPGGSLRLSCAASGGTFSFYGMGWFRQAPGKEREFVADIRTSAGRTYYADS
VKGRFTISRDNSKNTVYLQMNSLRPEDTALYYCAAEPSGISGWDYWGQGTLVTVSSGGGGSGGGGSGGGGSGGGG
SGGGGSGGGGSGGGGSEVQLVESGGGVVQPGNSLRLSCAASGFTFSSFGMSWVRQAPGKGLEWVSSISGSGSDTL
YADSVKGRFTISRDNAKTTLYLQMNSLRPEDTALYYCTIGGSLSRSSQGTLVTVSSA
(SEQ ID NO: 153)

FIG.15A

>F023701047.1 4CTLA011F01(L11V,A14P,Q45R,N73S,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDSS
KNTVYLQMNSLRPEDTALYYCAAEPSGISGWDYWGQGTLVTVSSAAADYKDHDGDYKDHDIDYKDDDDKGAAHHH
HHH (SEQ ID NO: 177)

>F023701048.1 4CTLA011F01(L11V,A14P,Q45R,N73V,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDVS
KNTVYLQMNSLRPEDTALYYCAAEPSGISGWDYWGQGTLVTVSSAAADYKDHDGDYKDHDIDYKDDDDKGAAHHH
HHH (SEQ ID NO: 178)

>F023701049.1 4CTLA011F01(L11V,A14P,Q45R,N73G,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDGS
KNTVYLQMNSLRPEDTALYYCAAEPSGISGWDYWGQGTLVTVSSAAADYKDHDGDYKDHDIDYKDDDDKGAAHHH
HHH (SEQ ID NO: 179)

>F023701050.1 4CTLA011F01(L11V,A14P,Q45R,N73R,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDRS
KNTVYLQMNSLRPEDTALYYCAAEPSGISGWDYWGQGTLVTVSSAAADYKDHDGDYKDHDIDYKDDDDKGAAHHH
HHH (SEQ ID NO: 180)

>F023701051.1 4CTLA011F01(L11V,A14P,Q45R,N73Q,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDQS
KNTVYLQMNSLRPEDTALYYCAAEPSGISGWDYWGQGTLVTVSSAAADYKDHDGDYKDHDIDYKDDDDKGAAHHH
HHH (SEQ ID NO: 181)

>F023701052.1 4CTLA011F01(L11V,A14P,Q45R,N73M,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDMS
KNTVYLQMNSLRPEDTALYYCAAEPSGISGWDYWGQGTLVTVSSAAADYKDHDGDYKDHDIDYKDDDDKGAAHHH
HHH (SEQ ID NO: 182)

FIG. 15B

>F023701053.1 4CTLA011F01(L11V,A14P,Q45R,N73H,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDHSKNTVYLQMNSLRPEDTALYYCAAEPSGISGWDYWGQGTLVTVSSAAADYKDHDGDYKDHDIDYKDDDDKGAAHHHHHH (SEQ ID NO: 183)

>F023701054.1 4CTLA011F01(L11V,A14P,Q45R,N73T,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDTSKNTVYLQMNSLRPEDTALYYCAAEPSGISGWDYWGQGTLVTVSSAAADYKDHDGDYKDHDIDYKDDDDKGAAHHHHHH (SEQ ID NO: 184)

>F023701055.1 4CTLA011F01(L11V,A14P,Q45R,N73D,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDDSKNTVYLQMNSLRPEDTALYYCAAEPSGISGWDYWGQGTLVTVSSAAADYKDHDGDYKDHDIDYKDDDDKGAAHHHHHH (SEQ ID NO: 185)

>F023701056.1 4CTLA011F01(L11V,A14P,Q45R,N73E,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDESKNTVYLQMNSLRPEDTALYYCAAEPSGISGWDYWGQGTLVTVSSAAADYKDHDGDYKDHDIDYKDDDDKGAAHHHHHH (SEQ ID NO: 186)

>F023701057.1 4CTLA011F01(L11V,A14P,Q45R,N73W,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDWSKNTVYLQMNSLRPEDTALYYCAAEPSGISGWDYWGQGTLVTVSSAAADYKDHDGDYKDHDIDYKDDDDKGAAHHHHHH (SEQ ID NO: 187)

>F023701058.1 4CTLA011F01(L11V,A14P,Q45R,N73W,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDFSKNTVYLQMNSLRPEDTALYYCAAEPSGISGWDYWGQGTLVTVSSAAADYKDHDGDYKDHDIDYKDDDDKGAAHHHHHH (SEQ ID NO: 188)

FIG. 15C

>F023701059.1 4CTLA011F01(L11V,A14P,Q45R,N73K,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDKS
KNTVYLQMNSLRPEDTALYYCAAEPSGISGWDYWGQGTLVTVSSAAADYKDHDGDYKDHDIDYKDDDDKGAAHHH
HHH
(SEQ ID NO: 189)

>F023701060.1 4CTLA011F01(L11V,A14P,Q45R,N73K,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDAS
KNTVYLQMNSLRPEDTALYYCAAEPSGISGWDYWGQGTLVTVSSAAADYKDHDGDYKDHDIDYKDDDDKGAAHHH
HHH
(SEQ ID NO: 190)

>F023701061.1 4CTLA011F01(L11V,A14P,Q45R,N73Y,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDYS
KNTVYLQMNSLRPEDTALYYCAAEPSGISGWDYWGQGTLVTVSSAAADYKDHDGDYKDHDIDYKDDDDKGAAHHH
HHH
(SEQ ID NO: 191)

>F023701062.1 4CTLA011F01(L11V,A14P,Q45R,N73P,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDPS
KNTVYLQMNSLRPEDTALYYCAAEPSGISGWDYWGQGTLVTVSSAAADYKDHDGDYKDHDIDYKDDDDKGAAHHH
HHH
(SEQ ID NO: 192)

>F023700912.1 4CTLA011F01(E1D,L11V,A14P,Q45R,A74S,K83R,V89L,M96P,Q108L)-
35GS-4CTLA011F01(L11V,A14P,Q45R,A74S,K83R,V89L,M96P,Q108L)-35GS-ALB11002-A
DVQLVESGGGVVQPGGSLRLSCAASGGTFSFYGMGWFRQAPGKEREFVADIRTSAGRTYYADSVKGRFTISRDNS
KNTVYLQMNSLRPEDTALYYCAAEPSGISGWDYWGQGTLVTVSSGGGGSGGGGSGGGGSGGGGSGGGGSGGGGSG
GGGSEVQLVESGGGVVQPGGSLRLSCAASGGTFSFYGMGWFRQAPGKEREFVADIRTSAGRTYYADSVKGRFTIS
RDNSKNTVYLQMNSLRPEDTALYYCAAEPSGISGWDYWGQGTLVTVSSGGGGSGGGGSGGGGSGGGGSGGGGSGG
GGSGGGGSEVQLVESGGGVVQPGNSLRLSCAASGFTFSSFGMSWVRQAPGKGLEWVSSISGSGSDTLYADSVKGR
FTISRDNAKTTLYLQMNSLRPEDTALYYCTIGGSLSRSSQGTLVTVSSA
(SEQ ID NO: 193)

>F023700914 4CTLA011F01(E1D,L11V,A14P,Q45R,A74S,K83R,V89L,M96P,Q108L)-35GS-
ALB11002-A
DVQLVESGGGVVQPGGSLRLSCAASGGTFSFYGMGWFRQAPGKEREFVADIRTSAGRTYYADSVKGRFTISRDNS
KNTVYLQMNSLRPEDTALYYCAAEPSGISGWDYWGQGTLVTVSSGGGGSGGGGSGGGGSGGGGSGGGGSGGGGSG
GGGSEVQLVESGGGVVQPGNSLRLSCAASGFTFSSFGMSWVRQAPGKGLEWVSSISGSGSDTLYADSVKGRFTIS
RDNAKTTLYLQMNSLRPEDTALYYCTIGGSLSRSSQGTLVTVSSA
(SEQ ID NO: 194)

FIG.15D

| NanoBody | Description |
|---|---|
| F023700906 | 4CTLA011F01(L11V,A14P,Q45R,A74S,K83R,V89L,M96P,Q108L)-FLAG3-HIS6 |
| F023700910 | 1PD102C12(E1D,L11V,A14P,A74S,K83R,I89L)-35GS-<br>4CTLA011F01(L11V,A14P,Q45R,A74S,K83R,V89L,M96P,Q108L)-35GS-<br>ALB11002-A |
| F023700912 | 4CTLA011F01(E1D,L11V,A14P,Q45R,A74S,K83R,V89L,M96P,Q108L)-35GS-<br>4CTLA011F01(L11V,A14P,Q45R,A74S,K83R,V89L,M96P,Q108L)-35GS-<br>ALB11002-A |
| F023700914 | 4CTLA011F01(E1D,L11V,A14P,Q45R,A74S,K83R,V89L,M96P,Q108L)-35GS-<br>ALB11002-A |
| F023700918 | 1PD102C12(E1D,L11V,A14P,A74S,K83R,I89L)-35GS-<br>1PD102C12(L11V,A14P,A74S,K83R,I89L)-35GS-<br>4CTLA011F01(L11V,A14P,Q45R,A74S,K83R,V89L,M96P,Q108L)-35GS-<br>ALB11002-A |
| F023700920 | 1PD102C12(E1D,L11V,A14P,A74S,K83R,I89L)-35GS-<br>4CTLA011F01(L11V,A14P,Q45R,A74S,K83R,V89L,M96P,Q108L)-35GS-<br>4CTLA011F01(L11V,A14P,Q45R,A74S,K83R,V89L,M96P,Q108L)-35GS-<br>ALB11002-A |
| F023700925 | 1PD102C12(E1D,L11V,A14P,A74S,K83R,I89L)-35GS-<br>1PD102C12(L11V,A14P,A74S,K83R,I89L)-35GS-<br>4CTLA011F01(L11V,A14P,Q45R,A74S,K83R,V89L,M96P,Q108L)-35GS-<br>4CTLA011F01(L11V,A14P,Q45R,A74S,K83R,V89L,M96P,Q108L)-35GS-<br>ALB11002-A |
| F023701047 | 4CTLA011F01(L11V,A14P,Q45R,N73S,A74S,K83R,V89L,M96P,Q108L)-FLAG3-<br>HIS6 |
| F023701048 | 4CTLA011F01(L11V,A14P,Q45R,N73V,A74S,K83R,V89L,M96P,Q108L)-FLAG3-<br>HIS6 |
| F023701049 | 4CTLA011F01(L11V,A14P,Q45R,N73G,A74S,K83R,V89L,M96P,Q108L)-FLAG3-<br>HIS6 |

FIG.16A

| | |
|---|---|
| F023701050 | 4CTLA011F01(L11V,A14P,Q45R,N73R,A74S,K83R,V89L,M96P,Q108L)-FLAG3-HIS6 |
| F023701051 | 4CTLA011F0 1(L11V,A14P,Q45R,N73Q,A74S,K83R,V89L,M96P,Q108L)-FLAG3-HIS6 |
| F023701052 | 4CTLA011F01(L11V,A14P,Q45R,N73M,A74S,K83R,V89L,M96P,Q108L)-FLAG3-HIS6 |
| F023701053 | 4CTLA011F01(L11V,A14P,Q45R,N73H,A74S,K83R,V89L,M96P,Q108L)-FLAG3-HIS6 |
| F023701054 | 4CTLA011F01(L11V,A14P,Q45R,N73T,A74S,K83R,V89L,M96P,Q108L)-FLAG3-HIS6 |
| F023701055 | 4CTLA011F01(L11V,A14P,Q45R,N73D,A74S,K83R,V89L,M96P,Q108L)-FLAG3-HIS6 |
| F023701056 | 4CTLA011F01(L11V,A14P,Q45R,N73E,A74S,K83R,V89L,M96P,Q108L)-FLAG3-HIS6 |
| F023701057 | 4CTLA011F0 1(L11V,A14P,Q45R,N73W,A74S,K83R,V89L,M96P,Q108L)-FLAG3-HIS6 |
| F023701058 | 4CTLA011F01(L11V,A14P,Q45R,N73F,A74S,K83R,V89L,M96P,Q108L)-FLAG3-HIS6 |
| F023701059 | 4CTLA011F01(L11V,A14P,Q45R,N73K,A74S,K83R,V89L,M96P,Q108L)-FLAG3-HIS6 |
| F023701060 | 4CTLA011F01(L11V,A14P,Q45R,N73A,A74S,K83R,V89L,M96P,Q108L)-FLAG3-HIS6 |
| F023701061 | 4CTLA011F01(L11V,A14P,Q45R,N73Y,A74S,K83R,V89L,M96P,Q108L)-FLAG3-HIS6 |
| F023701062 | 4CTLA011F01(L11V,A14P,Q45R,N73P,A74S,K83R,V89L,M96P,Q108L)-FLAG3-HIS6 |

PD1/CTLA4 BINDERS

This application claim the benefit of U.S. Provisional Patent Application No. 62/256,985, filed Nov. 18, 2015; which is herein incorporated by referenced in its entirety.

A computer readable format nucleotide/amino acid Sequence Listing is incorporated by reference in its entirety. The file containing the Sequence Listing is a 353 kbyte ASCII text file created Nov. 15, 2016 named "24236WOPCTSEQ".

FIELD OF THE INVENTION

The present invention relates, in part, to bispecific polypeptides binding to programmed cell death protein 1 ("PM") and cytotoxic T-lymphocyte-associated protein 4 ("CTLA4"). In particular, the present invention relates, in part, to bispecific polypeptides that comprise at least one (such as one or two) heavy-chain immunoglobulin single variable domains (also referred to herein as "ISVs" or "ISVDs") binding to PD1 and at least one (such as one or two) heavy-chain immunoglobulin single variable domains binding to CTLA4.

BACKGROUND OF THE INVENTION

Abrogating immune regulatory molecules such as cytotoxic T lymphocyte antigen 4 (CTLA4) represents a new and promising strategy to induce tumor regression, stabilize disease, and prolong survival by manipulation of the immune system. An anti-CTLA4 antibody, ipilimumab, is currently being sold for indications including melanoma. Evidence of tumor regression with prolonged time to progression has been seen in patients with melanoma who received CTLA4 antibodies and durable responses have been observed with ipilimumab in patients with melanoma, ovarian cancer, prostate cancer, and renal cell cancer.

Programmed death receptor 1 (PD1) is an immunoinhibitory receptor that is primarily expressed on activated T and B cells. Interaction with its ligands has been shown to attenuate T-cell responses both in vitro and in vivo. Blockade of the interaction between PD1 and one of its ligands, PD-L1, has been shown to enhance tumor-specific CD8+ T-cell immunity and may therefore be helpful in clearance of tumor cells by the immune system.

Blockade of the PD1/PD-L1 interaction could lead to enhanced tumor-specific T-cell immunity and therefore be helpful in clearance of tumor cells by the immune system. To address this issue, a number of studies were performed. In a murine model of aggressive pancreatic cancer, T. Nomi et al. (Clin. Cancer Res. 13: 2151-2157 (2007)) demonstrated the therapeutic efficacy of PD1/PD-L1 blockade. Administration of either PD1 or PD-L1 directed antibody significantly inhibited tumor growth. Antibody blockade effectively promoted tumor reactive CD8+ T cell infiltration into the tumor resulting in the up-regulation of anti-tumor effectors including IFN gamma, granzyme B and perforin. Additionally, the authors showed that PD1 blockade can be effectively combined with chemotherapy to yield a synergistic effect. In another study, using a model of squamous cell carcinoma in mice, antibody blockade of PD1 or PD-L1 significantly inhibited tumor growth (Tsushima F. et al., Oral Oncol. 42: 268-274 (2006)).

One method by which to inhibit CTLA4 and PD1-mediated downregulation of the immune response is by interfering with their interactions with their ligands by binding them with a multispecific Nanobody. The possibility exists that Nanobodies, originating in llamas, could cause an unwanted anti-drug immune response, e.g., by binding of the Nanobodies by pre-existing antibodies in the patient's serum. Thus, novel methods by which to humanize Nanobodies so as to decrease or eliminate such a response are particularly valuable as are Nanobodies that are created by such methods.

SUMMARY OF THE INVENTION

The present invention provides a PD1/CTLA4 binder or multispecific immunoglobulin single variable domain (ISVD) such as a Nanobody that binds to human PD1 and human CTLA4 by contacting human CTLA4 at one or more of the following residues VRVTVL (amino acids 33-38 of SEQ ID NO: 195), ADSQVTEVC (amino acids 41-49 of SEQ ID NO: 195) and CKVELMYPPPYYLG (amino acids 93-106 of SEQ ID NO: 195), e.g., all three sites. For example, the binder protects the residues from hydrogen-deuterium exchange in the presence of a deuterium source such as $D_2O$. In an embodiment of the invention, the ISVD binds to human CTLA4 and generates a binding heat map (e.g., as generated in a hydrogen-dueterium exchange assay) essentially as set forth in FIG. 17.

The present invention also provides a PD1/CTLA4 binder comprising: one or more ISVDs that bind to PD1 comprising: CDR1 comprising the amino acid sequence IHAMG (SEQ ID NO: 3) or GSIASIHAMG (SEQ ID NO: 6); CDR2 comprising the amino acid sequence VITXSGGITYYADS-VKG (SEQ ID NO: 4; wherein X is W or V) or VIT-WSGGITY (SEQ ID NO: 7); and CDR3 comprising the amino acid sequence DKHQSSXYDY (SEQ ID NO: 5; wherein X is W or F); and one or more ISVDs that bind to CTLA4 comprising: CDR1 comprising the amino acid sequence FYGMG (SEQ ID NO: 10) or GGTFSFYGMG (SEQ ID NO: 13); CDR2 comprising the amino acid sequence DIRTSAGRTYYADSVKG (SEQ ID NO: 11) or DIRTSAGRTY (SEQ ID NO: 14); and CDR3 comprising the amino acid sequence EXSGISGWDY (SEQ ID NO: 12; wherein X is M or P); and, optionally, a half-life extender and/or a C-terminal extender. In an embodiment of the invention, there is a peptide linker between each ISVD in the binder, e.g., a 35GS linker.

The present invention also provides a PD1/CTLA4 binder including an ISVD that binds to PD1 which comprises the amino acid sequence: DVQLVESGGG VVQPGGSLRL SCAASGSIAS IHAMGWFRQA PGKEREFVAV ITWSGGITYY ADSVKGRFTI SRDNSKNTVY LQMNSLRPED TALYYCAGDK HQSSWYDYWG QGTLVTVSS (SEQ ID NO: 135); and the ISVD that binds to CTLA4 comprises the amino acid sequence: XVQLVES-GGGVVQPGGSLRLSCAASGGTFSFYGMGWFRQAPG KEREFVADIRTSAGRTYYADSVKGRFTISRDNSKNT-VYLQMNSLRPEDTALYYCAAEPSGISGWDYWGQGT LVTVSS (SEQ ID NO: 143), wherein X is D or E; or $X_1$VQLVESGGGVVQPGGSLRLSCAASGGTFSFYGMG WFRQAPGKEREFVADIRTSAGRTYYADSVKGRFTISR D$X_2$SKNTVYLQMNSLRPEDTALYYCAAEPSGISGWD YWGQGTLVTVSS (SEQ ID NO: 196); wherein $X_1$ is D or E and wherein $X_2$ is S, V, G, R, Q, M, H, T, D, E, W, F, K, A, Y or P; and, optionally, a half-life extender and/or a C-terminal extender. In an embodiment of the invention, there is a peptide linker between each ISVD in the binder, e.g., a 35GS linker.

The present invention also provides a PD1/CTLA4 binder comprising:
- a PD1 ISVD comprising the amino acid sequence set forth in SEQ ID NO: 135;
- a 35GS linker comprising the amino acid sequence set forth in SEQ ID NO: 86;
- a CTLA4 ISVD comprising the amino acid sequence set forth in SEQ ID NO: 143 (D1E);
- a 35GS linker comprising the amino acid sequence set forth in SEQ ID NO: 86;
- a HSA ISVD comprising the amino acid sequence set forth in SEQ ID NO: 144; and
- a C-terminal Alanine.

or:
- a PD1 ISVD comprising the amino acid sequence set forth in SEQ ID NO: 135;
- a 35GS linker comprising the amino acid sequence set forth in SEQ ID NO: 86;
- a PD1 ISVD comprising the amino acid sequence set forth in SEQ ID NO: 135;
- a 35GS linker comprising the amino acid sequence set forth in SEQ ID NO: 86;
- a CTLA4 ISVD comprising the amino acid sequence set forth in SEQ ID NO: 143;
- a 35GS linker comprising the amino acid sequence set forth in SEQ ID NO: 86;
- a HSA ISVD comprising the amino acid sequence set forth in SEQ ID NO: 144; and
- a C-terminal Alanine.

or
- a PD1 ISVD comprising the amino acid sequence set forth in SEQ ID NO: 135;
- a 35GS linker comprising the amino acid sequence set forth in SEQ ID NO: 86;
- a CTLA4 ISVD comprising the amino acid sequence set forth in SEQ ID NO: 143 (D1E);
- a 35GS linker comprising the amino acid sequence set forth in SEQ ID NO: 86;
- a CTLA4 ISVD comprising the amino acid sequence set forth in SEQ ID NO: 143 (D1E);
- a 35GS linker comprising the amino acid sequence set forth in SEQ ID NO: 86;
- a HSA ISVD comprising the amino acid sequence set forth in SEQ ID NO: 144; and
- a C-terminal Alanine.

or
- a PD1 ISVD comprising the amino acid sequence set forth in SEQ ID NO: 135;
- a 35GS linker comprising the amino acid sequence set forth in SEQ ID NO: 86;
- a PD1 ISVD comprising the amino acid sequence set forth in SEQ ID NO: 135 (D1E);
- a 35GS linker comprising the amino acid sequence set forth in SEQ ID NO: 86;
- a CTLA4 ISVD comprising the amino acid sequence set forth in SEQ ID NO: 143 (D1E);
- a 35GS linker comprising the amino acid sequence set forth in SEQ ID NO: 86;
- a CTLA4 ISVD comprising the amino acid sequence set forth in SEQ ID NO: 143 (D1E);
- a 35GS linker comprising the amino acid sequence set forth in SEQ ID NO: 86;
- a HSA ISVD comprising the amino acid sequence set forth in SEQ ID NO: 144; and
- a C-terminal Alanine.

For example, the present invention provides a PD1/CTLA4 binder comprising the amino acid sequence set forth in SEQ ID NO: 146, 149, 151 or 153.

In an embodiment of the invention, the PD1/CTLA4 binder comprises a half-life extender, for example, an HSA binder, e.g. a human serum albumin ISVD which comprises: CDR1 comprising the amino acid sequence GFTFSSFGMS (SEQ ID NO: 177); CDR2 comprising the amino acid sequence SISGSGSDTL (SEQ ID NO: 178); and CDR3 comprising the amino acid sequence GGSLSR (SEQ ID NO: 179), for example, comprising the amino acid sequence: EVQLVESGGG VVQPGNSLRL SCAASGFTFS SFGMSWVRQA PGKGLEWVSS ISGSGSDTLYADSVKGRFTI SRDNAKTTLY LQMNSLRPED TALYYCTIGG SLSRSSQGTL VTVSSA (SEQ ID NO: 144).

In addition, the present invention provides a binder (e.g., an antibody, antigen-binding fragment thereof, ISVD or Nanobody) that cross-blocks the PD1/CTLA4 binder set forth herein from binding to PD1 and/or CTLA4.

The present invention provides a PD1/CTLA4 binder or multispecific binder (e.g., a multispecific ISVD such as Nanobody) that binds to PD1 and CTLA4 comprising: (i) a binding moiety which binds to PD1 that comprises the amino acid sequence set forth in SEQ ID NO: 1 or 2 but further comprising a mutation at one or more of positions 11, 89, 110 and 112 relative to the amino acid sequence in SEQ ID NO: 1 or 2 wherein said positions are numbered according to Kabat, and optionally further comprising any number of additional mutations that are set forth herein or otherwise, e.g., up to 10 (e.g., 1, 2, 3, 4, 5, 6, 7, 8, 9 or 10) additional mutations (e.g., point mutations, substitutions, deletions, insertions); and (ii) a binding moiety which binds to CTLA4 that comprises the amino acid sequence set forth in SEQ ID NO: 9 but further comprising a mutation at one or more of positions 11, 89, 110 and 112 relative to the amino acid sequence in SEQ ID NO: 9 wherein said positions are numbered according to Kabat, optionally further comprising any number of additional mutations that are set forth herein or otherwise, e.g., up to 10 (e.g., 1, 2, 3, 4, 5, 6, 7, 8, 9 or 10) additional mutations (e.g., point mutations, substitutions, deletions, insertions). In an embodiment of the invention, the binding moiety that binds to PD1 comprises one or more mutations relative to the amino acid sequence of SEQ ID NO: 1 or 2 wherein: the amino acid residue at position 11 is selected from L or V; the amino acid residue at position 89 is selected from T, V, I or L; the amino acid residue at position 110 is selected from T, K or Q; and/or the amino acid residue at position 112 is selected from S, K or Q; and wherein the binding moiety that binds to CTLA4 comprises one or more mutations relative to the amino acid sequence of SEQ ID NO: 9 wherein: the amino acid residue at position 11 is selected from L or V; the amino acid residue at position 89 is selected from T, V or L; the amino acid residue at position 110 is selected from T, K or Q; and/or the amino acid residue at position 112 is selected from S, K or Q. In an embodiment of the invention, binding moiety that binds to PD1 comprises one or more mutations relative to the amino acid sequence of SEQ ID NO: 1 or 2 wherein: position 89 is L and position 11 is V; or position 89 is L and position 110 is K or Q; or position 89 is L and position 112 is K or Q; or position 89 is L and position 11 is V and position 110 is K or Q; or position 89 is L and position 11 is V and position 112 is K or Q; or position 11 is V and position 110 is K or Q; or position 11 is V and position 112 is K or Q; and/or wherein the binding moiety that binds to CTLA4 comprises one or more mutations relative to the amino acid sequence of SEQ ID NO: 9 wherein: position 89 is L and position 11 is V; or position 89 is L and position 110 is K or Q; or position 89 is L and position 112 is K or Q; or position 89 is L and position 11 is V and position 110 is K or Q; or position 89 is L and position 11 is V and position 112 is K or Q; or position 11 is V and position 110 is K or Q; or position 11 is V and position 112 is K or Q. In an embodiment of the invention, the multispecific binder comprises mutations at positions 11, 89, 110 and 112, relative to SEQ ID NOs: 1, 2 and/or 9 are as any of those set forth in the table:

| | POSITION | | | | | POSITION | | |
|---|---|---|---|---|---|---|---|---|
| | 11 | 89 | 110 | 112 | | 11 | 89 | 110 | 112 |
| COM- | L | T | T | S | COM- | V | T | T | S |
| BINA- | L | T | T | K | BINA- | V | T | T | K |
| TION | L | T | T | Q | TION | V | T | T | Q |
| | L | T | K | S | | V | T | K | S |
| | L | T | Q | S | | V | T | Q | S |
| | L | V | T | K | | V | V | T | K |
| | L | V | T | Q | | V | V | T | Q |
| | L | V | K | S | | V | V | K | S |
| | L | V | Q | S | | V | V | Q | S |
| | L | I | T | K | | V | I | T | K |
| | L | I | T | Q | | V | I | T | Q |
| | L | I | K | S | | V | I | K | S |
| | L | I | Q | S | | V | I | Q | S |
| | | | | | | V | L | T | S |
| | L | L | T | K | | V | L | T | K |
| | L | L | T | Q | | V | L | T | Q |
| | L | L | K | S | | V | L | K | S |
| | L | L | Q | S | | V | L | Q | S |

In an embodiment of the invention (i) the binding moiety that binds to PD1 further comprises one or more mutations at a position selected from the group consisting of 1, 14, 41, 74, 83 and 87, relative to the amino acid sequence of SEQ ID NO: 1 or 2, wherein said positions are numbered according to Kabat; and/or (ii) the binding moiety that binds to CTLA4 further comprises one or more mutations at a position selected from the group consisting of 1, 14, 41, 74, 83 and 87, relative to the amino acid sequence of SEQ ID NO: 9, wherein said positions are numbered according to Kabat. In an embodiment of the invention, the multispecific binder comprises a C-terminal extension, e.g., of 1, 2, 3, 4, 5, 6, 7, 8, 9 or 10 amino acids. For example, in an embodiment of the invention, the C-terminal extension has the formula —X(n), wherein X and n are as follows: (a) n=1 and X=Ala; (b) n=2 and each X=Ala; (c) n=3 and each X=Ala; (d) n=2 and at least one X=Ala and wherein the remaining amino acid residue(s) X are independently chosen from any naturally occurring amino acid; (e) n=3 and at least one X=Ala and wherein the remaining amino acid residue(s) X are independently chosen from any naturally occurring amino acid; (f) n=3 and at least two X=Ala and wherein the remaining amino acid residue(s) X are independently chosen from any naturally occurring amino acid; (g) n=1 and X=Gly; (h) n=2 and each X=Gly; (i) n=3 and each X=Gly; (j) n=2 and at least one X=Gly wherein the remaining amino acid residue(s) X are independently chosen from any naturally occurring amino acid; (k) n=3 and at least one X=Gly wherein the remaining amino acid residue(s) X are independently chosen from any naturally occurring amino acid; (l) n=3 and at least two X=Gly wherein the remaining amino acid residue(s) X are independently chosen from any naturally occurring amino acid; (m) n=2 and each X=Ala or Gly; (n) n=3 and each X=Ala or Gly; (o) n=3 and at least one X=Ala or Gly wherein remaining amino acid residue(s) X are independently chosen from any naturally occurring amino acid; or (p) n=3 and at least two X=Ala or Gly wherein the remaining amino acid residue(s) X are independently chosen from any naturally occurring amino acid, e.g., a C-terminal extension selected from the group consisting of A, AA, AAA, G, GG, GGG, AG, GA, AAG, AGG, AGA, GGA, GAA and GAG.

The present invention also comprises a multispecific binder (e.g. a multispecific ISVD such as a Nanobody) which comprises (i) a binding moiety which binds to PD1 which comprises an amino acid sequence having at least 85% (e.g., 85, 86, 87, 88, 89, 90, 91, 92, 93, 94, 95, 96, 97, 98, 99, 99.5, 99.9 or 100%) sequence identity with the amino acid sequence set forth in a member selected from the group consisting of SEQ ID NOs: 1, 2 and 16-47 which comprises CDR1, CDR2 and CDR3 of an immunoglobulin comprising an amino acid sequence set forth in SEQ ID NO: 1 or 2, wherein said binding moiety comprises at least one mutation with respect to the amino acid sequence set forth in SEQ ID NO: 1 or 2, wherein said at least one mutation is at a position selected from the group consisting of 11, 89, 110 and 112, wherein said positions are numbered according to Kabat; and/or (ii) a binding moiety which binds to CTLA4 which comprises an amino acid sequence having at least 85% sequence identity with the amino acid sequence set forth in a member selected from the group consisting of SEQ ID NOs: 9 and 48-83 which comprises CDR1, CDR2 and CDR3 of an immunoglobulin comprising an amino acid sequence set forth in SEQ ID NO: 9, wherein said binding moiety comprises at least one mutation with respect to the amino acid sequence set forth in SEQ ID NO: 9, wherein said at least one mutation is at a position selected from the group consisting of 11, 89, 110 and 112, wherein said positions are numbered according to Kabat.

The present invention provides a multispecific binder or polypeptide comprising the amino acid sequence selected from the group consisting of SEQ ID NOs: 16-83 and 103-134.

The present invention includes a multispecific binder comprising (i) a binding moiety which binds to PD1 which comprises an amino acid sequence selected from the group consisting of SEQ ID NOs: 16-47, and (ii) a binding moiety which binds to CTLA4 which comprises an amino acid sequence selected from the group consisting of SEQ ID NOs: 48-83.

In an embodiment of the invention, the multispecific binder (e.g. a multispecific ISVD such as a Nanobody) is further linked to one or more immunoglobulin single variable domains, Nanobodies, antibodies or antigen-binding fragments thereof. In an embodiment of the invention, the multispecific binder includes one or more other binding moieties (e.g., immunoglobulin single variable domains, Nanobodies, antibodies or antigen-binding fragments thereof) that bind to CD27, LAG3, PD1, BTLA, TIM3, ICOS, B7-H3, B7-H4, CD137, GITR, PD-L1, PD-L2, ILT1, ILT2 CEACAM1, CEACAM5, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17 or TSLP.

The present invention includes a PD1/CTLA4 binder or multispecific binder in association with a further therapeutic agent such as pembrolizumab. The present invention also includes an injection device or vessel that comprises the PD1/CTLA4 binder or multispecific binder and, optionally, is in association with a further therapeutic agent such as pembrolizumab. The present invention also provides a polynucleotide encoding the PD1/CTLA4 binder or multispecific binder as set forth herein (e.g., comprising the nucleotide sequence set forth in SEQ ID NO: 145, 148, 150 or 152), as well as vectors comprising such polynucleotides and host cells (e.g., CHO cell or *Pichia* cell) including such polynucleotides and vectors.

The present invention provides a method for making a PD1/CTLA4 binder or multispecific binder as set forth herein comprising introducing a polynucleotide encoding the immunoglobulins into a host cell and culturing the host cell (e.g., CHO cell or *Pichia* cell) in a medium under conditions favorable to expression of said immunoglobulin from said polynucleotide and, optionally, purifying the immunoglobulin from said host cell and/or said medium. PD1/CTLA4 binder or multispecific binders produced by such a method are part of the present invention.

The present invention also provides a method for preventing PD1 from binding to PD-L1 and/or PD-L2 and for preventing CTLA4 on a T-cell from binding to CD80 and/or CD86 on an antigen-presenting cell comprising contacting PD1 with said PD1/CTLA4 binder or multispecific binder as described herein optionally in association with a further therapeutic agent.

The present invention provides a method for enhancing an immune response in a subject (e.g., mammal such as a human) comprising administering an effective amount of a PD1/CTLA4 binder or multispecific binder as set forth herein to the subject optionally in association with a further therapeutic agent.

The present invention also provides a method for treating or preventing cancer or an infectious disease in a subject comprising administering an effective amount of a PD1/CTLA4 binder or multispecific binder as set forth herein optionally in association with a further therapeutic agent to the subject. For example, in an embodiment of the invention, the cancer is metastatic cancer, a solid tumor, a hematologic cancer, leukemia, lymphoma, osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the infectious disease is a bacterial infection, a viral infection or a fungal infection. In an embodiment of the invention, wherein the subject is administered a further therapeutic agent and/or a therapeutic procedure in association with the PD1/CTLA4 binder or multispecific binder.

DESCRIPTION OF THE FIGURES

FIG. 1. A table listing some of the amino acid positions that will be specifically referred to herein and their numbering according to some alternative numbering systems (such as Aho and IMGT)

FIG. 2. Nanobody 102C12 and Reference A sequences (see WO 2008/071447, SEQ ID NO:348).

FIG. 3 (A1-A4 and B1-B2). (A1-A4) Sequences of PD1 binding moieties of the present invention. (B1-B2) alignment of PD1 binding moieties with the amino acid sequences of SEQ ID NOs: 1 and 2.

FIG. 4 (A4 and B1-B2). (A1-A4) Sequences of CTLA4 binding moieties of the present invention. (B1-B2) alignment of CTLA4 binding moieties with the amino acid sequences of SEQ ID NO: 9.

FIG. 5. Sequences which may be linked to the binders of the present invention.

FIG. 6 (1-9). Sequences of PD1/CTLA4 binders of the present invention.

FIG. 15 (A-D). Sequences of the present invention.

FIG. 16 (A-B). Description of binder constructs of the present invention.

DETAILED DESCRIPTION OF THE INVENTION

Figure 14A:
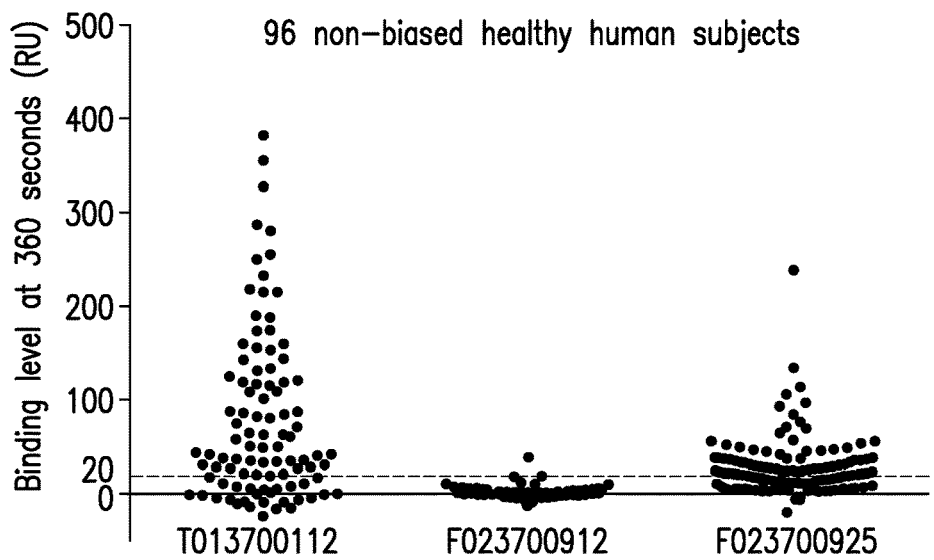
FIG. 14 (A-B). Binding of pre-existing antibodies from (a) health and (b) cancer patients to Nanobodies F023700912, F023700925 or a trivalent control Nanobody T013700112 (lacking mutations to reduce pre-existing antibody binding).
Figure 14B:
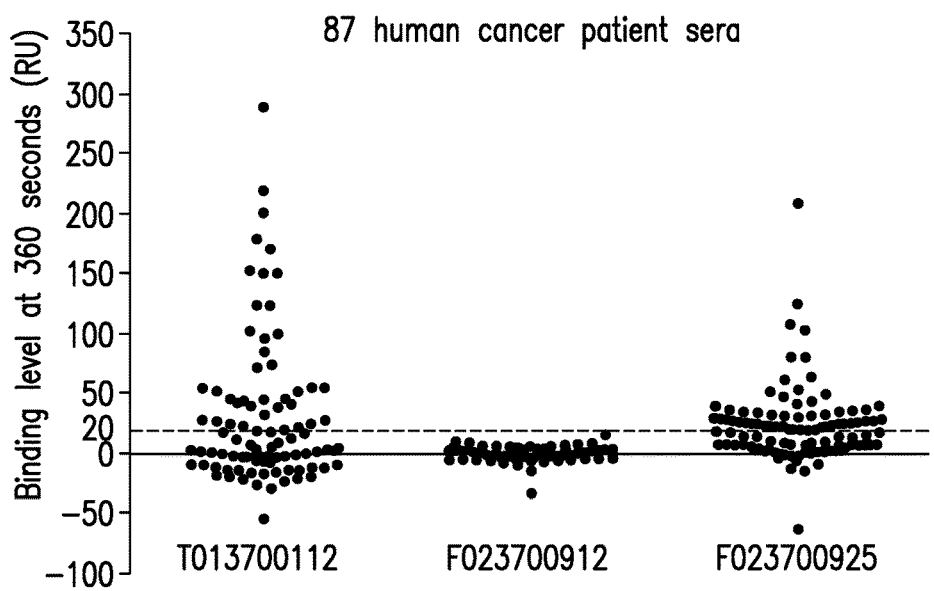

The present invention provides ISVDs that comprise mutations which block reactivity of pre-existing antibodies (pre-antibodies) to neo-epitopes within the ISVDs. Neoepitopes are epitopes within a protein which are revealed when the protein is m folding is altered. Pre-existing antibodies are antibodies existing in the body of a patient prior to receipt of an ISVD. The ISVDs of the present invention are based, in part, on llama antibodies whose C-terminal constant domains have been removed; thus, exposing the neo-epitopes in the C-terminus of the resulting VHH to pre-antibody binding. It has been discovered that the combination of mutations of residues 11 and 89 (e.g., L11V and I89L or V89L) led to a surprising lack of pre-antibody binding. Mutations in residue 112 have also been shown to remarkably reduce pre-antibody binding. Buyse & Boutton (WO2015/173325) included data showing that the combination of an L11V and V89L mutation provided a remarkable improvement in reducing pre-antibody binding compared to an L11V mutation alone or a V89L mutation alone. For example, Table H of Buyse & Boutton on page 97 showed comparative data for an ISVD with a V89L mutation alone (with or without C-terminal extension) and the same ISVD with a V89L mutation in combination with an L11V mutation (again, with or without a C-terminal extension). Also, although generated in two separate experiments, the data shown in Table H for the L11V/V89L combination as compared to the data given in Table B for an L11V mutation alone (in the same ISVD) showed that the pre-antibody binding reduction that is obtained by the L11V/V89L combination was greater than that for the L11V mutation alone. Since the llama antibody scaffold structure is known to be very highly conserved, the effect of the mutations at positions 11 and 89 is very likely to exist for any ISVD. Indeed, the effect was demonstrated, in FIG. 14, with the instant binders, F023700912, F023700925, which were shown to exhibit very low levels of pre-antibody binding.

In the present application, the amino acid residues/positions in an immunoglobulin heavy-chain variable domain will be indicated with the numbering according to Kabat. For the sake of convenience, FIG. 1 gives a table listing some of the amino acid positions that will be specifically referred to herein and their numbering according to some alternative numbering systems (such as Aho and IMGT. Note: unless explicitly indicated otherwise, for the present description and claims, Kabat numbering is decisive; other numbering systems are given for reference only).

With regards to the CDRs, as is well-known in the art, there are multiple conventions to define and describe the CDRs of a VH or VHH fragment, such as the Kabat definition (which is based on sequence variability and is the most commonly used) and the Chotia definition (which is based on the location of the structural loop regions). Reference is for example made to the website www.bioinf.org.uk/abs/. For the purposes of the present specification and claims, even though the CDRs according to Kabat may also be mentioned, the CDRs are most preferably defined on the basis of the Abm definition (which is based on Oxford Molecular's AbM antibody modelling software), as this is considered to be an optimal compromise between the Kabat and Chotia definitions. Reference is again made to the website www.bioinf.org.uk/abs/. See Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883; Chothia & Lesk (1987) J. Mol. Biol. 196: 901-917; Elvin A. Kabat, Tai Te Wu, Carl Foeller, Harold M. Perry, Kay S. Gottesman (1991) Sequences of Proteins of Immunological Interest; Protein Sequence and Structure Analysis of Antibody Variable Domains. In: Antibody Engineering Lab Manual (Ed.: Duebel, S. and Kontermann, R., Springer-Verlag, Heidelberg). In an embodiment of the invention, CDR determination is according to Kabat, e.g., wherein FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In an embodiment of the invention, CDRs are determined according to Kontermann and Dübel (Eds., Antibody Engineering, vol 2, Springer Verlag Heidelberg Berlin, Martin, Chapter 3, pp. 33-51, 2010).

The present invention aims to provide improved PD1/CTLA4 binders, in particular improved PD1/CTLA4 bispecific ISVDs and more in particular improved anti-PD1/CTLA4 bispecific Nanobodies. The PD1/CTLA4 binders of the present invention include those including CTLA4 binding moieties which include polypeptides which are variants of polypeptides comprising the amino acid sequence of SEQ ID NO: 9 which is mutated at position 1, 11, 14, 45, 73, 74, 83, 89, 96, 108, 110 and/or 112; and PD1 binding moieties which include polypeptides which are variants of polypeptides comprising the amino acid sequence of SEQ ID NO: 1 or 2 which is mutated at position 1, 11, 14, 52a, 73, 74, 83, 89, 100a, 110 and/or 112 (in either order). The improved PD1/CTLA4 bispecific binders provided by the invention are also referred to herein as the "PD1/CTLA4 bispecific binders of the invention" or "PD1/CTLA4 bispecific binders" or "PD1/CTLA4 binders". These terms encompass any molecule that includes a CTLA4 binding moiety and a PD1 binding moiety as set forth herein. For example, the terms include a molecule including a CTLA4 binding moiety (e.g., an ISVD that comprises an amino acid sequence set forth in a member selected from SEQ ID NOs: 143 or 196) and a PD1 binding moiety (e.g., an ISVD that comprises an amino acid sequence set forth in a member selected from the group consisting of SEQ ID NOs: 103-134, 135, 136, 137, 140, 141 and 142) which may be a fusion protein, and/or may be attached to a conventional antibody or antigen-binding fragment thereof. A PD1/CTLA4 binder includes any multispecific binder that comprises a CTLA4 binding moiety (e.g., including an amino acid sequence set forth in a member selected from the group consisting of SEQ ID NOs: 143 or 196) and a PD1 binding moiety (e.g., including an amino acid sequence set forth in a member selected from the group consisting of SEQ ID NOs: 103-134, 135, 136, 137, 140, 141 and 142) which also binds to another epitope such as CD27, LAG3, a different epitope of CTLA4, a different epitope of PD1, BTLA, TIM3, ICOS, B7-H3, B7-H4, CD137, GITR, PD-L1, PD-L2, ILT1, ILT2 CEACAM1, CEACAM5, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17 and/or TSLP.

As discussed the "PD1 binders" of the present invention are any of the molecules described herein that bind to PD1 (e.g., an ISVD such as a Nanobody) as well as any antibody or antigen-binding fragment thereof that binds to PD1 and includes any of the PD1 binding moieties described herein. A PD1 binder may be selective for PD1 or it may additionally include a binder that binds to LAG3, CD27, CTLA4, HSA, BTLA, TIM3, ICOS, B7-H3, B7-H4, CD137, GITR, PD-L1, PD-L2, ILT1, ILT2 CEACAM1, CEACAM5, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17, TSLP, e.g., comprising a LAG3 binding moiety and a CTLA4 binding moiety; a LAG3 binding moiety and a BTLA binding moiety; 1 or 2 PD1 binding moieties, 1 or 2 LAG3 binding moieties and a HSA binding moiety; or a LAG3 binding moiety and a BTLA binding moiety. An individual PD1 binder may be referred to as a PD1 binding moiety if it is part of a larger molecule, e.g., a multivalent molecule such as F023700910, F023700918, F023700920 or F023700925.

As discussed the "CTLA4 binders" of the present invention are any of the molecules described herein that bind to CTLA4 (e.g., an ISVD such as a Nanobody) as well as any antibody or antigen-binding fragment thereof that binds to CTLA4 and includes any of the CTLA4 binding moieties described herein. A CTLA4 binder may include a binder that binds to PD1, LAG3, CD27, HSA, BTLA, TIM3, ICOS, B7-H3, B7-H4, CD137, GITR, PD-L1, PD-L2, ILT1, ILT2 CEACAM1, CEACAM5, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17, TSLP, e.g., comprising a LAG3 binding moiety and a PD1 binding moiety; a LAG3 binding moiety and a BTLA binding moiety; 1 or 2 PD1 binding moieties, 1 or 2 LAG3 binding moieties and a HSA binding moiety; or a LAG3 binding moiety and a BTLA binding moiety. An individual CTLA4binder may be referred to as a CTLA4 binding moiety if it is part of a larger molecule, e.g., a multivalent molecule such as F023700910, F023700918, F023700920 or F023700925.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989). Examples of antigen-binding fragments include, but are not limited to, Fab, Fab', F(ab')$_2$, and Fv fragments, and single-chain Fv molecules.

The term "immunoglobulin single variable domain" (also referred to as "ISV" or "ISVD") is generally used to refer to immunoglobulin variable domains (which may be heavy chain or light chain domains, including VH, VHH or VL domains) that can form a functional antigen binding site without interaction with another variable domain (e.g. without a VH/VL interaction as is required between the VH and VL domains of conventional 4-chain monoclonal antibody). Examples of ISVDs will be clear to the skilled person and for example include Nanobodies (including a VHH, a humanized VHH and/or a camelized VHs such as camelized human VHs), IgNAR, domains, (single domain) antibodies (such as dAbs™) that are VH domains or that are derived from a VH domain and (single domain) antibodies (such as dAbs™) that are VL domains or that are derived from a VL domain. ISVDs that are based on and/or derived from heavy chain variable domains (such as VH or VHH domains) are generally preferred. Most preferably, an ISVD will be a Nanobody.

The term "Nanobody" is generally as defined in WO 2008/020079 or WO 2009/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®).

A multispecific binder is a molecule that comprises a first and second CTLA4 and PD1 (or PD1 and CTLA4) binding moiety (e.g., an ISVD or a Nanobody) and, optionally, one or more (e.g., 1, 2, 3, 4, 5) additional binding moieties (e.g., an ISVD or a Nanobody) that bind to an epitope other than that of the CTLA4 and PD1 binding moieties (e.g., CD27, LAG3 and/or BTLA). For example, F023700910, F023700918, F023700920 and F023700925 are multispecific PD1/CTLA4 binders that include an HSA binder.

A binding moiety or binding domain or binding unit is a molecule such as an ISVD or Nanobody that binds to an antigen. A binding moiety or binding domain or binding unit may be part of a larger molecule such as a multivalent or multispecific binder that includes more than one moiety, domain or unit and/or that comprises another functional element, such as, for example, a half-life extender (HLE), targeting unit and/or a small molecule such a polyethyleneglycol (PEG). For example, 102C12 (E1D,L11V,A14P, A74S,K83R,I89L) is a PD1 binding moiety ISVD of F023700910.

A monovalent CTLA4 or PD1 binder (e.g., ISVD such as a Nanobody) is a molecule that comprises a single antigen binding domain. A bivalent CTLA4/PD1 binder (e.g., ISVD such as a Nanobody) comprises two antigen binding domains (e.g., conventional antibodies including bispecific antibodies) that binds to CTLA4 and PD1. A multivalent binder comprises more than one antigen-binding domain. A trivalent binder comprises three antigen-binding domains.

A monospecific CTLA4 or PD1 binder (e.g., ISVD such as a Nanobody) binds a single antigen (CTLA4 or PD1); a bispecific CTLA4/PD1 binder binds to two different antigens (PD1 and CTLA4) and a multispecific binder binds to more than one antigen. A trispecific binder binds to three different antigens (e.g., PD1 and CTLA4 and, for example, CD27, LAG3 or BTLA).

A biparatopic binder (e.g., ISVD such as a Nanobody) is monospecific but binds to two different epitopes of the same antigen. A multiparatopic binder binds the same antigen but to more than one epitope in the antigen.

Also, as already indicated herein, the amino acid residues of a Nanobody are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein.

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

The term "half-life" as used herein relation to a binder such as a PD1/CTLA4 binder (e.g., comprising ISVDs (e.g., Nanobodies) that bind to PD1 and CTLA4) can generally be defined as described in paragraph o) on page 57 of WO 2008/020079 and as mentioned therein refers to the time taken for the serum concentration of the amino acid sequence, compound or polypeptide to be reduced by 50%, in vivo, for example due to degradation of the sequence or PD1/CTLA4 binder and/or clearance or sequestration of the sequence or PD1/CTLA4 binder by natural mechanisms. The in vivo half-life of a PD1/CTLA4 binder of the invention can be determined in any manner known per se, such as by pharmacokinetic analysis. Suitable techniques will be clear to the person skilled in the art, and may for example generally be as described in paragraph o) on page 57 of WO 2008/020079. As also mentioned in paragraph o) on page 57 of WO $^{2008}/_{020079}$, the half-life can be expressed using parameters such as the t½-alpha, t½-beta and the area under the curve (AUC). In this respect it should be noted that the term "half-life" as used herein in particular refers to the t½-beta or terminal half-life (in which the t½-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" are also as defined in paragraph o) on page 57 of WO 2008/020079 and in particular refer to an increase in the t½-beta, either with or without an increase in the t½-alpha and/or the AUC or both.

The phrase "control sequences" refers to polynucleotides necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another polynucleotide. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Isolated" PD1/CTLA4 binders (e.g., comprising ISVDs (e.g., Nanobodies) that bind to PD1 and CTLA4), polypeptides, polynucleotides and vectors, are at least partially free of other biological molecules from the cells or cell culture from which they are produced. Such biological molecules include nucleic acids, proteins, lipids, carbohydrates, or other material such as cellular debris and growth medium. An "isolated" PD1/CTLA4 binder may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

When a term is not specifically defined herein, it has its usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, N.Y. (2005), as well as to the general background art cited herein.

The following properties are associated with the indicated mutations in the PD1 binder 102C12:
E1D: Prevent pyroglutamic acid formation in the first amino acid of the construct E1
L11V: Decrease pre-antibody binding
A14P: Humanization
W52aV: Prevent oxidation of W52a
N73P: Prevent N73 deamidation
N73Q: Prevent N73 deamidation
N73 S: Prevent N73 deamidation
A74S: Humanization
K83R: Humanization
I89L: Decrease pre-antibody binding
W100aF: Prevent oxidation of W100a
or in the CTLA4 binder 11F1:
E1D: Prevent pyroglutamic acid formation in the first amino acid of the construct E1
L11V: Decrease pre-antibody binding
A14P: Humanization
Q45R: Mutated to increase stability
A74S: Humanization
K83R: Humanization
I89L: Decrease pre-antibody binding
M96P, Q or R: Prevent oxidation of M96
Q108L: Humanization The scope of the present invention includes the multivalent PD1/CTLA4 binders set forth in FIG. 15 or comprising the arrangement of moieties set forth in FIG. 16. The scope of the present invention also includes PD1/CTLA4 binders comprising any of the PD1 binders set forth in FIG. 15 (or any PD1 binder comprising CDR1, CDR2 and CDR3 of such a PD1 binder) or any of the multivalent PD1 binders (or one or more of any PD1 binding moieties thereof) comprising the arrangement of PD1 binding moieties set forth in FIG. 16 and/or any CTLA4 binder set forth in FIG. 15 (or any CTLA4 binder comprising CDR1, CDR2 and CDR3 of such a LAG3 binder) or any of the multivalent CTLA4 binders (or one or more of any CTLA4 binding moieties thereof) comprising the arrangement of CTLA4 binding moieties set forth in FIG. 16. The binders set forth in FIG. 15, in an embodiment of the invention, do not include the C-terminal extender (e.g., A), FLAG and/or HIS tags therein (e.g., HHHHHH (amino acids 148-153 of SEQ ID NO: 176); AAHHHHHH (amino acids 146-153 of SEQ ID NO: 176); or AAADYKDHDGDYKDHDIDYKDDDDKGAAHHH-HHH (amino acids 120-153 of SEQ ID NO: 176)). Any such binder or CDR may, in an embodiment of the invention, be a variant of what is set forth in FIG. 15, e.g., comprising 1, 2, 3, 4, 5, 6, 7, 8, 9 or 10 point mutations (e.g., conservative substitutions or deletions).

In an embodiment of the invention, CTLA4 is human CTLA4. In an embodiment of the invention, human CTLA4 comprises the amino acid sequence:

```
                                        (SEQ ID NO: 197)
MACLGFQRHK AQLNLATRTW PCTLLFFLLF IPVFCKAMHV

AQPAVVLASS RGIASFVCEY ASPGKATEVR VTVLRQADSQ

VTEVCAATYM MGNELTFLDD SICTGTSSGN QVNLTIQGLR

AMDTGLYICK VELMYPPPYY LGIGNGTQIY VIDPEPCPDS

DFLLWILAAV SSGLFFYSFL LTAVSLSKML KKRSPLTTGV

YVKMPPTEPE CEKQFQPYFI PIN
```

In an embodiment of the invention, PD1 is human PD1. In an embodiment of the invention, human PD1 comprises the amino acid sequence:

```
                                        (SEQ ID NO: 198)
MQIPQAPWPV VWAVLQLGWR PGWFLDSPDR PWNPPTFSPA

LLVVTEGDNA TFTCSFSNTS ESFVLNWYRM SPSNQTDKLA

AFPEDRSQPG QDCRFRVTQL PNGRDFHMSV VRARRNDSGT

YLCGAISLAP KAQIKESLRA ELRVTERRAE VPTAHPSPSP

RPAGQFQTLV VGVVGGLLGS LVLLVWVLAV ICSRAARGTI

GARRTGQPLK EDPSAVPVFS VDYGELDFQW REKTPEPPVP
```

```
-continued
CVPEQTEYAT IVFPSGMGTS SPARRGSADG PRSAQPLRPE

DGHCSWPL
```

PD1 Binding Moieties

The one or more (such as one or two) PD1 binding moieties present in the PD1/CTLA4 binders of the invention (e.g., comprising ISVDs (e.g., Nanobodies) that bind to PD1 and CTLA4) are preferably as follows (it should also be noted that when two or more PD1 binding moieties are present in a PD1/CTLA4 binders of the invention, they may be the same or different, and when they are different, they preferably all contain a suitable combination of mutations at positions 1, 11, 14, 52a, 73, 74, 83, 89, 100a, 110 and/or 112 as described herein, and preferably also have the same CDRs as described herein. The amino acid sequences of some preferred, but non-limiting examples of PD1 binding moieties that can be present in the PD1/CTLA4 binders of the invention are listed in FIG. 3A. FIG. 3B gives an alignment of these PD1 binding moiety with the amino acid sequences of SEQ ID NOs: 1 and 2.

As mentioned, the PD1 binding moieties present in the PD1/CTLA4 binders of the invention (e.g., comprising ISVDs (e.g., Nanobodies) that bind to PD1 and CTLA4) described herein can bind (and in particular, can specifically bind) to PD1. In particular, they can bind to PD1 and inhibit binding between PD1 and PD-L1 and/or PD-L2. For example, in an embodiment of the invention, the PD1/CTLA4 binders of the present invention, binds to PD1 and releases T-cells from PD1 pathway—mediated inhibition of the T-cell mediated immune response (e.g., by releasing the T-cells from PD1 mediated inhibition of proliferation and cytokine production).

As further described herein, the PD1 binders of the invention which are, in an embodiment of the invention in PD1/CTLA4 binders of the present invention, preferably have the same combination of CDRs (i.e. CDR1, CDR2 and CDR3) as are present in 102C12 or reference A or in a binder comprising the sequence of 102C12 or reference A (SEQ ID NO: 1 or 2). See Table A-1.

The present invention also includes PD1 binders which are variants of 102C12 which comprise an amino acid sequence as set forth below in Table A-2 below. The scope of the present invention includes PD1 binders that include CDR1, CDR2 and CDR3 of said variants set forth below in Table A-2.

In addition, the present invention includes PD1/CTLA4 binders comprising a PD1 binding moiety that includes CDR1, CDR2 and CDR3 or the amino acid sequence of 102C12 or of one of its variants set forth below in Table A-2.

TABLE A-1

PD1 Binder 102C12.

| SEQ ID NO | Description | Sequence |
|---|---|---|
| 1 | WO 2008/071447, SEQ ID NO: 348 (102C12) (may be referred to herein as "1PD102C12") | EVQLVESGGGLVQAGGSLRLSCAASGSIASIHAMGWFRQAPGKEREFVAVIT WSGGITYYADSVKGRFTISRDNAKNTVYLQMNSLKPEDTAIYYCAGDKHQSS WYDYWGQGTQVTVSS |
| 2 | reference A | EVQLVESGGGLVQAGGSLRLSCAASGSIASIHAMGWFRQAPGKEREFVAVIT WSGGITYYADSVKGRFTISRDNAKNTVYLQMNSLKPEDTAIYYCAGDKHQSS WYDYWGQGTLVTVSS |

TABLE A-2

Sequence Optimized Variant 102C12 PD1 Binders

| | | |
|---|---|---|
| SO 1PD102C12 monomer 102C12 (E1D, L11V, A14P, A74S, K83R, I89L)<br>Target: hPD-1<br>SEQ ID NO: 135 | | DVQLVESGGG VVQPGGSLRL SCAASGSIAS IHAMGWFRQA PGKEREFVA<u>V</u> ITWSGGITYY ADSVKGRFTI SRDNSKNTVY LQMNSLRPED TALYYCAGDK HQSSWYDYWG QGTLVTVSS |
| SEQ ID NO: 3 | PD1 binder CDR1 (Kabat) | IHAMG |
| SEQ ID NO: 4 | PD1 binder CDR2 (Kabat) | VITXSGGITYYADSVKG<br>wherein X is W or V<br>(e.g., VITwSGGITYYADSVKG or VITvSGGITYYADSVKG) |
| SEQ ID NO: 5 | PD1 binder CDR3 (Kabat/Abm) | DKHQSSXYDY<br>wherein X is W or F<br>(e.g., DKHQSSwYDY or DKHQSSfYDY) |
| SEQ ID NO: 6 | PD1 binder CDR1 (Abm) | GSIASIHAMG |
| SEQ ID NO: 7 | PD1 binder CDR2 (Abm) | VITXSGGITY<br>wherein X is W or V<br>(e.g., VITwSGGITY or VITvSGITY) |
| SEQ ID NO: 8 | PD1 binder CDR3 (Kabat/Abm) | DKHQSSXYDY<br>wherein X is W or F<br>(e.g., DKHQSSwYDY or DKHQSSfYDY) |
| Name: F023700275<br>Description: 1PD102C12 (A14P, A74S, K83R)<br>Target: hPD-1<br>SEQ ID NO: 136 | | EVQLVESGGGLVQPGGSLRLSCAASGSIASIHAMGWFRQAPGKEREFVAVITWS GGITYYADSVKGRFTISRDNSKNTVYLQMNSLRPEDTAIYYCAGDKHQSSWYDY WGQGTLVTVSS |
| SO 1PD102C12 monomer<br>Name: F023700706<br>Description: 1PD102C12 (L11V, A14P, A74S, K83R, I89L) | | EVQLVESGGGVVQPGGSLRLSCAASGSIASIHAMGWFRQAPGKEREFVAVITWS GGITYYADSVKGRFTISRDNSKNTVYLQMNSLRPEDTALYYCAGDKHQSSWYDY WGQGTLVTVSS |
| Target: hPD-1<br>SEQ ID NO: 137 | | |
| Monovalent SO 1PD102C12 + ALB201<br>Name: F023701127<br>Description: 1PD102C12 (E1D, L11V, A14P, A74S, K83R, I89L)-35GS- ALB11002-A<br>Target: hPD-1<br>SEQ ID NO: 138 | | DVQLVESGGGVVQPGGSLRLSCAASGSIASIHAMGWERQAPGKEREFVAVITWS GGITYYADSVKGRFTISRDNSKNTVYLQMNSLRPEDTALYYCAGDKHQSSWYDY WGQGTLVTVSSGGGGSGGGGSGGGGSGGGGSGGGGSGGGGSGGGGSEVQLVESG GGVVQPGNSLRLSCAASGETFSSFGMSWVRQAPGKGLEWVSSISGSGSDTLYAD SVKGRFTISRDNAKTTLYLQMNSLRPEDTALYYCTIGGSLSRSSQGTLVTVSSA |
| Bivalent SO 1PD102C12 + ALB201<br>Name: F023700933<br>Description: 1PD102C12 (E1D, L11V, A14P, A74S, K83R, I89L)-35GS- 1PD102C12(L11V, A14P, A74S, K83R, I89L)-35GS- ALB11002-A<br>Target: hPD-1<br>SEQ ID NO: 139 | | DVQLVESGGGVVQPGGSLRLSCAASGSIASIHAMGWFRQAPGKEREFVAVITWS GGITYYADSVKGRFTISRDNSKNTVYLQMNSLRPEDTALYYCAGDKHQSSWYDY WGQGTLVTVSSGGGGSGGGGSGGGGSGGGGSGGGGSGGGGSGGGGSEVQLVESG GGVVQPGGSLRLSCAASGSIASIHAMGWFRQAPGKEREFVAVITWSGGITYYAD SVKGRFTISRDNSKNTVYLQMNSLRPEDTALYYCAGDKHQSSWYDYWGQGTLVT VSSGGGGSGGGGSGGGGSGGGGSGGGGSGGGGSGGGGSEVQLVESGGGVVQPGN SLRLSCAASGFTFSSFGMSWVRQAPGKGLEWVSSISGSGSDTLYADSVKGRFTI SRDNAKTTLYLQMNSLRPEDTALYYCTIGGSLSRSSQGTLVTVSSA |
| Enhanced SO 1PD102C12 monomer<br>Name: F023701190<br>Description: 1PD102C12(E1D, L11V, A14P, W52aV, A74S, K83R, I89L, W100aF)<br>Target: hPD-1<br>SEQ ID NO: 140 | | DVQLVESGGGVVQPGGSLRLSCAASGSIASIHAMGWERQAPGKEREFVAVITVS GGITYYADSVKGRFTISRDNSKNTVYLQMNSLRPEDTALYYCAGDKHQSSFYDY WGQGTLVTVSS |

TABLE A-2-continued

Sequence Optimized Variant 102C12 PD1 Binders

Enhanced SO 1PD102C12 monomer
Name: F023701192
Description:
1PD102C12(E1D, L11V, A14P, W52aV, N73Q, A74S, K83R, I89L, W100aF)
Target: hPD-1
SEQ ID NO: 141

DVQLVESGGGVVQPGGSLRLSCAASGSIASIHAMGWFRQAPGKEREFVA**VITVS
GGITYYADSVKGRFTISRDQSKNTVYLQMNSLRPEDTALYYCAGDKHQSSFYDY**
WGQGTLVTVSS

Enhanced SO 1PD102C12 monomer
Name: F023701193
Description:
1PD102C12(E1D, L11V, A14P, W52aV, N73P, A74S, K83R, I89L, W100aF)
Target: hPD-1
SEQ ID NO: 142

DVQLVESGGGVVQPGGSLRLSCAASGSIASIHAMGWFRQAPGKEREFVA**VITVS
GGITYYADSVKGRFTISRDPSKNTVYLQMNSLRPEDTALYYCAGDKHQSSFYDY**
WGQGTLVTVSS

The present invention includes embodiments wherein one, two or three of the CDRs of a PD1 binder set forth above in Table A-1 or A-2 (e.g., wherein the binder comprises the amino acid sequence of SEQ ID NO: 1, 2, 135, 136, 137, 138, 139, 140, 141, 142 or 16-47)) or FIG. 3 wherein each CDR comprises 0, 1, 2, 3, 4, or 5 amino acid substitutions, e.g., conservative substitutions, and/or comprises 100, 99, 98, 97, 96 or 95% sequence identity relative to the CDR sequences set forth in Table A-1 or A-2 wherein the PD1 binder having such CDRs retain the ability to bind to PD1. In an embodiment of the invention, the first amino acid of a PD1 binder of the present invention is E. In an embodiment of the invention, the first amino acid of a PD1 binder of the present invention is D.

The Kabat residue numbers for certain residues of the PD1 ISVD set forth in Table A-1 are shown in the sequence below:

(SEQ ID NO: 2)
$E_1$VQLVESGGGL$_{11}$V$_{12}$Q$_{13}$A$_{14}$GGSLRLSCAASG$_{26}$S$_{27}$I$_{28}$A$_{29}$S$_{30}$I
HAMGW$_{36}$F$_{37}$R$_{38}$Q$_{39}$AP$_{41}$GKERE$_{46}$F$_{47}$V$_{48}$A$_{49}$VITWSGGITYYADS

VKGR$_{66}$F$_{67}$T$_{68}$I$_{69}$S$_{70}$RDNA$_{74}$KNTVYLQM$_{82}$N$_{82a}$S$_{82b}$L$_{82c}$K$_{83}$

P$_{84}$EDT$_{87}$A$_{88}$I$_{89}$Y$_{90}$Y$_{91}$CAGDKHQSSWYDYW$_{103}$G$_{104}$Q$_{105}$G$_{106}$

T$_{107}$L$_{108}$V$_{109}$T$_{110}$V$_{111}$S$_{112}$S$_{113}$

The Kabat residue numbers for certain residues of ISVD 102C12 (E1D, L11V, A14P, A74S, K83R, I89L) are shown in the sequence below:

(SEQ ID NO: 135)
D$_1$VQLVESGGG V$_{11}$VQP$_{14}$GGSLRL SCAASGSIAS IHAMGWFRQA

PGKEREFVAV ITWSGGITYY ADSVKGRFTI SRDNS$_{74}$KNTVY

LQMNSLR$_{83}$PED TAL$_{89}$YYCAGDK HQSSWYDYWG QGTLVTVSS

WO 2008/071447 describes Nanobodies that can bind to PD1 and uses thereof. SEQ ID NO: 348 of WO 2008/071447 disclosed a PD1 specific Nanobody called 102C12, the sequence of which is given herein as SEQ ID NO: 1. This sequence and its CDRs are also given in Table A below (see also FIG. 2). SEQ ID NO: 2 is a reference sequence that is based on SEQ ID NO:1 but with a humanizing Q108L mutation.

Mutations may be referred to herein and are designated by their Kabat number as shown above.

WO 2008/071447 also describes Nanobodies that can bind to CTLA4 and uses thereof. SEQ ID NO:1306 of WO 2008/071447 disclosed a CTLA4 specific Nanobody called 11F01, the sequence of which is given herein as SEQ ID NO: 9 (see also FIG. 2). This sequence and its CDRs are also given in Table B below.

In an embodiment of the invention, a PD1/CTLA4 binder has one or more of the following properties:
- Binds to CTLA4 (e.g., human and/or cynomolgous monkey CTLA4) (e.g., CTLA4-Fc fusion protein), e.g., with a KD of about 1 nM (e.g., about 1.2 nM);
- Binds to CTLA4 (e.g., human CTLA4) on the surface of a cell, e.g., a CHO cell;
- Binds to PD1 (e.g., human PD1) on the surface of a cell, e.g., a CHO cell;
- Blocks binding of CD80 and/or CD86 to CTLA4, e.g., cell surface expressed CTAL4, for example, on the surface of a CHO cell;
- Does not bind to CD28 (e.g., human), CD8 alpha (e.g., human), LAG3 (e.g., human) or BTLA (e.g., human), e.g., on the surface of a cell such as a CHO cell;
- Binds to human, rhesus monkey and/or monkey serum albumin (when the binder includes a serum albumin binder such as ALB11002);
- Inhibits tumor growth (e.g., of pancreatic tumors, e.g., human pancreatic tumors in an mouse harboring human immune cells)

The present invention includes PD1/CTLA4 binders (e.g., comprising ISVDs (e.g., Nanobodies) that bind to PD1 and CTLA4) comprising one or more PD1 binding moieties which are variants of SEQ ID NO: 1 or 2 (102C12, WO 2008/071447: SEQ ID NO: 348; reference A) that comprise the amino acid sequence of SEQ ID NO: 1 or 2 but comprising one or more of the following mutations relative to the sequence of SEQ ID NO: 1 or 2:
  1D or 1E;
  11V;
  14P;
  52aV;
  73Q, 73P or 73S;
  74S;
  83R;
  89T;
  89L; or
  100aF;

for example, wherein the PD1 binding moiety comprises one or more of the following sets of mutations:
- 1D or 1E in combination with 11V, 14P, 74S, 83R and 89L;
- 1D in combination with 11V, 14P, 52aV, 73S or 73Q or 73P, 74S, 83R, 89L and 100aF;
- 1E in combination with 11V, 14P, 52aV, 73S or 73Q or 73P, 74S, 83R, 89L and 100aF;
- 89L in combination with 11V, 14P, 52aV, 73S or 73Q or 73P, 74S, 83R and 100aF, and optionally, 1D;
- 89L in combination with 11V;
- 89L in combination with 110K or 110Q;
- 89L in combination with 112K or 112Q;
- 89L in combination with 11V, 14P, 74S, 83R, and, optionally, 1D;
- 110K or 110Q in combination with 11V, 14P, 52aV, 73S or 73Q or 73P, 74S, 83R, 89L and 100aF and 1D or 1E;
- 112K or 112Q in combination with 11V, 14P, 52aV, 73S or 73Q or 73P, 74S, 83R, 89L and 100aF and 1D or 1E;
- 1D or 1E in combination with 11V, 14P, 74S, 83R and 89L; and 112K or 112Q;
- 1D or 1E in combination with 11V, 14P, 74S, 83R and 89L; and 110K or 110Q;
- 89L in combination with 11V and 110K or 110Q;
- 89L in combination with 11V and 112K or 112Q;
- 11V in combination with 110K or 110Q; or
- 11V in combination with 112K or 112Q.

In particular, the PD1 binding moieties present in the PD1/CTLA4 binders of the invention (e.g., comprising ISVDs (e.g., Nanobodies) that bind to PD1 and CTLA4) comprise the amino acid sequence of SEQ ID NO: 1 or 2 wherein:

- the amino acid residue at position 1 is chosen from E and D;
- the amino acid residue at position 11 is chosen from L and V;
- the amino acid residue at position 14 is chosen from A and P;
- the amino acid residue at position 52a is chosen from W and V;
- the amino acid residue at position 73 is chosen from P, S, N and Q;
- the amino acid residue at position 74 is chosen from A and S;
- the amino acid residue at position 83 is chosen from K and R;
- the amino acid residue at position 89 is chosen from T, V, I and L;
- the amino acid residue at position 100a is chosen from W and F;
- the amino acid residue at position 110 is chosen from T, K and Q; and
- the amino acid residue at position 112 is chosen from S, K and Q;

such that, for example, one or more of the following is true:

- (i) position 1 is D;
- (ii) position 1 is E;
- (iii) position 11 is V;
- (iv) position 14 is P;
- (v) position 52a is V;
- (vi) position 73 is Q, P or S;
- (vii) position 74 is S;
- (viii) position 83 is R;
- (ix) position 89 is T;
- (x) position 89 is L;
- (xi) position 100a is F;

for example, wherein, in the PD1 binding moiety comprises one or more of the following sets of mutations:

- a. position 1 is D or E, position 11 is V, position 14 is P, position 74 is S, position 83 is R; and position 89 is L;
- b. position 1 is D or E, position 11 is V, position 14 is P, position 52a is V; position 73 is Q, P or S; position 74 is S, position 83 is R; position 89 is L; and position 100a is F;
- c. position 89 is L and position 11 is V;
- d. position 89 is L and position 110 is K or Q;
- e. position 89 is L and position 112 is K or Q;
- f. position 1 is D or E, position 11 is V, position 14 is P, position 52a is V; position 73 is Q, P or S; position 74 is S, position 83 is R; position 89 is L; position 100a is F and position 110 is K or Q;
- g. position 1 is D or E, position 11 is V, position 14 is P, position 52a is V; position 73 is Q, P or S; position 74 is S, position 83 is R; position 89 is L; position 100a is F and position 112 is K or Q;
- h. position 1 is D or E, position 11 is V, position 14 is P, position 74 is S, position 83 is R; position 89 is L and position 110 is K or Q;
- i. position 1 is D or E, position 11 is V, position 14 is P, position 74 is S, position 83 is R; position 89 is L; and position 112 is K or Q;
- j. position 89 is L and position 11 is V and position 110 is K or Q;
- k. position 89 is L and position 11 is V and position 112 is K or Q;
- l. position 11 is V and position 110 is K or Q; or
- m. position 11 is V and position 112 is K or Q;

relative to the amino acid sequence of SEQ ID NO: 1 or 2.

In particular embodiments, the PD1 binders (e.g., an ISVD such as a Nanobody) of the invention comprise amino acid sequences that are variants of SEQ ID NO: 1 or SEQ ID NO: 2 in which position 89 is T or L; or in which 1 is D or E, 11 is V, 14 is P, 52a is V; 73 is S, Q or P; 74 is S, 83 is R and 89 is L and/or 100a is F; or in which 1 is D or E, 11 is V, 14 is P, 74 is S, 83 is R and 89 is L; or in which position 11 is V and position 89 is L (optionally in suitable combination with a 110K or 110Q mutation and/or a 112K or 112Q mutation, and in particular in combination with a 110K or 110Q mutation) are particularly preferred. The present invention includes amino acid sequences in which position 11 is V and position 89 is L, optionally with a 110K or 110Q mutation.

The PD1 binding moieties (e.g. ISVDs such as Nanobodies) present in the PD1/CTLA4 binders of the invention preferably comprise the following CDRs (according to the Kabat convention):

- a CDR1 (according to Kabat) that is the amino acid sequence IHAMG (SEQ ID NO: 3); and
- a CDR2 (according to Kabat) that is the amino acid sequence VITXSGGITYYADSVKG (SEQ ID NO: 4; wherein X is W or V); and
- a CDR3 (according to Kabat) that is the amino acid sequence DKHQSSXYDY (SEQ ID NO: 5; wherein X is W or F).

Alternatively, when the CDRs are given according to the Abm convention, the PD1 binding moieties (e.g. ISVDs such as Nanobodies) present in the PD1/CTLA4 binders of the invention preferably comprise the following CDRs:

- a CDR1 (according to Abm) that is the amino acid sequence GSIASIHAMG (SEQ ID NO: 6); and
- a CDR2 (according to Abm) that is the amino acid sequence VITWSGGITY (SEQ ID NO: 7); and a CDR3 (according to Abm) that is the amino acid sequence DKHQSSXYDY (SEQ ID NO: 8, which is the same as SEQ ID NO:5; wherein X is W or F).

The above preferred CDRs are the same as are present in 102C12 (SEQ ID NO:1), in Reference A (SEQ ID NO: 2) or binder comprising the amino acid sequence of SEQ ID NO: 16-47 or 135-142. Binders having CDR1, CDR2 and CDR3 of such binders are part of the present invention.

A PD1 binding moiety (e.g. an ISVDs such as a Nanobody) that is present in a PD1/CTLA4 binder of the invention in an embodiment of the invention also has:

a degree of sequence identity with the reference amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment); and/or no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the reference amino acid sequence of SEQ ID NO: 1 or 2 (in which said amino acid differences, if present, may be present in the frameworks and/or the CDRs but are preferably present only in the frameworks and not in the CDRs).

With regards to the various aspects and preferred aspects of the PD1 binding moieties (e.g. ISVDs such as Nanobodies) present in the PD1/CTLA4 binders of the invention, when it comes to the degree of sequence identity with respect to SEQ ID NO: 1 or 2 and/or the number and kind of "amino acid differences" that may be present in such a binder of the invention (i.e., compared to the sequence of SEQ ID NO: 1 or 2), it should be noted that, when it is said that (i) a PD1 binding moiety has a degree of sequence identity with the sequence of SEQ ID NO: 1 or 2 of at least 85%, preferably at least 90%, more preferably at least 95% (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity); and/or when it is said that (ii) a PD1 binding moiety has no more than 7, preferably no more than 5, such as only 3, 2 or 1 "amino acid differences" with the sequence of SEQ ID NO: 1 or 2 (again, not taking into account any C-terminal extension that may be present and not taking into account the mutations at positions 1, 11, 14, 52a, 73, 74, 83, 89, 100a, 110 and/or 112 required by the specific aspect involved), then this also includes sequences that have no amino acid differences with the sequence of SEQ ID NO: 1 or 2 other than the mutations at positions 1, 11, 14, 52a, 73, 74, 83, 89, 100a, 110 and/or 112 required by the specific aspect involved) and any C-terminal extension that may be present.

Thus, in one specific aspect of the invention, the PD1 binding moieties (e.g. ISVDs such as Nanobodies) present in the PD1/CTLA4 binders of the invention may have 100% sequence identity with SEQ ID NO: 1 or 2 (including the CDRs, but not taking into account the mutation(s) or combination of mutations at positions 1, 11, 14, 52a, 73, 74, 83, 89, 100a, 110 and/or 112 disclosed herein and/or any C-terminal extension that may be present) and/or may have no amino acid differences with SEQ ID NO: 1 or 2 (i.e., other than the mutation(s) or combination of mutations at positions 1, 11, 14, 52a, 73, 74, 83, 89, 100a, 110 and/or 112 disclosed herein and any C-terminal extension that may be present).

When any amino acid differences are present (i.e., besides any C-terminal extension and the mutations at positions 1, 11, 14, 52a, 73, 74, 83, 89, 100a, 110 and/or 112 that are required by the specific aspect of the invention involved), these amino acid differences may be present in the CDRs and/or in the framework regions, but they are preferably present only in the framework regions (as defined by the Abm convention, i.e. not in the CDRs as defined according to the Abm convention), i.e., such that the PD1 binding moieties (e.g. ISVDs such as Nanobodies) present in the PD1/CTLA4 binders of the invention have the same CDRs (defined according to the Abm convention) as are present in SEQ ID NO: 1 or 2.

Also, when a PD1 binding moiety (e.g. an ISVD such as a Nanobody) present in a PD1/CTLA4 binder of the invention has one or more amino acid differences with the sequence of SEQ ID NO: 1 or 2 (besides the mutations at positions 1, 11, 14, 52a, 73, 74, 83, 89, 100a, 110 and/or 112 that are required by the specific aspect involved), then some specific, but non-limiting examples of such mutations/amino acid differences that may be present (i.e., compared to the sequences of SEQ ID NO: 1 or 2) are for example P41A, P41L, P41S or P41T (and in particular P41A) and/or T87A. Other examples of mutations are (a suitable combination of) one or more suitable "humanizing" substitutions; reference is for example made to WO 2009/138519 (or in the prior art cited in WO 2009/138519) and WO 2008/020079 (or in the prior art cited in WO 2008/020079), as well as Tables A-3 to A-8 from WO 2008/020079 (which are lists showing possible humanizing substitutions).

Also, when a PD1 binding moiety (e.g. an ISVD such as a Nanobody) is present at and/or forms the N-terminal part of the PD1/CTLA4 binder of the invention, then it preferably contains a D at position 1 (i.e., an E1D mutation compared to Reference A or 102C12). A preferred but non-limiting example of such an N-terminal PD1 binding moiety is given as SEQ ID NO: 31 (although other PD1 binding moieties with an E1D mutation can also be used). Similarly, when the PD1 binding moiety of SEQ ID NO:31 is not present at the N-terminal end but somewhere else in a PD1/CTLA4 binder of the invention, it preferably contains an D1E mutation). Accordingly, in a further aspect, the invention relates to a PD1/CTLA4 binder of the invention (which is as further described herein) that has a PD1 binding moiety (which is as further described herein) at its N-terminal end, wherein said PD1 binding moiety has a D at position 1, and is preferably SEQ ID NO: 31, 135, 140, 141 or 142.

The PD1 binding moieties (e.g. ISVDs such as Nanobodies) present in the PD1/CTLA4 binders of the invention according to the aspects described herein are preferably such that they contain a suitable combination of an L11V mutation, A14P mutation, an A74S mutation, a K83R mutation, and/or an I89L mutation and, optionally an E1D mutation, and preferably a suitable combination of any two of these mutations, such as all of these mutations. When the PD1 binding moiety is present at the N-terminal end of a PD1/CTLA4 binder of the invention, preferably also an E1D mutation-relative to the amino acid sequence of SEQ ID NO: 1 or 2. By means of preferred, but non-limiting examples, SEQ ID NOs: 30, 31, 46, 47, 135, 136, 137, 138, 139, 140, 141 or 142 are examples of PD1 binding moieties having further amino acid differences with SEQ ID NO: 1 or 2, i.e., A14P, A74S and K83R (in addition, as indicated in the previous paragraphs, SEQ ID NOs: 31 and 47 and 135 are example of those that also have an E1D mutation).

Thus, in a first aspect, a PD1 binding moiety (e.g. an ISVD such as a Nanobody) that is present in a PD1/CTLA4 binder of the invention has:
- a CDR1 (according to Kabat) that is the amino acid sequence IHAMG (SEQ ID NO: 3); and
- a CDR2 (according to Kabat) that is the amino acid sequence VITXSGGITYYADSVKG (SEQ ID NO: 4; wherein X is W or V); and
- a CDR3 (according to Kabat) that is the amino acid sequence DKHQSSXYDY (SEQ ID NO: 5; wherein X is W or F);

and has:
- a degree of sequence identity with the amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:
- no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and when present at the C-terminal end of the PD1/CTLA4 binders of the invention preferably has:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binders of the invention (e.g., comprising ISVDs (e.g., Nanobodies) that bind to PD1 and CTLA4) preferably has a D at position 1 (i.e., an E1D mutation compared to SEQ ID NO: 1 or 2), in which:
- the amino acid residue at position 1 of the PD1 binding moiety is chosen from E or D;
- the amino acid residue at position 11 of the PD1 binding moiety is chosen from L or V;
- the amino acid residue at position 14 of the PD1 binding moiety is chosen from A or P;
- the amino acid residue at position 52a of the PD1 binding moiety is chosen from W or V;
- the amino acid residue at position 73 of the PD1 binding moiety is chosen from N, P, S or Q;
- the amino acid residue at position 74 of the PD1 binding moiety is chosen from A or S;
- the amino acid residue at position 83 of the PD1 binding moiety is chosen from K or R;
- the amino acid residue at position 89 of the PD1 binding moiety is chosen from T, V, I or L;
- the amino acid residue at position 100a of the PD1 binding moiety is chosen from W or F;
- the amino acid residue at position 110 of the PD1 binding moiety is chosen from T, K or Q; and
- the amino acid residue at position 112 of the PD1 binding moiety is chosen from S, K or Q;

such that, for example, the PD1 binding moiety has one or more of the following:
- (i) position 1 is E or D;
- (ii) position 11 is V;
- (iii) position 14 is P;
- (iv) position 52a is V;
- (v) position 73 is Q, P or S;
- (vi) position 74 is S;
- (vii) position 83 is R;
- (viii) position 89 is L or T; or
- (ix) position 100a is F;

for example, wherein in the PD1 binding moiety comprises one or more of the following sets of mutations:
- a. position 89 is L and position 11 is V;
- b. position 89 is L and position 110 is K or Q;
- c. position 89 is L and position 112 is K or Q;
- d. position 1 is D or E, position 11 is V, position 14 is P, position 52a is V; position 73 is S, Q or P; position 74 is S, position 83 is R, position 89 is L and position 100a is F;
- e. position 1 is D, position 11 is V, position 14 is P, position 74 is S, position 83 is R and position 89 is L;
- f. position 1 is E, position 11 is V, position 14 is P, position 74 is S, position 83 is R and position 89 is L;
- g. position 89 is L and position 11 is V and position 110 is K or Q;
- h. position 89 is L and position 11 is V and position 112 is K or Q;
- i. position 1 is D, position 11 is V, position 14 is P, position 74 is S, position 83 is R, position 89 is L and position 112 is K or Q;
- j. position 1 is E, position 11 is V, position 14 is P, position 74 is S, position 83 is R, position 89 is L and position 112 is K or Q;
- k. position 1 is D, position 11 is V, position 14 is P, position 74 is S, position 83 is R, position 89 is L, and position 110 is K or Q;
- l. position 1 is D or E, position 11 is V, position 14 is P, position 52a is V, position 73 is S, Q or P, position 74 is S, position 83 is R, position 89 is L, position 100a if F and position 110 is K or Q;

m. position 1 is D or E, position 11 is V, position 14 is P, position 52a is V, position 73 is S, Q or P, position 74 is S, position 83 is R, position 89 is L, position 100a if F and position 112 is K or Q;

n. position 1 is E, position 11 is V, position 14 is P, position 74 is S, position 83 is R, position 89 is L and position 112 is K or Q;

o. position 11 is V and position 110 is K or Q; or p. position 11 is V and position 112 is K or Q.

In a further aspect, a PD1 binding moiety (e.g. an ISVD such as a Nanobody) that is present in a PD1/CTLA4 binder of the invention has:

a CDR1 (according to Kabat) that is the amino acid sequence IHAMG (SEQ ID NO: 3); and a CDR2 (according to Kabat) that is the amino acid sequence VITXSGGITYYADSVKG (SEQ ID NO: 4; wherein X is W or V); and a CDR3 (according to Kabat) that is the amino acid sequence DKHQSSXYDY (SEQ ID NO: 5; wherein X is W or F);

and has:

a degree of sequence identity with the amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:

no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and when present at the C-terminal end of the PD1/CTLA4 binder of the invention (e.g., comprising ISVDs (e.g., Nanobodies) that bind to PD1 and CTLA4) preferably has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e., an E1D mutation compared to SEQ ID NO: 1 or 2), such that said PD1 binding moiety comprises one or more of the following amino acid residues (i.e., mutations compared to the amino acid sequence of SEQ ID NO: 1 or 2) at the positions mentioned (numbering according to Kabat):

89T or 89L;
1D or 1E;
14P;
52aV;
73Q, 73S or 73P;
74S;
83R;
89L; or
100aF;

for example, wherein, the PD1 binding moiety comprises one or more of the following sets of mutations:

89L in combination with 1D, 11V, 14P, 74S and 83R;
89L in combination with 1E, 11V, 14P, 74S and 83R;
89L in combination with 1D, 11V, 14P, 52aV, 73S or 73Q or 73P; 74S, 83R and/or 100aF;
89L in combination with 1E, 11V, 14P, 52aV, 73S or 73Q or 73P; 74S, 83R and/or 100aF;
89L in combination with 11V;
89L in combination with 110K or 110Q;
89L in combination with 112K or 112Q;
89L in combination with 11V and 110K or 110Q;
89L in combination with 11V and 112K or 112Q;
112K or 112Q in combination with 1D, 11V, 14P, 74S, 83R and 89L;
110K or 110Q in combination with 1D, 11V, 14P, 74S, 83R and 89L;
112K or 112Q in combination with 1E, 11V, 14P, 74S, 83R and 89L;
110K or 110Q in combination with 1E, 11V, 14P, 74S, 83R and 89L;
112K or 112Q in combination with 1D, 11V, 14P, 52aV, 73S or 73P or 73Q, 74S, 83R, 89L, 100aF;
110K or 110Q in combination with 1D, 11V, 14P, 52aV, 73S or 73P or 73Q, 74S, 83R, 89L, 100aF;
112K or 112Q in combination with 1E, 11V, 14P, 52aV, 73S or 73P or 73Q, 74S, 83R, 89L, 100aF;
110K or 110Q in combination with 1E, 11V, 14P, 52aV, 73S or 73P or 73Q, 74S, 83R, 89L, 100aF;
11V in combination with 110K or 110Q; or
11V in combination with 112K or 112Q.

As mentioned, when a PD1 binding moiety (e.g. an ISVD such as a Nanobody) is present in a PD1/CTLA4 binder of the invention (at the C-terminal end, the PD1 binding moiety (and consequently, the resulting PD1/CTLA4 binder of the invention) preferably has a C-terminal extension X(n) as described herein and/or as described in WO 2012/175741 or PCT/EP2015/060643 (WO2015/173325).

As mentioned, in the invention, a PD1 binding moiety in which position 1 is E or D, position 11 is V, position 14 is P, position 74 is S, position 83 is R, and position 89 is L; or in which position 89 is T or in which position 1 is E or D, position 11 is V, position 14 is P, position 52a is V, position 73 is S, Q or P, position 74 is S, position 83 is R, position 89 is L and/or position 100a is F; or in which position 11 is V and position 89 is L (optionally, in suitable combination with a 110K or 110Q mutation and/or a 112K or 112Q mutation, and in particular in combination with a 110K or 110Q mutation) are preferred. Even more preferred are PD1 binding moieties in which position 11 is V and position 89 is L, optionally with a 110K or 110Q mutation.

Thus, in one preferred aspect, a PD1 binding moiety (e.g. a ISVD such as a Nanobody) that is present in a PD1/CTLA4 binder of the invention has:

a CDR1 (according to Kabat) that is the amino acid sequence IHAMG (SEQ ID NO:3); and a CDR2 (according to Kabat) that is the amino acid sequence VITXSGGITYYADSVKG (SEQ ID NO:4; wherein X is W or V); and a CDR3 (according to Kabat) that is the amino acid sequence DKHQSSXYDY (SEQ ID NO:5; wherein X is W or F);

and has:

a degree of sequence identity with the amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:

no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and when present at the C-terminal end of the PD1/CTLA4 binder of the invention preferably has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I); and when present at the N-terminal end of the PD1/CTLA4 binder of the invention preferably has a D at position 1 (i.e., an E1D mutation compared to SEQ ID NO: 1 or 2), in which:

the amino acid residue at position 1 of the PD1 binding moiety is chosen from E and D;

the amino acid residue at position 11 of the PD1 binding moiety is chosen from L and V;

the amino acid residue at position 14 of the PD1 binding moiety is chosen from A and P;

the amino acid at position 52a of the PD1 binding moiety is chosen from W and V;

the amino acid at position 73 of the PD1 binding moiety is chosen from N, P, S and Q;

the amino acid residue at position 74 of the PD1 binding moiety is chosen from A and S;

the amino acid residue at position 83 of the PD1 binding moiety is chosen from K and R;

the amino acid residue at position 89 of the PD1 binding moiety is chosen from T, L, I and V;

the amino acid at position 100a is preferably chosen from W and F;

the amino acid residue at position 110 of the PD1 binding moiety is chosen from T, K and Q (and is preferably T); and the amino acid residue at position 112 of the PD1 binding moiety is chosen from S, K and Q (and in preferably S).

In another preferred aspect, a PD1 binding moiety (e.g. an ISVD such as a Nanobody) that is present in a PD1/CTLA4 binder of the invention that bind to PD1 and CTLA4) has:

a CDR1 (according to Kabat) that is the amino acid sequence IHAMG (SEQ ID NO:3); and a CDR2 (according to Kabat) that is the amino acid sequence VITXSGGITYYADSVKG (SEQ ID NO:4; wherein X is W or V); and a CDR3 (according to Kabat) that is the amino acid sequence DKHQSSXYDY (SEQ ID NO:5; wherein X is W or F);

and has:

a degree of sequence identity with the amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:

no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and when present at the C-terminal end of the PD1/CTLA4 binder of the invention preferably has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e. an E1D mutation compared to SEQ ID NO: 1 or 2), in which one or more of the following is true:

the amino acid residue at position 1 of the PD1 moiety is E or D;

the amino acid residue at position 11 of the PD1 moiety is V;

the amino acid residue at position 14 of the PD1 moiety is P;

the amino acid residue at position 52a of the PD1 moiety is V;

the amino acid residue at position 73 of the PD1 moiety is S, Q or P;
the amino acid residue at position 74 of the PD1 moiety is S;
the amino acid residue at position 83 of the PD1 moiety is R
the amino acid residue at position 89 of the PD1 moiety is L;
the amino acid residue at position 100a of the PD1 moiety is F;
the amino acid residue at position 110 of the PD1 moiety is preferably chosen from T, K or Q; or
the amino acid residue at position 112 of the PD1 moiety is preferably chosen from S, K or Q.

In one specific, but non-limiting aspect, the PD1 moieties (e.g. ISVDs such as Nanobodies) present in the PD1/CTLA4 binders of the invention comprise the following sets of mutations (i.e. mutations compared to the sequence of SEQ ID NO: 1 or 2) at the positions mentioned (numbering according to Kabat):

11V in combination with 89L;
11V in combination with 89L, 1E, 14P, 52aV, 73S or 73Q or 73P, 74S, 83R and 100aF;
11V in combination with 89L, 1D, 14P, 52aV, 73S or 73Q or 73P, 74S, 83R and 100aF;
11V in combination with 89L, 1D, 14P, 74S and 83R;
11V in combination with 89L, 1E, 14P, 74S and 83R;
11V in combination with 110K or 110Q;
11V in combination with 112K or 112Q;
11V in combination with 89L, 1D, 14P, 74S, 83R and 110K or 110Q;
11V in combination with 89L, 1D, 14P, 74S, 83R and 112K or 112Q;
11V in combination with 89L, 1E, 14P, 74S, 83R and 110K or 110Q;
11V in combination with 89L, 1E, 14P, 74S, 83R and 112K or 112Q;
11V in combination with 89L, 1E, 14P, 52aV, 73S or 73Q or 73P, 74S, 83R, 100aF and 110K or 110Q;
11V in combination with 89L, 1E, 14P, 52aV, 73S or 73Q or 73P, 74S, 83R, 100aF and 112K or 112Q;
11V in combination with 89L, 1D, 14P, 52aV, 73S or 73Q or 73P, 74S, 83R, 100aF and 110K or 110Q;
11V in combination with 89L, 1D, 14P, 52aV, 73S or 73Q or 73P, 74S, 83R, 100aF and 112K or 112Q;
11V in combination with 89L and 110K or 110Q; or
11V in combination with 89L and 112K or 112Q;
and have CDRs such as those set forth in SEQ ID NO: 1, 2, 16-47 or 135-142 (e.g., according to Kabat) and have an overall degree of sequence identity with the amino acid sequence of SEQ ID NO: 1, 2, 16-47 or 135-142 that are as described herein.

In another specific, but non-limiting aspect, the PD1 binding moieties (e.g. ISVDs such as Nanobodies) present in the PD1/CTLA4 binders of the invention comprise the following sets of mutations (i.e., mutations compared to the sequence of SEQ ID NO: 1 or 2) at the positions mentioned (numbering according to Kabat):

89L in combination with 11V;
89L in combination with 89L, 1D, 11V, 14P, 74S and 83R;
89L in combination with 89L, 1E, 11V, 14P, 74S and 83R;
89L in combination with 11V, 14P, 52aV, 73S or 73Q or 73P, 74S, 83R, 100aF and/or 1D or 1E;
89L in combination with 110K or 110Q;
89L in combination with 112K or 112Q;
89L in combination with 89L, 1D, 11V, 14P, 74S, 83R; and 110K or 110Q;
89L in combination with 89L, 1E, 11V, 14P, 74S, 83R; and 112K or 112Q;
89L in combination with 11V, 14P, 52aV, 73S or 73Q or 73P, 74S, 83R, 89L, 100aF, 110K or 110Q and/or 1D or 1E;
89L in combination with 11V, 14P, 52aV, 73S or 73Q or 73P, 74S, 83R, 89L, 100aF, 112K or 112Q and/or 1D or 1E;
89L in combination with 11V and 110K or 110Q; or
89L in combination with 11V and 112K or 112Q;
and have CDRs such as those set forth in SEQ ID NO: 1, 2, 16-47 or 135-142 (e.g., according to Kabat) and have an overall degree of sequence identity with the amino acid sequence of SEQ ID NO: 1 or 2 that are as described herein.

In another specific, but non-limiting aspect, the PD1 binding moieties (e.g. ISVDs such as Nanobodies) present in the PD1/CTLA4 binders of the invention (comprise the following sets of mutations (i.e. mutations compared to the sequence of SEQ ID NO: 1 or 2) at the positions mentioned (numbering according to Kabat):

110K or 110Q in combination with 1E;
110K or 110Q in combination with 1D;
110K or 110Q in combination with 11V;
110K or 110Q in combination with 14P;
110K or 110Q in combination with 52aV;
110K or 110Q in combination with 73S or 73Q or 73P;
110K or 110Q in combination with 74S;
110K or 110Q in combination with 83R;
110K or 110Q in combination with 89L;
110K or 110Q in combination with 100aF; or
110K or 110Q in combination with 11V and 89L;
and have CDRs such as those set forth in SEQ ID NO: 1, 2, 116-47 or 135-142 (according to Kabat) and have an overall degree of sequence identity with the amino acid sequence of SEQ ID NO: 1, 2, 16-47 or 135-142 that are as described herein.

In another specific, but non-limiting aspect, the PD1 binding moieties (e.g. ISVDs such as Nanobodies) present in the PD1/CTLA4 binders of the invention comprise the following sets of mutations (i.e. mutations compared to the sequence of SEQ ID NO: 1 or 2) at the positions mentioned (numbering according to Kabat):

112K or 112Q in combination with 1D;
112K or 112Q in combination with 1E;
112K or 112Q in combination with 11V;
112K or 112Q in combination with 14P;
112K or 112Q in combination with 52aV;
112K or 112Q in combination with 73S or 73Q or 73P;
112K or 112Q in combination with 74S;
112K or 112Q in combination with 83R;
112K or 112Q in combination with 89L;
112K or 112Q in combination with 100aF; or
112K or 112Q in combination with 11V and 89L;
and have CDRs such as those set forth in SEQ ID NO: 1, 2, 16-47 or 135-142 (e.g., according to Kabat) and have an overall degree of sequence identity with the amino acid sequence of SEQ ID NO: 1 or 2 that are as described herein.

In another aspect, the PD1 binding moieties (e.g. ISVDs such as Nanobodies) present in the PD1/CTLA4 binders of the invention comprise a T at position 89 and have CDRs such as those set forth in SEQ ID NO: 1, 2, 16-47 or 135-142 (e.g., according to Kabat) and have an overall degree of sequence identity with the amino acid sequence of SEQ ID NO: 1 or 2 that are as described herein.

In another aspect, the PD1 binding moieties (e.g. ISVDs such as Nanobodies) present in the PD1/CTLA4 binders of the invention comprise a V at position 11 and an L at position 89 and have CDRs such as those set forth in SEQ ID NO: 1, 2, 16-47 or 135-142 (e.g., according to Kabat) and have an overall degree of sequence identity with the amino acid sequence of SEQ ID NO: 1 or 2 that are as described herein.

As mentioned, the PD1 binding moieties (e.g. ISVDs such as Nanobodies) present in the PD1/CTLA4 binders of the invention according to the aspects described herein are preferably such that they contain a suitable combination of an L11V mutation, an A14P mutation, an A74S mutation a K83R mutation and/or an I89L mutation and optionally an E1D mutation, and preferably a suitable combination of any two of these mutations, such as all of these mutations (and again, when the PD1 binding moiety is present at the N-terminal end of a polypeptide of the invention, preferably also an E1D mutation) (relative to the amino acid sequence of SEQ ID NO: 1 or 2).

In another aspect, a PD1 binding moiety (e.g. an ISVD such as a Nanobody) that is present in a PD1/CTLA4 binders of the invention (e.g., comprising ISVDs (e.g., Nanobodies) that bind to PD1 and CTLA4) has:
- a CDR1 (according to Abm) that is the amino acid sequence GSIASIHAMG (SEQ ID NO: 6); and
- a CDR2 (according to Abm) that is the amino acid sequence VITXSGGITY (SEQ ID NO: 7; wherein X is W or V); and
- a CDR3 (according to Abm) that is the amino acid sequence DKHQSSXYDY (SEQ ID NO: 5; wherein X is W or F);

and has:
- a degree of sequence identity with the amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:
- no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and when present at the C-terminal end of the PD1/CTLA4 binder of the invention preferably has:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e., an E1D mutation compared to SEQ ID NO: 1 or 2), in which:
- the amino acid residue at position 1 of the PD1 binding moiety is chosen from E or D;
- the amino acid residue at position 11 of the PD1 binding moiety is chosen from L or V;
- the amino acid residue at position 14 of the PD1 binding moiety is chosen from A or P;
- the amino acid residue at position 52a of the PD1 binding moiety is chosen from W and V;
- the amino acid residue at position 73 of the PD1 binding moiety is chosen from P, S, N and Q;
- the amino acid residue at position 74 of the PD1 binding moiety is chosen from A or S;
- the amino acid residue at position 83 of the PD1 binding moiety is chosen from K or R;
- the amino acid residue at position 89 of the PD1 binding moiety is chosen from T, V, I or L;
- the amino acid residue at position 100a of the PD1 binding moiety is chosen from W and F;
- the amino acid residue at position 110 of the PD1 binding moiety is chosen from T, K or Q; and
- the amino acid residue at position 112 of the PD1 binding moiety is chosen from S, K or Q;

such that, for example in the PD1 binding moiety comprises one or more of the following mutations or sets of mutations:
(i) position 89 is T or L;
(ii) position 89 is L and position 11 is V;
(iii) position 1 is D, position 11 is V, position 14 is P, position 74 is S, position 83 is R and position 89 is L;
(iv) position 1 is E, position 11 is V, position 14 is P, position 74 is S, position 83 is R and position 89 is L;
(v) position 1 is D or E, position 11 is V, position 14 is P, position 52a is V, position 73 is S, Q or P, position 74 is S, position 83 is R, position 89 is L and position 100a is F;
(vi) position 89 is L and position 110 is K or Q;
(vii) position 89 is L and position 112 is K or Q;
(viii) position 89 is L and position 11 is V and position 110 is K or Q;
(ix) position 89 is L and position 11 is V and position 112 is K or Q;
(x) position 1 is D, position 11 is V, position 14 is P, position 74 is S, position 83 is R, position 89 is L; and position 110 is K or Q;
(xi) position 1 is E, position 11 is V, position 14 is P, position 74 is S, position 83 is R, position 89 is L; and position 110 is K or Q;
(xii) position 1 is D, position 11 is V, position 14 is P, position 74 is S, position 83 is R, position 89 is L; and position 112 is K or Q;
(xiii) position 1 is E, position 11 is V, position 14 is P, position 74 is S, position 83 is R, position 89 is L; and position 112 is K or Q;
(xiv) position 1 is D or E, position 11 is V, position 14 is P, position 52a is V, position 73 is S, P or Q, position 74 is S, position 83 is R, position 89 is L; position 100a is F and position 110 is K or Q;
(xv) position 1 is D or E, position 11 is V, position 14 is P, position 52a is V, position 73 is S, P or Q, position 74 is S, position 83 is R, position 89 is L; position 100a is F and position 112 is K or Q;
(xvi) position 11 is V and position 110 is K or Q; or
(xvii) position 11 is V and position 112 is K or Q.

In a further aspect, a PD1 binding moiety (e.g. an ISVD such as a Nanobody) that is present in a binding moiety of the invention has:
- a CDR1 (according to Abm) that is the amino acid sequence GSIASIHAMG (SEQ ID NO:6); and
- a CDR2 (according to Abm) that is the amino acid sequence VITXSGGITY (SEQ ID NO:7; wherein X is W or V); and
- a CDR3 (according to Abm) that is the amino acid sequence DKHQSSXYDY (SEQ ID NO:5; wherein X is W or F);

and has:
- a degree of sequence identity with the amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:
- no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);

and when present at the C-terminal end of the PD1/CTLA4 binder of the invention preferably has:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e. an E1D mutation compared to SEQ ID NO: 1 or 2), such that said PD1 binding moiety comprises the following sets of mutations (i.e. mutations compared to the amino acid sequence of SEQ ID NO: 1 or 2) at the positions mentioned (numbering according to Kabat):

89T or 89L;
89L in combination with 11V;
89L in combination with 1D, 11V, 14P, 74S and 83R;
89L in combination with 1E, 11V, 14P, 74S and 83R;
89L in combination with 1D, 11V, 14P, 52aV, 73S or 73P or 73Q, 74S, 83R and 100aF;
89L in combination with 1E, 11V, 14P, 52aV, 73S or 73Q or 73P, 74S, 83R and 100aF;
89L in combination with 110K or 110Q;
89L in combination with 112K or 112Q;
89L in combination with 11V and 110K or 110Q;
89L in combination with 11V and 112K or 112Q;
89L in combination with 1D, 11V, 14P, 74S, 83R and 110K or 110Q;
89L in combination with 1E, 11V, 14P, 74S, 83R and 110K or 110Q;
89L in combination with 1D, 11V, 14P, 74S, 83R and 112K or 112Q;
89L in combination with 1E, 11V, 14P, 74S, 83R and 112K or 112Q;
89L in combination with 1E, 11V, 14P, 52aV, 73S or 73P or 73Q, 74S, 83R, 100aF and 110K or 110Q;
89L in combination with 1D, 11V, 14P, 52aV, 73S or 73P or 73Q, 74S, 83R, 100aF and 112K or 112Q;
11V in combination with 110K or 110Q; or
11V in combination with 112K or 112Q.

As mentioned, when a PD1 binding moiety (e.g. an ISVD such as a Nanobody) that is present in a PD1/CTLA4 binder of the invention is used in a monovalent format and/or is present at the C-terminal end of a PD1/CTLA4 binder of the invention (as defined herein), the PD1 binding moiety (and consequently, the resulting PD1/CTLA4 binder of the invention) preferably has a C-terminal extension X(n), which C-terminal extension may be as described herein for the PD1/CTLA4 binder of the invention and/or as described in WO 2012/175741 or PCT/EP2015/060643 (WO2015/173325).

As mentioned, in the invention, PD1 binding moieties (e.g. ISVDs such as Nanobodies) in which position 1 is E or D, position 11 is V, position 14 is P, position 74 is S, position 83 is R and position 89 is L, or in which position 89 is T or in which position 1 is E or D, position 11 is V, position 14 is P, position 52a is V, position 73 is S, P or Q, position 74 is S, position 83 is R, position 89 is L and/or position 100a is F or in which position 11 is V and position 89 is L (optionally in suitable combination with a 110K or 110Q mutation and/or a 112K or 112Q mutation, and in particular in combination with a 110K or 110Q mutation) are preferred. Also preferred are PD1 binding moieties in which position 11 is V and position 89 is L, optionally with a 110K or 110Q mutation (relative to the amino acid sequence of SEQ ID NO: 1 or 2).

Thus, in one preferred aspect, a PD1 binding moiety (e.g. a ISVD such as a Nanobody) that is present in a PD1/CTLA4 binder of the invention has:
- a CDR1 (according to Abm) that is the amino acid sequence GSIASIHAMG (SEQ ID NO:6); and
- a CDR2 (according to Abm) that is the amino acid sequence VITXSGGITY (SEQ ID NO:7; wherein X is W or V); and
- a CDR3 (according to Abm) that is the amino acid sequence DKHQSSXYDY (SEQ ID NO:5; wherein X is W or F);

and has:
- a degree of sequence identity with the amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);
and/or has:
no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);
and when present at the C-terminal end of the PD1/CTLA4 binder of the invention preferably has:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
and when present at the N-terminal end of the PD1/CTLA4 binder of the invention preferably has a D at position 1 (i.e., an E1D mutation compared to SEQ ID NO: 1 or 2),
in which
the amino acid residue at position 1 of the PD1 binding moiety is chosen from E or D;
the amino acid residue at position 11 of the PD1 binding moiety is chosen from L or V;
the amino acid residue at position 14 of the PD1 binding moiety is chosen from A or P;
the amino acid residue at position 52a of the PD1 binding moiety is chosen from W and V;
the amino acid residue at position 73 of the PD1 binding moiety is chosen from P, N, S and Q;
the amino acid residue at position 74 of the PD1 binding moiety is chosen from A or S;
the amino acid residue at position 83 of the PD1 binding moiety is chosen from K or R;
the amino acid residue at position 89 of the PD1 binding moiety is T, V I or L;
the amino acid residue at position 100a of the PD1 binding moiety is chosen from W and F;
the amino acid residue at position 110 of the PD1 binding moiety is chosen from T, K or Q (and is preferably T); and
the amino acid residue at position 112 of the PD1 binding moiety is chosen from S, K or Q (and is preferably S).
In another preferred aspect, a PD1 binding moiety that is present in a PD1/CTLA4 binder of the invention has:
a CDR1 (according to Abm) that is the amino acid sequence GSIASIHAMG (SEQ ID NO: 6); and
a CDR2 (according to Abm) that is the amino acid sequence VITXSGGITY (SEQ ID NO: 7; wherein X is W or V); and
a CDR3 (according to Abm) that is the amino acid sequence DKHQSSXYDY (SEQ ID NO: 5; wherein X is W or F);
and has:
a degree of sequence identity with the amino acid sequence of SEQ ID NO: 1 or 2 (in which the CDRs, any C-terminal extension that may be present, as well as the mutations at positions 1, 11, 14, 52a, 73, 74, 83, 89, 100a, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);
and/or has:
no more than 7, such as no more than 5, preferably no more than 3, such as only 3, 2 or 1 "amino acid differences" (as defined herein, and not taking into account any of the above-listed mutations at position(s) 1, 11, 14, 52a, 73, 74, 83, 89, 100a, 110 and/or 112 that may be present and not taking into account any C-terminal extension that may be present) with the amino acid sequence of SEQ ID NO: 1 or 2 (in which said amino acid differences, if present, may be present in the frameworks and/or the CDRs but are preferably present only in the frameworks and not in the CDRs);
and when present at the C-terminal end of the PD1/CTLA4 binder of the invention preferably has:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
and when present at the N-terminal end of the PD1/CTLA4 binder of the invention preferably has a D at position 1 (i.e. an E1D mutation compared to SEQ ID NO: 1 or 2),
in which one or more of the following is true:
the amino acid residue at position 1 of the PD1 binding moiety is D or E;
the amino acid residue at position 11 of the PD1 binding moiety is V;
the amino acid residue at position 14 of the PD1 binding moiety is P;
the amino acid residue at position 52a of the PD1 binding moiety is V;
the amino acid residue at position 73 of the PD1 binding moiety is S, P or Q;
the amino acid residue at position 74 of the PD1 binding moiety is S;
the amino acid residue at position 83 of the PD1 binding moiety is R;
the amino acid residue at position 89 of the PD1 binding moiety is L;
the amino acid residue at position 100a of the PD1 binding moiety is F;
the amino acid residue at position 110 of the PD1 binding moiety is chosen from T, K and Q; or
the amino acid residue at position 112 of the PD1 binding moiety is chosen from S, K and Q.
In one specific, but non-limiting aspect, the PD1 binding moiety (e.g. a ISVD such as a Nanobody) present in the PD1/CTLA4 binder of the invention (e.g., comprising ISVDs (e.g., Nanobodies) that bind to PD1 and CTLA4) comprise the following sets of mutations (i.e. mutations compared to the sequence of SEQ ID NO: 1 or 2) at the positions mentioned (numbering according to Kabat):
11V in combination with 89L;
11V in combination with 1D, 14P, 74S, 83R and 89L;
11V in combination with 1E, 14P, 74S, 83R and 89L;

11V in combination with 14P, 52aV, 73S or 73Q or 73P, 74S, 83R, 89L, 100aF and 1E or 1D;
11V in combination with 110K or 110Q;
11V in combination with 112K or 112Q;
11V in combination with 14P, 52aV, 73S or 73Q or 73P, 74S, 83R, 89L, 100aF, 110K or 110Q and 1E or 1D;
11V in combination with 14P, 52aV, 73S or 73Q or 73P, 74S, 83R, 89L, 100aF, 112K or 112Q and 1E or 1D;
11V in combination with 89L and 110K or 110Q;
11V in combination with 89L and 112K or 112Q;
110K or 110Q in combination with 1D, 11V, 14P, 74S, 83R and 89L;
110K or 110Q in combination with 1E, 11V, 14P, 74S, 83R and 89L;
112K or 112Q in combination with 1D, 11V, 14P, 74S, 83R and 89L; or
112K or 112Q in combination with 1E, 11V, 14P, 74S, 83R and 89L and have CDRs such as those set forth in SEQ ID NO: 1, 2, 16-47 or 135-142 (e.g., according to Abm) and have an overall degree of sequence identity with the amino acid sequence of SEQ ID NO: 1 or 2 that are as described herein.

In another specific, but non-limiting aspect, the PD1 binding moiety (e.g. an ISVD such as a Nanobody) present in the PD1/CTLA4 binder of the invention comprise the following sets of mutations (i.e., mutations compared to the sequence of SEQ ID NO: 1 or 2) at the positions mentioned (numbering according to Kabat):
89L in combination with 11V;
89L in combination with 1E, 11V, 14P, 74S and 83R;
89L in combination with 1D, 11V, 14P, 74S and 83R;
89L in combination with 11V, 14P, 52aV, 73S or 73Q or 73P, 74S, 83R, 100aF and 1E or 1D;
89L in combination with 110K or 110Q;
89L in combination with 112K or 112Q;
89L in combination with 1E, 11V, 14P, 74S, 83R and 110K or 110Q;
89L in combination with 1D, 11V, 14P, 74S, 83R and 110K or 110Q;
89L in combination with 1E, 11V, 14P, 74S, 83R and 112K or 112Q;
89L in combination with 1D, 11V, 14P, 74S, 83R and 112K or 112Q;
89L in combination with 11V, 14P, 52aV, 73S or 73Q or 73P, 74S, 83R, 100aF, 110K or 110Q and 1E or 1D;
89L in combination with 11V, 14P, 52aV, 73S or 73Q or 73P, 74S, 83R, 100aF, 112K or 112Q and 1E or 1D;
89L in combination with 11V and 110K or 110Q; or
89L in combination with 11V and 112K or 112Q;

and have CDRs such as those set forth in SEQ ID NO: 1, 2, 16-47 or 135-142 (e.g., according to Abm) and have an overall degree of sequence identity with the amino acid sequence of SEQ ID NO: 1 or 2 that are as described herein.

In another specific, but non-limiting aspect, the PD1 binding moiety (e.g. an ISVD such as a Nanobody) present in the PD1/CTLA4 binder of the invention comprise the following sets of mutations (i.e. mutations compared to the sequence of SEQ ID NO:2) at the positions mentioned (numbering according to Kabat):
110K or 110Q in combination with 11V;
110K or 110Q in combination with 1E, 11V, 14P, 74S, 83R and 89L;
110K or 110Q in combination with 1D, 11V, 14P, 74S, 83R and 89L;
110K or 110Q in combination with 11V, 14P, 52aV, 73S or 73Q or 73P, 74S, 83R, 89L and 100aF, and 1E or 1D.
110K or 110Q in combination with 89L; or
110K or 110Q in combination with 11V and 89L;

and have CDRs such as those set forth in SEQ ID NO: 1, 2, 16-47 or 135-142 (e.g., according to Abm) and have an overall degree of sequence identity with the amino acid sequence of SEQ ID NO: 1 or 2 that are as described herein.

In another specific, but non-limiting aspect, the PD1 binding moieties (e.g. ISVDs such as Nanobodies) present in the PD1/CTLA4 binders of the invention (e.g., comprising ISVDs (e.g., Nanobodies) that bind to PD1 and CTLA4) comprise the following sets of mutations (i.e. mutations compared to the sequence of SEQ ID NO: 1 or 2) at the positions mentioned (numbering according to Kabat):
112K or 112Q in combination with 11V;
112K or 112Q in combination with 1E, 11V, 14P, 74S, 83R and 89L;
112K or 112Q in combination with 1D, 11V, 14P, 74S, 83R and 89L;
112K or 112Q in combination with 11V, 14P, 52aV, 73S or 73Q or 73P, 74S, 83R, 89L and 100aF, and 1E or 1D;
112K or 112Q in combination with 89L; or
112K or 112Q in combination with 11V and 89L;

and have CDRs such as those set forth in SEQ ID NO: 1, 2, 16-47 or 135-142 (e.g., according to Abm) and have an overall degree of sequence identity with the amino acid sequence of SEQ ID NO: 1 or 2 that are as described herein.

In another aspect, the PD1 binder(s) present in the PD1/CTLA4 binder of the invention (e.g., comprising ISVDs (e.g., Nanobodies) that bind to PD1 and CTLA4) comprise a T or an L at position 89 and have CDRs such as those set forth in SEQ ID NO: 1, 2, 16-47 or 135-142 (e.g., according to Abm) and have an overall degree of sequence identity with the amino acid sequence of SEQ ID NO: 1 or 2 that are as described herein.

In another aspect, the PD1 binding moiety (e.g. an ISVD such as a Nanobody) present in the PD1/CTLA4 binder of the invention comprise a V at position 11 and an L at position 89 and have CDRs such as those set forth in SEQ ID NO: 1, 2, 16-47 or 135-142 (e.g., according to Abm) and have an overall degree of sequence identity with the amino acid sequence of SEQ ID NO: 1 or 2 that are as described herein.

As mentioned, the PD1 binding moiety (e.g. an ISVD such as a Nanobody) present in the PD1/CTLA4 binder of the invention according to the aspects described herein are preferably such that they contain a suitable combination of an optional E1D mutation, an L11V mutation, A14P mutation, an A74S mutation, a K83R mutation, and/or an I89L mutation; and preferably a suitable combination of any two of these mutations, such as all five or six of these mutations (when the PD1 binding moiety is present at the N-terminal end of a polypeptide of the invention, preferably also an E1D mutation) (relative to the amino acid sequence of SEQ ID NO: 1 or 2).

Some preferred but non-limiting examples of PD1 binding moieties that can be present in the PD1/CTLA4 binders of the invention are given in SEQ ID NOs: 16 to 47 or 135-142, and PD1/CTLA4 binder of the invention that suitably comprise one or more of these sequences form further aspects of the invention.

Some preferred PD1 binding moieties that can be present in the PD1/CTLA4 binder of the invention are the sequences of SEQ ID NOs: 30, 31, 16-47 or 135-142. Of these, SEQ ID NO: 31 is particularly suited to be present at the N-terminal end of a PD1/CTLA4 binder of the invention, and SEQ ID NO: 46 is particularly suited to be present at the C-terminal end of a PD1/CTLA4 binder of the invention.

When a PD1 binding moiety (e.g. an ISVD such as a Nanobody) is present at and/or forms the C-terminal end of a PD1/CTLA4 binder of the invention, it preferably has a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting examples of such C-terminal extensions $X_{(n)}$, X and n can be as further described herein for the PD1/CTLA4 binders of the invention (e.g., comprising ISVDs (e.g., Nanobodies) that bind to PD1 and CTLA4).

In an embodiment of the invention, when the PD1 binding moieties (e.g. ISVDs such as Nanobodies) present in the PD1/CTLA4 binder of the invention (e.g., comprising ISVDs (e.g., Nanobodies) that bind to PD1 and CTLA4) contain mutations at positions 110 or 112 (relative to the amino acid sequence of SEQ ID NO: 1 or 2) (optionally in combination with mutations at positions 1, 11, 14, 74, 83 and/or 89 as described herein), the 5 C-terminal amino acid residues of framework 4 (starting from position 109) can be substituted as follows:
(i) if no C-terminal extension is present: VTVKS (SEQ ID NO:88), VTVQS (SEQ ID NO:89), VKVSS (SEQ ID NO: 90) or VQVSS (SEQ ID NO: 91); or
(ii) if a C-terminal extension is present: VTVKSX$_{(n)}$ (SEQ ID NO: 92), VTVQSX(n) (SEQ ID NO: 93), VKVSSX (n) (SEQ ID NO: 94) or VQVSSX$_{(n)}$ (SEQ ID NO: 95), such as VTVKSA (SEQ ID NO: 96), VTVQSA (SEQ ID NO: 97), VKVSSA (SEQ ID NO: 98) or VQVSSA (SEQ ID NO: 99).

In an embodiment of the invention, when the PD1 binding moieties (e.g. ISVDs such as Nanobodies) present in the PD1/CTLA4 binders of the invention (e.g., comprising ISVDs (e.g., Nanobodies) that bind to PD1 and CTLA4) do not contain mutations at positions 110 or 112 (but only mutations at position 1 (optionally), 11, 14, 74, 83 and/or 89 as described herein) (relative to the amino acid sequence of SEQ ID NO: 1 or 2), the C-terminal 5 amino acid residues of framework 4 (starting from position 109) will usually be substituted as follows:
(i) when no C-terminal extension is present: VTVSS (SEQ ID NO: 100) (as in the sequence of SEQ ID NO:2); or
(ii) when a C-terminal extension is present: VTVSSX$_{(n)}$ (SEQ ID NO: 101) such as VTVSSA (SEQ ID NO:102). In these C-terminal sequences, X and n are as defined herein for the C-terminal extensions.

CTLA4 Binding Moieties

The one or more (such as one or two) CTLA4 binding moieties present in the PD1/CTLA4 binders of the invention (e.g., comprising ISVDs (e.g., Nanobodies) that bind to PD1 and CTLA4) are preferably as follows (it should also be noted that when two or more CTLA4 binding moieties are present in a PD1/CTLA4 binder of the invention, they may be the same or different, and when they are different, they preferably all contain (a suitable combination of) mutations at positions 1, 11, 14, 45, 74, 83 89, 96, 108, 110 and/or 112 as described herein, and preferably also have the same CDRs as described herein) (relative to the amino acid sequence of SEQ ID NO: 9). The amino acid sequences of some preferred, but non-limiting examples of CTLA4 binders that can be present in the polypeptides (e.g., PD1/CTLA4 binders) of the invention are listed in FIG. 4A. FIG. 4B gives an alignment of these CTLA4 binding moieties with the sequence of SEQ ID NO: 9.

As further described herein, the CTLA4 binders of the invention which are, in an embodiment of the invention in PD1/CTLA4 binders of the present invention, preferably have the same combination of CDRs (i.e. CDR1, CDR2 and CDR3) as are present in 11F1 or in a binder comprising the sequence of 11F1 (SEQ ID NO: 9). See Table B-1.

The present invention also includes CTLA4 binders which are variants of 11F1 which comprise an amino acid sequence as set forth below in Table B-2 below. The scope of the present invention includes CTLA4 binders that include CDR1, CDR2 and CDR3 of said variants set forth below in Table B-2.

In addition, the present invention includes PD1/CTLA4 binders comprising a CTLA4 binding moiety that includes CDR1, CDR2 and CDR3 or the amino acid sequence of 11F1 or of one of its variants set forth below in Table B-2.

TABLE B-1

CTLA4 Binder 11F1 (11F01).

| SEQ ID NO | Description | Sequence |
|---|---|---|
| 9 | Reference A WO 2008/071447 SEQ ID NO: 1306 (11F01 or 4CTLA011F01) | EVQLVESGGGLVQAGGSLRLSCAASGGTFSF YGMGWFRQAPGKEQEFVADIRTSAGRTYYAD SVKGRFTISRDNAKNTVYLQMNSLKPEDTAV YYCAAEMSGISGWDYWGQGTQVTVSS |

TABLE B-2

CTLA4 Binder 11F1 Variants.

| | | |
|---|---|---|
| 14 | 11F01 (E1D, L11V, A14P, Q45R, A74S, K83R, V89L, M96P, Q108L) | DVQLVESGGGVVQPGGSLRLSCAASGGTFSFYGMG WFRQAPGKEREFVADIRTSAGRTYYADSVKGRFTISRDNSKNTVYLQMNSLRP EDTALYYCAAEPSGISGWDYWGQGTLVTVSS |
| 10 | CDR1 (Kabat) | FYGMG |
| 11 | CDR2 (Kabat) | DIRTSAGRTYYADSVKG |
| 12 | CDR3 (Kabat/Abm) | EXSGISGWDY; wherein X is M or P (e.g., EMSGISGWDY or EPSGISGWDY) |
| 13 | CDR1 (Abm) | GGTFSFYGMG |
| 14 | CDR2 (Abm) | DIRTSAGRTY |

TABLE B-2-continued

CTLA4 Binder 11F1 Variants.

| 15CDR3 (Kabat/Abm) | EXSGISGWDY; wherein X is M or P (e.g., EMSGISGWDY or EPSGISGWDY) |
|---|---|
| 19611F01(L11V, A14P, Q45R, N73X, A74S, K83R, V89L, M96P, Q108L) | EVQLVESGGGVVQPGGSLRLSCAASGGTFSFYGMGWFRQAPGKEREFVADIRT SAGRTYYADSVKGRFTISRDXSKNTVYLQMNSLRPEDTALYYCAAEPSGISGW DYWGQGTLVTVSS; wherein X is S, V, G, R, Q, M, H, T, D, E, W, F, K, A, Y or P |

Note:
SEQ ID NO: 12 is identical to SEQ ID NO: 15
*CDRs underscored and/or bold.

The present invention includes embodiments wherein one, two or three of the CDRs of a CTLA4 binder set forth above in Table B-1 or B-2 (e.g., of 11F01 or 11F01 (E1D, L11V, A14P, Q45R, A74S, K83R, V89L, M96P, Q108L)) wherein each CDR comprises 0, 1, 2, 3, 4, or 5 amino acid substitutions, e.g., conservative substitutions, and/or comprises 100, 99, 98, 97, 96 or 95% sequence identity relative to the CDR sequences set forth in Table B-1 or B-2 wherein the CTLA4 binder having such CDRs retain the ability to bind to CTLA4. In an embodiment of the invention, the first amino acid of a CTLA4 binder of the present invention is E. In an embodiment of the invention, the first amino acid of a PD1 binder of the present invention is D.

Residue 1 or SEQ ID NO: 104 can be D or E. If residue 1 is D, the CTLA4 binder may be designated as 1D and if residue 1 is E, the CTLA4 binder may be designated as 1E.

The Kabat residue numbers for certain residues of the CTLA4 binders (e.g., ISVD such as a Nanobody) that are based on Nanobody 11F01 which are set forth herein are shown in the sequence below:

(SEQ ID NO: 9)
$E_1$VQLVESGGGL$_{11}$V$_{12}$Q$_{13}$A$_{14}$GGSLRLSCAASG$_{26}$G$_{27}$T$_{28}$F$_{29}$S$_{30}$F

YGMGW$_{36}$F$_{37}$R$_{38}$Q$_{39}$APGKEQ$_{45}$E$_{46}$F$_{47}$V$_{48}$A$_{49}$DIRTSAGRTYYADS

VKGR$_{66}$F$_{67}$T$_{68}$I$_{69}$S$_{70}$RDN$_{73}$A$_{74}$KNTVYLQMN$_{82a}$S$_{82b}$L$_{82c}$K$_{83}$

P$_{84}$EDT$_{87}$A$_{88}$V$_{89}$Y$_{90}$Y$_{91}$CAAEM$_{96}$SGISGWDYW$_{103}$G$_{104}$Q$_{105}$

G$_{106}$TQ$_{108}$V$_{109}$T$_{110}$V$_{111}$S$_{112}$S$_{113}$

The Kabat residue numbers for certain residues of the CTLA4 binder 11F01 (E1D, L11V, A14P, Q45R, A74S, K83R, V89L, M96P, Q108L) which are set forth herein are shown in the sequence below:

(SEQ ID NO: 143)
D$_1$VQLVESGGGV$_{11}$VQP$_{14}$GGSLRLSCAASGGTFSFYGMGWFRQAPGKE

R$_{45}$EFVADIRTSAGRTYYADSVKGRFTISRDN$_{73}$S$_{74}$KNTVYLQMNSL

R$_{83}$PEDTAL$_{89}$YYCAAEP$_{96}$SGISGWDYWGQGTL$_{108}$VTVSS

Mutations may be referred to herein and are designated by their Kabat number as shown above.

In an embodiment of the invention, the CTLA4 binder 11F01 comprises a mutation at position 73, e.g, N73X wherein X is S, V, G, R, Q, M, H, T, D, E, W, F, K, A, Y or P (or any amino acid other than N).

As mentioned, CTLA4 binding moieties (e.g. ISVDs such as Nanobodies) present in the PD1/CTLA4 binders of the invention described herein can bind (and in particular, can specifically bind) to CTLA4. In particular, they can bind to CTLA4 and thereby prevent CD80 and/or CD86 e.g., on antigen-presenting cells, from binding to CTLA4, e.g., on T cells. In an embodiment of the invention, the resulting blockade of CTLA4 signaling prolongs T-cell activation, restores T-cell proliferation, and thus amplifies T-cell-mediated immunity, which theoretically enhances the patient's capacity to mount an antitumor immune response.

Generally, the CTLA4 binding moieties (e.g. ISVDs such as Nanobodies) present in the PD1/CTLA4 binders of the invention are variants of SEQ ID NO: 9 (11F01, WO 2008/071447: SEQ ID NO:1306) that comprise the following mutations or sets of mutations (i.e., mutations compared to the sequence of SEQ ID NO: 9):

89T or 89L;
89L in combination with 1D, 11V, 14P, 45R, 74S, 83R, 96P and 108L;
89L in combination with 1E, 11V, 14P, 45R, 74S, 83R, 96P and 108L;
89L in combination with 11V;
89L in combination with 110K or 110Q;
89L in combination with 112K or 112Q;
89L in combination with 11V and 110K or 110Q;
89L in combination with 11V and 112K or 112Q;
89L in combination with 1D, 11V, 14P, 45R, 74S, 83R, 89L, 96P, 108L and 110K or 110Q;
89L in combination with 1E, 11V, 14P, 45R, 74S, 83R, 89L, 96P, 108L and 110K or 110Q;
89L in combination with 1D, 11V, 14P, 45R, 74S, 83R, 89L, 96P, 108L and 112K or 112Q; or
89L in combination with 1E, 11V, 14P, 45R, 74S, 83R, 89L, 96P, 108L and 112K or 112Q;
11V in combination with 110K or 110Q; or
11V in combination with 112K or 112Q.

In an embodiment of the invention, in the CTLA4 binding moieties (e.g. ISVDs such as Nanobodies) present in the PD1/CTLA4 binders of the invention:

the amino acid residue at position 1 is chosen from E or D;
the amino acid residue at position 11 is chosen from L or V;
the amino acid residue at position 14 is chosen from A or P;
the amino acid residue at position 45 is chosen from Q or R;
the amino acid residue at position 74 is chosen from A or S;
the amino acid residue at position 83 is chosen from K or R;
the amino acid residue at position 89 is chosen from T, V or L;
the amino acid residue at position 96 is chosen from M or P;
the amino acid residue at position 108 is chosen from Q or L;

the amino acid residue at position 110 is chosen from T, K or Q; and the amino acid residue at position 112 is chosen from S, K or Q;

such that, for example, CTLA4 binding moiety comprises one or more of the following mutations or sets of mutations:
  (i) position 89 is T or L;
  (ii) position 89 is L and position 11 is V;
  (iii) position 89 is L, position 1 is D, position 11 is V, position 14 is P, position 45 is R, position 74 is S, position 83 is R, position 96 is P and position 108 is L;
  (iv) position 89 is L, position 1 is E, position 11 is V, position 14 is P, position 45 is R, position 74 is S, position 83 is R, position 96 is P and position 108 is L;
  (v) position 89 is L and position 110 is K or Q;
  (vi) position 89 is L and position 112 is K or Q;
  (vii) position 89 is L and position 11 is V and position 110 is K or Q;
  (viii) position 89 is L and position 11 is V and position 112 is K or Q;
  (ix) position 89 is L, position 1 is D, position 11 is V, position 14 is P, position 45 is R, position 74 is S, position 83 is R, position 96 is P, position 108 is L and position 110 is K or Q
  (x) position 89 is L, position 1 is E, position 11 is V, position 14 is P, position 45 is R, position 74 is S, position 83 is R, position 96 is P, position 108 is L and position 110 is K or Q
  (xi) position 89 is L, position 1 is D, position 11 is V, position 14 is P, position 45 is R, position 74 is S, position 83 is R, position 96 is P, position 108 is L and position 112 is K or Q;
  (xii) position 89 is L, position 1 is E, position 11 is V, position 14 is P, position 45 is R, position 74 is S, position 83 is R, position 96 is P, position 108 is L and position 112 is K or Q;
  (xiii) position 11 is V and position 110 is K or Q; or
  (xiv) position 11 is V and position 112 is K or Q.

The presence of a CTLA4 binding moieties in which position 89 is T or in which position 1 is E or D, position 11 is V, position 14 is P, position 45 is R, position 74 is S, position 83 is R, position 89 is L, position 96 is P, position 108 is L or in which position 11 is V and position 89 is L (optionally in suitable combination with a 110K or 110Q mutation and/or a 112K or 112Q mutation, and in particular in combination with a 110K or 110Q mutation) are preferred. Also preferred are CTLA4 binding moieties in which position 11 is V and position 89 is L, optionally with a 110K or 110Q mutation.

The CTLA4 binding moieties (e.g. ISVDs such as Nanobodies) present in the PD1/CTLA4 binders of the invention preferably comprise the following CDRs (according to the Kabat convention):
  a CDR1 (according to Kabat) that is the amino acid sequence FYGMG (SEQ ID NO: 10); and
  a CDR2 (according to Kabat) that is the amino acid sequence DIRT SAGRTYYADSVKG (SEQ ID NO: 11); and
  a CDR3 (according to Kabat) that is the amino acid sequence EXSGISGWDY (SEQ ID NO: 12; wherein X is M or P).

Alternatively, when the CDRs are given according to the Abm convention, the CTLA4 binding moieties (e.g. ISVDs such as Nanobodies) present in the PD1/CTLA4 binders of the invention preferably comprise the following CDRs:
  a CDR1 (according to Abm) that is the amino acid sequence GGTFSFYGMG (SEQ ID NO: 13); and
  a CDR2 (according to Abm) that is the amino acid sequence DIRTSAGRTY (SEQ ID NO: 14); and
  a CDR3 (according to Abm) that is the amino acid sequence EXSGISGWDY (SEQ ID NO: 15, which is the same as SEQ ID NO: 4; wherein X is M or P).

The above preferred CDRs are the same as are present in 11F01 (SEQ ID NO: 9).

CTLA4 binding moieties (e.g. ISVDs such as Nanobodies) present in the PD1/CTLA4 binders of the preferably also have:
  a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment); and/or
  no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs).

With regards to the various aspects and preferred aspects of the when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment) of the invention provided by the invention, when it comes to the degree of sequence identity with respect to SEQ ID NO: 9 and/or the number and kind of "amino acid differences" that may be present in such a binder of the invention (i.e. compared to the sequence of SEQ ID NO: 9), it should be noted that, when it is said that
  (i) CTLA4 binding moiety has a degree of sequence identity with the sequence of SEQ ID NO: 9 of at least 85%, preferably at least 90%, more preferably at least 95% (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity); and/or when it is said that
  (ii) a CTLA4 binding moiety has no more than 7, preferably no more than 5, such as only 3, 2 or 1 "amino acid differences" with the sequence of SEQ ID NO: 9 (again, not taking into account any C-terminal extension that may be present and not taking into account the mutations at positions 1, 11, 14, 45, 74, 83 89, 96, 108, 110 and/or 112 required by the specific aspect involved), then this also includes sequences that have no amino acid differences with the sequence of SEQ ID NO: 9 other than the mutations at positions 1, 11, 14, 45, 74, 83 89, 96, 108, 110 and/or 112 required by the specific aspect involved) and any C-terminal extension that may be present.

Thus, in one specific aspect of the invention, the CTLA4 binding moieties (e.g. ISVDs such as Nanobodies) present in the PD1/CTLA4 binders of the invention may have 100% sequence identity with SEQ ID NO: 9 (including the CDRs, but not taking into account the mutation(s) or combination of mutations at positions 1, 11, 14, 45, 74, 83, 89, 96, 108, 110 and/or 112 disclosed herein and/or any C-terminal extension that may be present) and/or may have no amino acid differences with SEQ ID NO: 9 (i.e., other than the mutation(s) or combination of mutations at positions 1, 11, 14, 45, 74, 83, 89, 96, 108, 110 and/or 112 disclosed herein and any C-terminal extension that may be present).

When any amino acid differences are present (i.e. besides any C-terminal extension and the mutations at positions 1, 11, 14, 45, 74, 83 89, 96, 108, 110 and/or 112 that are required by the specific aspect of the invention involved), these amino acid differences may be present in the CDRs and/or in the framework regions, but they are preferably present only in the framework regions (as defined by the Abm convention, i.e. not in the CDRs as defined according to the Abm convention), i.e. such that the CTLA4 binding moieties present in the PD1/CTLA4 binders of the invention have the same CDRs (defined according to the Abm convention) as are present in SEQ ID NO: 48-83 or 143.

Also, when a CTLA4 binding moieties (e.g. ISVDs such as Nanobodies) present in the PD1/CTLA4 binders of the invention according to any aspect of the invention has one or more amino acid differences with the sequence of SEQ ID NO: 9 (besides the mutations at positions 1, 11, 14, 45, 74, 83 89, 96, 108, 110 and/or 112 that are required by the specific aspect involved), then some specific, but non-limiting examples of such mutations/amino acid differences that may be present (i.e. compared to the sequences of SEQ ID NO: 9) are for example P41A, P41L, P41S or P41T (and in particular P41A) and/or T87A (relative to the amino acid sequence of SEQ ID NO: 9). Other examples of mutations are (a suitable combination of) one or more suitable "humanizing" substitutions such as Q108L; reference is for example made to WO 2009/138519 (or in the prior art cited in WO 2009/138519) and WO 2008/020079 (or in the prior art cited in WO 2008/020079), as well as Tables A-3 to A-8 from WO 2008/020079 (which are lists showing possible humanizing substitutions). Preferably, the CTLA4 binder(s) present in the polypeptides of the invention contain at least a Q108L humanizing substitution. Also, the methionine residue at position 96 (Kabat numbering) may be replaced by another naturally occurring amino acid residue such as Pro (except Cys, Asp or Asn).

Also, when a CTLA4 binding moiety (e.g. an ISVD such as a Nanobody) is present at and/or forms the N-terminal part of the PD1/CTLA4 binders of the invention, then it preferably contains a D at position 1 (i.e. an E1D mutation compared to SEQ ID NO: 9). A preferred but non-limiting example of such N-terminal CTLA4 binding moieties are given as SEQ ID NOs: 64 and 65 and 143 (although other CTLA4 binding moieties with an E1D mutation can also be used. Similarly, when the CTLA binding moieties of SEQ ID NO: 64 or 65 or 143 is not present at the N-terminal end but somewhere else in a PD1/CTLA4 binder of the invention, it preferably contains an D1E mutation (1E). Accordingly, in a further aspect, the invention relates to a PD1/CTLA4 binder of the invention (which is as further described herein) that has a CTLA4 binding moiety (which is as further described herein) at its N-terminal end, wherein said CTLA4 binding moiety has a D at position 1 (1D), and is preferably SEQ ID NOs: 64 or 65 or 143.

The CTLA4 binding moieties present in the PD1/CTLA4 binders of the invention (e.g., comprising ISVDs (e.g., Nanobodies) that bind to PD1 and CTLA4) according to the aspects described herein are preferably such that they contain a suitable combination of an optional E1D mutation, L11V mutation, A14P mutation, a Q45R mutation, an A74S mutation, a K83R mutation, V89L mutation, M96P mutation and a Q108L mutation. In an embodiment of the invention, such CTLA4 binding moieties comprise a suitable combination of Q108L with any one of the other E1D (optionally), L11V, A14P, Q45R, A74S, K83R, V89L, M96P, Q108L mutations. Preferably the CTLA4 binding moieties comprise a combination of any of such mutations, e.g. any two of these other mutations, more preferably with any three of these mutations (such as with the combination A14P, A74S and K83R), such as with all four or nine or 10 of these mutations (and again, when the CTLA4 binding moiety is monovalent or present at the N-terminal end of a PD1/CTLA4 binder of the invention, preferably also an E1D mutation) (relative to the amino acid sequence of SEQ ID NO: 9). Also, in an embodiment of the invention, the methionine residue of a CTLA4 binding moiety, at position 96 (Kabat numbering), may be replaced by another naturally occurring amino acid residue such as Pro (except, for example, Cys, Asp or Asn). By means of preferred, but non-limiting examples, SEQ ID NOs: 62 to 65 and 80 to 83 and 143 are examples of CTLA4 binding moieties having further amino acid differences with SEQ ID NO: 9, e.g., E1D (optionally), L11V, A14P, Q45R, A74S, K83R, V89L, M96P and Q108L (in addition, as indicated in the previous paragraphs, SEQ ID NOs: 64, 65 and 82 and 83 also have an E1D mutation).

Thus, in a first aspect, a CTLA4 binding moiety (e.g. an ISVD such as a Nanobody) present in the PD1/CTLA4 binder of the invention has:
  a CDR1 (according to Kabat) that is the amino acid sequence FYGMG (SEQ ID NO: 10); and
  a CDR2 (according to Kabat) that is the amino acid sequence DIRTSAGRTYYADSVKG (SEQ ID NO: 11); and
  a CDR3 (according to Kabat) that is the amino acid sequence EXSGISGWDY (SEQ ID NO: 12; wherein X is M or P);
and has:
  a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);
and/or has:
  no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs);

and when present at the C-terminal end of the PD1/CTLA4 binder of the invention preferably has:

a C-terminal extension (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e. an E1D mutation compared to SEQ ID NO: 9), in which:

the amino acid residue at position 1 of the CTLA4 binding moiety is chosen from E or D;

the amino acid residue at position 11 of the CTLA4 binding moiety is chosen from L or V;

the amino acid residue at position 14 of the CTLA4 binding moiety is chosen from A or P;

the amino acid residue at position 45 of the CTLA4 binding moiety is chosen from Q or R;

the amino acid residue at position 74 of the CTLA4 binding moiety is chosen from A or S;

the amino acid residue at position 83 of the CTLA4 binding moiety is chosen from K or R;

the amino acid residue at position 89 of the CTLA4 binding moiety is chosen from T, V or L;

the amino acid residue at position 96 of the CTLA4 binding moiety is chosen from M or P;

the amino acid residue at position 108 of the CTLA4 binding moiety is chosen from Q or L;

the amino acid residue at position 110 of the CTLA4 binding moiety is chosen from T, K or Q; and the amino acid residue at position 112 of the CTLA4 binding moiety is chosen from S, K or Q;

such that, for example, the CTLA4 binding moiety comprises one or more of the following mutations:

(i) position 1 is E or D;
(ii) position 11 is V;
(iii) position 14 is P;
(iv) position 45 is R;
(v) position 74 is S;
(vi) position 83 is R;
(vii) position 89 is L or T;
(viii) position 96 is P;
(ix) position 108 is L;

for example, wherein, the CTLA4 binding moiety comprises one or more of the following sets of mutations:

a. position 89 is L and position 11 is V;
b. position 89 is L and position 110 is K or Q;
c. position 89 is L and position 112 is K or Q;
d. position 89 is L and position 11 is V and position 110 is K or Q;
e. position 89 is L and position 11 is V and position 112 is K or Q;
f. position 1 is D, position 11 is V, position 14 is P, position 45 is R, position 74 is S, position 83 is R, position 89 is L, position 96 is P and position 108 is L position;
g. position 1 is E, position 11 is V, position 14 is P, position 45 is R, position 74 is S, position 83 is R, position 89 is L, position 96 is P and position 108 is L;
h. position 1 is D, position 11 is V, position 14 is P, position 45 is R, position 74 is S, position 83 is R, position 89 is L, position 96 is P, position 108 is L position and 110 is K or Q;
i. position 1 is E, position 11 is V, position 14 is P, position 45 is R, position 74 is S, position 83 is R, position 89 is L, position 96 is P, position 108 is L position and 110 is K or Q;
j. position 1 is D, position 11 is V, position 14 is P, position 45 is R, position 74 is S, position 83 is R, position 89 is L, position 96 is P, position 108 is L and position 112 is K or Q;
k. position 1 is E, position 11 is V, position 14 is P, position 45 is R, position 74 is S, position 83 is R, position 89 is L, position 96 is P, position 108 is L and position 112 is K or Q;
l. position 11 is V and position 110 is K or Q; or
m. position 11 is V and position 112 is K or Q.

In a further aspect, a CTLA4 binding moiety present in the PD1/CTLA4 binder of the invention (e.g., comprising ISVDs (e.g., Nanobodies) that bind to PD1 and CTLA4) has:

a CDR1 (according to Kabat) that is the amino acid sequence FYGMG (SEQ ID NO: 10); and a CDR2 (according to Kabat) that is the amino acid sequence DIRTSAGRTYYADSVKG (SEQ ID NO: 11); and a CDR3 (according to Kabat) that is the amino acid sequence EXSGISGWDY (SEQ ID NO: 12; wherein X is M or P);

and has:

a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:

no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs);

and when present at the C-terminal end of the PD1/CTLA4 binder of the invention preferably has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e. an E1D mutation compared to SEQ ID NO: 9), such that said CTLA4 binding moiety comprises one or more of the following amino acid residues (i.e. mutations compared to the amino acid sequence of SEQ ID NO: 9) at the positions mentioned (numbering according to Kabat):

1D or 1E;
11V;
14P;
45R;
74S;
83R;
89L or 8T;
96P;
108L;

for example, wherein the CTLA4 binding moiety comprises one or more of the following sets of mutations:

1E in combination with 11V; 14P; 45R; 74S; 83R; 89L; 96P; and 108L;
1D in combination with 11V; 14P; 45R; 74S; 83R; 89L; 96P; and 108L;
89L in combination with 11V;
89L in combination with 110K or 110Q;
89L in combination with 112K or 112Q;
89L in combination with 11V and 110K or 110Q;
89L in combination with 11V and 112K or 112Q;
1E in combination with 11V; 14P; 45R; 74S; 83R; 89L; 96P; 108L and 110K or 110Q;
1D in combination with 11V; 14P; 45R; 74S; 83R; 89L; 96P; 108L and 110K or 110Q;
1E in combination with 11V; 14P; 45R; 74S; 83R; 89L; 96P; 108 L and 112K or 112Q;
1D in combination with 11V; 14P; 45R; 74S; 83R; 89L; 96P; 108L and 112K or 112Q;
11V in combination with 110K or 110Q; or
11V in combination with 112K or 112Q.

As mentioned, when a CTLA4 binding moiety (e.g. an ISVD such as a Nanobody) present in the PD1/CTLA4 binders of the invention is used in a monovalent format and/or is present at the C-terminal end of a PD1/CTLA4 binder of the invention (as defined herein), the CTLA4 binding moiety (and consequently, the resulting PD1/CTLA4 binder of the invention) preferably has a C-terminal extension X(n) as described and/or as described in WO 2012/175741 or PCT/EP2015/060643 (WO2015/173325).

As mentioned, in the invention, CTLA4 binding moieties in which position 89 is T or in which position 1 is E or D, position 11 is V; position 14 is P; position 45 is R; position 74 is S; position 83 is R; position 89 is L; position 96 is P; and position 108 is L or in which position 11 is V and position 89 is L (optionally in suitable combination with a 110K or 110Q mutation and/or a 112K or 112Q mutation, and in particular in combination with a 110K or 110Q mutation) are preferred. Also preferred are CTLA4 moieties in which position 11 is V and position 89 is L, optionally with a 110K or 110Q mutation.

Thus, in one preferred aspect, a CTLA4 binding moiety (e.g. an ISVD such as a Nanobody) that is present in a PD1/CTLA4 binder of the invention has:

a CDR1 (according to Kabat) that is the amino acid sequence FYGMG (SEQ ID NO: 10); and
a CDR2 (according to Kabat) that is the amino acid sequence DIRTSAGRTYYADSVKG (SEQ ID NO: 11); and
a CDR3 (according to Kabat) that is the amino acid sequence EXSGISGWDY (SEQ ID NO: 12; wherein X is M or P);

and has:

a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:

no more than 7, such as no more than 5, preferably no more than 3, such as only 3, 2 or 1 "amino acid differences" (as defined herein, and not taking into account any of the above-listed mutations at position(s) 1, 11, 14, 45, 74, 83 89, 96, 108, 110 and/or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs);

and when present at the C-terminal end of the PD1/CTLA4 binder of the invention preferably has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e. an E1D mutation compared to SEQ ID NO: 9), in which:

the amino acid residue at position 1 of the CTLA4 binding moiety is chosen from E or D
the amino acid residue at position 11 of the CTLA4 binding moiety is chosen from L or V;
the amino acid residue at position 14 of the CTLA4 binding moiety is chosen from A or P;
the amino acid residue at position 45 of the CTLA4 binding moiety is chosen from Q or R;
the amino acid residue at position 74 of the CTLA4 binding moiety is chosen from A or S;
the amino acid residue at position 83 of the CTLA4 binding moiety is chosen from K or R;
the amino acid residue at position 89 of the CTLA4 binding moiety is chosen from T, V or L;

the amino acid residue at position 96 of the CTLA4 binding moiety is chosen from M or P;

the amino acid residue at position 108 of the CTLA4 binding moiety is chosen from Q or L;

the amino acid residue at position 110 of the CTLA4 binding moiety is preferably chosen from T, K or Q (and is preferably T); and the amino acid residue at position 112 of the CTLA4 binding moiety is preferably chosen from S, K or Q (and is preferably S).

In another preferred aspect, a CTLA4 binding moiety (e.g. an ISVD such as a Nanobody) that is present in a PD1/CTLA4 binder of the has:

a CDR1 (according to Kabat) that is the amino acid sequence FYGMG (SEQ ID NO: 10); and a CDR2 (according to Kabat) that is the amino acid sequence DIRTSAGRTYYADSVKG (SEQ ID NO: 11); and a CDR3 (according to Kabat) that is the amino acid sequence EXSGISGWDY (SEQ ID NO: 12; wherein X is M or P);

and has:

a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:

no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs); and when present at the C-terminal end of the PD1/CTLA4 binder of the invention preferably has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e. an E1D mutation compared to SEQ ID NO: 9), in which one or more of the following is true:

the amino acid residue at position 1 of the CTLA4 binding moiety is E or D;

the amino acid residue at position 11 of the CTLA4 binding moiety is V;

the amino acid residue at position 14 of the CTLA4 binding moiety is P;

the amino acid residue at position 45 of the CTLA4 binding moiety is R;

the amino acid residue at position 74 of the CTLA4 binding moiety is S;

the amino acid residue at position 83 of the CTLA4 binding moiety is R;

the amino acid residue at position 89 of the CTLA4 binding moiety is L;

the amino acid residue at position 96 of the CTLA4 binding moiety is P;

the amino acid residue at position 108 of the CTLA4 binding moiety is L;

the amino acid residue at position 110 of the CTLA4 binding moiety is chosen from T, K or Q; or the amino acid residue at position 112 of the CTLA4 binding moiety is chosen from S, K or Q.

In one specific, but non-limiting aspect, the CTLA4 binding moieties (e.g. ISVDs such as Nanobodies) present in the PD1/CTLA4 binders of the invention comprise the following sets of mutations (i.e. mutations compared to the sequence of SEQ ID NO: 9) at the positions mentioned (numbering according to Kabat):

11V in combination with 89L;

11V in combination with 1D, 14P, 45R, 74S, 83R, 89L, 96P and 108L;

11V in combination with 1E, 14P, 45R, 74S, 83R, 89L, 96P and 108L;

11V in combination with 110K or 110Q;

11V in combination with 112K or 112Q;

11V in combination with 1D, 14P, 45R, 74S, 83R, 89L, 96P, 108L and 110K or 110Q;

11V in combination with 1E, 14P, 45R, 74S, 83R, 89L, 96P, 108L and 110K or 110Q;

11V in combination with 1D, 14P, 45R, 74S, 83R, 89L, 96P, 108L and 112K or 112Q;

11V in combination with 1E, 14P, 45R, 74S, 83R, 89L, 96P, 108L and 112K or 112Q;

11V in combination with 89L and 110K or 110Q; or 11V in combination with 89L and 112K or 112Q;

and have CDRs such as those set forth in SEQ ID NO: 9 or 48-83 or 143 (e.g., according to Kabat) and have an overall degree of sequence identity with the amino acid sequence of SEQ ID NO: 9 that are as described herein.

In another specific, but non-limiting aspect, the CTLA4 binding moieties (e.g. ISVDs such as Nanobodies) present in the PD1/CTLA4 binders of the comprise the following sets of mutations (i.e. mutations compared to the sequence of SEQ ID NO: 9) at the positions mentioned (numbering according to Kabat):

89L in combination with 11V;

89L in combination with 1D, 11V, 14P, 45R, 74S, 83R, 96P and 108L;

89L in combination with 1E, 11V, 14P, 45R, 74S, 83R, 96P and 108L;

89L in combination with 110K or 110Q;

89L in combination with 112K or 112Q;

89L in combination with 1D, 11V, 14P, 45R, 74S, 83R, 96P, 108L and 110K or 110Q;

89L in combination with 1E, 11V, 14P, 45R, 74S, 83R, 96P, 108L and 110K or 110Q;

89L in combination with 1D, 11V, 14P, 45R, 74S, 83R, 96P, 108L and 112K or 112Q;

89L in combination with 1E, 11V, 14P, 45R, 74S, 83R, 96P, 108L and 112K or 112Q;

89L in combination with 11V and 110K or 110Q; or 89L in combination with 11V and 112K or 112Q;

and have CDRs such as those set forth in SEQ ID NO: 9 or 48-83 or 143 (e.g., according to Kabat) and have an overall degree of sequence identity with the amino acid sequence of SEQ ID NO: 9 that are as described herein.

In another specific, but non-limiting aspect, the CTLA4 binding moieties (e.g. ISVDs such as Nanobodies) present in the PD1/CTLA4 binders of the invention comprise the following sets of mutations (i.e. mutations compared to the sequence of SEQ ID NO: 9) at the positions mentioned (numbering according to Kabat):

110K or 110Q in combination with 11V;
110K or 110Q in combination with 1D, 11V, 14P, 45R, 74S, 83R, 89L 96P and 108L;
110K or 110Q in combination with 1E, 11V, 14P, 45R, 74S, 83R, 89L 96P and 108L;
110K or 110Q in combination with 89L; or
110K or 110Q in combination with 11V and 89L;

and have CDRs such as those set forth in SEQ ID NO: 9 or 48-83 or 143 (e.g., according to Kabat) and have an overall degree of sequence identity with the amino acid sequence of SEQ ID NO: 9 that are as described herein.

In another specific, but non-limiting aspect, the CTLA4 binding moieties (e.g. ISVDs such as Nanobodies) present in the PD1/CTLA4 binders of the invention comprise the following sets of mutations (i.e. mutations compared to the sequence of SEQ ID NO: 9) at the positions mentioned (numbering according to Kabat):

112K or 112Q in combination with 11V;
112K or 112Q in combination with 1D, 11V, 14P, 45R, 74S, 83R, 89L 96P and 108L;
112K or 112Q in combination with 1E, 11V, 14P, 45R, 74S, 83R, 89L 96P and 108L;
112K or 112Q in combination with 89L; or
112K or 112Q in combination with 11V and 89L;

and have CDRs such as those set forth in SEQ ID NO: 9 or 48-83 or 143 (e.g., according to Kabat) and have an overall degree of sequence identity with the amino acid sequence of SEQ ID NO: 9 that are as described herein.

In another aspect, the CTLA4 binding moieties (e.g. ISVDs such as Nanobodies) present in the PD1/CTLA4 binders of the invention comprise a T or L at position 89 (e.g., 1D or 1E, 11V, 14P, 45R, 74S, 83R, 89L 96P and 108L) and have CDRs such as those set forth in SEQ ID NO: 9 or 48-83 or 143 (according to Kabat) and have an overall degree of sequence identity with the amino acid sequence of SEQ ID NO: 9 that are as described herein.

In another aspect, the CTLA4 binding moieties (e.g. ISVDs such as Nanobodies) present in the PD1/CTLA4 binders of the invention comprise a V at position 11 and an L at position 89 (e.g., 1D or 1E, 11V, 14P, 45R, 74S, 83R, 89L 96P and 108L) and have CDRs such as those set forth in SEQ ID NO: 9 or 48-83 or 143 (e.g., according to Kabat) and have an overall degree of sequence identity with the amino acid sequence of SEQ ID NO: 9 that are as described herein.

As mentioned, the CTLA4 binding moieties (e.g. ISVDs such as Nanobodies) present in the PD1/CTLA4 binders of the invention according to the aspects described herein are preferably such that they contain a suitable combination of an optional E1D mutation, an L11V mutation, an A14P mutation, a Q45R mutation, an A74S mutation, a K83R mutation, a V89L mutation, an M96P mutation and/or a Q108L mutation, and preferably a suitable combination of Q108L with any one of the other A14P, Q45R, A74S and K83R mutations, and preferably in combination with any two of these other mutations, more preferably with any three of these mutations (such as with the combination A14P, A74S and K83R), such as with all four of these mutations (and again, when the CTLA4 binder is monovalent or present at the N-terminal end of a compound or polypeptide of the invention, preferably also an E1D mutation) (relative to the amino acid sequence of SEQ ID NO: 9). Also, the methionine residue at position 96 (Kabat numbering) may be replaced by another naturally occurring amino acid residue such as Pro (except Cys, Asp or Asn).

In another aspect, a CTLA4 binding moiety (e.g. an ISVD such as a Nanobody) present in a PD1/CTLA4 binder of the invention has:

a CDR1 (according to Abm) that is the amino acid sequence GGTFSFYGMG (SEQ ID NO: 13); and
a CDR2 (according to Abm) that is the amino acid sequence DIRTSAGRTY (SEQ ID NO: 14); and
a CDR3 (according to Abm) that is the amino acid sequence EXSGISGWDY (SEQ ID NO: 12; wherein X is M or P);

and has:

a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:

no more than 7, such as no more than 5, preferably no more than 3, such as only 3, 2 or 1 "amino acid differences" (as defined herein, and not taking into account any of the above-listed mutations at position(s) 1, 11, 14, 45, 74, 83 89, 96, 108, 110 and/or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs);

and when present at the C-terminal end of the PD1/CTLA4 binder of the invention preferably has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e. an E1D mutation compared to SEQ ID NO: 9), in which:

the amino acid residue at position 1 of the CTLA4 binding moiety is chosen from E or D;
the amino acid residue at position 11 of the CTLA4 binding moiety is chosen from L or V;
the amino acid residue at position 14 of the CTLA4 binding moiety is chosen from A or P;

the amino acid residue at position 45 of the CTLA4 binding moiety is chosen from Q or R;
the amino acid residue at position 74 of the CTLA4 binding moiety is chosen from A or S;
the amino acid residue at position 83 of the CTLA4 binding moiety is chosen from K or R;
the amino acid residue at position 89 of the CTLA4 binding moiety is chosen from T, V or L;
the amino acid residue at position 96 of the CTLA4 binding moiety is chosen from M or P;
the amino acid residue at position 108 of the CTLA4 binding moiety is chosen from Q or L;
the amino acid residue at position 110 of the CTLA4 binding moiety is chosen from T, K or Q; and
the amino acid residue at position 112 of the CTLA4 binding moiety is chosen from S, K or Q;

such that for example, one or more of the following is true:
(i) position 1 is E or D;
(ii) position 11 is V;
(iii) position 14 is P;
(iv) position 45 is R;
(v) position 74 is S;
(vi) position 83 is R;
(vii) position 89 is L or T;
(viii) position 96 is P;
(ix) position 108 is L;

for example, wherein the CTLA4 binder comprises one or more of the following sets of mutations:
a. position 89 is L and position 11 is V;
b. position 89 is L and position 110 is K or Q;
c. position 89 is L and position 112 is K or Q;
d. position 89 is L and position 11 is V and position 110 is K or Q;
e. position 89 is L and position 11 is V and position 112 is K or Q;
f. position 1 is D, position 11 is V, position 14 is P, position 45 is R, position 74 is S, position 83 is R, position 89 is L, position 96 is P and position 108 is L position;
g. position 1 is E, position 11 is V, position 14 is P, position 45 is R, position 74 is S, position 83 is R, position 89 is L, position 96 is P and position 108 is L;
h. position 1 is D, position 11 is V, position 14 is P, position 45 is R, position 74 is S, position 83 is R, position 89 is L, position 96 is P, position 108 is L position and 110 is K or Q;
i. position 1 is E, position 11 is V, position 14 is P, position 45 is R, position 74 is S, position 83 is R, position 89 is L, position 96 is P, position 108 is L position and 110 is K or Q;
j. position 1 is D, position 11 is V, position 14 is P, position 45 is R, position 74 is S, position 83 is R, position 89 is L, position 96 is P, position 108 is L and position 112 is K or Q;
k. position 1 is E, position 11 is V, position 14 is P, position 45 is R, position 74 is S, position 83 is R, position 89 is L, position 96 is P, position 108 is L and position 112 is K or Q;
l. position 11 is V and position 110 is K or Q; or
m. position 11 is V and position 112 is K or Q.

In a further aspect, a CTLA4 binding moiety (e.g. an ISVD such as a Nanobody) that is present in a PD1/CTLA4 binder of the invention has:
a CDR1 (according to Abm) that is the amino acid sequence GGTFSFYGMG (SEQ ID NO: 13); and
a CDR2 (according to Abm) that is the amino acid sequence DIRTSAGRTY (SEQ ID NO: 14); and
a CDR3 (according to Abm) that is the amino acid sequence EXSGISGWDY (SEQ ID NO: 12; wherein X is M or P);

and has:
a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:
no more than 7, such as no more than 5, preferably no more than 3, such as only 3, 2 or 1 "amino acid differences" (as defined herein, and not taking into account any of the above-listed mutations at position(s) 1, 11, 14, 45, 74, 83 89, 96, 108, 110 and/or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs);

and when present at the C-terminal end of the polypeptide of the invention preferably has:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the PD1/CTLA4 binder of the invention preferably has a D at position 1 (i.e. an E1D mutation compared to SEQ ID NO: 9), such that said CTLA4 binding moiety comprises one or more of the following amino acid residues (i.e. mutations compared to the amino acid sequence of SEQ ID NO: 9) at the positions mentioned (numbering according to Kabat):
1E or 1D;
11V;
14P;
45R;
74S;
83R;
89L or 89T;
96P; or
108L;

for example, wherein the CTLA4 binding moiety comprises one or more of the following sets of mutations:
89L in combination with 11V;
89L in combination with 110K or 110Q;
89L in combination with 112K or 112Q;
89L in combination with 11V and 110K or 110Q;
89L in combination with 11V and 112K or 112Q;
1E in combination with 11V; 14P; 45R; 74S; 83R; 89L; 96P; and 108L;

1D in combination with 11V; 14P; 45R; 74S; 83R; 89L; 96P; and 108L;
1E in combination with 11V; 14P; 45R; 74S; 83R; 89L; 96P; 108L and 110K or 110Q;
1D in combination with 11V; 14P; 45R; 74S; 83R; 89L; 96P; 108L and 110K or 110Q;
1E in combination with 11V; 14P; 45R; 74S; 83R; 89L; 96P; 108 L and 112K or 112Q;
1D in combination with 11V; 14P; 45R; 74S; 83R; 89L; 96P; 108L and 112K or 112Q;
11V in combination with 110K or 110Q; or
11V in combination with 112K or 112Q.

As mentioned, when a CTLA4 moiety (e.g. an ISVD such as a Nanobody) that is present in the PD1/CTLA4 binders of the invention is used in a monovalent format and/or is present at the C-terminal end of a polypeptide of the invention (as defined herein), the CTLA4 binder (and consequently, the resulting polypeptide of the invention) preferably has a C-terminal extension X(n), which C-terminal extension may be as described herein for the CTLA4 binder(s) present in the polypeptides of the invention and/or as described in WO 2012/175741 or PCT/EP2015/060643 (WO2015/173325).

As mentioned, in the invention, CTLA4 moiety in which position 89 is T or in which position 11 is V and position 89 is L (optionally in suitable combination with a 110K or 110Q mutation and/or a 112K or 112Q mutation, and in particular in combination with a 110K or 110Q mutation) are preferred. Also preferred are CTLA4 binders in which position 11 is V and position 89 is L, optionally with a 110K or 110Q mutation; or in which position 1 is D or E, position 11 is V; position 14 is P; position 45 is R; position 74 is S; position 83 is R; position 89 is L; position 96 is P and position 108 is L.

Thus, in one preferred aspect, a CTLA4 moiety (e.g. an ISVD such as a Nanobody) that is present in the PD1/CTLA4 binders of the invention has:
  a CDR1 (according to Abm) that is the amino acid sequence GGTFSFYGMG (SEQ ID NO: 13); and
  a CDR2 (according to Abm) that is the amino acid sequence DIRTSAGRTY (SEQ ID NO: 14); and
  a CDR3 (according to Abm) that is the amino acid sequence EXSGISGWDY (SEQ ID NO: 12; wherein X is M or P);
and has:
  a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);
and/or has:
  no more than 7, such as no more than 5, preferably no more than 3, such as only 3, 2 or 1 "amino acid differences" (as defined herein, and not taking into account any of the above-listed mutations at position(s) 1, 11, 14, 45, 74, 83 89, 96, 108, 110 and/or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs);
and when present at the C-terminal end of the PD1/CTLA4 binder of the invention preferably has:
  a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
and when present at the N-terminal end of the PD1/CTLA4 binder of the invention preferably has a D at position 1 (i.e. an E1D mutation compared to SEQ ID NO: 9),
in which
  the amino acid residue at position 1 of the CTLA4 binding moiety is chosen from E and D;
  the amino acid residue at position 11 of the CTLA4 binding moiety is chosen from L and V;
  the amino acid residue at position 14 of the CTLA4 binding moiety is chosen from A and P;
  the amino acid residue at position 45 of the CTLA4 binding moiety is chosen from Q and R;
  the amino acid residue at position 74 of the CTLA4 binding moiety is chosen from A and S;
  the amino acid residue at position 83 of the CTLA4 binding moiety is chosen from K and R;
  the amino acid residue at position 89 of the CTLA4 binding moiety is chosen from T, V and L;
  the amino acid residue at position 96 of the CTLA4 binding moiety is chosen from M and P;
  the amino acid residue at position 108 of the CTLA4 binding moiety is chosen from Q and L;
  the amino acid residue at position 110 of the CTLA4 binding moiety is chosen from T, K and Q (and is preferably T); and
  the amino acid residue at position 112 of the CTLA4 binding moiety is chosen from S, K and Q (and is preferably S).

In another preferred aspect, a CTLA4 binding moiety (e.g. an ISVD such as a Nanobody) that is present in a PD1/CTLA4 binder of the invention has:
  a CDR1 (according to Abm) that is the amino acid sequence GGTFSFYGMG (SEQ ID NO: 13); and
  a CDR2 (according to Abm) that is the amino acid sequence DIRTSAGRTY (SEQ ID NO: 14); and
  a CDR3 (according to Abm) that is the amino acid sequence EXSGISGWDY (SEQ ID NO: 12; wherein X is M or P);
and has:
  a degree of sequence identity with the amino acid sequence of SEQ ID NO: 9 (in which the CDRs, any C-terminal extension that may be present, as well as the mutations at positions 1, 11, 14, 45, 74, 83 89, 96, 108, 110 and/or 112 required by the specific aspect involved, are not taken into account for determining the degree of sequence identity) of at least 85%, preferably at least 90%, more preferably at least 95% when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or has:

no more than 7, such as no more than 5, preferably no more than 3, such as only 3, 2 or 1 "amino acid differences" (as defined herein, and not taking into account any of the above-listed mutations at position(s) 1, 11, 14, 45, 74, 83 89, 96, 108, 110 and/or 112 that may be present and not taking into account any C-terminal extension that may be present) with the amino acid sequence of SEQ ID NO: 9 (in which said amino acid differences, if present, may be present in the frameworks and/or the CDRs but are preferably present only in the frameworks and not in the CDRs);

and when present at the C-terminal end of the PD1/CTLA4 binder of the invention preferably has:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and when present at the N-terminal end of the polypeptide of the invention preferably has a D at position 1 (i.e. an E1D mutation compared to SEQ ID NO: 9), in which one or more of the following is true:

the amino acid residue at position 1 of the CTLA4 binding moiety is E or D;

the amino acid residue at position 11 of the CTLA4 binding moiety is V;

the amino acid residue at position 14 of the CTLA4 binding moiety is P;

the amino acid residue at position 45 of the CTLA4 binding moiety is R;

the amino acid residue at position 74 of the CTLA4 binding moiety is S;

the amino acid residue at position 83 of the CTLA4 binding moiety is R;

the amino acid residue at position 89 of the CTLA4 binding moiety is L;

the amino acid residue at position 96 of the CTLA4 binding moiety is P;

the amino acid residue at position 108 of the CTLA4 binding moiety is L;

the amino acid residue at position 110 of the CTLA4 binding moiety is preferably chosen from T, K and Q; or the amino acid residue at position 112 of the CTLA4 binding moiety is preferably chosen from S, K and Q.

In one specific, but non-limiting aspect, the CTLA4 binding moieties (e.g. ISVDs such as Nanobodies) present in the PD1/CTLA4 binders of the invention (e.g., comprising ISVDs (e.g., Nanobodies) that bind to PD1 and CTLA4) comprise the following sets of mutations (i.e. mutations compared to the sequence of SEQ ID NO: 9) at the positions mentioned (numbering according to Kabat):

11V in combination with 89L;
11V in combination with 1D, 14P, 45R, 74S, 83R, 89L, 96P and 108L;
11V in combination with 1E, 14P, 45R, 74S, 83R, 89L, 96P and 108L;
11V in combination with 110K or 110Q;
11V in combination with 112K or 112Q;
11V in combination with 1D, 14P, 45R, 74S, 83R, 89L, 96P, 108L and 110K or 110Q;
11V in combination with 1E, 14P, 45R, 74S, 83R, 89L, 96P, 108L and 110K or 110Q;
11V in combination with 1D, 14P, 45R, 74S, 83R, 89L, 96P, 108L and 112K or 112Q;
11V in combination with 1E, 14P, 45R, 74S, 83R, 89L, 96P, 108L and 112K or 112Q;
11V in combination with 89L and 110K or 110Q; or
11V in combination with 89L and 112K or 112Q;

and have CDRs such as those set forth in SEQ ID NO: 9 or 48-83 or 143 (e.g., according to Abm) and have an overall degree of sequence identity with the amino acid sequence of SEQ ID NO: 9 that are as described herein.

In another specific, but non-limiting aspect, the CTLA4 binding moieties (e.g. ISVDs such as Nanobodies) present in the PD1/CTLA4 binders of the invention comprise the following sets of mutations (i.e. mutations compared to the sequence of SEQ ID NO: 9) at the positions mentioned (numbering according to Kabat):

89L in combination with 11V;
89L in combination with 1D, 11V, 14P, 45R, 74S, 83R, 96P and 108L;
89L in combination with 1E, 11V, 14P, 45R, 74S, 83R, 96P and 108L;
89L in combination with 110K or 110Q;
89L in combination with 112K or 112Q;
89L in combination with 1D, 11V, 14P, 45R, 74S, 83R, 96P, 108L and 110K or 110Q;
89L in combination with 1E, 11V, 14P, 45R, 74S, 83R, 96P, 108L and 110K or 110Q;
89L in combination with 1D, 11V, 14P, 45R, 74S, 83R, 96P, 108L and 112K or 112Q;
89L in combination with 1E, 11V, 14P, 45R, 74S, 83R, 96P, 108L and 112K or 112Q;
89L in combination with 11V and 110K or 110Q; or
89L in combination with 11V and 112K or 112Q;

and have CDRs such as those set forth in SEQ ID NO: 9 or 48-83 or 143 (e.g., according to Abm) and have an overall degree of sequence identity with the amino acid sequence of SEQ ID NO: 9 that are as described herein.

In another specific, but non-limiting aspect, the CTLA4 binding moieties (e.g. ISVDs such as Nanobodies) present in the PD1/CTLA4 binders of the invention comprise the following sets of mutations (i.e. mutations compared to the sequence of SEQ ID NO: 9) at the positions mentioned (numbering according to Kabat):

110K or 110Q in combination with 11V;
110K or 110Q in combination with 1D, 11V, 14P, 45R, 74S, 83R, 89L 96P and 108L;
110K or 110Q in combination with 1E, 11V, 14P, 45R, 74S, 83R, 89L 96P and 108L;
110K or 110Q in combination with 89L; or
110K or 110Q in combination with 11V and 89L;

and have CDRs such as those set forth in SEQ ID NO: 9 or 48-83 or 143 (e.g., according to Abm) and have an overall degree of sequence identity with the amino acid sequence of SEQ ID NO: 9 that are as described herein.

In another specific, but non-limiting aspect, the CTLA4 binding moieties (e.g. ISVDs such as Nanobodies) present in the PD1/CTLA4 binders of the invention comprise the following sets of mutations (i.e. mutations compared to the sequence of SEQ ID NO: 9) at the positions mentioned (numbering according to Kabat):

112K or 112Q in combination with 11V;
112K or 112Q in combination with 1D, 11V, 14P, 45R, 74S, 83R, 89L 96P and 108L;
112K or 112Q in combination with 1E, 11V, 14P, 45R, 74S, 83R, 89L 96P and 108L;
112K or 112Q in combination with 89L; or
112K or 112Q in combination with 11V and 89L;

and have CDRs such as those set forth in SEQ ID NO: 9 or 48-83 or 143 (e.g., according to Abm) and have an overall degree of sequence identity with the amino acid sequence of SEQ ID NO: 9 that are as described herein.

In another aspect, the CTLA4 binding moieties (e.g. ISVDs such as Nanobodies) present in the PD1/CTLA4 binders of the invention comprise a T or L at position 89 (e.g., 1D or 1E, 11V, 14P, 45R, 74S, 83R, 89L 96P and 108L) and have CDRs such as those set forth in SEQ ID NO: 9 or 48-83 or 143 (e.g., according to Abm) and have an overall degree of sequence identity with the amino acid sequence of SEQ ID NO: 9 that are as described herein.

In another aspect, the CTLA4 binding moieties (e.g. ISVDs such as Nanobodies) present in the PD1/CTLA4 binders of the invention comprise a V at position 11 and an L at position 89 (e.g., 1D or 1E, 11V, 14P, 45R, 74S, 83R, 89L 96P and 108L) and have CDRs such as those set forth in SEQ ID NO: 9 or 48-83 or 143 (e.g., according to Abm) and have an overall degree of sequence identity with the amino acid sequence of SEQ ID NO: 9 that are as described herein.

As mentioned, the CTLA4 binding moieties present in the PD1/CTLA4 binders of the invention according to the aspects described herein are preferably such that they contain a suitable combination of an optional E1D mutation, an L11V mutation, A14P mutation, a Q45R mutation, an A74S mutation, a K83R mutation, a V89L mutation, an M96P mutation and a Q108L mutation, and preferably a suitable combination of Q108L with any one of the other A14P, Q45R, A74S and K83R mutations, and preferably in combination with any two of these other mutations, more preferably with any three of these mutations (such as with the combination A14P, A74S and K83R), such as with all four of these mutations (and again, when the CTLA4 binding moieties is monovalent or present at the N-terminal end of a compound or polypeptide of the invention, preferably also an E1D mutation) (relative to the amino acid sequence of SEQ ID NO: 9). Also, the methionine residue at position 96 (Kabat numbering) may be replaced by another naturally occurring amino acid residue such as Pro (except Cys, Asp or Asn).

Some preferred but non-limiting examples of CTLA4 binding moieties (e.g. ISVDs such as Nanobodies) that can be present in the PD1/CTLA4 binders of the invention are given in SEQ ID NOs: 50 to 83 and 143, and PD1/CTLA4 binders of the invention that suitably comprise one or more of these sequences form further aspects of the invention.

Examples of CTLA4 binding moieties (e.g. ISVDs such as Nanobodies) that can be present in the PD1/CTLA4 binders of the invention are the sequences of SEQ ID NOs: 62 to 65 and 80 to 83 and 143. Of these, SEQ ID NOs: 64 and 65 are particularly suited to be present at the N-terminal end of a PD1/CTLA4 binders of the invention, and SEQ ID NOs:80 and 81 is particularly suited to be present at the C-terminal end of a PD1/CTLA4 binders of the invention.

When a CTLA4 binding moiety (e.g. an ISVD such as a Nanobody) is present at and/or form the C-terminal end of the PD1/CTLA4 binder in which they are present (or when they otherwise have an "exposed" C-terminal end in such PD1/CTLA4 binder by which is generally meant that the C-terminal end of the ISVD is not associated with or linked to a constant domain (such as a CH1 domain); reference is again made to WO 2012/175741 and PCT/EP2015/60643 (WO2015173325)), preferably also have a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting examples of such C-terminal extensions $X_{(n)}$, X and n can be as further described herein for the PD1/CTLA4 binders of the invention. (e.g., comprising ISVDs (e.g., Nanobodies) that bind to PD1 and CTLA4).

When the CTLA4 binding moieties (e.g. ISVDs such as Nanobodies) present in the PD1/CTLA4 binders of the invention contain mutations at positions 110 or 112 (optionally in combination with mutations at position 11 and/or 89 as described herein) (relative to the amino acid sequence of SEQ ID NO: 9), the 5 C-terminal amino acid residues of framework 4 (starting from position 109) can be substituted as follows:
  (i) if no C-terminal extension is present: VTVKS (SEQ ID NO:88), VTVQS (SEQ ID NO:89), VKVSS (SEQ ID NO: 90) or VQVSS (SEQ ID NO: 91); or
  (ii) if a C-terminal extension is present: VTVKSX$_{(n)}$ (SEQ ID NO: 92), VTVQSX(n) (SEQ ID NO: 93), VKVSSX(n) (SEQ ID NO: 94) or VQVSSX$_{(n)}$ (SEQ ID NO: 95), such as VTVKSA (SEQ ID NO: 96), VTVQSA (SEQ ID NO: 97), VKVSSA (SEQ ID NO: 98) or VQVSSA (SEQ ID NO: 99).

When the CTLA4 binding moieties (e.g. ISVDs such as Nanobodies) present in the PD1/CTLA4 binders of the invention do not contain mutations at positions 110 or 112 (but only mutations at position 1, 11, 14, 45, 74, 83, 89, 96 and/or 108 as described herein), the C-terminal amino acid residues of framework 4 (starting from position 109) will usually be either:
  (i) when no C-terminal extension is present: VTVSS (SEQ ID NO:100) (as in the sequence of SEQ ID NO:2); or
  (ii) when a C-terminal extension is present: VTVSSX$_{(n)}$ (SEQ ID NO:101) such as VTVSSA (SEQ ID NO:102).
  In these C-terminal sequences, X and n are as defined herein for the C-terminal extensions.

PD1/CTLA4 Binders

As further described herein, the PD1/CTLA4 binders provided by the invention (e.g., comprising ISVDs (e.g., Nanobodies) that bind to PD1 and CTLA4) comprise at least one (such as one or two) PD1 binding moiety as described herein and at least one (such as one or two) CTLA4 binding moiety as described herein and, optionally, a half-life extender such as an ISVD that binds to a serum protein such as a serum albumin, e.g., human serum albumin (HSA), e.g., ALB11002. The present invention provides the PD1/CTLA4 binders F023700910, F023700918, F023700920 and F023700925 as set forth herein.

The present invention aims to provide improved PD1/CTLA4 binders, in particular improved PD1/CTLA4 bispecific ISVDs and more in particular improved PD1/CTLA4 bispecific Nanobodies. The PD1/CTLA4 binders of the present invention include those including CTLA4 binding moieties which include polypeptides which are variants of polypeptides comprising the amino acid sequence of SEQ ID NO: 9 which is mutated at position 11, 14, 45, 74, 83, 89, 96, 108, 110 and/or 112 (e.g., SEQ ID NO: 143); and PD1 binding moieties which include polypeptides which are variants of polypeptides comprising the amino acid sequence of SEQ ID NO: 1 or 2 which is mutated at position 1, 11, 14, 52a, 73, 74, 83, 89, 100a, 110 and/or 112 (e.g., SEQ ID NO: 135, 136, 137, 138, 139, 140, 141 or 142). In an embodiment of the invention, the PD1/CTLA4 binders comprise the amino acid sequences set forth in SEQ ID NOs: 103-134, 146, 149, 151 or 153.

In particular, both the PD1 binder(s) present in the polypeptides of the invention as well as the CTLA4 binder(s) present in the polypeptides of the invention will comprise (a combination of mutations at positions 11, 89, 110 and/or 112 that are as further described herein (using Kabat numbering).

The PD1/CTLA4 binders (e.g., comprising ISVDs (e.g., Nanobodies) that bind to PD1 and CTLA4) of the invention, in an embodiment of the invention, also comprise a C-terminal extension X(n) as further described herein. As described in WO 2012/175741 (but also for example in WO 2013/024059 and PCT/EP2015/060643 (WO2015/173325)), a C-terminal alanine extension can prevent the binding of so-called "pre-existing antibodies" (assumed to be IgGs) to a putative epitope that is situated at the C-terminal region of the PD1/CTLA4 binders (e.g., ISVD, e.g., Nanobody). This epitope is assumed to include, among other residues, the surface-exposed amino acid residues of the C-terminal sequence VTVSS (SEQ ID NO: 100) as well as the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as position 107).

However, although the presence of such a C-terminal alanine (or a C-terminal extension generally) can greatly reduce (and in some cases essentially fully prevent) the binding of the "pre-existing antibodies" that can be found in the sera from a range of subjects (both healthy subjects as patients), it has been found that the sera from some subjects (such as the sera from patients with some immune diseases such as SLE) can contain pre-existing antibodies that can bind to the C-terminal region of an ISVD (when such region is exposed) even when the ISVD contains such a C-terminal alanine (or more generally, such C-terminal extension). Reference is again made to the co-pending non-prepublished PCT application PCT/EP2015/060643 (WO2015/173325) by Assignee filed on May 13, 2015 and entitled "Improved immunoglobulin variable domains".

Accordingly, one specific objective of the invention is to provide PD1/CTLA4 binders (e.g., comprising ISVDs (e.g., Nanobodies) that bind to PD1 and CTLA4) that have low (or reduced) binding by so-called "pre-existing antibodies", and in particular of the kind described in PCT/EP2015/060643 (WO2015/173325) (for example, those pre-existing antibodies that can bind to an exposed C-terminal region of an ISV even in the presence of a C-terminal extension).

According to the invention, this objective is achieved by:
(i) the presence, in the PD1/CTLA4 binders of the invention (e.g., comprising ISVDs (e.g., Nanobodies) that bind to PD1 and CTLA4), of a C-terminal extension X(n); in combination with
(ii) the presence, in one or more and preferably all of the PD1/CTLA4 binders of the invention (e.g., comprising ISVDs (e.g., Nanobodies) that bind to PD1 and CTLA4), of certain amino acid residues/mutations at positions 11, 89, 110 and/or 112 (relative to SEQ ID NOs: 1, 2 and 9 set forth above) of the PD1/CTLA4 binders, which residues/mutations are as further described herein. Preferably, said mutations are present in at least the C-terminal PD1 or CTLA4 binding moiety of the PD1/CTLA4 binders of the invention, and more preferably in all of the binding moieties present in the PD1/CTLA4 binders of the invention, i.e., in the PD1 binding moieties and in the CTLA4 binding moieties and also in the serum albumin binding moiety (if present).

Table C lists some preferred but non-limiting possible combinations of the amino acid residues that can be present at positions 11, 89, 110 and 112 of the PD1/CTLA4 binders (e.g., comprising ISVDs (e.g., Nanobodies) that bind to PD1 and CTLA4) that are present in the polypeptides of the invention.

TABLE C

Possible Combinations of Mutations at Amino Acid Positions 11, 89, 110 and 112 in PD1 and CTLA4 Binding Moieties of SEQ ID NOs: 1, 2 and/or 9.

| | POSITION | | | | | POSITION | | | |
|---|---|---|---|---|---|---|---|---|---|
| | 11 | 89 | 110 | 112 | | 11 | 89 | 110 | 112 |
| COM-BINA-TION | L | T | T | S | COM-BINA-TION | V | T | T | S |
| | L | T | T | K | | V | T | T | K |
| | L | T | T | Q | | V | T | T | Q |
| | L | T | K | S | | V | T | K | S |
| | L | T | Q | S | | V | T | Q | S |
| | L | V(*) | T | K | | V | V(*) | T | K |
| | L | V(*) | T | Q | | V | V(*) | T | Q |
| | L | V(*) | K | S | | V | V(*) | K | S |
| | L | V(*) | Q | S | | V | V(*) | Q | S |
| | | | | | | V | L | T | S |
| | L | L | T | K | | V | L | T | K |
| | L | L | T | Q | | V | L | T | Q |
| | L | L | K | S | | V | L | K | S |
| | L | L | Q | S | | V | L | Q | S |

(*)Note:
in the PD1 binders, the amino acid residue at position 89 can also be an I instead of a V.

In an embodiment of the invention, the binding moiety that binds to PD1 and/or CTLA4 comprises 1, 2, 3, 4, 5, 6, 7, 8, 9 or 10 or more additional mutations, e.g., each independently chosen from substitutions, insertions and deletions.

The C-terminal extension present in the PD1/CTLA4 binders of invention (e.g., comprising ISVDs (e.g., Nanobodies) that bind to PD1 and CTLA4) may be as described in WO 2012/175741 and PCT/EP2015/60643 (WO2015/173325), and preferably is of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting examples of such C-terminal extensions $X_{(n)}$, X and n can be as follows:
(a) n=1 and X=Ala;
(b) n=2 and each X=Ala;
(c) n=3 and each X=Ala;
(d) n=2 and at least one X=Ala (with the remaining amino acid residue(s) X being independently chosen from any naturally occurring amino acid but preferably being independently chosen from Val, Leu and/or Ile);

(e) n=3 and at least one X=Ala (with the remaining amino acid residue(s) X being independently chosen from any naturally occurring amino acid but preferably being independently chosen from Val, Leu and/or Ile);
(f) n=3 and at least two X=Ala (with the remaining amino acid residue(s) X being independently chosen from any naturally occurring amino acid but preferably being independently chosen from Val, Leu and/or Ile);
(g) n=1 and X=Gly;
(h) n=2 and each X=Gly;
(i) n=3 and each X=Gly;
(j) n=2 and at least one X=Gly (with the remaining amino acid residue(s) X being independently chosen from any naturally occurring amino acid but preferably being independently chosen from Val, Leu and/or Ile);
(k) n=3 and at least one X=Gly (with the remaining amino acid residue(s) X being independently chosen from any naturally occurring amino acid but preferably being independently chosen from Val, Leu and/or Ile);
(l) n=3 and at least two X=Gly (with the remaining amino acid residue(s) X being independently chosen from any naturally occurring amino acid but preferably being independently chosen from Val, Leu and/or Ile);
(m) n=2 and each X=Ala or Gly;
(n) n=3 and each X=Ala or Gly;
(o) n=3 and at least one X=Ala or Gly (with the remaining amino acid residue(s) X being independently chosen from any naturally occurring amino acid but preferably being independently chosen from Val, Leu and/or Ile); or
(p) n=3 and at least two X=Ala or Gly (with the remaining amino acid residue(s) X being independently chosen from any naturally occurring amino acid but preferably being independently chosen from Val, Leu and/or Ile);

with aspects (a), (b), (c), (g), (h), (i), (m) and (n) being preferred, with aspects in which n=1 or 2 being preferred and aspects in which n=1 being preferred.

It should also be noted that, preferably, any C-terminal extension present in a PD1/CTLA4 binders of the invention (e.g., comprising ISVDs (e.g., Nanobodies) that bind to PD1 and CTLA4) does not contain a (free) cysteine residue (unless said cysteine residue is used or intended for further functionalization, for example for PEGylation).

Some specific, but non-limiting examples of useful C-terminal extensions are the following amino acid sequences: A, AA, AAA, G, GG, GGG, AG, GA, AAG, AGG, AGA, GGA, GAA or GAG.

The PD1/CTLA4 binders of the invention (e.g., comprising ISVDs (e.g., Nanobodies) that bind to PD1 and CTLA4) also, in an embodiment of the invention, comprise an aspartic acid residue (D) at position 1 (i.e., the first amino acid residue at the N-terminal end of the polypeptide is preferably D).

In an embodiment of the invention, a half-life extender is an ISVD (e.g., a Nanobody) that binds to a serum protein such as serum albumin, e.g., human serum albumin (HSA). In particular, such a serum albumin binding ISVD or Nanobody may be a (single) domain antibody or dAb against human serum albumin as described in for example EP 2 139 918, WO 2011/006915, WO 2012/175400, WO 2014/111550 and may in particular be a serum albumin binding Nanobody as described in WO 2004/041865, WO 2006/122787, WO 2012/175400 or PCT/EP2015/060643 (WO2015/173325). Preferred serum albumin binding ISVDs are the Nanobody Alb-1 (see WO 2006/122787) or its humanized variants such as Alb-8 (WO 2006/122787, SEQ ID NO:62), Alb-23 (WO 2012/175400, SEQ ID NO:1) and other humanized (and preferably also sequence-optimized) variants of Alb-1 and/or variants of Alb-8 or Alb-23 (or more generally ISVDs that have essentially the same CDRs as Alb-1, Alb-8 and Alb-23). The amino acid sequences of some preferred but non-limiting serum albumin binders that can be present in the PD1/CTLA4 binders of the invention are given in FIG. 5 as SEQ ID NOs: 84 and 85. In an embodiment of the invention, the HSA binding ISVD is ALB11002.

Such a serum albumin binding ISVD, when present, may contain within its sequence one or more framework mutations that reduce binding by pre-existing antibodies. In particular, when such a serum albumin binding ISVD is a Nanobody or a (single) domain antibody that is, essentially consist of and/or is derived from a VH domain, the serum albumin binding ISVD may contain (a suitable combination of) amino acid residues/mutations at positions 11, 89, 110 and/or 112 that are as described in PCT/EP2015/060643 (WO2015/173325) and/or that essentially are as described herein for the CTLA4 and PD1 binding moieties present in the PD1/CTLA4 binders of the invention (e.g., comprising ISVDs (e.g., Nanobodies) that bind to PD1 and CTLA4). For example, PCT/EP2015/060643 (WO2015/173325) describes a number of variants of Alb-1, Alb-8 and Alb-23 that contain amino acid residues/mutations at positions 11, 89, 110 and/or 112 that reduce binding by pre-existing antibodies that can be used in the compounds of the invention.

When such a serum albumin binding ISVD is present at the C-terminal end of a PD1/CTLA4 binder of the invention (e.g., comprising ISVDs (e.g., Nanobodies) that bind to PD1 and CTLA4), the serum albumin binding ISVD (and as a result, the compound of the invention), in an embodiment of the invention, has a C-terminal extension X(n), which C-terminal extension may be as described herein for the PD1 or CTLA4 binding moieties present in the PD1/CTLA4 binders of the invention and/or as described in WO 2012/175741 or PCT/EP2015/060643 (WO2015/173325). It also, in an embodiment of the invention, has mutations that reduce the binding of pre-existing antibodies, like (a suitable combination of) the amino acid residues/mutations at positions 11, 89, 110 and/or 112 described in PCT/EP2015/060643 (WO2015/173325).

Although the presence/use of a serum albumin binding ISVD is the preferred way of providing the PD1/CTLA4 binders of the invention (e.g., comprising ISVDs (e.g., Nanobodies) that bind to PD1 and CTLA4) with an increased half-life, other means of increasing the half-life of a PD1/CTLA4 binder of the invention, such as the use of other binding domains binding to serum albumin, the use of ISVDs binding to other serum proteins such as transferrin or IgG, PEGylation, fusion to human albumin (e.g., HSA) or a suitable fragment thereof, or the use of a suitable serum albumin-binding peptide are also included in the scope of the invention.

Thus, in a further aspect, the invention relates to PD1/CTLA4 binders (e.g., comprising ISVDs (e.g., Nanobodies) that bind to PD1 and CTLA4) that comprise at least one (such as one or two) PD1 binding moieties as described herein and at least one (such as one or two) CTLA4 binding moieties as described herein, and, optionally, one or more (such as one or two) half-life extenders, such as one or two ISVDs that bind to a serum protein such as serum albumin, e.g., HSA (e.g., ALB11002), wherein said PD1/CTLA4 binder has a half-life (as defined herein) in human subjects of at least 1 day, preferably at least 3 days, more preferably at least 7 days, such as at least 10 days.

As mentioned, the PD1/CTLA4 binders of the invention (e.g., comprising ISVDs (e.g., Nanobodies) that bind to PD1 and CTLA4) preferably also have an increased half-life (as defined herein), by which is generally meant that the polypeptide has a half-life (as defined herein) that is at least 2 times, preferably at least 5 times, for example at least 10 times or more than 20 times, greater than the half-life of the monovalent PD1 binder that is present in the polypeptide of the invention as well as a half-life (as defined herein) that is at least 2 times, preferably at least 5 times, for example at least 10 times or more than 20 times, greater than the half-life of the monovalent CTLA4 binding moiety that is present in the PD1/CTLA4 binders of the invention (as measured in either in man and/or a suitable animal model, such as mouse or cynomolgus monkey).

In an embodiment of the invention, the half-life extender is an ISVD (e.g., Nanobody) that binds to human serum albumin, e.g., ALB11002 is summarized below in Table D or FIG. 5.

differences" with the amino acid sequence of SEQ ID NO: 84, 85 or 144 (in which said amino acid differences, if present, may be present in the frameworks and/or the CDRs but are preferably present only in the frameworks and not in the CDRs);

and optionally having:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I).

In the PD1/CTLA4 binders of the invention (e.g., comprising ISVDs (e.g., Nanobodies) that bind to PD1 and CTLA4), the PD1 binding moieties, CTLA4 binding moieties (and the serum albumin binding ISV, if present) can be directly linked to each other or via one or more suitable linkers. Some preferred but non-limiting linkers are a 9GS,

TABLE D

Human Serum Albumin (HSA) Binder ALB11002

| SEQ ID NO | Description | Sequence |
|---|---|---|
| 144 | ALB11002 | EVQLVESGGG XVQPGNSLRL SCAASGFTFS SFGMSWVRQA PGKGLEWVSS ISGSGSDTLY ADSVKGRFTI SRDNAKTTLY LQMNSLRPED TAXYYCTIGG SLSRSSQGTL VTVSSA; wherein X at residues 11 and 93 are L or V |
| 199 | CDR1 | GFTFSSFGMS (optionally, wherein residue 5 of the CDR is mutated from S to R) or SFGMS (amino acids 6-10 of SEQ ID NO: 199) |
| 200 | CDR2 | SISGSGSDTLYADSVKG or SISGSGSDTL (amino acids 1-10 of SEQ ID NO: 200) |
| 201 | CDR3 | GGSLSR |
| 84 | HSA binder | EVQLVESGGGLVQPGNSLRLSCAASGFTFSSFGMSWVRQAPGKGLEWVSSISGSG SDTLYADSVKGRFTISRDNAKTTLYLQMNSLRPEDTAV YYCTIGGSLSRSSQGTLVTVSS |
| 85 | HSA binder | EVQLLESGGGVVQPGGSLRLSCAASGFTFRSFGMSWVRQAPGKGPEWVSSIS GSGSDTLYADSVKGRFTISRDNSKNTLYLQMNSLRPEDTALYYCTIGGSLS RSSQGTLVTVSS |

* CDRs underscored and/or bold. Optionally, ALB11002 lacks the C-terminal Alanine. Optionally, the HSA binder comprises the amino acid sequence set forth in SEQ ID NO: 144 but which comprises 11L and/or an 93V, for example, EVQLVESGGGVVQPGGSLRLSCAASGFTFSSFGMSWVRQAPGKGLEWVSSISGSGSDTLY-ADSVKGRFTISRDNAKTT LYLQMNSLRPEDTALYYCTIGGSLSRSSQGTLVTVSS (SEQ ID NO: 144)

In an embodiment of the invention, the half-life extender is an HSA ISVD (e.g., a Nanobody) comprising:
a CDR1 that comprises the amino acid sequence GFTF-SSFGMS (SEQ ID NO: 199) or SFGMS (amino acids 6-10 of SEQ ID NO: 199); and
a CDR2 that comprises the amino acid sequence SISGSGSDTL (SEQ ID NO: 200) or SISGSGSDTL (amino acids 1-10 of SEQ ID NO: 200); and
a CDR3 that comprises the amino acid sequence GGSLSR (SEQ ID NO: 201);
and, optionally, having:
a degree of sequence identity with the amino acid sequence of SEQ ID NO: 84, 85 or 144 (in which any C-terminal extension that may be present as well as the CDRs are not taken into account for determining the degree of sequence identity) of at least 85%, preferably at least 90%, more preferably at least 95%;
and/or
no more than 7, such as no more than 5, preferably no more than 3, such as only 3, 2 or 1 "amino acid 15GS or 35GS linker (any combination of 9, 15 or 35 G and S amino acids such as, for example, GGGG SGGGGSGGGGSGGGGSGGGGSGGGGSGGGGS) (SEQ ID NO: 86). In an embodiment of the invention, the linker is $(GGGGS)_n$ (SEQ ID NO: 180), wherein n is 1, 2, 3, 4, 5, 6, 7, 8, 9 or 10.

The present invention includes the PD1/CTLA4 binders of the invention (e.g., comprising ISVDs (e.g., Nanobodies) that bind to PD1 and CTLA4) that can, besides the one or more PD1 binding moieties, the one or more CTLA4 binding moieties and the optional serum albumin binding ISVD (if present), contain one or more other amino acid sequences, chemical entities or moieties. These other amino acid sequences, chemical entities or moieties can confer one or more desired properties to the (resulting) PD1/CTLA4 binders of the invention and/or can alter the properties of the (resulting) PD1/CTLA4 binders of the invention in a desired manner, for example to provide the (resulting) PD1/CTLA4 binders of the invention with a desired biological and/or therapeutic activity (for example, to provide the resulting compound of the invention with affinity and preferably potency against another therapeutically relevant target than PD1 and CTLA4 such that the resulting compound becomes "trispecific" with respect to PD1, CTLA4 and that other therapeutically relevant target, to modify or improve pharmacokinetic and/or pharmacodynamic properties, to target the PD1/CTLA4 binder of the invention to specific cells, tissues or organs (including cancer cells and cancer tissues), to provide a cytotoxic effect and/or to serve as a detectable tag or label. Some non-limiting examples of such other amino acid sequences, chemical entities or moieties are:

- one or more binding domains or binding units that are directed against a therapeutically relevant target other than PD1 and CTLA4 (i.e. so as to provide a PD1/CTLA4 binder of the invention that is trispecific for PD1, CTLA4 and the other therapeutically relevant target, e.g., CD27, LAG3, BTLA, TIM3, ICOS, B7-H3, B7-H4, CD137, GITR, PD-L1, PD-L2, ILT1, ILT2 CEACAM1, CEACAM5, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17 or TSLP); and/or
- one or more binding domains or binding units that target the PD1/CTLA4 binders of the invention to a desired cell, tissue or organ (such as a cancer cell); and/or
- one or more binding domains or binding units that provide for increased specificity against PD1 (usually, these will be able to bind to PD1 but will generally by themselves essentially not be functional against PD1); and/or
- one or more binding domains or binding units that provide for increased specificity against CTLA4 (usually, these will be able to bind to CTLA4 but will generally by themselves essentially not be functional against CTLA4); and/or
- a binding domain, binding unit or other chemical entity that allows for the PD1/CTLA4 binder of the invention to be internalized into a (desired) cell (for example, an internalizing anti-EGFR Nanobody as described in WO 2005/044858); and/or
- a payload such as a cytotoxic payload; and/or
- a detectable label or tag, such as a radiolabel or fluorescent label; and/or
- a tag that can help with immobilization, detection and/or purification of the PD1/CTLA4 binder of the invention, such as a HIS or FLAG3 tag; and/or
- a tag that can be functionalized, such as a C-terminal GGC or GGGC tag.

The scope of the invention includes that the PD1/CTLA4 binders of the invention (e.g., comprising ISVDs (e.g., Nanobodies) that bind to PD1 and CTLA4) can also contain one or more parts or fragments of a (preferably human) conventional antibody (such as an Fc part or a functional fragment thereof or one or more constant domains) and/or from a Camelid heavy-chain only antibody (such as one or more constant domains).

When the PD1/CTLA4 binders of the invention (e.g., comprising ISVDs (e.g., Nanobodies) that bind to PD1 and CTLA4) contain one or more further binding domains or binding units (e.g. as described in the previous paragraphs), these other binding domains or binding units preferably comprise one or more ISVDs, and more preferably are all ISVDs. For example and without limitation, these one or more further binding domains or binding units can be one or more Nanobodies (including a VHH, a humanized VHH and/or a camelized VHs such as camelized human VHs), a (single domain) antibody is a VH domain or that is derived from a VH domain, a dAb that is or essentially consists of a VH domain or that is derived from a VH domain, or even a (single) domain antibody or a dAb that is or essentially consists of VL domain. In particular, these one or more binding domains or binding units, when present, may comprise one or more Nanobodies, and more in particular are all Nanobodies.

When a PD1/CTLA4 binder of the invention has an ISVD at its C-terminal end (which C-terminal binding moiety (e.g., ISVD such as a Nanobody) may be a PD1 binding moiety, a CTLA4 binding moiety, a human serum albumin binding moiety (e.g., an ISVD such as a Nanobody, e.g., ABL1002) or another ISVD as referred to in the previous paragraphs), then the PD1/CTLA4 binder of the invention (i.e., said C-terminal ISVD) preferably has a C-terminal extension X(n) as described herein.

When a PD1/CTLA4 binder of the invention (e.g., comprising ISVDs (e.g., Nanobodies) that bind to PD1 and CTLA4) contains, in addition to the one or more PD1 binding moieties, the one or more CTLA4 binding moieties and the serum albumin binding binding moiety (e.g., ISVD such as a Nanobody) (if present) any further binding moiety (e.g., ISVDs) (as referred to in the previous paragraphs), and where such further ISVDs are Nanobodies or are ISVDs that are, that essentially consist of and/or that are derived from VH sequences, then according to a preferred aspect of the invention said one or more (and preferably all) of such ISVDs present in the PD1/CTLA4 binder of the invention will contain within their sequence one or more framework mutations that reduce binding by pre-existing antibodies. In particular, according to this aspect of the invention, such further ISVDs may contain (a suitable combination of) amino acid residues/mutations at positions 11, 89, 110 and/or 112 that are as described in PCT/EP2015/060643 (WO2015/173325) and/or that essentially are as described herein for the PD1 binding moieties and CTLA4 binding moieties. In one specific aspect, when the polypeptide of the invention has an ISVD at its C-terminal end (which C-terminal ISVD may be a PD1 binder, a CTLA4 binding moieties, a serum albumin binding moiety (e.g., ISVD) or another ISVD as referred to in the previous paragraphs), then at least said ISVD that is present at and/or forms the C-terminal has such framework mutations that reduce binding by pre-existing antibodies (and said C-terminal ISVD will preferably also have a C-terminal extension X(n) as described herein).

In another aspect, the invention relates to a PD1/CTLA4 binder (e.g., comprising ISVDs (e.g., Nanobodies) that bind to PD1 and CTLA4) that comprises at least one PD1 binding moiety (e.g., ISVD) and at least one CTLA4 binding moiety (e.g., ISVD) (which PD1/CTLA4 binder is as further described herein), in which the PD1 binding moiety (e.g., ISVD) is chosen from SEQ ID NOs: 16 to 47 and 135-142 and in which the CTLA4 binding moiety (e.g., ISVD) is chosen from SEQ ID NOs: 50 to 83, 143 and 196.

In another aspect, the invention relates to a PD1/CTLA4 binder (e.g., comprising ISVDs (e.g., Nanobodies) that bind to PD1 and CTLA4) that comprises at least one PD1 binding moiety (e.g., ISVD) and at least one CTLA4 binding moiety (e.g., ISVD) (which PD1/CTLA4 binder is as further described herein), in which the PD1 binding moiety (e.g., ISVD) is chosen from SEQ ID NOs: 30, 31, 46, 47 and 135 and in which the CTLA4 binding moiety (e.g., ISVD) is chosen from SEQ ID NOs: 62 to 65 and/or 80 to 83 and/or 143.

Again, all these PD1/CTLA4 binders (e.g., comprising ISVDs (e.g., Nanobodies) that bind to PD1 and CTLA4) preferably contain a C-terminal extension X(n) (as described herein) and a D at position 1, and as further described herein may contain a serum albumin binding moiety (e.g. ISVD).

It will be clear from the disclosure herein that PD1/CTLA4 binders of the invention (e.g., comprising ISVDs (e.g., Nanobodies) that bind to PD1 and CTLA4) comprise at least two binding moieties (e.g., ISVDs such as Nanobodies) (i.e. are at least bivalent) and are at least directed to PD1 and CTLA4 (i.e. are at least bispecific). The PD1/CTLA4 binders can further have different "formats", i.e., essentially be bivalent, trivalent or multivalent, can be bispecific, trispecific or multispecific, and can be biparatopic (as defined herein and in for example WO 2009/068625) with respect to PD1 and/or CTLA4. For example and without limitation, a PD1/CTLA4 binders of the invention can:

- essentially consist of one PD1 binding moiety (as described herein) and one CTLA binding moiety (as described herein);
- essentially consist of two PD1 binding moieties (as described herein) and one CTLA binding moiety (as described herein);
- essentially consist of one PD1 binding moiety (as described herein) and two CTLA binding moieties (as described herein);
- essentially consist of two PD1 binding moieties (as described herein) and two CTLA binding moieties (as described herein);
- essentially consist of one PD1 binding moiety (as described herein), one CTLA binding moiety (as described herein) and one binding moiety (e.g., ISVD) against human serum albumin (as described herein);
- essentially consist of two PD1 binding moieties (as described herein), one CTLA binding moiety (as described herein) and one ISVD binding moiety (e.g., ISVD) against human serum albumin (as described herein);
- essentially consist of one PD1 binding moiety (as described herein), two CTLA binding moieties (as described herein) and one binding moiety (e.g., ISVD) against human serum albumin (as described herein);
- essentially consist of two PD1 binding moieties (as described herein), two CTLA binding moieties (as described herein) and one binding moiety (e.g., ISVD) against human serum albumin (as described herein);
- essentially consist of one PD1 binding moiety (as described herein), one CTLA binding moiety (as described herein) and one further binding moiety (e.g., ISVD) against PD1 (which may or may not be functional with respect to PD1);
- essentially consist of one PD1 binding moiety (as described herein), one CTLA binding moiety (as described herein) and one further binding moiety (e.g., ISVD) against CTLA4 (which may or may not be functional with respect to CTLA4);
- essentially consist of one PD1 binding moiety (as described herein), one CTLA binding moiety (as described herein), one further binding moiety (e.g., ISVD) against PD1 (which may or may not be functional with respect to PD1) and one binding moiety (e.g., ISVD) against human serum albumin (as described herein); or
- essentially consist of one PD1 binding moiety (as described herein), one CTLA binding moiety (as described herein), one further binding moiety (e.g., ISVD) against CTLA4 (which may or may not be functional with respect to CTLA4) and one binding moiety (e.g., ISVD) against human serum albumin (as described herein)

Other suitable formats for a PD1/CTLA4 binder of the invention (e.g., comprising ISVDs (e.g., Nanobodies) that bind to PD1 and CTLA4) will be clear to the skilled person based on the disclosure herein.

As will be clear to the skilled person, when a PD1/CTLA4 binder of the invention (e.g., comprising ISVDs (e.g., Nanobodies) that bind to PD1 and CTLA4) is intended for topical use (i.e. on the skin or in the eye) or is for example meant to have a (localized) therapeutic action somewhere in for example the GI tract (i.e., after oral administration or administration by suppository) or in the lungs (i.e. after administration by inhalation) or is otherwise meant to be directly applied to its intended place of action (for example, by direct injection), a PD1/CTLA4 binder of the invention will usually not require half-life extension. In these cases, the use of a bivalent bispecific PD1/CTLA4 binder of the invention or of another PD1/CTLA4 binder of the invention without half-life extension may be preferred.

Some preferred, but non-limiting examples of polypeptides of the invention without half-life extension are schematically represented in Table C-1 below, and each of these forms a further aspect of the invention. Other examples of suitable polypeptides of the invention without half-life extension will be clear to the skilled person based on the disclosure herein. Again, these polypeptides preferably have a D at position 1.

TABLE C-1

Schematic Representation of CTLA4/PD1 Binders of the Invention without a Half-Life Extending ISVD.

[PD1 binding moiety]-[CTLA4 binding moiety]
[PD1 binding moiety]-[CTLA4 binding moiety]-X(n)
[PD1 binding moiety]-[PD1 binding moiety]-[CTLA4 binding moiety]
[PD1 binding moiety]-[PD1 binding moiety]-[CTLA4 binding moiety]-X(n)
[PD1 binding moiety]-[CTLA4 binding moiety]-[PD1 binding moiety]
[PD1 binding moiety]-[CTLA4 binding moiety]-[PD1 binding moiety]-X(n)
[PD1 binding moiety]-[CTLA4 binding moiety]-[CTLA4 binding moiety]
[PD1 binding moiety]-[CTLA4 binding moiety]-[CTLA4 binding moiety]-X(n)
[CTLA4 binding moiety]-[PD1 binding moiety]
[CTLA4 binding moiety]-[PD1 binding moiety]-X(n)
[CTLA4 binding moiety]-[CTLA4 binding moiety]-[PD1 binding moiety]
[CTLA4 binding moiety]-[CTLA4 binding moiety]-[PD1 binder]-X(n)
[CTLA4 binding moiety]-[PD1 binding moiety]-[CTLA4 binding moiety]
[CTLA4 binding moiety]-[PD1 binding moiety]-[CTLA4 binding moiety]-X(n)
[CTLA4 binder]-[PD1 binding moiety]-[PD1 binding moiety]

TABLE C-1-continued

Schematic Representation of CTLA4/PD1 Binders of
the Invention without a Half-Life Extending ISVD.

[CTLA4 binding moiety]-[PD1 binder]-[PD1 binding moiety]-X(n)
[PD1 binding moiety]-[other PD1 binding moiety]-[CTLA4 binding moiety]
[PD1 binding moiety]-[other PD1 binding moiety]-[CTLA4 binding moiety]-X(n)
[PD1 binding moiety]-[CTLA4 binding moiety]-[other PD1 binding moiety]
[PD1 binding moiety]-[CTLA4 binding moiety]-[other PD1 binding moiety] -X(n)
[other PD1 binding moiety]-[PD1 binding moiety]-[CTLA4 binding moiety]
[other PD1 binding moiety]-[PD1 binding moiety]-[CTLA4 binding moiety]-X(n)
[other PD1 binding moiety]-[CTLA4 binding moiety]-[PD1 binding moiety]
[other PD1 binding moiety]-[CTLA4 binding moiety]-[PD1 binding moiety]-X(n)
[CTLA4 binding moiety]-[other CTLA4 binding moiety]-[PD1 binding moiety]
[CTLA4 binding moiety]-[other CTLA4 binding moiety]-[PD1 binding moiety]-X(n)
[CTLA4 binding moiety]-[PD1 binding moiety]-[other CTLA4 binding moiety]
[CTLA4 binding moiety]-[PD1 binding moiety]-[other CTLA4 binding moiety]-X(n)
[other CTLA4 binding moiety]-[CTLA4 binding moiety]-[PD1 binding moiety]
[other CTLA4 binding moiety]-[CTLA4 binding moiety]-[PD1 binding moiety]-X(n)
[other CTLA4 binding moiety]-[PD1 binding moiety]-[CTLA4 binding moiety]
[other CTLA4 binding moiety]-[PD1 binding moiety]-[CTLA4 binding moiety]-X(n)
[PD1 binding moiety]-[Targeting domain]-[CTLA4 binding moiety]
[PD1 binding moiety]-[Targeting domain]-[CTLA4 binding moiety]-X(n)
[PD1 binding moiety]-[CTLA4 binding moiety]-[Targeting domain]
[PD1 binding moiety]-[CTLA4 binding moiety]-[Targeting domain]-X(n)
[Targeting domain]-[PD1 binding moiety]-[CTLA4 binding moiety]
[Targeting domain]-[PD1 binding moiety]-[CTLA4 binding moiety]-X(n)
[Targeting domain]-[CTLA4 binding moiety]-[PD1 binding moiety]
[Targeting domain]-[CTLA4 binding moiety]-[PD1 binding moiety]-X(n)
[CTLA4 binding moiety]-[Targeting domain]-[PD1 binding moiety]
[CTLA4 binding moiety]-[Targeting domain]-[PD1 binding moiety]-X(n)
[CTLA4 binding moiety]-[PD1 binding moiety]-[Targeting domain]
[CTLA4 binding moiety]-[PD1 binding moiety]-[Targeting domain]-X(n)
[Targeting domain]-[CTLA4 binding moiety]-[PD1 binding moiety]
[Targeting domain]-[CTLA4 binding moiety]-[PD1 binding moiety]-X(n)
[Targeting domain]-[PD1 binding moiety]-[CTLA4 binding moiety]
[Targeting domain]-[PD1 binding moiety]-[CTLA4 binding moiety]-X(n)

Legend:
"[PD1 binding moiety]" = PD1 binding domain or unit (e.g., an ISVD such as a Nanobody), for example as set forth herein, e.g., any of SEQ ID NOs: 16-47 or 135-142.
"[CTLA4 binding moiety]" = CTLA4 binding domain or unit (e.g., an ISVD such as a Nanobody), for example as set forth herein, e.g., any of SEQ ID NOs: 48-83 or 143 or 196
"[other PD1 binding moiety]" = (functional or non-functional) binding unit or domain (e.g., ISVD such as a Nanobody) against PD1, e.g., other than the PD1 binding moiety as described herein
"[other CTLA4 binding moiety]" = (functional or non-functional) binding unit or domain (e.g., ISVD such as a Nanobody) against CTLA4, e.g., other than the CTLA4 binding moiety as described herein
"[targeting domain]" = binding domain or unit (such as an ISVD, e.g., a Nanobody) that targets the PD1/CTLA4 binder of the invention to a specific cell, tissue or organ
"-" = suitable linker (such as 9GS, 15GS or 35GS)

As will be clear to the skilled person, when a PD1/CTLA4 binder of the invention (e.g., comprising ISVDs (e.g., Nanobodies) that bind to PD1 and CTLA4) is intended for systemic administration and/or for prevention and/or treatment of a chronic disease or disorder, it will usually be preferred that said PD1/CTLA4 binder of the invention has increased half-life (as defined herein), i.e. compared to the CTLA4 and PD1 binding moieties present in such PD1/CTLA4 binder of the invention. More preferably, such a PD1/CTLA4 binder of the invention will contain a half-life extending binding moiety such as, preferably, an ISVD and in particular a Nanobody binding to human serum albumin (as described herein).

Some preferred, but non-limiting examples of such PD1/CTLA4 binders of the invention (e.g., comprising ISVDs (e.g., Nanobodies) that bind to PD1 and CTLA4) are schematically represented in Table C-2 below, and each of these forms a further aspect of the invention. Other examples of suitable PD1/CTLA4 binders of the invention with half-life extension will be clear to the skilled person based on the disclosure herein. Generally, for PD1/CTLA4 binder of the invention with half-life extension, the presence of a C-terminal extension is much preferred. Again, these polypeptides preferably have a D at position 1.

TABLE C-2

Schematic Representation of Some CTLA4/PD1 Binders
of the Invention with a Half-Life Extending Moiety.

[PD1 binding moiety]-[CTLA4 binding moiety]-[HLE]
[PD1 binding moiety]-[CTLA4 binding moiety]-[HLE]-X(n)
[PD1 binding moiety]-[HLE]-[CTLA4 binding moiety]
[PD1 binding moiety]-[HLE]-[CTLA4 binding moiety]-X(n)
[HLE]-[PD1 binding moiety-[CTLA4 binding moiety]
[HLE]-[PD1 binding moiety]-[CTLA4 binding moiety]-X(n)
[CTLA4 binding moiety]-[PD1 binding moiety]-[HLE]
[CTLA4 binding moiety]-[PD1 binding moiety]-[HLE]-X(n)
[CTLA4 binding moiety]-[HLE]-[PD1 binding moiety]
[CTLA4 binding moiety]-[HLE]-[PD1 binding moiety]-X(n)

TABLE C-2-continued

Schematic Representation of Some CTLA4/PD1 Binders
of the Invention with a Half-Life Extending Moiety.

[HLE]-[CTLA4 binding moiety]-[PD1 binding moiety]
[HLE]-[CTLA4 binding moiety]-[PD1 binding moiety]-X(n)
[PD1 binding moiety]-[PD1 binding moiety]-[CTLA4 binding moiety]-[HLE]-X(n)
[PD1 binding moiety]-[CTLA4 binding moiety]-[PD1 binding moiety]-[HLE]-X(n)
[PD1 binding moiety]-[CTLA4 binding moiety]-[CTLA4 binding moiety]-[HLE]-X(n)
[CTLA4 binding moiety]-[CTLA4 binding moiety]-[PD1binder]-[HLE]-X(n)
[CTLA4 binding moiety]-[PD1 binding moiety]-[CTLA4 binding moiety]-[HLE]-X(n)
[CTLA4 binding moiety]-[PD1binder]-[PD1 binding moiety]-[HLE]-X(n)
[PD1 binding moiety]-[other ISVD against PD1]-[CTLA4 binding moiety ]-[HLE]-X(n)
[PD1 binding moiety]-[PD1 binding moiety]-[CTLA4 binding moiety]-[CTLA4 binding moiety]-[HLE]-X(n)
[CTLA4 binding moiety]-[CTLA4 binding moiety]-[PD1 binding moiety]-[PD1 binding moiety]-[HLE]-X(n)
[CTLA4 binding moiety]-[other ISVD against CTLA4]-[PD1 binding moiety ]-[HLE]-X(n)
[PD1 binding moiety]-[Targeting domain ]-[CTLA4 binding moiety ]-[HLE]-X(n)
[Targeting domain]-[PD1 binding moiety]-[CTLA4 binding moiety ]-[HLE]-X(n)

Legend:
"[PD1 binding moiety]" = PD1 binding domain or unit (e.g., an ISVD such as a Nanobody), for example as set forth herein, e.g., any of SEQ ID NOs: 16-47 or 135-142.
"[CTLA4 binding moiety]" = CTLA4 binding domain or unit (e.g., an ISVD such as a Nanobody), for example as set forth herein, e.g., any of SEQ ID NOs: 48-83 or 143 or 196
"[HLE]" = serum albumin binding moiety e.g., an ISVD such as a Nanobody
"[Other ISVD against PD1]" = (functional or non-functional) binding unit or domain (e.g., an ISVD such as a Nanobody) against PD1, e.g., other than the PD1 binding moiety
"[Other ISVD against CTLA4]" = (functional or non-functional) binding unit or domain (e.g., an ISVD such as a Nanobody) against CTLA4, e.g., other than the CTLA4 binding moiety
"[targeting domain]" = domain (such as an ISVD, e.g., a Nanobody) that targets the PD1/CTLA4 binder of the invention to a specific cell, tissue or organ
"-" = suitable linker (such as 9GS, 15GS or 35GS)

In an embodiment of the invention, the PD1/CTLA4 binder comprises the structure:

[PD1 binding moiety]-[PD1 binding moiety]-[CTLA4 binding moiety]-[CTLA4 binding moiety]-[Albumin binding moiety];

[CTLA4 binding moiety]-[CTLA4 binding moiety]-[PD1 binding moiety]-[PD1 binding moiety]-[Albumin binding moiety];

[PD1 binding moiety]-[CTLA4 binding moiety]-[Albumin binding moiety];

[CTLA4 binding moiety]-[PD1 binding moiety]-[Albumin binding moiety];

[PD1 binding moiety]-[CTLA4 binding moiety]-[CTLA4 binding moiety]-[Albumin binding moiety];

[CTLA4 binding moiety]-[CTLA4 binding moiety]-[PD1 binding moiety]-[Albumin binding moiety];

[PD1 binding moiety]-[PD1 binding moiety]-[CTLA4 binding moiety]-[Albumin binding moiety]; or

[CTLA4 binding moiety]-[PD1 binding moiety]-[PD1 binding moiety]-[Albumin binding moiety];

each optionally, including a C-terminal Alanine.

Some preferred, but non-limiting examples of PD1/CTLA4 binders of the invention (e.g., comprising ISVDs (e.g., Nanobodies) that bind to PD1 and CTLA4) are given in FIG. 6 or SEQ ID NOs: 103-134, 146, 149, 151 or 153.

In an embodiment of the invention, the PD1/CTLA4 binder of the present invention is F023700910, F023700918, F023700920 or F023700925 as follows.

F023700910 may be encoded by a polynucleotide comprising the nucleotide sequence:

(SEQ ID NO: 145)

```
          10        20        30        40        50        60
----:----|----:----|----:----|----:----|----:----|----:----|
gacgtgcaattggtggagtctggtggcggagttgtccagcctggcggcagtctgcggtta 70        80        90       100       110       120
----:----|----:----|----:----|----:----|----:----|----:----|
tcttgcgccgcttctggcagcattgccagtattcacgctatgggttggttcaggcaggct 130       140       150       160       170       180
----:----|----:----|----:----|----:----|----:----|----:----|
cctggtaaagaacgtgagtttgtggctgtgattacttggtccggtggtattacttactac 190       200       210       220       230       240
----:----|----:----|----:----|----:----|----:----|----:----|
gctgatagcgttaagggccggtttacaatttcccgtgataatagcaaaaataccgtctat 250       260       270       280       290       300
----:----|----:----|----:----|----:----|----:----|----:----|
ctgcaaatgaacagtctgcgcccggaagataccgccctgtattactgtgcgggcgataaa 310       320       330       340       350       360
----:----|----:----|----:----|----:----|----:----|----:----|
catcagtcctcatggtatgactactgggggcaagggaccctggtcacggtctcctccgga
```

```
                   370       380       390       400       410       420
          ----:----|----:----|----:----|----:----|----:----|----:----|
          ggcggtgggtcaggtggcggaggcagcggtggaggaggtagtggcggtggcggtagtggg
                   430       440       450       460       470       480
          ----:----|----:----|----:----|----:----|----:----|----:----|
          ggtggaggcagcggaggcggaggcagtgggggcggtggatccgaggtgcagttggtggag
                   490       500       510       520       530       540
          ----:----|----:----|----:----|----:----|----:----|----:----|
          tctgggggaggagtggtgcagccggggggctctctgagactctcctgtgcagcctctggt
                   550       560       570       580       590       600
          ----:----|----:----|----:----|----:----|----:----|----:----|
          ggcaccttcagtttctatggcatgggctggttccgccaggctccagggaaggagcgcgag
                   610       620       630       640       650       660
          ----:----|----:----|----:----|----:----|----:----|----:----|
          tttgtagcagatattagaaccagtgctggtaggacatactatgcagactccgtgaagggc
                   670       680       690       700       710       720
          ----:----|----:----|----:----|----:----|----:----|----:----|
          cgattcaccatctccagagacaacagcaagaacacggtgtatctgcaaatgaacagcctg
                   730       740       750       760       770       780
          ----:----|----:----|----:----|----:----|----:----|----:----|
          cgccctgaggacacggccctgtattactgtgcagcagagccaagtggaataagtggttgg
                   790       800       810       820       830       840
          ----:----|----:----|----:----|----:----|----:----|----:----|
          gactactggggccaggggaccctggtcacggtctcgagcggaggcggtgggtcaggtggc
                   850       860       870       880       890       900
          ----:----|----:----|----:----|----:----|----:----|----:----|
          ggaggcagcggtggaggaggtagtggcggtggcggtagtgggggtggaggcagcggaggc
                   910       920       930       940       950       960
          ----:----|----:----|----:----|----:----|----:----|----:----|
          ggaggcagtgggggcggtggctcagaggtacaactagtggagtctggaggtggcgttgtg
                   970       980       990      1000      1010      1020
          ----:----|----:----|----:----|----:----|----:----|----:----|
          caaccgggtaacagtctgcgccttagctgcgcagcgtctggctttaccttcagctccttt
                  1030      1040      1050      1060      1070      1080
          ----:----|----:----|----:----|----:----|----:----|----:----|
          ggcatgagctgggttcgccaggctccgggaaaaggactggaatgggtttcgtctattagc
                  1090      1100      1110      1120      1130      1140
          ----:----|----:----|----:----|----:----|----:----|----:----|
          ggcagtggtagcgatacgctctacgcggactccgtgaagggccgtttcaccatctcccgc
                  1150      1160      1170      1180      1190      1200
          ----:----|----:----|----:----|----:----|----:----|----:----|
          gataacgccaaaactacactgtatctgcaaatgaatagcctgcgtcctgaagatacggcc
                  1210      1220      1230      1240      1250      1260
          ----:----|----:----|----:----|----:----|----:----|----:----|
          ctgtattactgtactattggtggctcgttaagccgttcttcacagggtaccctggtcacc
                  1270
          ----:----|--
          gtctcctcagcg
```

F023700910 comprises the amino acid sequence:

(SEQ ID NO: 146)

DVQLVESGGGVVQPGGSLRLSCAASGSIASIHAMG

WFRQAPGKEREFVAVITWSGGITYYADSVKG

RFTISRDNSKNTVYLQMNSLRPEDTALYY

CAGDKHQSSWYDYWGQGTLVTVSSGGGGSGG

GGSGGGGSGGGGSGGGGSGGGGSGGGGSE

VQLVESGGGVVQPGGSLRLSCAASGGTFS

FYGMGWFRQAPGKEREFVADIRTSAGRTYYA

DSVKGRFTISRDNSKNTVYLQMNSLRPEDTA

LYYCAAEPSGISGWDYWGQGTLVTVSSGG

GGSGGGGSGGGGSGGGGSGGGGSGGGGSG

GGGSEVQLVESGGGVVQPGNSLRLSCAASGF

TFSSFGMSWVRQAPGKGLEWVSSISGSGS

-continued

DTLYADSVKGRFTISRDNAKTTLYLQMNSLR

PEDTALYYCTIGGSLSRSSQGTLVTVSSA;
optionally comprising a signal peptide such as (SEQ ID NO: 147)
MRFPSIFTAVLFAASSALAAPVNTTTEDETAQIPAEAVI

GYSDLEGDFDVAVLPFSNSTNNGLLFINTTIASIAAKEE

GVSLEKR

F023700910 comprises the following moieties:
PD1 binder 102C12 (E1D,L11V,A14P,A74S,K83R, I89L);
Peptide linker;
CTLA4 binder 11F01 (L11V,A14P,Q45R,A74S,K83R, V89L,M96P,Q108L);
Peptide linker;
human serum albumin binder ALB11002;
C-terminal extender Alanine.
For example:
PD1 binder SEQ ID NO: 135;
35GS linker SEQ ID NO: 86;
CTLA4 binder SEQ ID NO: 143 (optionally, D1E);
35GS linker SEQ ID NO: 86;
HSA binder SEQ ID NO: 144;
Alanine F023700918 may be encoded by a polynucleotide comprising the nucleotide sequence:

```
                                              (SEQ ID NO: 148)
         10        20        30        40        50        60
----:----|----:----|----:----|----:----|----:----|----:----|
gacgtgcaattggtggagtctggtggcggagttgtccagcctggcggcagtctgcggtta 70        80        90       100       110       120
----:----|----:----|----:----|----:----|----:----|----:----|
tcttgcgccgcttctggcagcattgccagtattcacgctatgggttggttcaggcaggct 130       140       150       160       170       180
----:----|----:----|----:----|----:----|----:----|----:----|
cctggtaaagaacgtgagtttgtggctgtgattacttggtccggtggtattacttactac 190       200       210       220       230       240
----:----|----:----|----:----|----:----|----:----|----:----|
gctgatagcgttaagggccggtttacaatttcccgtgataatagcaaaaataccgtctat 250       260       270       280       290       300
----:----|----:----|----:----|----:----|----:----|----:----|
ctgcaaatgaacagtctgcgcccggaagataccgccctgtattactgtgcgggcgataaa 310       320       330       340       350       360
----:----|----:----|----:----|----:----|----:----|----:----|
catcagtcctcatggtatgactactgggggcaagggaccctggtcacggtctcctccgga 370       380       390       400       410       420
----:----|----:----|----:----|----:----|----:----|----:----|
ggcggtgggtcaggtggcggaggcagcggtggaggaggtagtggcggtggcggtagtggg 430       440       450       460       470       480
----:----|----:----|----:----|----:----|----:----|----:----|
ggtggaggcagcggaggcggaggcagtgggggcggtggatcagaggtgcagttggtggag 490       500       510       520       530       540
----:----|----:----|----:----|----:----|----:----|----:----|
tctggtggcggagttgtccagcctggcggcagtctgcggttatcttgcgccgcttctggc 550       560       570       580       590       600
----:----|----:----|----:----|----:----|----:----|----:----|
agcattgccagtattcacgctatgggttggttcaggcaggctcctggtaaagaacgtgag 610       620       630       640       650       660
----:----|----:----|----:----|----:----|----:----|----:----|
tttgtggctgtgattacttggtccggtggtattacttactacgctgatagcgttaagggc 670       680       690       700       710       720
----:----|----:----|----:----|----:----|----:----|----:----|
cggtttacaatttcccgtgataatagcaaaaataccgtctatctgcaaatgaacagtctg 730       740       750       760       770       780
----:----|----:----|----:----|----:----|----:----|----:----|
cgcccggaagataccgccctgtattactgtgcgggcgataaacatcagtcctcatggtat 790       800       810       820       830       840
----:----|----:----|----:----|----:----|----:----|----:----|
gactactgggggcaagggaccctggtcacggtctcctcaggaggcggtgggtcaggtggc 850       860       870       880       890       900
----:----|----:----|----:----|----:----|----:----|----:----|
ggaggcagcggtggaggaggtagtggcggtggcggtagtgggggtggaggcagcggaggc
```

```
                910       920       930       940       950       960
       ----:----|----:----|----:----|----:----|----:----|----:----|
       ggaggcagtgggggcggtggatccgaggtgcagttggtggagtctggggggaggagtggtg 970       980       990      1000      1010      1020
       ----:----|----:----|----:----|----:----|----:----|----:----|
       cagccggggggctctctgagactctcctgtgcagcctctggtggcaccttcagtttctat 1030      1040      1050      1060      1070      1080
       ----:----|----:----|----:----|----:----|----:----|----:----|
       ggcatgggctggttccgccaggctccagggaaggagcgcgagtttgtagcagatattaga 1090      1100      1110      1120      1130      1140
       ----:----|----:----|----:----|----:----|----:----|----:----|
       accagtgctggtaggacatactatgcagactccgtgaagggccgattcaccatctccaga 1150      1160      1170      1180      1190      1200
       ----:----|----:----|----:----|----:----|----:----|----:----|
       gacaacagcaagaacacggtgtatctgcaaatgaacagcctgcgccctgaggacacggcc 1210      1220      1230      1240      1250      1260
       ----:----|----:----|----:----|----:----|----:----|----:----|
       ctgtattactgtgcagcagagccaagtggaataagtggttgggactactggggccagggg 1270      1280      1290      1300      1310      1320
       ----:----|----:----|----:----|----:----|----:----|----:----|
       accctggtcacggtctcgagcggaggcggtgggtcaggtggcggaggcagcggtggagga 1330      1340      1350      1360      1370      1380
       ----:----|----:----|----:----|----:----|----:----|----:----|
       ggtagtggcggtggcggtagtgggggtggaggcagcggaggcggaggcagtggggcggt 1390      1400      1410      1420      1430      1440
       ----:----|----:----|----:----|----:----|----:----|----:----|
       ggctcagaggtacaactagtggagtctggaggtggcgttgtgcaaccgggtaacagtctg 1450      1460      1470      1480      1490      1500
       ----:----|----:----|----:----|----:----|----:----|----:----|
       cgccttagctgcgcagcgtctggctttaccttcagctcctttggcatgagctgggttcgc 1510      1520      1530      1540      1550      1560
       ----:----|----:----|----:----|----:----|----:----|----:----|
       caggctccgggaaaaggactggaatgggtttcgtctattagcggcagtggtagcgatacg 1570      1580      1590      1600      1610      1620
       ----:----|----:----|----:----|----:----|----:----|----:----|
       ctctacgcggactccgtgaagggccgtttcaccatctcccgcgataacgccaaaactaca 1630      1640      1650      1660      1670      1680
       ----:----|----:----|----:----|----:----|----:----|----:----|
       ctgtatctgcaaatgaatagcctgcgtcctgaagatacggccctgtattactgtactatt 1690      1700      1710      1720      1730
       ----:----|----:----|----:----|----:----|----:----|----
       ggtggctcgttaagccgttcttcacagggtaccctggtcaccgtctcctcagcg
```

F023700918 comprises the amino acid sequence:

(SEQ ID NO: 149)

DVQLVESGGGVVQPGGSLRLSCAASGSIASIHAMG

WFRQAPGKEREFVAVITWSGGITYYADSVKG

RFTISRDNSKNTVYLQMNSLRPEDTALYY

CAGDKHQSSWYDYWGQGTLVTVSSGGGGSGGGGSGG

GGSGGGGSGGGGSGGGGSGGGGSE

VQLVESGGGVVQPGGSLRLSCAASGSIAS

IHAMGWFRQAPGKEREFVAVITWSGGITYYA

DSVKGRFTISRDNSKNTVYLQMNSLRPEDTA

LYYCAGDKHQSSWYDYWGQGTLVTVSSGG

GGSGGGGSGGGGSGGGGSGGGGSGGGGSG

GGGSEVQLVESGGGVVQPGGSLRLSCAASGG

TFSFYGMGWFRQAPGKEREFVA

DIRTSAGRTYYADSVKGRFTISRDNSKNTVYLQMNSLR

PEDTALYYCAAEPSGISGWDYWGQGTLVTVSS

GGGGSGGGGSGGGGSGGGGSGGGGSGGG

GSGGGGSEVQLVESGGGVVQPGNSLRLSCA

ASGFTFSSFGMSWVRQAPGKGLEWVSSISG

SGSDTLYADSVKGRFTISRDNAKTTLYLQM

-continued
NSLRPEDTALYYCTIGGSLSRSSQGTLVTV
SSA;
optionally comprising a signal peptide such as (SEQ ID NO: 147)
MRFPSIFTAVLFAASSALAAPVNTTTEDETAQIPAEAVI

GYSDLEGDFDVAVLPFSNSTNNGLLFINTTIASIAAKEE

GVSLEKR

F023700918 comprises the following moieties:
  PD1 binder 102C12 (E1D,L11V,A14P,A74S,K83R, I89L);
  peptide linker;
  PD1 binder 102C12 (L11V,A14P,A74S,K83R,I89L);
  peptide linker;
  CTLA4 binder 11F01 (L11V,A14P,Q45R,A74S,K83R, V89L,M96P,Q108L);
  peptide linker;
  human serum albumin binder ALB11002;
  C-terminal extender Alanine.
For example:
  PD1 binder SEQ ID NO: 135 (optionally, D1E);
  35GS linker SEQ ID NO: 86;
  PD1 binder SEQ ID NO: 135 (optionally, D1E);
  35GS linker SEQ ID NO: 86;
  CTLA4 binder SEQ ID NO: 143 (optionally, D1E);
  35GS linker SEQ ID NO: 86;
  HSA binder SEQ ID NO: 144;
  Alanine F023700920 can be encoded by a polynucleotide comprising the nucleotide sequence:

```
                                               (SEQ ID NO: 150)
         10        20        30        40        50        60
----:----|----:----|----:----|----:----|----:----|----:----|
gacgtgcaattggtggagtctggtggcggagttgtccagcctggcggcagtctgcggtta 70        80        90       100       110       120
----:----|----:----|----:----|----:----|----:----|----:----|
tcttgcgccgcttctggcagcattgccagtattcacgctatgggttggttcaggcaggct 130       140       150       160       170       180
----:----|----:----|----:----|----:----|----:----|----:----|
cctggtaaagaacgtgagtttgtggctgtgattacttggtccggtggtattacttactac 190       200       210       220       230       240
----:----|----:----|----:----|----:----|----:----|----:----|
gctgatagcgttaagggccggtttacaatttcccgtgataatagcaaaaataccgtctat 250       260       270       280       290       300
----:----|----:----|----:----|----:----|----:----|----:----|
ctgcaaatgaacagtctgcgcccggaagataccgccctgtattactgtgcgggcgataaa 310       320       330       340       350       360
----:----|----:----|----:----|----:----|----:----|----:----|
catcagtcctcatggtatgactactgggggcaagggaccctggtcacggtctcctccgga 370       380       390       400       410       420
----:----|----:----|----:----|----:----|----:----|----:----|
ggcggtgggtcaggtggcggaggcagcggtggaggaggtagtggcggtggcggtagtggg 430       440       450       460       470       480
----:----|----:----|----:----|----:----|----:----|----:----|
ggtggaggcagcggaggcggaggcagtggggcggtggatccgaggtgcagttggtggag 490       500       510       520       530       540
----:----|----:----|----:----|----:----|----:----|----:----|
tctggggggaggagtggtgcagccggggggctctctgagactctcctgtgcagcctctggt 550       560       570       580       590       600
----:----|----:----|----:----|----:----|----:----|----:----|
ggcaccttcagtttctatggcatgggctggttccgccaggctccagggaaggagcgcgag 610       620       630       640       650       660
----:----|----:----|----:----|----:----|----:----|----:----|
tttgtagcagatattagaaccagtgctggtaggacatactatgcagactccgtgaagggc 670       680       690       700       710       720
----:----|----:----|----:----|----:----|----:----|----:----|
cgattcaccatctccagagacaacagcaagaacacggtgtatctgcaaatgaacagcctg 730       740       750       760       770       780
----:----|----:----|----:----|----:----|----:----|----:----|
cgccctgaggacacggccctgtattactgtgcagcagagccaagtggaataagtggttgg 790       800       810       820       830       840
----:----|----:----|----:----|----:----|----:----|----:----|
gactactggggccaggggaccctggtcacggtctcgagcggaggcggtgggtcaggtggc
```

```
                850       860       870       880       890       900
        ----:----|----:----|----:----|----:----|----:----|----:----|
        ggaggcagcggtggaggaggtagtggcggtggcggtagtgggggtggaggcagcggaggc 910       920       930       940       950       960
        ----:----|----:----|----:----|----:----|----:----|----:----|
        ggaggcagtgggggcggtggatcagaggtgcagttggtggagtctgggggaggagtggtg 970       980       990      1000      1010      1020
        ----:----|----:----|----:----|----:----|----:----|----:----|
        cagccggggggctctctgagactctcctgtgcagcctctggtggcaccttcagtttctat 1030      1040      1050      1060      1070      1080
        ----:----|----:----|----:----|----:----|----:----|----:----|
        ggcatgggctggttccgccaggctccagggaaggagcgcgagtttgtagcagatattaga 1090      1100      1110      1120      1130      1140
        ----:----|----:----|----:----|----:----|----:----|----:----|
        accagtgctggtaggacatactatgcagactccgtgaagggccgattcaccatctccaga 1150      1160      1170      1180      1190      1200
        ----:----|----:----|----:----|----:----|----:----|----:----|
        gacaacagcaagaacacggtgtatctgcaaatgaacagcctgcgccctgaggacacggcc 1210      1220      1230      1240      1250      1260
        ----:----|----:----|----:----|----:----|----:----|----:----|
        ctgtattactgtgcagcagagccaagtggaataagtggttgggactactggggccagggg 1270      1280      1290      1300      1310      1320
        ----:----|----:----|----:----|----:----|----:----|----:----|
        accctggtcacggtctcctcaggaggcggtgggtcaggtggcggaggcagcggtggagga 1330      1340      1350      1360      1370      1380
        ----:----|----:----|----:----|----:----|----:----|----:----|
        ggtagtggcggtggcggtagtgggggtggaggcagcggaggcggaggcagtggggcggt 1390      1400      1410      1420      1430      1440
        ----:----|----:----|----:----|----:----|----:----|----:----|
        ggatcagaggtgcaactagtggagtctggaggtggcgttgtgcaaccgggtaacagtctg 1450      1460      1470      1480      1490      1500
        ----:----|----:----|----:----|----:----|----:----|----:----|
        cgccttagctgcgcagcgtctggctttaccttcagctcctttggcatgagctgggttcgc 1510      1520      1530      1540      1550      1560
        ----:----|----:----|----:----|----:----|----:----|----:----|
        caggctccgggaaaaggactggaatgggtttcgtctattagcggcagtggtagcgatacg 1570      1580      1590      1600      1610      1620
        ----:----|----:----|----:----|----:----|----:----|----:----|
        ctctacgcggactccgtgaagggccgtttcaccatctcccgcgataacgccaaaactaca 1630      1640      1650      1660      1670      1680
        ----:----|----:----|----:----|----:----|----:----|----:----|
        ctgtatctgcaaatgaatagcctgcgtcctgaagatacggccctgtattactgtactatt 1690      1700      1710      1720      1730
        ----:----|----:----|----:----|----:----|----:----|----
        ggtggctcgttaagccgttcttcacagggtaccctggtcaccgtctcctcagcg
```

F023700920 comprises the amino acid sequence:

(SEQ ID NO: 151)
DVQLVESGGGVVQPGGSLRLSCAASGSIASIHAMG

WFRQAPGKEREFVAVITWSGGITYYADSVKGRFTISRDNSKNTVYLQMNS

LRPEDTALYYCAGDKHQSSWYDYWGQGTLVTVSSGGGGSGGGGSGGGGSG

GGGSGGGGSGGGGSGGGGSEVQLVESGGGVVQPGGSLRLSCAASGGTFSF

YGMGWFRQAPGKEREFVADIRTSAGRTYYADSVKGRFTISRDNSKNTVYL

QMNSLRPEDTALYYCAAEPSGISGWDYWGQGTLVTVSSGGGGSGGGGSGG

GSGGGGSGGGGSGGGGSGGGGSEVQLVESGGGVVQPGGSLRLSCAASGG

TFSFYGMGWFRQAPGKEREFVADIRTSAGRTYYADSVKGRFTISRDNSKN

TVYLQMNSLRPEDTALYYCAAEPSGISGWDYWGQGTLVTVSSGGGGSGGG

GSGGGGSGGGGSGGGGSGGGGSEVQLVESGGGVVQPGNSLRLSCA

ASGFTFSSFGMSWVRQAPGKGLEWVSSISGSGSDTLYADSVKGRFTISRD

NAKTTLYLQMNSLRPEDTALYYCTIGGSLSRSSQGTLVTVSSA;

optionally comprising a signal peptide such as (SEQ ID NO: 147)
MRFPSIFTAVLFAASSALAAPVNTTTEDETAQIPAEAVIGYSDLEGDFDV

AVLPFSNSTNNGLLFINTTIASIAAKEEGVSLEKR

F023700920 comprises the following moieties:
PD1 binder 102C12 (E1D,L11V,A14P,A74S,K83R, I89L);
peptide linker;
CTLA4 binder 11F01 (L11V,A14P,Q45R,A74S,K83R, V89L,M96P,Q108L);

peptide linker;
CTLA4 binder 11F01 (L11V,A14P,Q45R,A74S,K83R, V89L,M96P,Q108L);
peptide linker;
human serum albumin binder ALB11002;
C-terminal extender Alanine
For example:
PD1 binder SEQ ID NO: 135;
35GS linker SEQ ID NO: 86;
CTLA4 binder SEQ ID NO: 143 (optionally, D1E);
35GS linker SEQ ID NO: 86;
CTLA4 binder SEQ ID NO: 143 (optionally, D1E);
35GS linker SEQ ID NO: 86;
HSA binder SEQ ID NO: 144;
Alanine F023700925 may be encoded by a polynucleotide comprising the nucleotide sequence:

```
                                                   (SEQ ID NO: 152)
         10        20        30        40        50        60
----:----|----:----|----:----|----:----|----:----|----:----|
gacgtgcaattggtggagtctggtggcggagttgtccagcctggcggcagtctgcggtta 70        80        90       100       110       120
----:----|----:----|----:----|----:----|----:----|----:----|
tcttgcgccgcttctggcagcattgccagtattcacgctatgggttggttcaggcaggct 130       140       150       160       170       180
----:----|----:----|----:----|----:----|----:----|----:----|
cctggtaaagaacgtgagtttgtggctgtgattacttggtccggtggtattacttactac 190       200       210       220       230       240
----:----|----:----|----:----|----:----|----:----|----:----|
gctgatagcgttaagggccggtttacaatttcccgtgataatagcaaaaataccgtctat 250       260       270       280       290       300
----:----|----:----|----:----|----:----|----:----|----:----|
ctgcaaatgaacagtctgcgcccggaagataccgccctgtattactgtgcgggcgataaa 310       320       330       340       350       360
----:----|----:----|----:----|----:----|----:----|----:----|
catcagtcctcatggtatgactactgggggcaagggaccctggtcacggtctcctccgga 370       380       390       400       410       420
----:----|----:----|----:----|----:----|----:----|----:----|
ggcggtgggtcaggtggcggaggcagcggtggaggaggtagtggcggtggcggtagtggg 430       440       450       460       470       480
----:----|----:----|----:----|----:----|----:----|----:----|
ggtggaggcagcggaggcggaggcagtgggggcggtggatcagaggtgcagttggtggag 490       500       510       520       530       540
----:----|----:----|----:----|----:----|----:----|----:----|
tctggtggcggagttgtccagcctggcggcagtctgcggttatcttgcgccgcttctggc 550       560       570       580       590       600
----:----|----:----|----:----|----:----|----:----|----:----|
agcattgccagtattcacgctatgggttggttcaggcaggctcctggtaaagaacgtgag 610       620       630       640       650       660
----:----|----:----|----:----|----:----|----:----|----:----|
tttgtggctgtgattacttggtccggtggtattacttactacgctgatagcgttaagggc 670       680       690       700       710       720
----:----|----:----|----:----|----:----|----:----|----:----|
cggtttacaatttcccgtgataatagcaaaaataccgtctatctgcaaatgaacagtctg 730       740       750       760       770       780
----:----|----:----|----:----|----:----|----:----|----:----|
cgcccggaagataccgccctgtattactgtgcgggcgataaacatcagtcctcatggtat 790       800       810       820       830       840
----:----|----:----|----:----|----:----|----:----|----:----|
gactactgggggcaagggaccctggtcacggtctcctcaggaggcggtgggtcaggtggc 850       860       870       880       890       900
----:----|----:----|----:----|----:----|----:----|----:----|
ggaggcagcggtggaggaggtagtggcggtggcggtagtgggggtggaggcagcggaggc 910       920       930       940       950       960
----:----|----:----|----:----|----:----|----:----|----:----|
ggaggcagtgggggcggtggatccgaggtgcagttggtggagtctgggggaggagtggtg 970       980       990      1000      1010      1020
----:----|----:----|----:----|----:----|----:----|----:----|
cagccggggggctctctgagactctcctgtgcagcctctggtggcaccttcagtttctat
```

-continued

```
          1030      1040      1050      1060      1070      1080
     ----:----|----:----|----:----|----:----|----:----|----:----|
     ggcatgggctggttccgccaggctccagggaaggagcgcgagtttgtagcagatattaga 1090      1100      1110      1120      1130      1140
     ----:----|----:----|----:----|----:----|----:----|----:----|
     accagtgctggtaggacatactatgcagactccgtgaagggccgattcaccatctccaga 1150      1160      1170      1180      1190      1200
     ----:----|----:----|----:----|----:----|----:----|----:----|
     gacaacagcaagaacacggtgtatctgcaaatgaacagcctgcgccctgaggacacggcc 1210      1220      1230      1240      1250      1260
     ----:----|----:----|----:----|----:----|----:----|----:----|
     ctgtattactgtgcagcagagccaagtggaataagtggttgggactactggggccagggg 1270      1280      1290      1300      1310      1320
     ----:----|----:----|----:----|----:----|----:----|----:----|
     accctggtcacggtctcgagcggaggcggtgggtcaggtggcggaggcagcggtggagga 1330      1340      1350      1360      1370      1380
     ----:----|----:----|----:----|----:----|----:----|----:----|
     ggtagtggcggtggcggtagtgggggtggaggcagcggaggcggaggcagtggggcggt 1390      1400      1410      1420      1430      1440
     ----:----|----:----|----:----|----:----|----:----|----:----|
     ggatcagaggtgcagttggtggagtctgggggaggagtggtgcagccggggggctctctg 1450      1460      1470      1480      1490      1500
     ----:----|----:----|----:----|----:----|----:----|----:----|
     agactctcctgtgcagcctctggtggcaccttcagtttctatggcatgggctggttccgc 1510      1520      1530      1540      1550      1560
     ----:----|----:----|----:----|----:----|----:----|----:----|
     caggctccagggaaggagcgcgagtttgtagcagatattagaaccagtgctggtaggaca 1570      1580      1590      1600      1610      1620
     ----:----|----:----|----:----|----:----|----:----|----:----|
     tactatgcagactccgtgaagggccgattcaccatctccagagacaacagcaagaacacg 1630      1640      1650      1660      1670      1680
     ----:----|----:----|----:----|----:----|----:----|----:----|
     gtgtatctgcaaatgaacagcctgcgccctgaggacacggccctgtattactgtgcagca 1690      1700      1710      1720      1730      1740
     ----:----|----:----|----:----|----:----|----:----|----:----|
     gagccaagtggaataagtggttgggactactggggccaggggaccctggtcacggtctcc 1750      1760      1770      1780      1790      1800
     ----:----|----:----|----:----|----:----|----:----|----:----|
     tcaggaggcggtgggtcaggtggcggaggcagcggtggaggaggtagtggcggtggcggt 1810      1820      1830      1840      1850      1860
     ----:----|----:----|----:----|----:----|----:----|----:----|
     agtgggggtggaggcagcggaggcggaggcagtggggcggtggatcagaggtgcaacta 1870      1880      1890      1900      1910      1920
     ----:----|----:----|----:----|----:----|----:----|----:----|
     gtggagtctggaggtggcgttgtgcaaccgggtaacagtctgcgccttagctgcgcagcg 1930      1940      1950      1960      1970      1980
     ----:----|----:----|----:----|----:----|----:----|----:----|
     tctggctttaccttcagctcctttggcatgagctgggttcgccaggctccgggaaaagga 1990      2000      2010      2020      2030      2040
     ----:----|----:----|----:----|----:----|----:----|----:----|
     ctggaatgggtttcgtctattagcggcagtggtagcgatacgctctacgcggactccgtg 2050      2060      2070      2080      2090      2100
     ----:----|----:----|----:----|----:----|----:----|----:----|
     aagggccgtttcaccatctcccgcgataacgccaaaactacactgtatctgcaaatgaat 2110      2120      2130      2140      2150      2160
     ----:----|----:----|----:----|----:----|----:----|----:----|
     agcctgcgtcctgaagatacggccctgtattactgtactattggtggctcgttaagccgt 2170      2180      2190
     ----:----|----:----|----:----|----:-
     tcttcacagggtaccctggtcaccgtctcctcagcg
```

F023700925 comprises the amino acid sequence:

(SEQ ID NO: 153)
```
DVQLVESGGGVVQPGGSLRLSCAASGSIASIHAMG
WFRQAPGKEREFVAVITWSGGITYYADSVKGRFTISRDNSKNTVYLQMNS
LRPEDTALYYCAGDKHQSSWYDYWGQGTLVTVSSGGGGSGGGGSGGGGSG
GGGSGGGGSGGGGSGGGGSEVQLVESGGGVVQPGGSLRLSCAASGSIASI
HAMGWERQAPGKEREFVAVITWSGGITYYADSVKGRFTISRDNSKNTVYL
QMNSLRPEDTALYYCAGDKHQSSWYDYWGQGTLVTVSSGGGGSGGGGSGG
GGSGGGGSGGGGSGGGGSGGGGSEVQLVESGGGVVQPGGSLRLSCAASGG
TFSFYGMGWFRQAPGKEREFVADIRTSAGRTYYADSVKGRFTISRDNSKN
TVYLQMNSLRPEDTALYYCAAEPSGISGWDYWGQGTLVTVSSGGGGSGGG
GSGGGGSGGGGSGGGGSGGGGSGGGGSEVQLVESGGGVVQPGGSLRLSCA
ASGGTFSFYGMGWERQAPGKEREFVADIRTSAGRTYYADSVKGRFTISRD
NSKNTVYLQMNSLRPEDTALYYCAAEPSGISGWDYWGQGTLVTVSSGGGG
SGGGGSGGGGSGGGGSGGGGSGGGGSGGGGSEVQLVESGGGVVQPGNSLR
LSCAASGFTFSSFGMSWVRQAPGKGLEWVSSISGSGSDTLYADSVKGRFT
ISRDNAKTTLYLQMNSLRPEDTALYYCTIGGSLSRSSQGTLVTVSSA;
optionally comprising a signal peptide such as
                                  (SEQ ID NO: 147)
MRFPSIFTAVLFAASSALAAPVNTTTEDETAQIPAEAVIGYSDLEGDFDV
AVLPFSNSTNNGLLFINTTIASIAAKEEGVSLEKR
```

Figure 17:
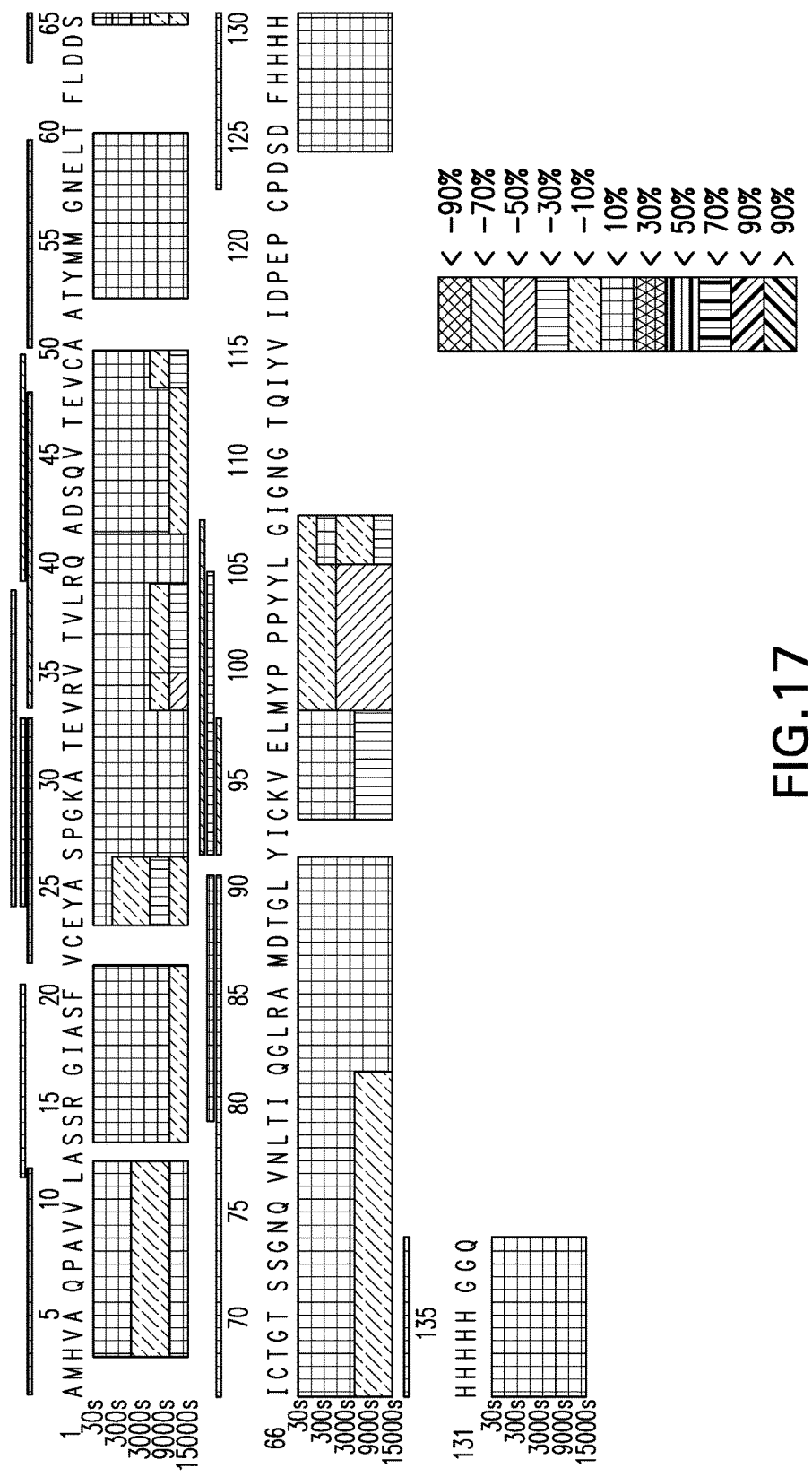
FIG. 17. Deuterium labeling difference heatmap of human CTLA4 binding by F023700912 CTLA4 binder.

F023700925 comprises the following moieties:
PD1 binder 102C12 (E1D, Lily, A14P, A74S, K83R, I89L);
peptide linker;
PD1 binder 102C12 (Lily, A14P, A74S, K83R, I89L);
peptide linker;
CTLA4 binder 11F01 (L11V, A14P, Q45R, A74S, K83R, V89L, M96P, Q108L);
peptide linker;
CTLA4 binder 11F01 (L11V, A14P, Q45R, A74S, K83R, V89L, M96P, Q108L);
peptide linker;
human serum albumin binder ALB11002;

C-terminal extender Alanine.

For example:

PD1 binder SEQ ID NO: 135;

35GS linker SEQ ID NO: 86;

PD1 binder SEQ ID NO: 135 (optionally, D1E);

35GS linker SEQ ID NO: 86;

CTLA4 binder SEQ ID NO: 143 (optionally, D1E);

35GS linker SEQ ID NO: 86;

CTLA4 binder SEQ ID NO: 143 (optionally, D1E);

35GS linker SEQ ID NO: 86;

HSA binder SEQ ID NO: 144;

Alanine.

The present invention includes any binder comprising the PD1, CTLA4 and HSA binding moieties of F023700910, F023700918, F023700920 or F023700925.

The present invention includes embodiments wherein the PD1/CTLA4 binders of the present invention comprise 0, 1, 2, 3, 4, 5, 6, 7, 8, 9 or 10 amino acid substitutions, e.g., conservative amino acid substitutions, and/or comprises 80, 85, 90, 91, 92, 93, 94, 95, 96, 97, 98 or 99% sequence identity relative to the sequences set forth in SEQ ID NO: 146, 149, 151 or 153, e.g., wherein the PD1/CTLA4 binder having such substitutions and/or sequence identity retain the ability to bind to PD1 and CTLA4. In an embodiment of the invention, the first amino acid of a PD1/CTLA4 binder of the present invention is E. In an embodiment of the invention, the first amino acid of a PD1/CTLA4 binder of the present invention is D.

The present invention also provides an injection device comprising any of the PD1/CTLA4 binders (e.g., comprising ISVDs (e.g., Nanobodies) that bind to PD1 and CTLA4), polypeptides or polynucleotides set forth herein or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the PD1/CTLA4 binder or a pharmaceutical composition thereof), a needle for piecing skin and/or blood vessels for injection of the fluid; and a plunger for pushing the fluid out of the cylinder and through the needle bore. In an embodiment of the invention, an injection device that comprises an PD1/CTLA4 binder or a pharmaceutical composition thereof is an intravenous (IV) injection device. Such a device includes the PD1/CTLA4 binder or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the subject through the cannula or trocar/needle. The PD1/CTLA4 binder or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the PD1/CTLA4 binder or a pharmaceutical composition thereof to a patient's body. External infusion pumps are medical devices that deliver the PD1/CTLA4 binder or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

Epitope Binding and Cross-Blocking

The present invention provides PD1/CTLA4 binders of the present invention (e.g., F023700910, F023700918, F023700920 or F023700925) as well as binders, e.g., ISVDs (e.g., Nanobodies) and antibodies and antigen-binding fragments thereof that bind to the same PD1 and/or CTLA4 epitope of such binders. For example, the present invention includes binders that bind to human CTLA4 by contacting the same residues as F023700912 (SEQ ID NO: 193) or which contact the same residues as the CTLA4 binding moiety thereof (11F01 (E1D,L11V, A14P,Q45R,A74S, K83R,V89L,M96P,Q108L)) For example, the present invention provides binders that bind to human CTLA4 at residues VRVTVL (Residues 33-38 of SEQ ID NO: 195), ADSQVTEVC (Residues 41-49 of SEQ ID NO: 195) and/or CKVELMYPPPYYLG (Residues 93-106 of SEQ ID NO: 195), e.g., all three sites, of human CTLA4. In an embodiment of the invention, the binder demonstrates binding to human CTLA4 at these residues in a hydrogen-deuterium exchange assay, e.g., protects the residues from exchange of hydrogen for deuterium in the presence of deuterium such as $D_2O$, e.g., as represented by a binding heat map essentially as set forth in FIG. 17.

The present invention also provides cross-blocking binders that are able to cross-block binding of any of the binders disclosed herein (e.g., F023700910, F023700918, F023700920 or F023700925). Such cross-blocking binders may be any molecule that exhibits such cross-blocking, e.g., an ISVD, Nanobody, antibody or antigen-binding fragment thereof.

In general, a binder (e.g., ISVD such as Nanobody) or antibody or antigen-binding fragment thereof that "cross-blocks" a reference binder or "cross competes with" a reference binder (e.g., such as F023700910, F023700918, F023700920 or F023700925)) refers to a binder (e.g., ISVD such as Nanobody) or antibody or antigen-binding fragment thereof that blocks binding of the reference binder to its antigen in a cross-blocking assay by 50% or more, and conversely, the reference binder blocks binding of the binder (e.g., ISVD such as Nanobody) or antibody or antigen-binding fragment thereof to its antigen in a cross-blocking assay by 50% or more. Cross-blocking can be determined using any assay known in the art, including surface plasmon resonance (SPR), ELISA and flow cytometry.

In an embodiment of the invention, cross-blocking is determined by use of a Biacore assay. For convenience reference is made to two binders, the scope of the present invention includes antibodies and antigen binding fragments thereof, e.g., Fab fragments, that cross-block a binder of the present invention. A Biacore machine (for example the Biacore 3000) is operated in line with the manufacturer's recommendations.

Thus, in one cross-blocking assay, PD1 or CTLA4 is coupled to a CMS Biacore chip using standard amine coupling chemistry to generate a PD1 or LAG3-coated surface. For example, 200-800 resonance units of PD1 or CTLA4 would be coupled to the chip (or any amount that gives easily measurable levels of binding but that is readily saturable by the concentrations of test reagent being used).

The two binders (termed A* and B*) to be assessed for their ability to cross-block each other are mixed at a one to one molar ratio of binding sites in a suitable buffer to create the test mixture.

The concentration of each binder in the test mix should be high enough to readily saturate the binding sites for that binder on the PD1 or CTLA4 molecules captured on the Biacore chip. The binders in the mixture are at the same molar concentration.

Separate solutions containing binder A* alone and binder B* alone are also prepared. Binder A* and binder B* in these solutions should be in the same buffer and at the same concentration as in the test mix.

The test mixture is passed over the PD1 or CTLA4-coated Biacore chip and the total amount of binding recorded. The chip is then treated in such a way as to remove the bound binders without damaging the chip-bound PD1 or CTLA4. In an embodiment of the invention, this is done by treating the chip with 30 mM HCl for 60 seconds.

The solution of binder A* alone is then passed over the PD1 or CTLA4-coated surface and the amount of binding recorded. The chip is again treated to remove all of the bound binder without damaging the chip-bound PD1 or CTLA4.

The solution of binder B* alone is then passed over the PD1 or CTLA4-coated surface and the amount of binding recorded.

The maximum theoretical binding of the mixture of binder A* and binder B* is next calculated, and is the sum of the binding of each binder when passed over the PD1 or CTLA4 surface alone. If the actual recorded binding of the mixture is less than this theoretical maximum, then the two binders are cross-blocking each other.

Thus, in general, a cross-blocking binder according to the invention is one which will bind to PD1 or CTLA4 in the above Biacore cross-blocking assay such that, during the assay and in the presence of a second binder, the recorded binding is between, for example, 80% and 0.1% (e.g., 80% to 4%) of the maximum theoretical binding, for example between 75% and 0.1% (e.g., 75% to 4%) of the maximum theoretical binding, for example, between 70% and 0.1% (e.g., 70% to 4%) of maximum theoretical binding (as just defined above) of the two binders in combination.

In an embodiment of the invention, an ELISA assay is used for determining whether a PD1 and/or CTLA4 binder cross-blocks or is capable of cross-blocking according to the invention.

The general principal of the assay is to have an PD1 or CTLA4 binder coated onto the wells of an ELISA plate. An excess amount of a second, potentially cross-blocking, anti-PD1 or CTLA4 binder is added in solution (i.e., not bound to the ELISA plate). A limited amount of PD1 or CTLA4 is then added to the wells. The coated binder and the binder in solution compete for binding of the limited number of PD1 or CTLA4 molecules. The plate is washed to remove PD1 or CTLA4 that has not been bound by the coated binder and to also remove the second, solution phase binder as well as any complexes formed between the second, solution phase binder and PD1 or CTLA4. The amount of bound PD1 or CTLA4 is then measured using an appropriate PD1 or CTLA4 detection reagent. A binder in solution that is able to cross-block the coated binder will be able to cause a decrease in the number of PD1 or CTLA4 molecules that the coated binder can bind relative to the number of PD1 or CTLA4 molecules that the coated binder can bind in the absence of the second, solution phase, binder.

Expression Methods

The present invention includes recombinant methods for making an PD1/CTLA4 binders (e.g., an ISVD such as a Nanobody) of the present invention (e.g., F023700910, F023700918, F023700920 or F023700925) comprising (i) introducing a polynucleotide encoding the amino acid sequence of said PD1/CTLA4 binder, for example, wherein the polynucleotide is in a vector and/or is operably linked to a promoter; (ii) culturing the host cell (e.g., CHO or *Pichia* or *Pichia pastoris*) under condition favorable to expression of the polynucleotide and, (iii) optionally, isolating the PD1/CTLA4 binder from the host cell and/or medium in which the host cell is grown. See e.g., WO 04/041862, WO 2006/122786, WO 2008/020079, WO 2008/142164 or WO 2009/068627.

The invention also relates to polynucleotides that encode PD1/CTLA4 binders (e.g., comprising ISVDs (e.g., Nanobodies) that bind to PD1 and CTLA4) described herein (e.g., F023700910, F023700918, F023700920 or F023700925). The polynucleotides may, in an embodiment of the invention, be operably linked to one or more control sequences. The polynucleotide may be in the form of a plasmid or vector. Again, such polynucleotides can be generally as described in the published patent applications of Ablynx N.V., such as for example WO 04/041862, WO 2006/122786, WO 2008/020079, WO 2008/142164 or WO 2009/068627.

The invention also relates to nucleotide sequences or nucleic acids that encode the PD1/CTLA4 binders of the invention (e.g., comprising ISVDs (e.g., Nanobodies) that bind to PD1 and CTLA4) (e.g., F023700910, F023700918, F023700920 or F023700925). The invention further includes genetic constructs that include the foregoing nucleotide sequences or nucleic acids and one or more elements for genetic constructs known per se. The genetic construct may be in the form of a plasmid or vector. Again, such constructs can be generally as described in the published patent applications of Ablynx N.V., such as for example WO 2004/041862, WO 2006/122786, WO 2008/020079, WO 2008/142164 or WO 2009/068627.

The invention also relates to hosts or host cells that contain such nucleotide sequences or nucleic acids, and/or that express (or are capable of expressing), PD1/CTLA4 binders of the invention (e.g., comprising ISVDs (e.g., Nanobodies) that bind to PD1 and CTLA4) (e.g., F023700910, F023700918, F023700920 or F023700925). Again, such host cells can be generally as described in the published patent applications of Ablynx N.V., such as for example WO 2004/041862, WO 2006/122786, WO 2008/020079, WO 2008/142164 or WO 2009/068627.

The PD1/CTLA4 binder (e.g., comprising ISVDs (e.g., Nanobodies) that bind to PD1 and CTLA4) (e.g., F023700910, F023700918, F023700920 or F023700925), polypeptides, compounds, and polynucleotides (e.g., vectors) described herein are preferably administered to the circulation. As such, they can be administered in any suitable manner that allows the PD1/CTLA4 binders, polypeptides, compounds, and polynucleotides to enter the circulation, such as intravenously, via injection or infusion, or in any other suitable manner (including oral administration, subcutaneous administration, intramuscular administration, administration through the skin, intranasal administration, administration via the lungs, etc.) that allows the PD1/CTLA4 binders, polypeptides, compounds, and polynucleotides to enter the circulation. Suitable methods and routes of administration will be clear to the skilled person, again for example also from the teaching of the published patent applications of Ablynx N.V., such as for example WO 04/041862, WO 2006/122786, WO 2008/020079, WO 2008/142164 or WO 2009/068627.

Eukaryotic and prokaryotic host cells, including mammalian cells as hosts for expression of the PD1/CTLA4 binders (e.g., comprising ISVDs (e.g., Nanobodies) that bind to PD1 and CTLA4 (e.g., F023700910, F023700918, F023700920 or F023700925)) are well known in the art and include many immortalized cell lines available from the American Type Culture Collection (ATCC). These include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens* and *Neurospora crassa*. *Pichia* sp., any *Saccharomyces* sp., *Hansenula polymorpha*, any *Kluyveromyces* sp., *Candida albicans*, any *Aspergillus* sp., *Trichoderma reesei*, *Chrysosporium lucknowense*, any *Fusarium* sp., *Yarrowia lipolytica*, and *Neurospora crassa*.

Further, expression of a PD1/CTLA4 binder (e.g., comprising ISVDs (e.g., Nanobodies) that bind to PD1 and CTLA4) (e.g., F023700910, F023700918, F023700920 or F023700925) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

The present invention includes methods for purifying a PD1/CTLA4 binder (e.g., comprising ISVDs (e.g., Nanobodies) that bind to PD1 and CTLA4) (e.g., F023700910, F023700918, F023700920 or F023700925) comprising introducing a sample (e.g., culture medium, cell lysate or cell lysate fraction, e.g., a soluble fraction of the lysate) comprising the PD1/CTLA4 binder to a purification medium (e.g., cation-exchange medium, anion-exchange medium, hydrophobic exchange medium, affinity purification medium (e.g., protein-A, protein-G, protein-A/G, protein-L)) and either collecting purified PD1/CTLA4 binder from the flow-through fraction of said sample that does not bind to the medium; or, discarding the flow-through fraction and eluting bound PD1/CTLA4 binder from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium; or wherein the PD1/CTLA4 binder is secreted into the culture medium by the host cell and the medium or a fraction thereof is applied to the purification medium.

In general, glycoproteins produced in a particular cell line or transgenic animal will have a glycosylation pattern that is characteristic for glycoproteins produced in the cell line or transgenic animal. Therefore, the particular glycosylation pattern of a PD1/CTLA4 binder (e.g., comprising ISVDs (e.g., Nanobodies) (e.g., F023700910, F023700918, F023700920 or F023700925) that bind to PD1 and CTLA4) will depend on the particular cell line or transgenic animal used to produce the PD1/CTLA4 binder. PD1/CTLA4 binders comprising only non-fucosylated N-glycans are part of the present invention and may be advantageous, because non-fucosylated antibodies have been shown to typically exhibit more potent efficacy than their fucosylated counterparts both in vitro and in vivo (See for example, Shinkawa et al., J. Biol. Chem. 278: 3466-3473 (2003); U.S. Pat. Nos. 6,946,292 and 7,214,775). These PD1/CTLA4 binders with non-fucosylated N-glycans are not likely to be immunogenic because their carbohydrate structures are a normal component of the population that exists in human serum IgG.

Figure 7:
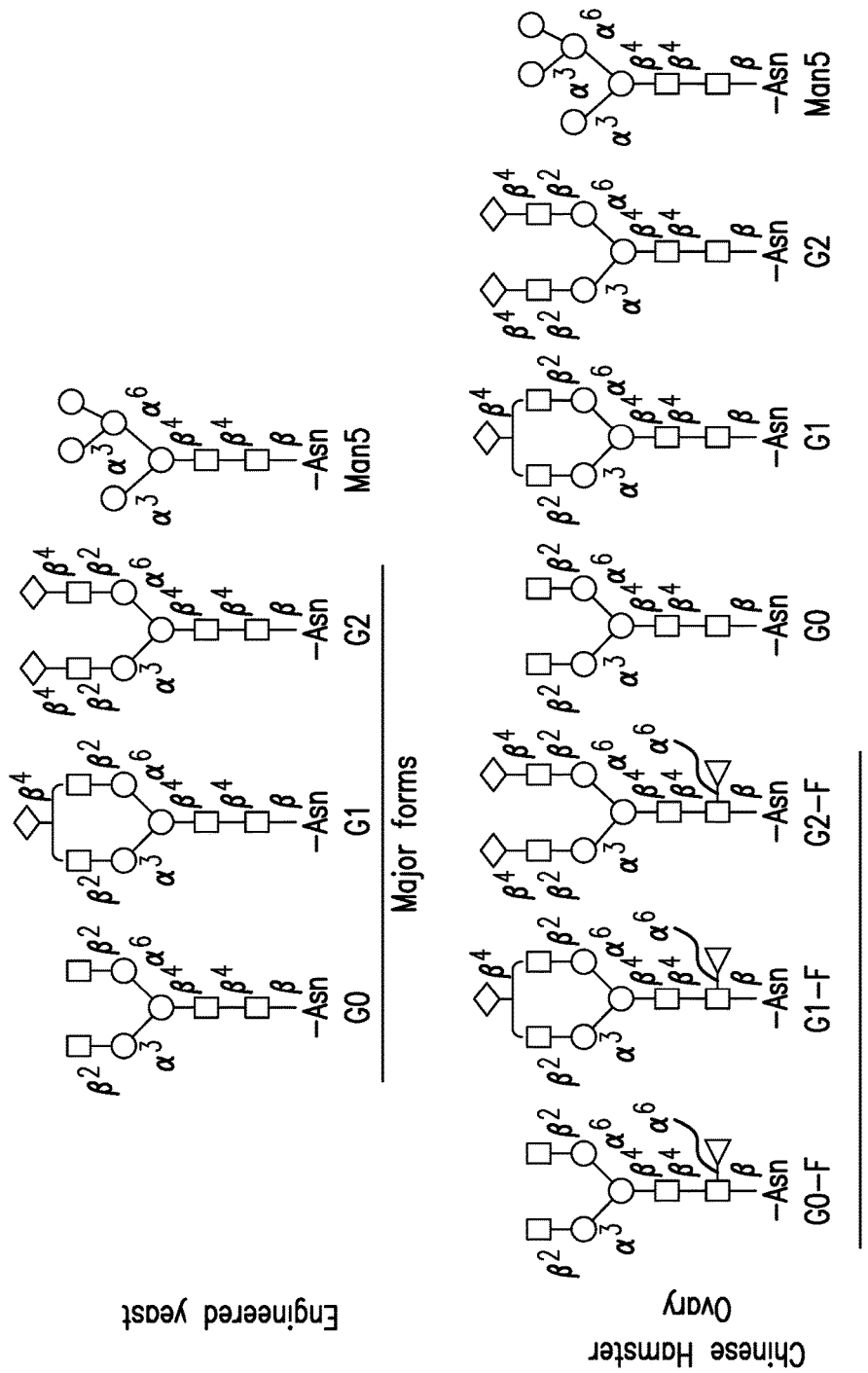
FIG. 7. Predominant N-linked glycans for monoclonal antibodies produced in Chinese hamster ovary cells (CHO N-linked glycans) and in engineered yeast cells (engineered yeast N-linked glycans): squares: N-acetylglucosamine (GlcNac); circles: mannose (Man); diamonds: galactose (Gal); triangles: fucose (Fuc).

The present invention includes PD1/CTLA4 binders (e.g., comprising ISVDs (e.g., Nanobodies) that bind to PD1 and CTLA4) (e.g., F023700910, F023700918, F023700920 or F023700925) comprising N-linked glycans that are typically added to immunoglobulins produced in Chinese hamster ovary cells (CHO N-linked glycans) or to engineered yeast cells (engineered yeast N-linked glycans), such as, for example, *Pichia pastoris*. For example, in an embodiment of the invention, the PD1/CTLA4 binder comprises one or more of the "engineered yeast N-linked glycans" or "CHO N-linked glycans" that are set forth in FIG. 7 (e.g., G0 and/or G0-F and/or G1 and/or G1-F and/or G2-F and/or Man5). In an embodiment of the invention, the PD1/CTLA4 binder comprises the engineered yeast N-linked glycans, i.e., G0 and/or G1 and/or G2, optionally, further including Man5. In an embodiment of the invention, the PD1/CTLA4 binders comprise the CHO N-linked glycans, i.e., G0-F, G1-F and G2-F, optionally, further including G0 and/or G1 and/or G2 and/or Man5. In an embodiment of the invention, about 80% to about 95% (e.g., about 80-90%, about 85%, about 90% or about 95%) of all N-linked glycans on the PD1/CTLA4 binders are engineered yeast N-linked glycans or CHO N-linked glycans. See Nett et al. Yeast. 28(3): 237-252 (2011); Hamilton et al. Science. 313(5792): 1441-1443 (2006); Hamilton et al. Curr Opin Biotechnol. 18(5): 387-392 (2007). For example, in an embodiment of the invention, an engineered yeast cell is GFI5.0 or YGLY8316 or strains set forth in U.S. Pat. No. 7,795,002 or Zha et al. Methods Mol Biol. 988:31-43 (2013). See also international patent application publication no. WO2013/066765.

Combinations

In particular embodiments, the PD1/CTLA4 binders (e.g., comprising ISVDs (e.g., Nanobodies) that bind to PD1 and CTLA4) (e.g., F023700910, F023700918, F023700920 or F023700925) may be used alone, or in association with other, further therapeutic agents and/or therapeutic procedures, for treating or preventing any disease such as cancer, e.g., as discussed herein, in a subject in need of such treatment or prevention. Compositions or kits, e.g., pharmaceutical compositions comprising a pharmaceutically acceptable carrier, comprising such binders in association with further therapeutic agents are also part of the present invention.

The term "in association with" indicates that the components, a PD1/CTLA4 binders (e.g., comprising ISVDs (e.g., Nanobodies) that bind to PD1 and CTLA4) (e.g., F023700910, F023700918, F023700920 or F023700925) along with another agent such as pembrolizumab or nivolumab, can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route (e.g., wherein a PD1/CTLA4 binder of the present invention is administered parenterally and paclitaxel is administered orally).

In particular embodiments, the PD1/CTLA4 binders (e.g., comprising ISVDs (e.g., Nanobodies) that bind to PD1 and CTLA4) (e.g., F023700910, F023700918, F023700920 or F023700925) may be used in association with an anti-cancer therapeutic agent or immunomodulatory drug such as an immunomodulatory receptor inhibitor, e.g., an antibody or antigen-binding fragment thereof that specifically binds to the receptor.

In an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is in association with one or more of an inhibitors (e.g., a small organic molecule or an antibody or antigen-binding fragment thereof) such as: an MTOR (mammalian target of rapamycin) inhibitor, a cytotoxic agent, a platinum agent a BRAF inhibitor, a CDK4/6 inhibitor an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is in association with one or more of: anti-CTLA4 antibodies or antigen-binding fragments thereof (e.g., ipilimumab), anti-PD1 antibody or antigen-binding fragment thereof (e.g., pembrolizumab, nivolumab, CT-011), anti-PDL1, anti-CTLA4, anti-TIM3, anti-CS1, (e.g., elotuzumab), anti-KIR2DL1/2/3 (e.g., lirilumab), anti-CD27, anti-CD137 (e.g., urelumab), anti-GITR (e.g., TRX518), anti-PD-L1 (e.g., BMS-936559, MSB0010718C or MPDL3280A), anti-PD-L2, anti-ILT1, anti-ILT2, anti-ILT3, anti-ILT4, anti-ILT5, anti-ILT6, anti-ILT7, anti-ILT8, anti-CD40, anti-OX40, anti-CD137, anti-KIR2DL1, anti-KIR2DL2/3, anti-KIR2DL4, anti-KIR2DL5A, anti-KIR2DL5B, anti-KIR3DL1, anti-KIR3DL2, anti-KIR3DL3, anti-NKG2A, anti-NKG2C, anti-NKG2E, or any small organic molecule inhibitor of such targets; IL-10, anti-IL10, anti-TSLP (thymic stromal lymphopoietin) or PEGylated IL-10.

In an embodiment of the invention, the molecular weight of the polyethylene glycol (PEG) moiety, on a PEGylated IL-10 molecule, is about 12,000 daltons or about 20,000 daltons. In an embodiment of the invention, PEGylated IL-10 (e.g., PEGylated human IL-10) comprises one or more polyethylene glycol molecules covalently attached via a linker (e.g., $C_{2-12}$ alkyl such as —$CH_2CH_2CH_2$—) to a single amino acid residue of a single subunit of IL-10, wherein said amino acid residue is the alpha amino group of the N-terminal amino acid residue or the epsilon amino group of a lysine residue. In an embodiment of the invention PEGylated IL-10 is: $(PEG)_b$-L-NH-IL-10; wherein b is 1-9 and L is a $C_{2-12}$ alkyl linker moiety covalently attached to a nitrogen (N) of the single amino acid residue of the IL-10. In an embodiment of the invention, the IL-10 of PEGylated IL-10 has the formula: $[X—O(CH_2CH_2O)_n]_b$-L-NH-IL-10, wherein X is H or $C_{1-4}$ alkyl; n is 20 to 2300; b is 1 to 9; and L is a $C_{1-11}$ alkyl linker moiety which is covalently attached to the nitrogen (N) of the alpha amino group at the amino terminus of one IL-10 subunit; provided that when b is greater than 1, the total of n does not exceed 2300. See U.S. Pat. No. 7,052,686.

In an embodiment of the invention, the anti-IL-10 antibody or antigen-binding fragment thereof (e.g., humanized antibody) comprises the CDRs set forth below:

```
                               (SEQ ID NO: 154)
CDR-L1: KTSQNIFENLA;

(SEQ ID NO: 155)
CDR-L2: NASPLQA;

(SEQ ID NO: 156)
CDR-L3: HQYYSGYT;

(SEQ ID NO: 157)
CDR-H1: GFTFSDYHMA;

(SEQ ID NO: 158)
CDR-H2: SITLDATYTYYRDSVRG;

(SEQ ID NO: 159)
CDR-H3: HRGFSVWLDY
```

(See U.S. Pat. No. 7,662,379)

In an embodiment of the invention, the anti-TSLP antibody or antigen-binding fragment thereof (e.g., humanized antibody) comprises the CDRs set forth below:

```
                               (SEQ ID NO: 160)
CDR-H1: GYIFTDYAMH;

(SEQ ID NO: 161)
CDR-H2: TFIPLLDTSDYNQNFK;

(SEQ ID NO: 162)
CDR-H3: MGVTHSYVMDA;

(SEQ ID NO: 163)
CDR-L1: RASQPISISVH;

(SEQ ID NO: 164)
CDR-L2: FASQSIS;

(SEQ ID NO: 165)
CDR-L3: QQTFSLPYT
```

(see WO2008/76321)

In an embodiment of the invention, the anti-CD27 antibody or antigen-binding fragment thereof (e.g., humanized antibody) comprises the CDRs set forth below:

```
                               (SEQ ID NO: 166)
CDR-H1: GFIIKATYMH;

(SEQ ID NO: 167)
CDR-H2: RIDPANGETKYDPKFQV;

(SEQ ID NO: 168)
CDR-H3: YAWYFDV;
```

```
                               (SEQ ID NO: 169)
CDR-L1: RASENIYSFLA;

(SEQ ID NO: 170)
CDR-L2: HAKTLAE;

(SEQ ID NO: 171)
CDR-L3: QHYYGSPLT;
```

(See WO2012/04367).

Thus, the present invention includes compositions comprising a PD1/CTLA4 binders (e.g., comprising ISVDs (e.g., Nanobodies) (e.g., F023700910, F023700918, F023700920 or F023700925) that bind to PD1 and CTLA4) in association with pembrolizumab; as well as methods for treating or preventing cancer in a subject comprising administering an effective amount of the PD1/CTLA4 binder in association with pembrolizumab (e.g., pembrolizumab dosed at 200 mg once every three weeks) to the subject. Optionally, the subject is also administered in association with a another further therapeutic agent.

In an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is in association with a pembrolizumab antibody which comprises an immunoglobulin heavy chain (or CDR-H1, CDR-H2 and CDR-H3 thereof) comprising the amino acid sequence:

```
                                           (SEQ ID NO: 172)
QVQLVQSGVEVKKPGASVKVSCKASGYTFTNYYMYWVRQAPGQGLEWMGG

INPSNGGTNFNEKFKNRVTLTTDSSTTTAYMELKSLQFDDTAVYYCARRD

YRFDMGFDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK;
``` and an immunoglobulin light chain (or CDR-L1, CDR-L2 and CDR-L3 thereof) comprising the amino acid sequence:

```
                                           (SEQ ID NO: 173)
EIVLTQSPATLSLSPGERATLSCRASKGVSTSGYSYLHWYQQKPGQAPRL

LIYLASYLESGVPARFSGSGSGTDFTLTISSLEPEDFAVYYCQHSRDLPL

TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

In an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is in association with an antibody comprising an immunoglobulin heavy chain (or CDR-H1, CDR-H2 and CDR-H3 thereof) comprising the amino acid sequence:

(SEQ ID NO: 174)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK;

and an immunoglobulin light chain (or CDR-L1, CDR-L2 and CDR-L3 thereof) comprising the amino acid sequence:

(SEQ ID NO: 175)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is in association with any one or more of: 13-cis-retinoic acid, 3-[5-(methylsulfonylpiperadinemethyl)-indolyl]-quinolone, 4-hydroxytamoxifen, 5-deooxyuridine, 5'-deoxy-5-fluorouridine, 5-fluorouracil, 6-mecaptopurine, 7-hydroxystaurosporine, A-443654, abiraterroneacetate, abraxane, ABT-578, acolbifene, ADS-100380, aflibercept, ALT-110, altretamine, amifostine, aminoglutethimide, amrubicin, amsacrine, anagrelide, anastrozole, angiostatin, AP-23573, ARQ-197, arzoxifene, AS-252424, AS-605240, asparaginase, ATI3387, AT-9263, atrasentan, axitinib, AZD1152, Bacillus Calmette-Guerin (BCG) vaccine, batabulin, BC-210, besodutox, bevacizumab, BGJ398, bicalutamide, Bio111, BIO140, BKM120, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, CEA (recombinant vaccinia-carcinoembryonic antigen vaccine), cediranib, CG-1521, CG-781, chlamydocin, chlorambucil, chlorotoxin, cilengitide, cimitidine, cisplatin, cladribine, clodronate, cobimetnib, COL-3, CP-724714, cyclophosphamide, cyproterone, cyproteroneacetate, cytarabine, cytosinearabinoside, dabrafenib, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, DNE03, docetaxel, dovitinib, doxorubicin, droloxifene, edotecarin, yttrium-90 labeled-edotreotide, edotreotide, EKB-569, EMD121974, encorafenib, endostatin, enzalutamide, enzastaurin, epirubicin, epithilone B, ERA-923, erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, fulvestrant, galeterone, ganetespib, gefitinib, gemcitabine, gimatecan, glucopyranosyl lipid A, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, imiquimod, INC280, INCB24360, INO1001, interferon, interleukin-2, interleukin-12, ipilimumab, irinotecan, JNJ-16241199, ketoconazole, KRX-0402, lapatinib, lasofoxifene, LEE011, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, LY3009120, marimastat, mechlorethamine, medroxyprogesteroneacetate, megestrolacetate, MEK162, melphalan, mercaptopurine, mesna, methotrexate, mithramycin, mitomycin, mitotane, mitoxantrone, a suspension of heat killed *Mycobacterium obuense*, tozasertib, MLN8054, natitoclax, neovastat, Neratinib, neuradiab, nilotinib, nilutimide, nolatrexed, NVP-BEZ235, oblimersen, octreotide, ofatumumab, oregovomab, ornatuzumab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, poly-ICLC, porfimer, prednisone, procarbazine, progestins, PSK protein bound polysaccharide (derived from *Basidiomycete coriolus versicolor*), PLX8394, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, 6-thioguanine, thiotepa, ticilimumab, tipifarnib, tivozanib, TKI-258, TLK286, TNF ☐(tumor necrosis factor alpha), topotecan, toremifene citrate, trabectedin, trametinib, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vemurafenib, vinblastine, vincristine, vindesine, vinorelbine, vitaxin, vitespan, vorinostat, VX-745, wortmannin, Xr311, Z-100 hot water extract of *Bacillus* tuberculosis, zanolimumab, ZK186619, ZK-304709, ZM336372 or ZSTK474.

In an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline;

Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is in association with an agent which treats or prevents such a deficiency, such as, e.g., filgrastim, PEG-filgrastim, erythropoietin, epoetin alfa or darbepoetin alfa.

In an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is in association with a vaccine. In an embodiment of the invention, the vaccine is an anti-cancer vaccine, a peptide vaccine, an RNA vaccine or a DNA vaccine. For example, in an embodiment of the invention, the vaccine is a tumor cell (e.g., an irradiated tumor cell) or a dendritic cell (e.g., a dendritic cell pulsed with a tumor peptide).

In an embodiment of the invention, a PD1/CTLA4 binders (e.g., comprising ISVDs (e.g., Nanobodies) that bind to PD1 and CTLA4) (e.g., F023700910, F023700918, F023700920 or F023700925) is administered in association with a therapeutic procedure. A therapeutic procedure is one or more steps carried out by a physician or clinician in treating a subject which is intended to alleviate one or more symptoms (e.g., of cancer and/or infectious disease) in the treated subject, whether by inducing the regression or elimination of such symptoms or by inhibiting the progression of such symptom(s), e.g., cancer symptoms such as tumor growth or metastasis, by any clinically measurable degree.

In an embodiment of the invention, a therapeutic procedure is anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures.

In an embodiment of the invention, the radiation therapy is brachytherapy: the temporary placement of radioactive materials within the body, usually employed to give an extra dose—or boost—of radiation to an area.

In an embodiment of the invention, a surgical procedure administered in association with a PD1/CTLA4 binders (e.g., comprising ISVDs (e.g., Nanobodies) that bind to PD1 and CTLA4) is surgical tumorectomy.

Therapeutic Uses

The invention includes a method for the preventing and/or treating at least one disease or disorder that can be prevented or treated by the use of a PD1/CTLA4 binders (e.g., comprising ISVDs (e.g., Nanobodies) that bind to PD1 and CTLA4) (e.g., F023700910, F023700918, F023700920 or F023700925) of the present invention, optionally in association with a further therapeutic agent or therapeutic procedure, which method comprises administering, to a subject in need thereof, a pharmaceutically active amount of the PD1/CTLA4 binder, and/or of a pharmaceutical composition comprising the same.

"Treat" or "treating" means to administer a PD1/CTLA4 binders (e.g., comprising ISVDs (e.g., Nanobodies) that bind to PD1 and CTLA4) (e.g., F023700910, F023700918, F023700920 or F023700925) of the present invention, to a subject (e.g., a mammal such as a human) having one or more symptoms of a disease for which the PD1/CTLA4 binders are effective, e.g., in the treatment of a subject having cancer or an infectious disease, or being suspected of having cancer or infectious disease, for which the agent has therapeutic activity. Typically, the PD1/CTLA4 binder is administered in an "effective amount" or "effective dose" which will alleviate one or more symptoms (e.g., of cancer or infectious disease) in the treated subject or population, whether by inducing the regression or elimination of such symptoms or by inhibiting the progression of such symptom(s), e.g., cancer symptoms such as tumor growth or metastasis, by any clinically measurable degree. The effective amount of the PD1/CTLA4 binder may vary according to factors such as the disease stage, age, and weight of the patient, and the ability of the drug to elicit a desired response in the subject.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

To prepare pharmaceutical or sterile compositions of the PD1/CTLA4 binders (e.g., comprising ISVDs (e.g., Nanobodies) that bind to PD1 and CTLA4) of the present invention (e.g., F023700910, F023700918, F023700920 or F023700925), the PD1/CTLA4 binders is admixed with a pharmaceutically acceptable carrier or excipient. See, e.g., Remington's Pharmaceutical Sciences and U.S. Pharmacopeia: National Formulary, Mack Publishing Company, Easton, Pa. (1984). Such compositions are part of the present invention.

The scope of the present invention includes dessicated, e.g., freeze-dried, compositions comprising an PD1/CTLA4 binders (e.g., comprising ISVDs (e.g., Nanobodies) that bind to PD1 and CTLA4) (e.g., F023700910, F023700918, F023700920 or F023700925) or a pharmaceutical composition thereof that includes a pharmaceutically acceptable carrier but substantially lacks water.

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, N.Y.; Lieberman, et al. (eds.) (1990) Pharmaceutical Dosage Forms: Tablets, Marcel Dekker, N.Y.; Lieberman, et al. (eds.) (1990) Pharmaceutical Dosage Forms: Disperse Systems, Marcel Dekker, N.Y.; Weiner and Kotkoskie (2000) Excipient Toxicity and Safety, Marcel Dekker, Inc., New York, N.Y.).

Generally, for the prevention and/or treatment of the diseases and disorders mentioned herein and depending on the specific disease or disorder to be treated, the potency and/or the half-life of the PD1/CTLA4 binders (e.g., comprising ISVDs (e.g., Nanobodies) that bind to PD1 and CTLA4) (e.g., F023700910, F023700918, F023700920 or F023700925) to be used, the specific route of administration and the specific pharmaceutical formulation or composition used, the PD1/CTLA4 binders of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

The mode of administration of a PD1/CTLA4 binders (e.g., comprising ISVDs (e.g., Nanobodies) that bind to PD1 and CTLA4) (e.g., F023700910, F023700918, F023700920 or F023700925) to a subject can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

Determination of the appropriate dose is made by the clinician, e.g., using parameters or factors known or suspected in the art to affect treatment. Generally, in determining the dose, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable. Guidance in selecting appropriate doses is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343: 1594-1602).

Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

The subject to be treated may be any mammal, such as a dog, cat, horse, rabbit, mouse cow, monkey or gorilla, preferably as a human. As will be clear to the skilled person, the subject to be treated will in particular be a person suffering from, or at risk from, the diseases and disorders mentioned herein.

Generally, the treatment regimen will be followed until the desired therapeutic effect is achieved and/or for as long as the desired therapeutic effect is to be maintained. Again, this can be determined by the clinician.

As the PD1/CTLA4 binders (e.g., comprising ISVDs (e.g., Nanobodies) that bind to PD1 and CTLA4) of the present invention (e.g., F023700910, F023700918, F023700920 or F023700925) are capable of binding to PD1 and CTLA4, they can in particular be used for treatment or prevention of cancer, metastatic cancer, a solid tumor, a hematologic cancer, leukemia, lymphoma, osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer and gastric cancer.

PD1/CTLA4 binders (e.g., comprising ISVDs (e.g., Nanobodies) that bind to PD1 and CTLA4) of the present invention (e.g., F023700910, F023700918, F023700920 or F023700925) can be used for treatment or prevention of infectious diseases such as, for example, viral infection, bacterial infection, fungal infection or parasitic infection. In an embodiment of the invention, the viral infection is infection with a virus selected from the group consisting of human immunodeficiency virus (HIV), ebola virus, hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus. In an embodiment of the invention, the bacterial infection is infection with a bacteria selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtheriae, Salmonella*, bacilli, *Vibrio cholerae, Clostridium tetan, Clostridium botulinum, Bacillus anthricis, Yersinia pestis, Mycobacterium leprae, Mycobacterium lepromatosis,* and *Borriella*. In an embodiment of the invention, the fungal infection is infection with a fungus selected from the group consisting of *Candida* (*albicans, krusei, glabrata, tropicalis,* etc.), *Cryptococcus neoformans, Aspergillus* (*fumigatus, niger,* etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*. In an embodiment of the invention, the parasitic infection is infection with a parasite selected from the group consisting of *Entamoeba histolytica, Balantidium coli, Naegleria fowleri, Acanthamoeba, Giardia Zambia, Cryptosporidium, Pneumocystis carinii, Plasmodium vivax, Babesia microti, Trypanosoma brucei, Trypanosoma cruzi, Leishmania donovani, Toxoplasma gondii, Nippostrongylus brasiliensis*.

The invention also relates to methods of treatment of the aforementioned diseases and disorders, which generally comprise administering to a subject in need thereof (i.e. suffering from one of the aforementioned diseases) a therapeutically effective amount of a PD1/CTLA4 binders (e.g., comprising ISVDs (e.g., Nanobodies) that bind to PD1 and CTLA4) of the invention (e.g., F023700910, F023700918, F023700920 or F023700925). The invention also relates to a PD1/CTLA4 binders (e.g., comprising ISVDs (e.g., Nanobodies) that bind to PD1 and CTLA4) for use in the prevention or treatment of one of the aforementioned diseases or disorders.

Other aspects, embodiments, advantages and applications of the invention will become clear from the further description herein.

EXAMPLES

These examples are intended to exemplify the present invention are not a limitation thereof. Compositions and methods set forth in the Examples form part of the present invention.

Example 1: F023700906 Nanobody Binding to CTLA-4-Fc

Monovalent F023700906 Nanobody (CTLA4 binder 11F01 (L11V,A14P,Q45R,A74S,K83R,V89L,M96P, Q108L)-FLAG3-HIS6), a building block of F023700925, demonstrated binding to CTLA-4-Fc fusion molecule from both human and cynomolgus monkey. On-rate, off-rate and affinity were determined using human and cynomolgus monkey CTLA4-hFc (Table below).

TABLE E

Binding of F023700906 to Human and Cynomolgous Monday CTLA4

| | Human CTLA-4-Fc | | | Cynomolgus CTLA-4-Fc | | |
|---|---|---|---|---|---|---|
| | Ka (1/Ms) | Kd (1/s) | KD (M) | Ka (1/Ms) | Kd (1/s) | KD (M) |
| F023700906 | 4.8E+06 | 5.9E−03 | 1.2E−09 | 4.7E+06 | 5.7E−03 | 1.2E−09 |

Example 2: F023700918 and F023700925 Binding to Human CTLA-4

Figure 8:
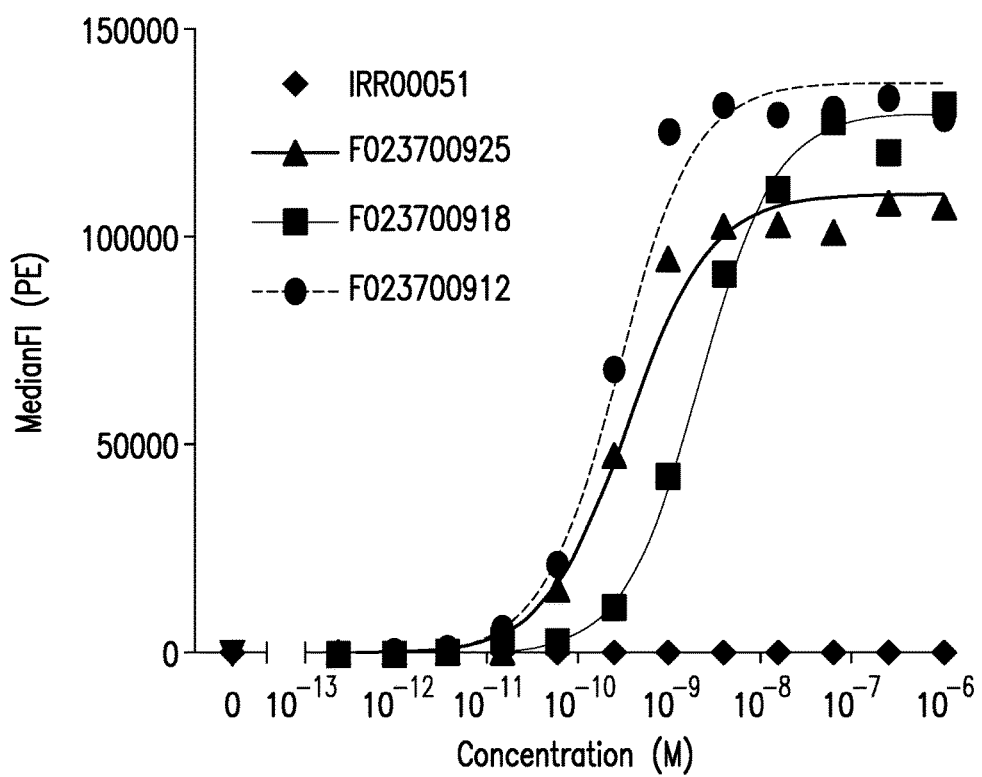
FIG. 8. Binding of Nanobodies F023700925, F023700918 and F023700912 and control Nanobody (IRR00051; anti-HER2/ERBB2 (bivalent anti-HER2 with 35GS connected to albumin binder)) to CHO-K1 cells expressing human CTLA4

F023700918 and F023700925 demonstrated binding to human CTLA-4 expressed on cell surface. Binding of F023700918 (filled squares), F023700925 (filled triangles), F023700912 (filled circles) and an irrelavant Nb (diamonds) to hCTLA4-overexpressing CHO-K1 cells was studied by flow cytometry. Nanobodies were detected via the ALB11-binding mAB ABH0074. The flow cytometry data generated in this experiment are in FIG. 8.

Example 3: Human PD-1 Cell Surface Binding by F023700925

Figure 9:
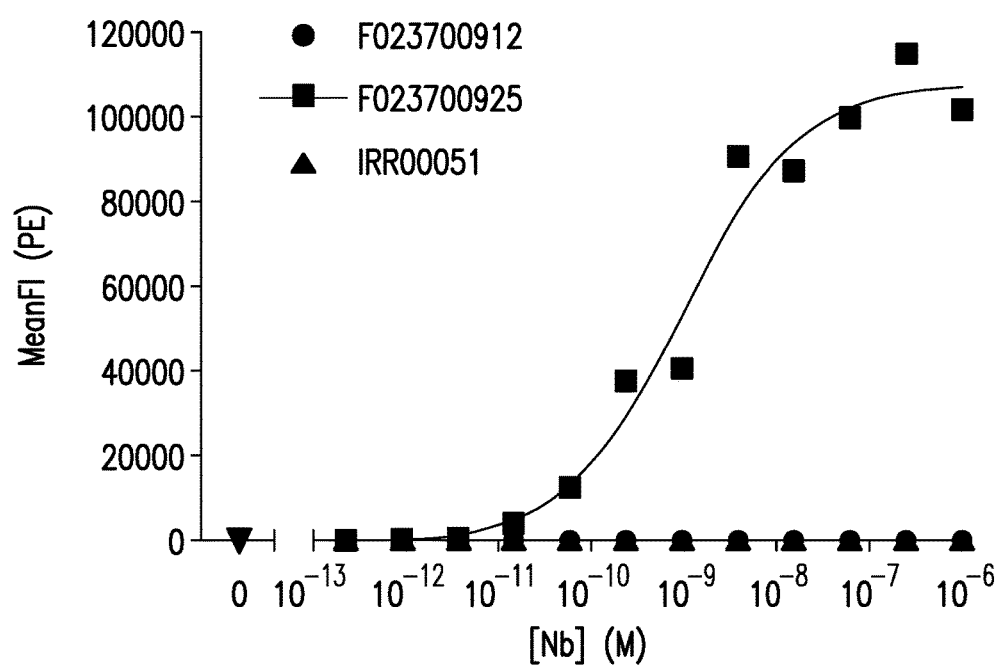
FIG. 9. Binding of Nanobodies F023700925, F023700912 and control Nanobody (IRR00051) to CHO-K1 cells expressing human PD1.

F023700925 demonstrated binding to human PD-1 expressed on cell surface. Binding of batches of F023700925 (filled squares) and F023700912 (filled circles) and irrelavant Nb IRR00051 (filled triangles) to hPD1-overexpressing CHO-K1 cells was studied by flow cytometry. Nbs were detected via the ALB11-binding mAB ABH0074. The flow cytometry data generated in this experiment are in FIG. 9.

Example 4: Human CTLA-4/CD80 and CD86 Blocking Assay

Figure 10A:
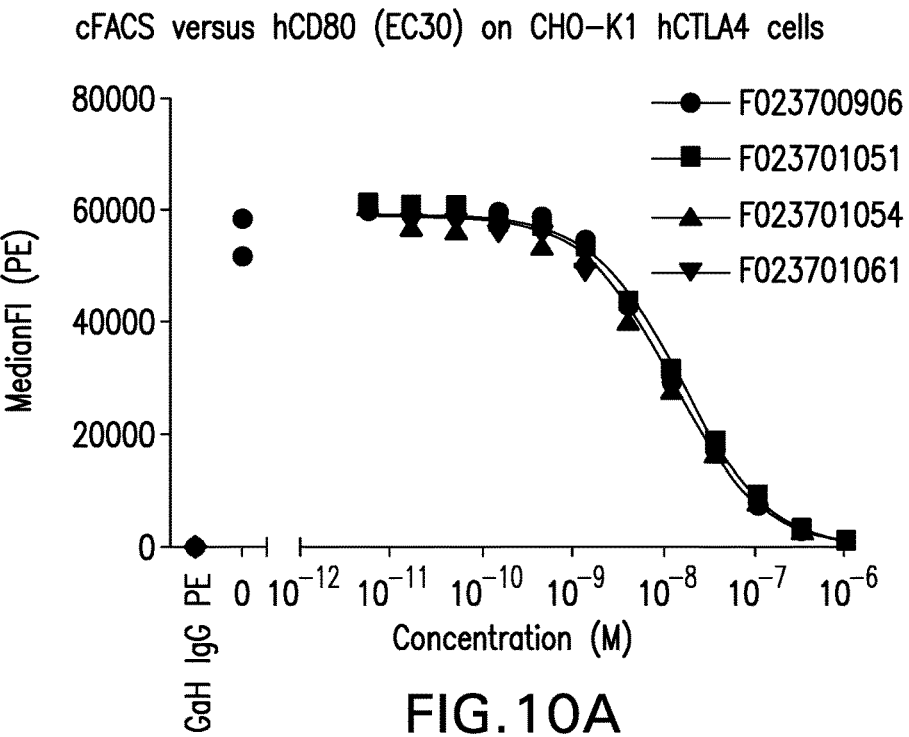
FIG. 10 (A-B). Blockage of binding of human CTLA4 (on CHO-K1 cells) to (A) human CD80 or (B) human CD86 by F023700906, F023701051, F023701054 and F023701061.
Figure 10B:
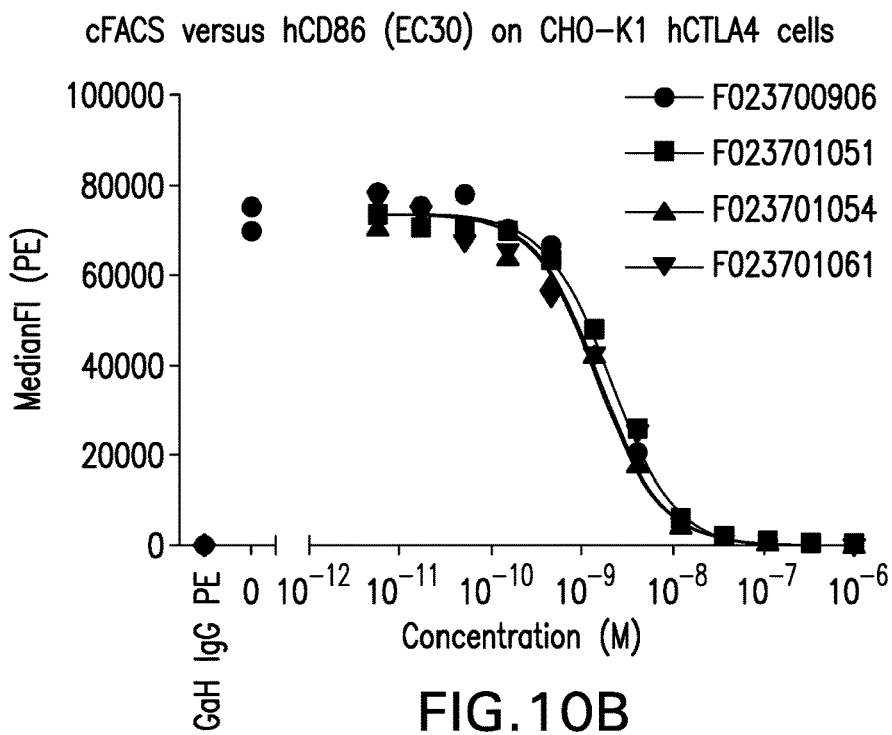
Figure 11A:
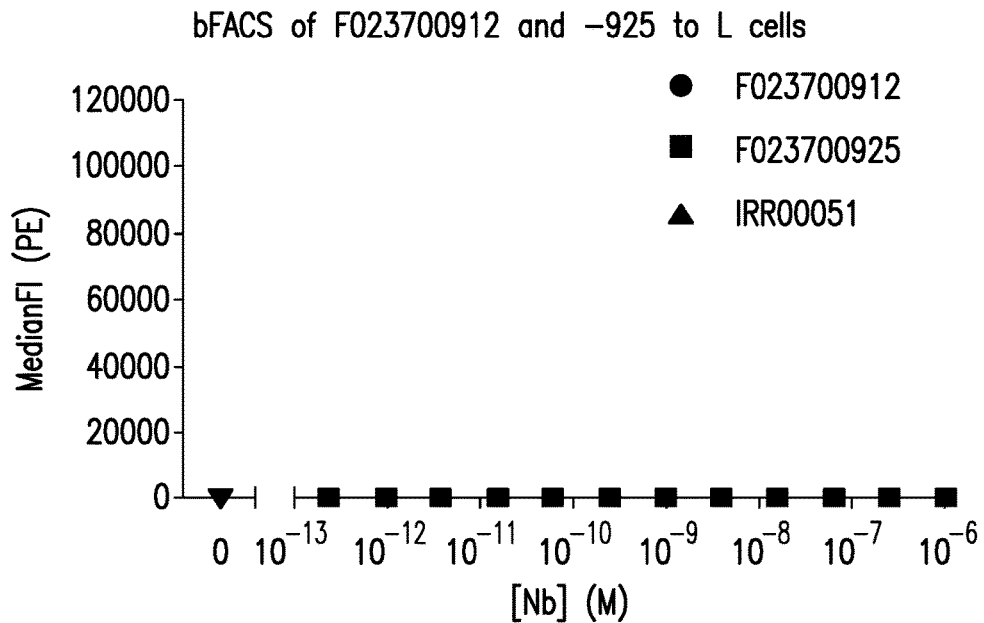
FIG. 11 (A-H). Binding of Nanobodies F023700912 or F023700925 or control Nanobody (IRR00051) to (A) negative control L cells, (B) negative control CHO-K1 cells, (C) huCD28+ L cells, (D) huCD8alpha+ L cells, (E) huLag-3+ CHO-K1 cells, (F) huBTLA+ CHO-K1 cells, (G) huCTLA-4+ CHO-K cells, or (H) huPD-1+ CHO-K1 cells.
Figure 11B:
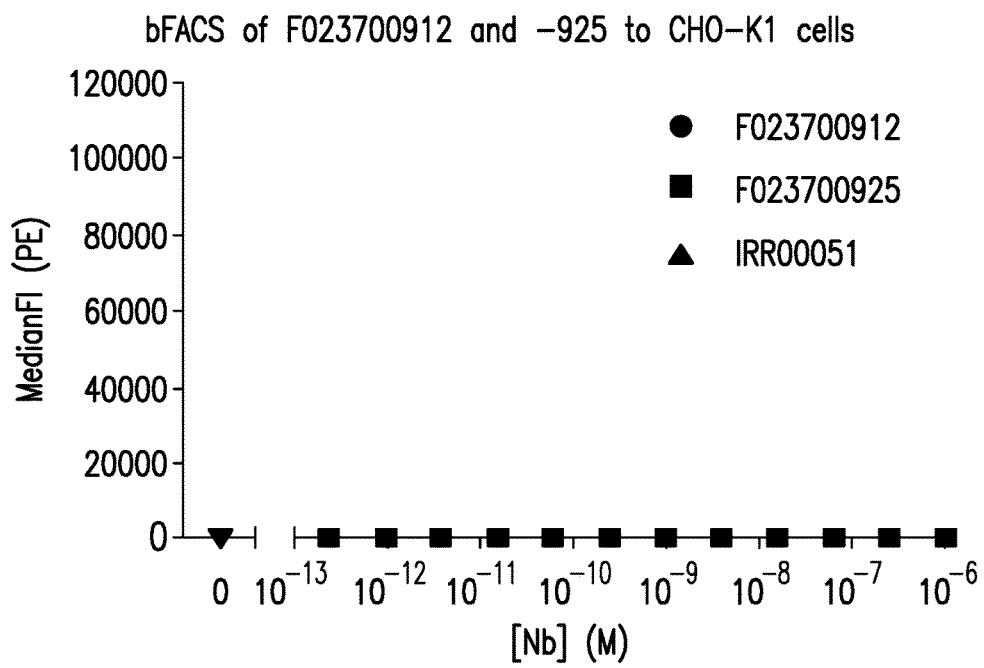
Figure 11C:
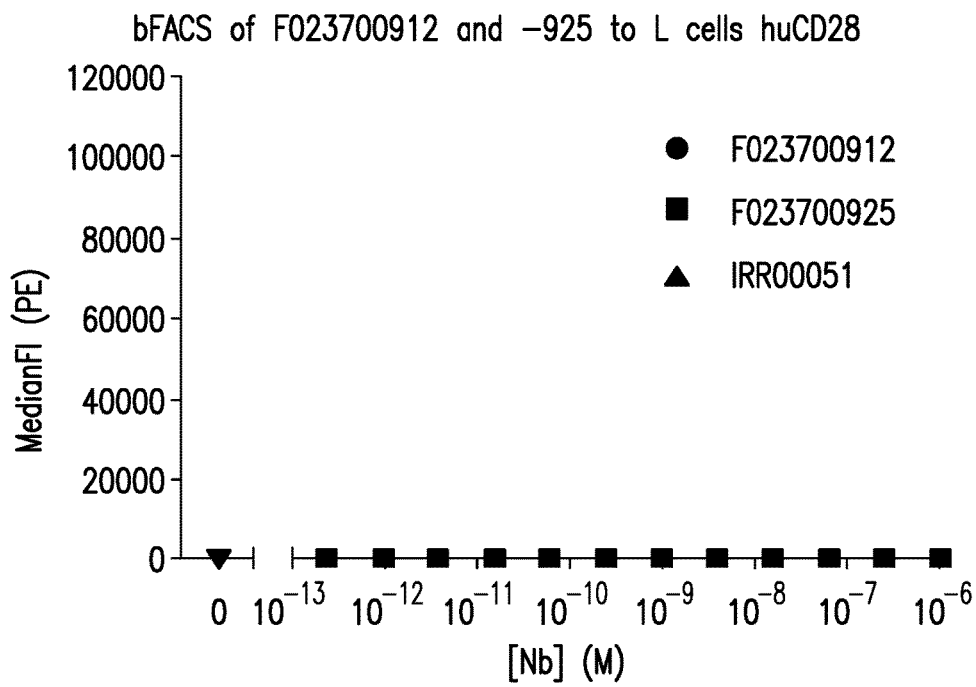
Figure 11D:
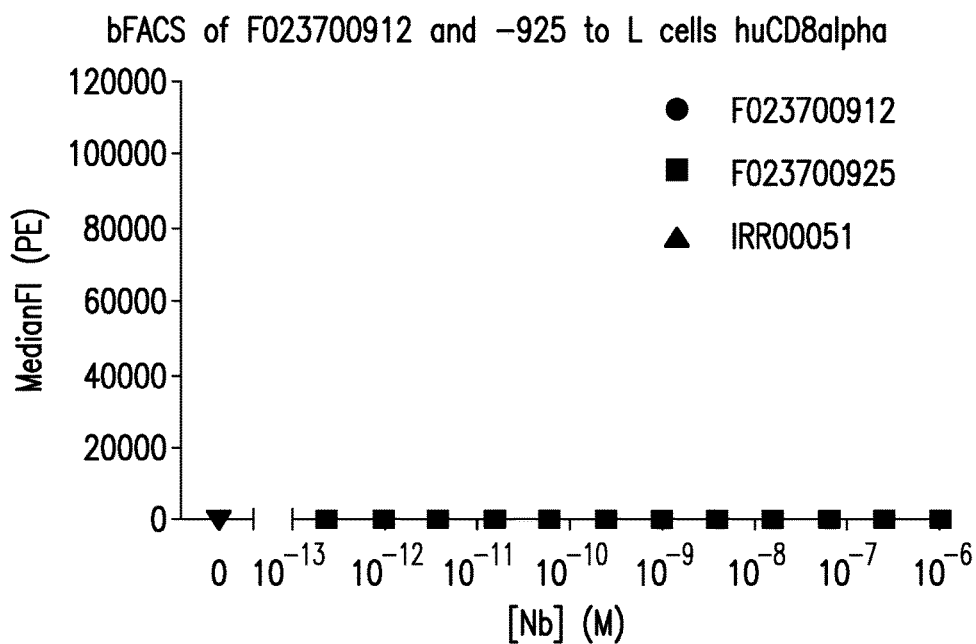
Figure 11E:
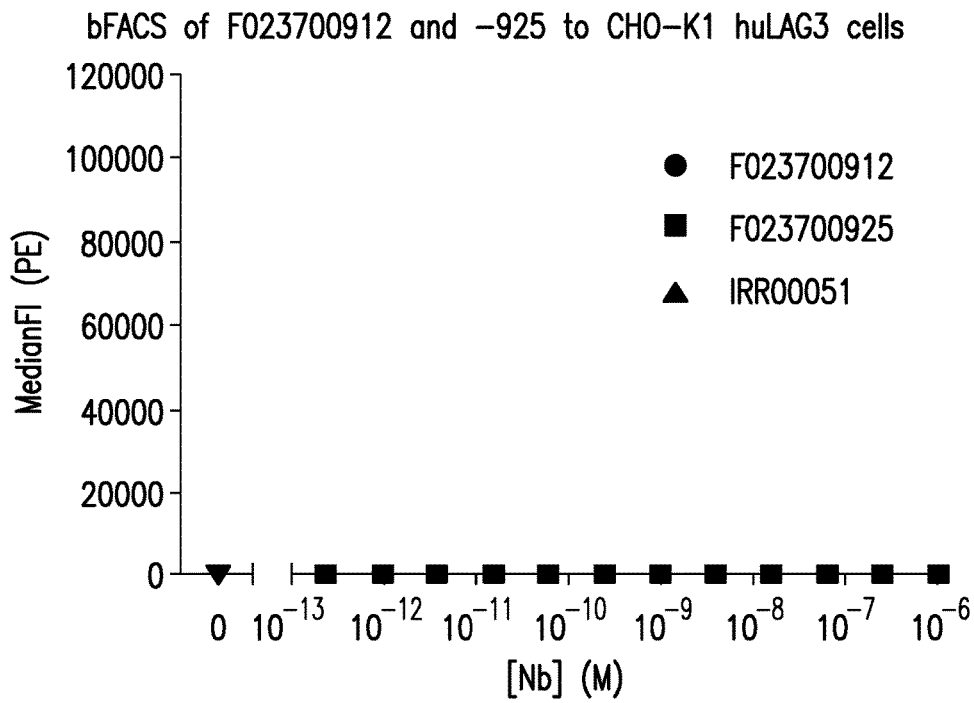
Figure 11F:
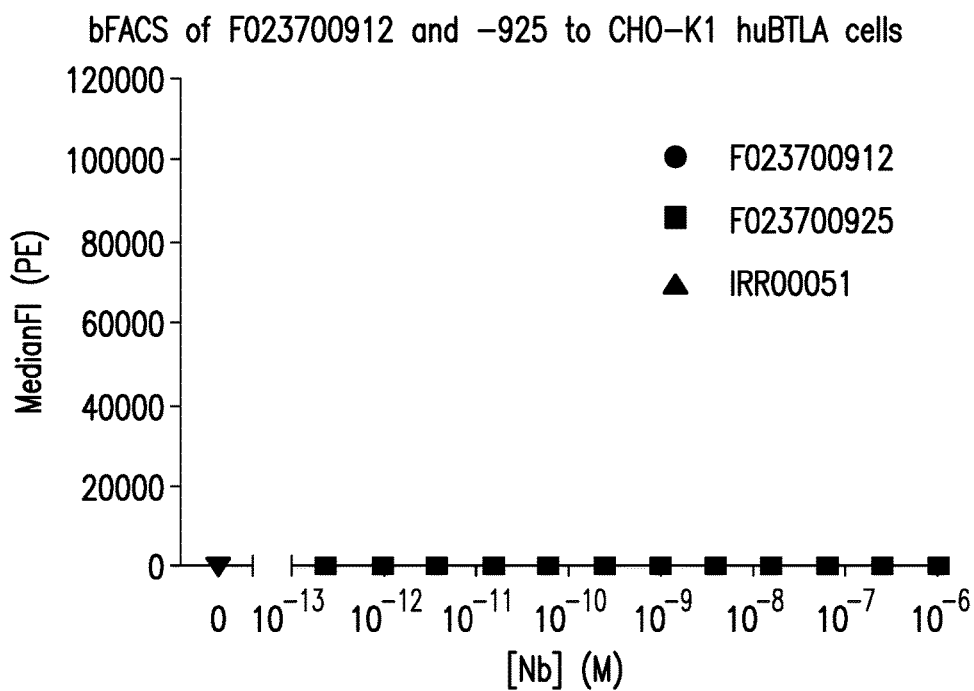
Figure 11G:
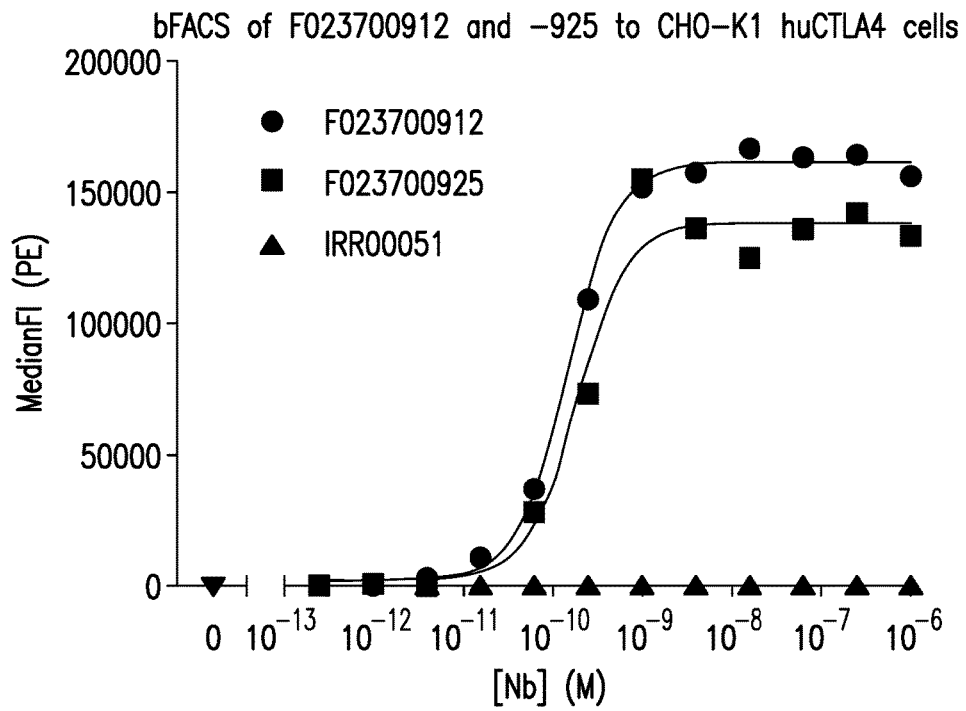
Figure 11H:
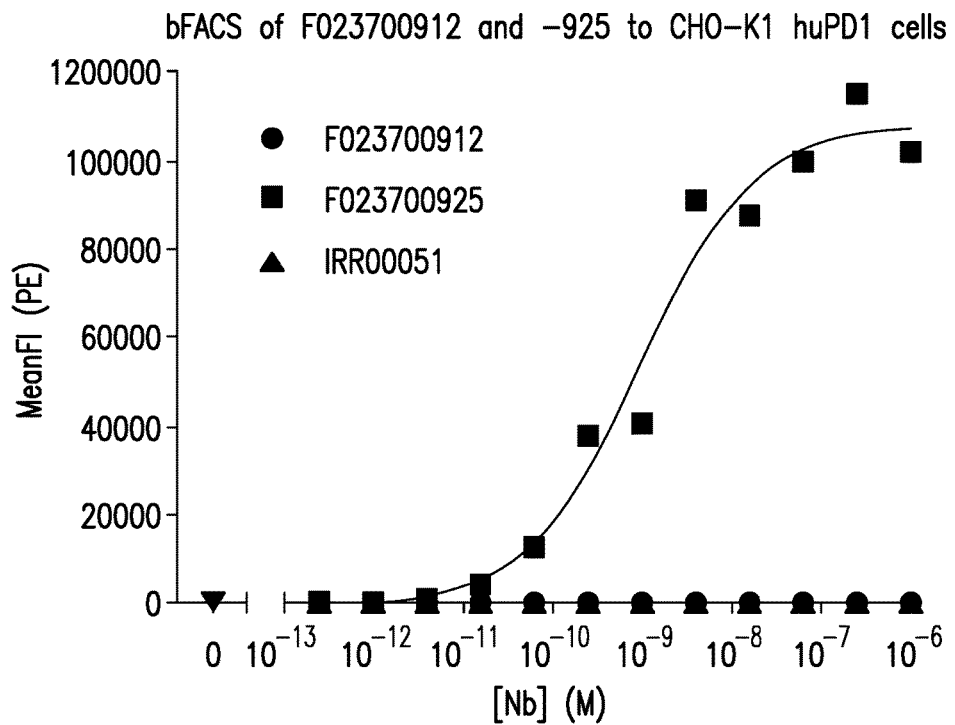

F023700906, a building block of F023700925, as well as F023701051, F023701054 and F023701061 blocked binding of human CTLA-4 to its ligands CD80 and CD86. Flow cytometry analysis of discovery batches of N73X variants (filled squares, filled triangles, filled triangles upside-down) of Nb F023700906 (filled circles) with fixed concentrations (EC30) of (A) hCD80-hFc or (B) hCD86-hFc on hCTLA4-overexpressing CHO-K1 cells. The ligands were detected via the human IgG Fc fusion protein. The flow cytometry data generated in this experiment are in FIG. 10 (A-B).

Example 5: Binding Specificity Assay

Specificity assessment F023700925 predicted selective binding to CTLA-4 and PD-1. Specificity assessment against BTLA, CD8, CTLA4, LAG3, and CD28 was performed on overexpressing cells using flow cytometry, whereas ICOS binding was evaluated in ELISA as a recombinant protein (hICOS-hFc). Expression of BTLA, CD8, PD1, CTLA4, LAG3, CD28 was assessed via directly-labelled target-specific Abs. Anti-hICOS and anti-hCTLA4/anti-hPD1 positive controls were all positive. No binding to hICOS was observed in the ELISA assays. FIG. 11 (A-H) showed binding to negative control L cells, negative control CHO-K1 cells, huCD28+ L cells, huCD8alpha+ L cells, huLag-3+ CHO-K1 cells, huBTLA+ CHO-K1 cells, huCTLA-4+ CHO-K cells, and huPD-1+CHO-K1 cells, respectively. No binding to BTLA, CD8, LAG3, CD28 could be observed for F023700925, whereas potent binding of F023700925 was observed on PD-1+ or CTLA-4+ CHO-K1 cells. The flow cytometry data generated in this experiment are in FIG. 11 (A-H).

Example 6: Serum Albumin Binding Assay

F023700925 bound to human, rhesus monkey and mouse albumin, predicting prolonged half-life when compared to non-albumin-binding Nanobodies. Binding to human, rhesus monkey and mouse serum albumin was observed, when analyzed using surface plasmon resonance (SPR).

TABLE F

Binding Analyses of F023700925 to human, Rhesus Monkey and Mouse Serum Albumin

| | Human serum albumin | | | Rhesus serum albumin | | | Mouse serum albumin | | |
|---|---|---|---|---|---|---|---|---|---|
| | Ka (1/Ms) | Kd (1/s) | KD (M) | Ka (1/Ms) | Kd (1/s) | KD (M) | Ka (1/Ms) | Kd (1/s) | KD (M) |
| F023700912 | 9.4E+04 | 8.8E−03 | 9.3E−08 | 9.5E+04 | 8.9E−03 | 9.3E−08 | 1.2E+05 | 1.8E−01 | 1.5E−06 |
| F023700925 | 3.4E+04 | 7.6E−03 | 2.2E−07 | 3.3E+04 | 8.1E−03 | 2.4E−07 | 4.8E+04 | 1.5E−01 | 3.1E−06 |

Figure 12A:
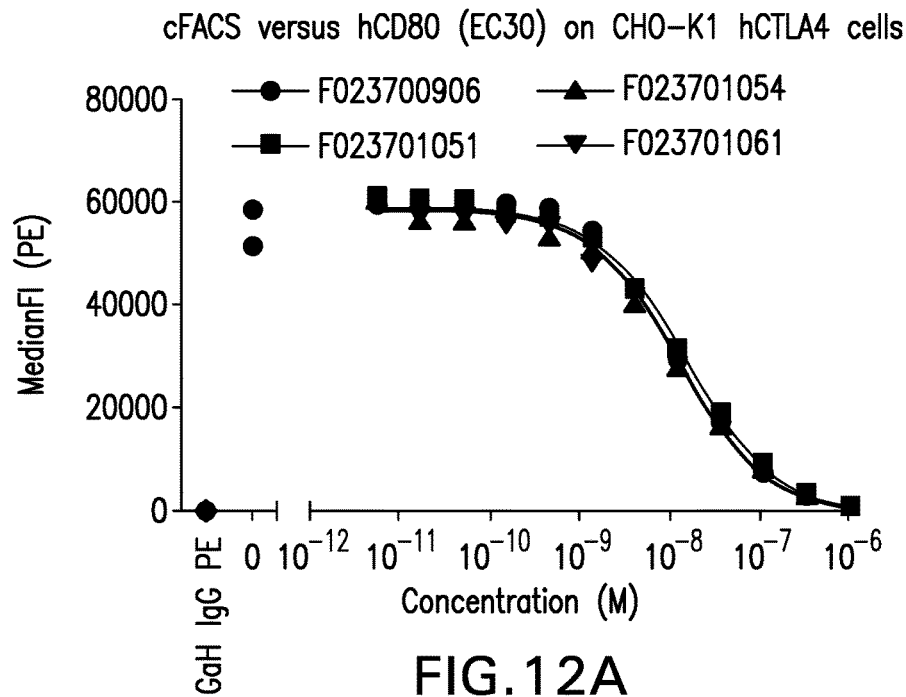
FIG. 12 (A-B). Blockage of binding of human CTLA4 (on CHO-K1 cells) to (A) human CD80 or (B) human CD86 by Nanobodies F02370906, F02371051, F023701054 or F023701061.
Figure 12B:
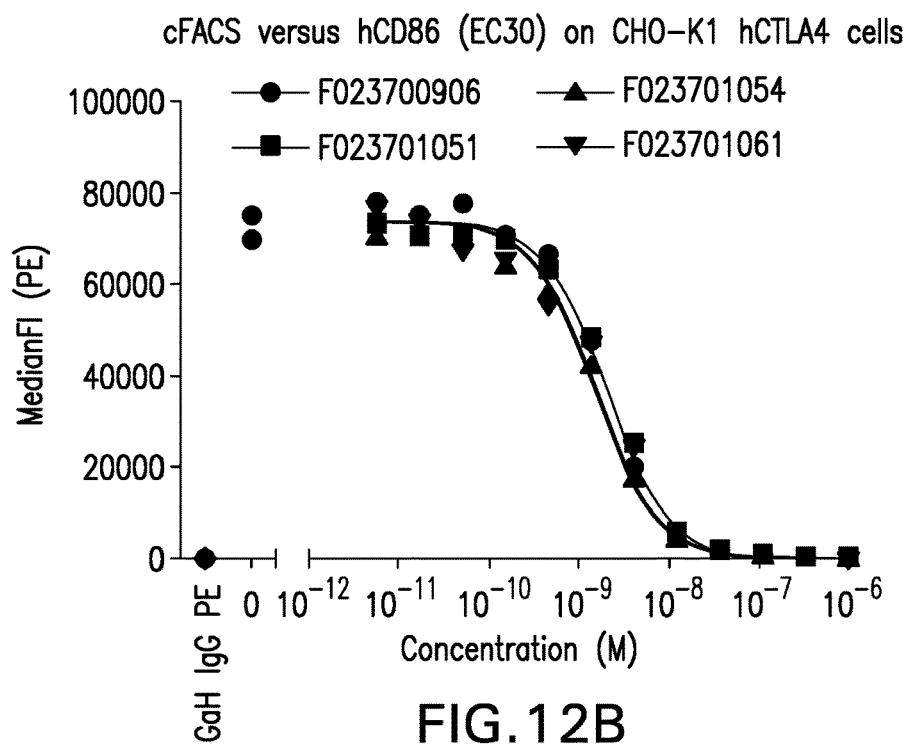
Figure 13A:
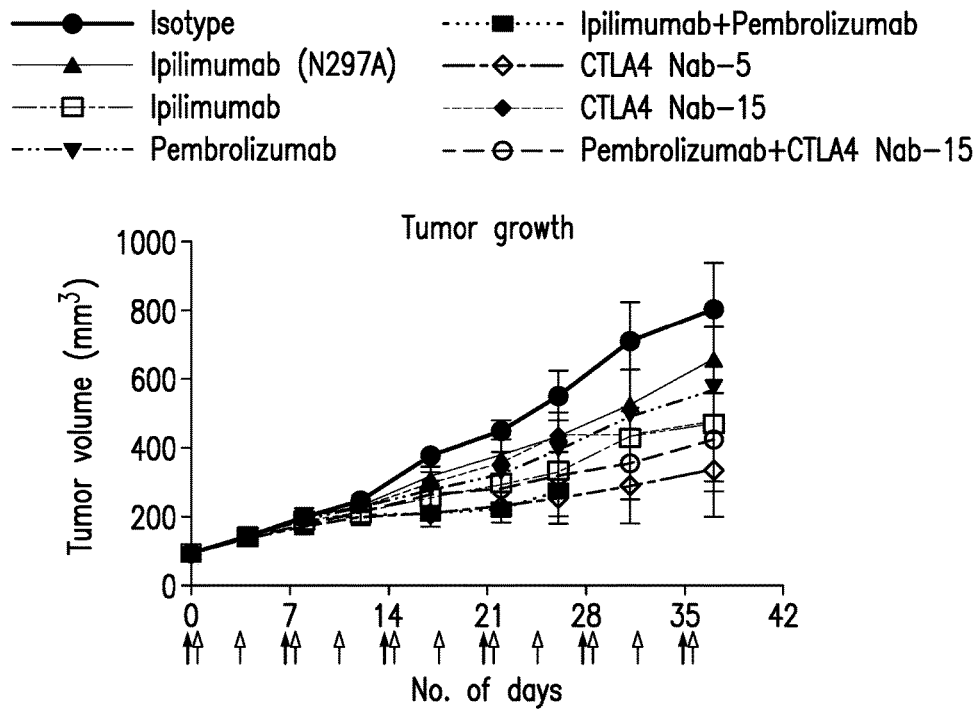
FIG. 13 (A-J). Average panc08/.13 tumor volumes±SEM (A), and individual tumor volumes on day 37 (B), and tumor volumes in individual humanized mice over the course of the experiment in mice treated with (C) isotype control antibody, (D) ipilimumab (N297A), (E) ipilimumab, (F) pembrolizumab, (G) ipilimumab+pembrolizumab, (H) CTLA4 Nanobody F023700912 (5 mpk), (I) CTLA4 Nanobody F023700912 (15 mpk) or (J) pembrolizumab+CTLA4 Nanobody F023700912 (15 mpk).
Figure 13B:
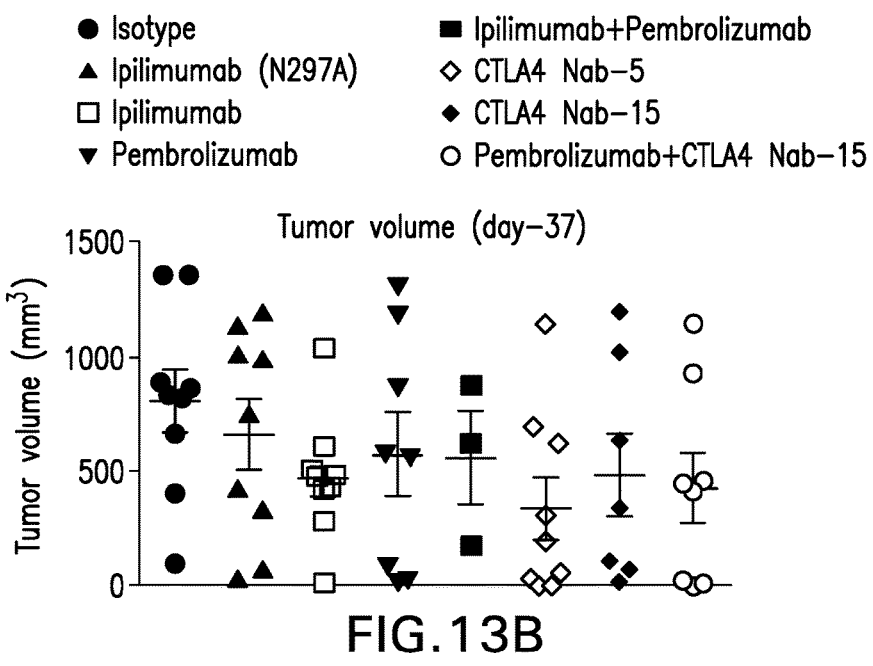
Figure 13C:
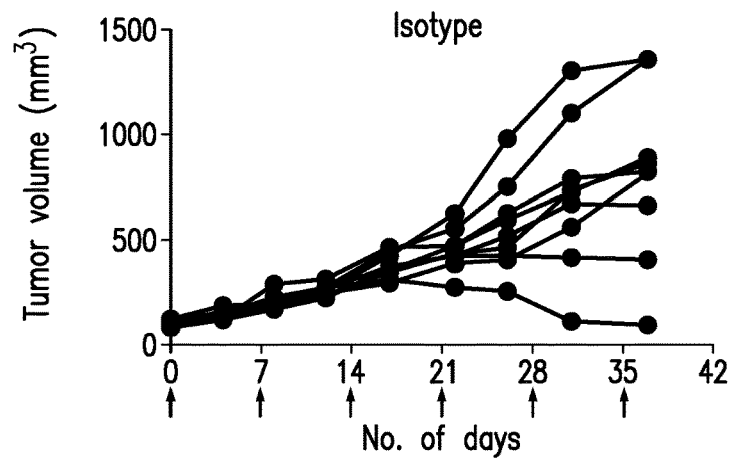
Figure 13D:
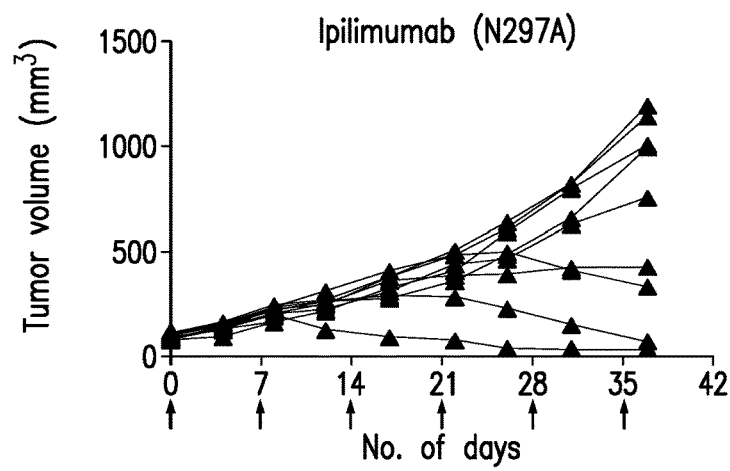
Figure 13E:
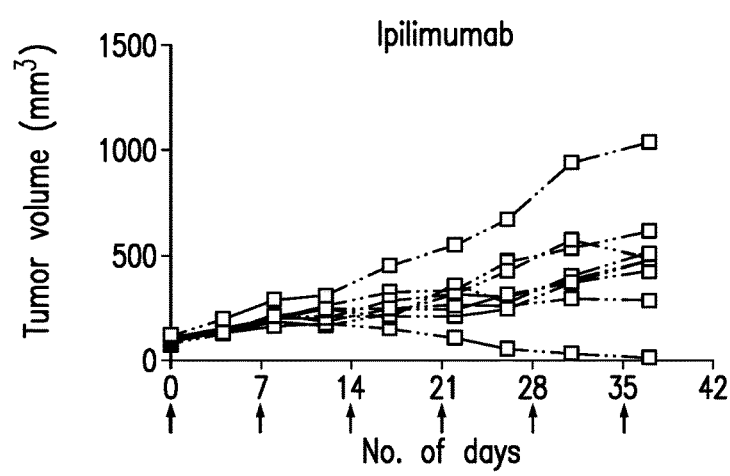
Figure 13F:
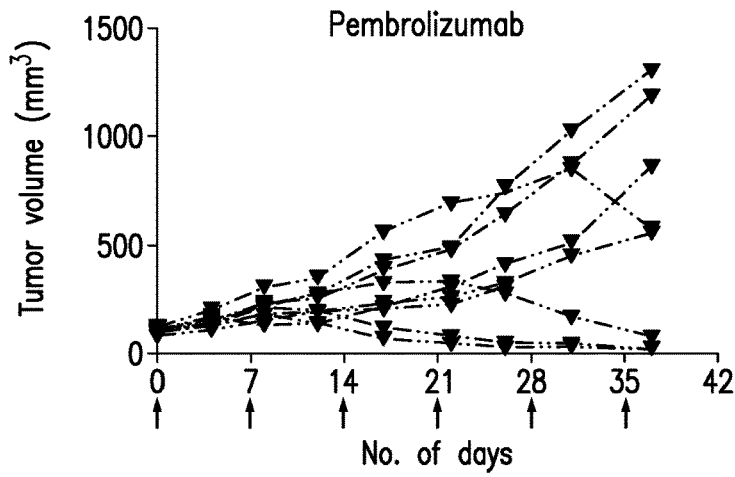
Figure 13G:
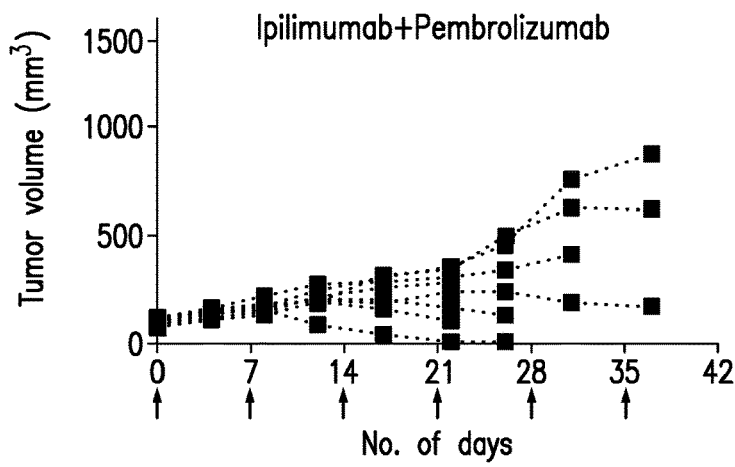
Figure 13H:
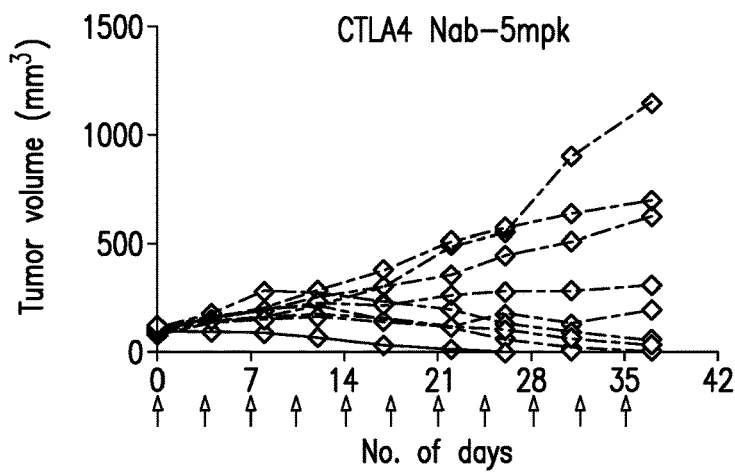
Figure 13I:
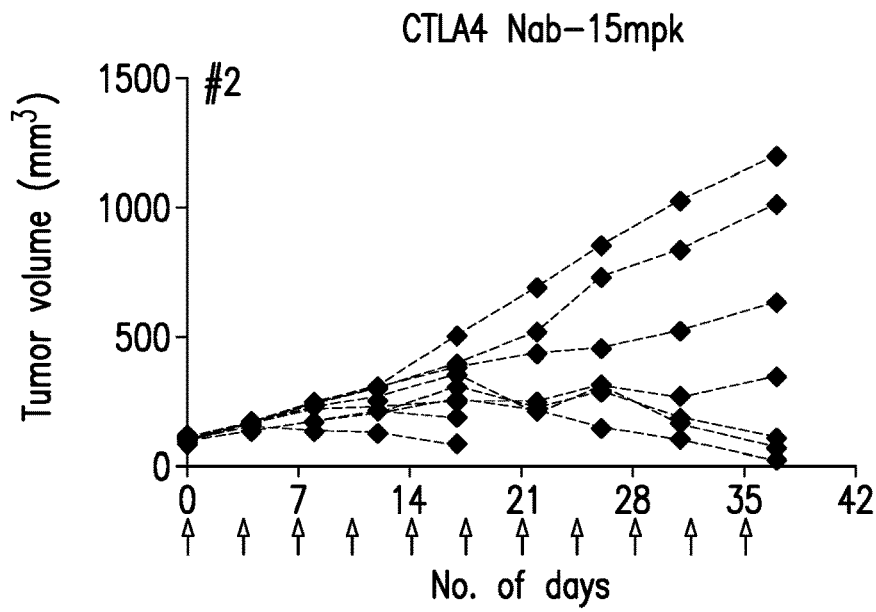
Figure 13J:
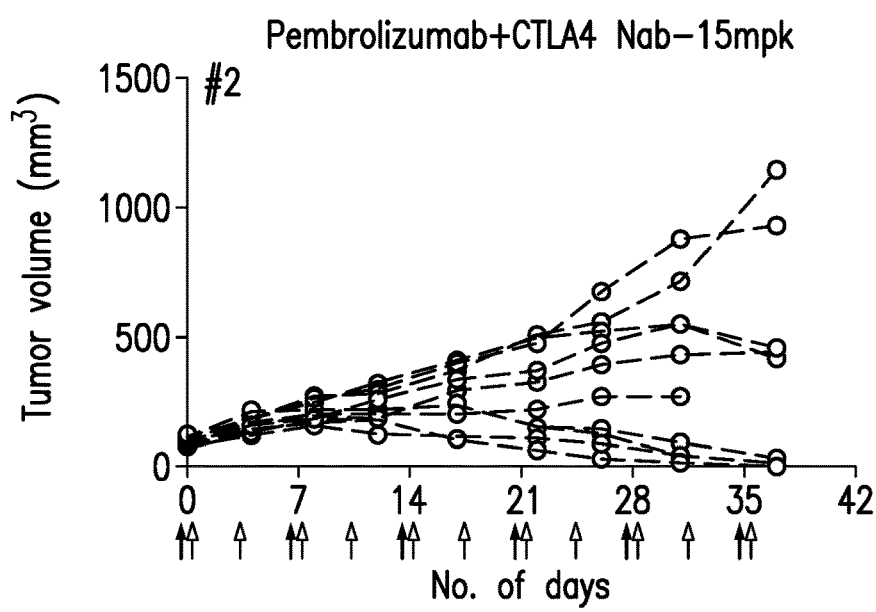

Human serum albumin: cat A3782, Sigma, lot. SLBD7204V
Rhesus monkey serum albumin: BioWorld, cat 22070099-1, lot L15091001DA,
Mouse plasma albumin: Innovative Research, lot 1012,
Instrument and sensor chip: Biacore T100 (GE Healthcare); CMS (ID T160713-2, GE Healthcare, lot 10242599
F023700912 is 11F01 (E1D, Lily, A14P, Q45R, A74S, K83R, V89L, M96P, Q108L)-35GS-11F01 (Lily, A14P, Q45R, A74S, K83R, V89L, M96P, Q108L)-35GS-ALB11002-A Examples 7: Binding Kinetic Analyses of Variants Several variants of F023700906, a building block of F023700925, at position N73 were generated to avoid deamidation at this site. All possible substitutions were evaluated in off-rate along with the current SO F023700906 (Table G). Variants F023701051 [11F01 (L11V,A14P,Q45R,N73Q,A74S,K83R,V89L,M96P,Q108L)-FLAG3-HIS6], F023701054 [11F01 (L11V,A14P,Q45R,N73T,A74S,K83R,V89L,M96P,Q108L)-FLAG3-HIS6], and F023701061 [11F01 (L11V,A14P,Q45R,N73Y, A74S,K83R,V89L,M96P, Q108L)-FLAG3-HIS6] were compared to F023700906 for their ability to block binding of (A) CD80 or (B) CD86 to CTLA-4 expressing CHO-K1 cells. All these variants were able to block binding of CD80 and CD84 to CTLA-4. The flow cytometry data generated in this experiment are in FIG. 12 (A-B).

Example 8: F023700912 Eradicates Established Solid Tumors in Humanized Mice

Humanized mice (Jackson Laboratories) were implanted with Panc 08.13 tumor cells. Mice with established tumors (~100 mm$^3$, n=9-10/group) were treated as follows: 1-Isotype controls (hIgG1-2 mg/kg and hIgG4-3 mg/kg); 2-Ipilimumab-N297A (3 mg/kg); 3-Ipilimumab (3 mg/kg); 4-Pembrolizumab (2 mg/kg); 5-Ipilimumab (3 mg/kg)+Pembrolizumab (2 mg/kg); 6-F023700912 (5 mg/kg; indicated as CTLA4-Nab 5), 7-F023700912 (15 mg/kg; indicated as CTLA4-Nab-15), and 8-F023700912 (15 mg/kg)+Pembrolizumab (2 mg/kg). All the antibodies were injected subcutaneously every 7 days for 6 doses. F023700912 was administered subcutaneously every 3.5 days for 11 doses. Tumor volume and body weight were measured every 4-5 days. Shown are average tumor volumes±SEM (A), individual tumor volumes on day-37 (B), and tumor volumes in individual mice over the course of the experiment (C). Average (mean±SEM) (D) and individual (E) body weight changes in each treatment group were also shown. Number of mice that were found dead or humanely euthanized due to body weight loss is indicated as '#' '↑' indicates antibody and '↑' indicates Nanobody dosing schedule. The tumor volume data generated in this experiment are in FIG. 13 (A-J). These data demonstrated that F023700912 was highly effective at inhibiting tumor growth.

Example 9: Binding of F023700912 and F023700925 to Pre-Existing Antibodies from Healthy Subjects and Cancer Patients Trivalent reference Nanobody, 013700112 (not modified for reducing the binding of pre-existing antibodies) demonstrated binding to several serum samples derived from (FIG. 14A) healthy subjects or (FIG. 14B) cancer patients. Sequence optimized trivalent Nanobody of similar size, F023700912, demonstrated a lower frequency of binding to the same serum samples. F023700925 comprised the same building blocks as F023700912. Despite the larger size, the pentavalent F023700925 Nanobody exhibited no more binding to pre-existing Abs than the reference Nanobody 013700112. Binding of pre-existing antibodies to Nanobodies captured on human serum albumin (HSA) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 μl/min) and HSA was injected at 10 μg/ml in ProteOn Acetate buffer pH4.5 (flow rate 100 μl/min) to render immobilization levels of approximately 3600 RU. After immobilization, surfaces were deactivated with ethanolamine HCl (flow rate 30 μl/min). Nanobodies were injected for 2 minutes at 45 μl/min over the HSA surface to render a Nanobody capture level of approximately 600 RU for trivalent F023700912 and approximately 1000 RU for pentavalent F023700925. The samples containing pre-existing antibodies were diluted 1:10 in PBS-Tween20 (0.005%) before being injected for 2 minutes at 45 μl/min followed by a subsequent 400 seconds dissociation step. After each cycle (i.e., before a new Nanobody capture and blood sample injection step) the HSA surfaces were regenerated with a 2 minute injection of HCl (100 mM) at 45 μl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-HSA dissociation and 2) non-specific binding to reference ligand lane containing HSA only. Binding levels of pre-existing antibodies were determined by setting report points at 125 seconds (5 seconds after end of association). As a reference, the samples containing pre-existing antibodies were also tested for binding to a trivalent Nanobody not modified for reducing the binding of these pre-existing antibodies (T013700112).

Example 10: Epitope Mapping of Anti-hCTLA4 Nanobody by Hydrogen Deuterium Exchange Mass Spectrometry Contact areas between anti-hCTLA4 Nanobody, F023700912 were determined by use of hydrogen deuterium exchange mass spectrometry (HDX-MS) analysis. HDX-MS measured the incorporation of deuterium into the amide backbone of the protein and changes in this incorporation are influenced by the hydrogen's solvent exposure. A comparison of the deuterium exchange levels in antigen-alone samples and Nanobody-bound samples was done to identify antigen regions that may be in contact with the Nanobody.

The human CTLA4 residues most strongly protected from deuteration by the Nanobody, F023700912 were VRVTVL (Residues 33-38 of SEQ ID NO: 195), ADSQVTEVC (Residues 41-49 of SEQ ID NO: 195) and CKVELMYPP-PYYLG (Residues 93-106 of SEQ ID NO: 195).

TABLE G

Amino Acid Sequences (SEQ ID NO: 195)

Human CTLA4 AMHVAQPAVVLASSRGIASFVCEYASPGKATEVRVTVLR
QADSQVTEVCAATYMMGNELTFLDDSICTGTSSGNQVNL
TIQGLRAMDTGLYICKVELMYPPPYYLGIGNGTQIYVID
PEPCPDSDFHHHHHHHHHGGQ

We claim:

1. A PD1/CTLA4 binder comprising one or more ISVDs that bind to PD1 comprising the amino acid sequence:

```
                                          (SEQ ID NO: 135)
DVQLVESGGG VVQPGGSLRL SCAASGSIAS IHAMGWFRQA

PGKEREFVAV ITWSGGITYY ADSVKGRFTI SRDNSKNTVY

LQMNSLRPED TALYYCAGDK HQSSWYDYWG QGTLVTVSS;
``` or variant SEQ ID NO: 135 wherein D1 substituted with E; and
  one or more ISVDs that bind to CTLA4 comprising the amino acid sequence:

```
                                          (SEQ ID NO: 143)
XVQLVESGGGVVQPGGSLRLSCAASGGTFSFYGMG

WFRQAPGKEREFVADIRTSAGRTYYADSVKGRFTISRDNSKNTVYLQMNS

LRPEDTALYYCAAEPSGISGWDYWGQGTLVTVSS, or (SEQ ID NO: 196)
X1VQLVESGGGVVQPGGSLRLSCAASGGTFSFYGMGWFRQAPGKEREFVA

DIRTSAGRTYYADSVKGRFTISRDX2SKNTVYLQMNSLRPEDTALYYCAA

EPSGISGWDYWGQGTLVTVSS,
``` wherein $X_1$ is D or E and wherein $X_2$ is S, V, G, R, Q, M, H, T, D, E, W, F, K, A, Y or P;
  and, optionally, a half-life extender and/or a C-terminal extender.

2. The PD1/CTLA4 binder of claim 1, wherein the PD1/CTLA4 binder comprises a peptide linker between each ISVD.

3. The PD1/CTLA4 binder of claim 1, wherein the PD1/CTLA4 binder comprises:
  a PD1 ISVD comprising the amino acid sequence set forth in SEQ ID NO: 135;
  a 35GS linker comprising the amino acid sequence set forth in SEQ ID NO: 86;
  a CTLA4 ISVD comprising the amino acid sequence set forth in SEQ ID NO: 143 or variant of SEQ ID NO: 196 wherein $X_1$ is substituted with E;
  a 35GS linker comprising the amino acid sequence set forth in SEQ ID NO: 86;
  a HSA ISVD comprising the amino acid sequence set forth in SEQ ID NO: 144; and
  a C-terminal Alanine.

4. The PD1/CTLA4 binder of claim 1, wherein the PD1/CTLA4 binder comprises
  a PD1 ISVD comprising the amino acid sequence set forth in SEQ ID NO: 135;
  a 35GS linker comprising the amino acid sequence set forth in SEQ ID NO: 86;
  a PD1 ISVD comprising the amino acid sequence set forth in SEQ ID NO: 135 or variant of SEQ ID NO: 135 wherein D1 is substituted with E;
  a 35GS linker comprising the amino acid sequence set forth in SEQ ID NO: 86;
  a CTLA4 ISVD comprising the amino acid sequence set forth in SEQ ID NO: 143 or variant of SEQ ID NO: 196 wherein $X_1$ is substituted with E;
  a 35GS linker comprising the amino acid sequence set forth in SEQ ID NO: 86;
  a HSA ISVD comprising the amino acid sequence set forth in SEQ ID NO: 144; and
  a C-terminal Alanine.

5. The PD1/CTLA4 binder of claim 1, wherein the PD1/CTLA4 binder comprises
  a PD1 ISVD comprising the amino acid sequence set forth in SEQ ID NO: 135;
  a 35GS linker comprising the amino acid sequence set forth in SEQ ID NO: 86;
  a CTLA4 ISVD comprising the amino acid sequence set forth in SEQ ID NO: 143 or variant of SEQ ID NO: 196 wherein $X_1$ is substituted with E;
  a 35GS linker comprising the amino acid sequence set forth in SEQ ID NO: 86;
  a CTLA4 ISVD comprising the amino acid sequence set forth in SEQ ID NO: 143 or variant of SEQ ID NO: 196 wherein $X_1$ is substituted with E;
  a 35GS linker comprising the amino acid sequence set forth in SEQ ID NO: 86;
  a HSA ISVD comprising the amino acid sequence set forth in SEQ ID NO: 144; and
  a C-terminal Alanine.

6. The PD1/CTLA4 binder of claim 1, wherein the PD1/CTLA4 binder comprises
  a PD1 ISVD comprising the amino acid sequence set forth in SEQ ID NO: 135;
  a 35GS linker comprising the amino acid sequence set forth in SEQ ID NO: 86;
  a PD1 ISVD comprising the amino acid sequence set forth in SEQ ID NO: 135 or variant of SEQ ID NO: 135 wherein D1 is substituted with E;
  a 35GS linker comprising the amino acid sequence set forth in SEQ ID NO: 86;
  a CTLA4 ISVD comprising the amino acid sequence set forth in SEQ ID NO: 143 or variant of SEQ ID NO: 196 wherein $X_1$ is substituted with E;
  a 35GS linker comprising the amino acid sequence set forth in SEQ ID NO: 86;
  a CTLA4 ISVD comprising the amino acid sequence set forth in SEQ ID NO: 143 or variant of SEQ ID NO: 196 wherein $X_1$ is substituted with E;
  a 35GS linker comprising the amino acid sequence set forth in SEQ ID NO: 86;
  a HSA ISVD comprising the amino acid sequence set forth in SEQ ID NO: 144; and
  a C-terminal Alanine.

7. The PD1/CTLA4 binder of claim 2, wherein the PD1/CTLA4 binder comprises a peptide linker wherein the peptide linker comprises the amino acid sequence GGGGSGGGGSGGGGSGGGGSGGGGSGGGGSGGGGS (SEQ ID NO: 86).

8. The PD1/CTLA4 binder of claim 1, wherein the PD1/CTLA4 binder comprises the amino acid sequence set forth in SEQ ID NO: 146, 149, 151 or 153.

9. The PD1/CTLA4 binder of claim 1, wherein the PD1/CTLA4 binder comprises a half-life extender which is a human serum albumin ISVD which comprises:
- CDR1 comprising the amino acid sequence GFTFSSFGMS (SEQ ID NO: 199) or SFGMS (amino acids 6-10 of SEQ ID NO: 199);
- CDR2 comprising the amino acid sequence SISGSGSDTL (SEQ ID NO: 200) or SISGSGSDTL (amino acids 1-10 of SEQ ID NO: 200); and
- CDR3 comprising the amino acid sequence GGSLSR (SEQ ID NO: 201).

10. The PD1/CTLA4 binder of claim 1, wherein the PD1/CTLA4 binder comprises a half-life extender which is an ISVD that binds to human serum albumin and comprises the amino acid sequence:

```
                                        (SEQ ID NO: 144)
EVQLVESGGG VVQPGNSLRL SCAASGFTFS SFGMSWVRQA

PGKGLEWVSS ISGSGSDTLYADSVKGRFTI SRDNAKTTLY

LQMNSLRPED TALYYCTIGG SLSRSSQGTL VTVSSA.
```

11. The PD1/CTLA4 binder of claim 1, wherein the PD1/CTLA4 binder comprises a C-terminal extender which is an Alanine.

12. A PD1/CTLA4 binder produced by introducing a polynucleotide encoding the PD1/CTLA4 binder of claim 1 into a host cell and culturing the host cell in a medium under conditions favorable to expression of said PD1/CTLA4 binder from said polynucleotide and, optionally, purifying the PD1/CTLA4 binder from said host cell and/or said medium.

13. A composition comprising the PD1/CTLA4 binder of claim 1 and a pharmaceutically accepted carrier.

14. A PD1/CTLA4 binder comprising the amino acid sequence set forth in SEQ ID NO:146, SEQ ID NO:149; SEQ ID NO:151, or SEQ ID NO:153.

15. A composition comprising the PD1/CTLA4 binder of claim 14 and a pharmaceutically acceptable carrier.

* * * * *

SEQUENCE LISTING

<160> NUMBER OF SEQ ID NOS: 201

<210> SEQ ID NO 1
<211> LENGTH: 119
<212> TYPE: PRT
<213> ORGANISM: Artificial Sequence
<220> FEATURE:
<223> OTHER INFORMATION: humanized lama

<400> SEQUENCE: 1

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Gln Val Thr Val Ser Ser
        115

<210> SEQ ID NO 2
<211> LENGTH: 119
<212> TYPE: PRT
<213> ORGANISM: Artificial Sequence
<220> FEATURE:
<223> OTHER INFORMATION: humanized lama

<400> SEQUENCE: 2

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

```
Ala Gly Asp Lys His Gln Ser Ser Trp Tyr Asp Tyr Trp Gly Gln Gly
            100                 105                 110
Thr Leu Val Thr Val Ser Ser
        115

<210> SEQ ID NO 3
<211> LENGTH: 5
<212> TYPE: PRT
<213> ORGANISM: Lama

<400> SEQUENCE: 3

Ile His Ala Met Gly
1               5

<210> SEQ ID NO 4
<211> LENGTH: 17
<212> TYPE: PRT
<213> ORGANISM: Lama
<220> FEATURE:
<221> NAME/KEY: MISC_FEATURE
<222> LOCATION: (4)..(4)
<223> OTHER INFORMATION: X is W or V

<400> SEQUENCE: 4

Val Ile Thr Xaa Ser Gly Gly Ile Thr Tyr Tyr Ala Asp Ser Val Lys
1               5                   10                  15
Gly

<210> SEQ ID NO 5
<211> LENGTH: 10
<212> TYPE: PRT
<213> ORGANISM: Lama
<220> FEATURE:
<221> NAME/KEY: MISC_FEATURE
<222> LOCATION: (7)..(7)
<223> OTHER INFORMATION: X is W or F

<400> SEQUENCE: 5

Asp Lys His Gln Ser Ser Xaa Tyr Asp Tyr
1               5                   10

<210> SEQ ID NO 6
<211> LENGTH: 10
<212> TYPE: PRT
<213> ORGANISM: Lama

<400> SEQUENCE: 6

Gly Ser Ile Ala Ser Ile His Ala Met Gly
1               5                   10

<210> SEQ ID NO 7
<211> LENGTH: 10
<212> TYPE: PRT
<213> ORGANISM: Lama
<220> FEATURE:
<221> NAME/KEY: MISC_FEATURE
<222> LOCATION: (4)..(4)
<223> OTHER INFORMATION: X is W or V

<400> SEQUENCE: 7

Val Ile Thr Xaa Ser Gly Gly Ile Thr Tyr
1               5                   10

<210> SEQ ID NO 8
<211> LENGTH: 10
<212> TYPE: PRT
```

```
<213> ORGANISM: Lama
<220> FEATURE:
<221> NAME/KEY: MISC_FEATURE
<222> LOCATION: (7)..(7)
<223> OTHER INFORMATION: X is W or F

<400> SEQUENCE: 8

Asp Lys His Gln Ser Ser Xaa Tyr Asp Tyr
1               5                  10

<210> SEQ ID NO 9
<211> LENGTH: 119
<212> TYPE: PRT
<213> ORGANISM: Artificial Sequence
<220> FEATURE:
<223> OTHER INFORMATION: humanized lama

<400> SEQUENCE: 9

Glu Val Gln Leu Val Glu Ser Gly Gly Gly Leu Val Gln Ala Gly Gly
1               5                  10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Ser Ser
        115

<210> SEQ ID NO 10
<211> LENGTH: 5
<212> TYPE: PRT
<213> ORGANISM: Lama

<400> SEQUENCE: 10

Phe Tyr Gly Met Gly
1               5

<210> SEQ ID NO 11
<211> LENGTH: 17
<212> TYPE: PRT
<213> ORGANISM: Lama

<400> SEQUENCE: 11

Asp Ile Arg Thr Ser Ala Gly Arg Thr Tyr Tyr Ala Asp Ser Val Lys
1               5                  10                  15

Gly

<210> SEQ ID NO 12
<211> LENGTH: 10
<212> TYPE: PRT
<213> ORGANISM: Lama
<220> FEATURE:
<221> NAME/KEY: MISC_FEATURE
<222> LOCATION: (2)..(2)
<223> OTHER INFORMATION: X is M or P
```

```
<400> SEQUENCE: 12

Glu Xaa Ser Gly Ile Ser Gly Trp Asp Tyr
1               5                   10

<210> SEQ ID NO 13
<211> LENGTH: 10
<212> TYPE: PRT
<213> ORGANISM: Lama

<400> SEQUENCE: 13

Gly Gly Thr Phe Ser Phe Tyr Gly Met Gly
1               5                   10

<210> SEQ ID NO 14
<211> LENGTH: 10
<212> TYPE: PRT
<213> ORGANISM: Lama

<400> SEQUENCE: 14

Asp Ile Arg Thr Ser Ala Gly Arg Thr Tyr
1               5                   10

<210> SEQ ID NO 15
<211> LENGTH: 10
<212> TYPE: PRT
<213> ORGANISM: Lama
<220> FEATURE:
<221> NAME/KEY: MISC_FEATURE
<222> LOCATION: (2)..(2)
<223> OTHER INFORMATION: X is M or P

<400> SEQUENCE: 15

Glu Xaa Ser Gly Ile Ser Gly Trp Asp Tyr
1               5                   10

<210> SEQ ID NO 16
<211> LENGTH: 119
<212> TYPE: PRT
<213> ORGANISM: Artificial Sequence
<220> FEATURE:
<223> OTHER INFORMATION: humanized lama

<400> SEQUENCE: 16

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 17
<211> LENGTH: 119
```

```
<212> TYPE: PRT
<213> ORGANISM: Artificial Sequence
<220> FEATURE:
<223> OTHER INFORMATION: humanized lama

<400> SEQUENCE: 17

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Lys Val Ser Ser
        115

<210> SEQ ID NO 18
<211> LENGTH: 119
<212> TYPE: PRT
<213> ORGANISM: Artificial Sequence
<220> FEATURE:
<223> OTHER INFORMATION: humanized lama

<400> SEQUENCE: 18

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Gln Val Ser Ser
        115

<210> SEQ ID NO 19
<211> LENGTH: 119
<212> TYPE: PRT
<213> ORGANISM: Artificial Sequence
<220> FEATURE:
<223> OTHER INFORMATION: humanized lama

<400> SEQUENCE: 19

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
```

```
                        20                  25                  30
Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Lys Ser
        115

<210> SEQ ID NO 20
<211> LENGTH: 119
<212> TYPE: PRT
<213> ORGANISM: Artificial Sequence
<220> FEATURE:
<223> OTHER INFORMATION: humanized lama

<400> SEQUENCE: 20

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser
        115

<210> SEQ ID NO 21
<211> LENGTH: 119
<212> TYPE: PRT
<213> ORGANISM: Artificial Sequence
<220> FEATURE:
<223> OTHER INFORMATION: humanized lama

<400> SEQUENCE: 21

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Lys Val Ser Ser
        115

<210> SEQ ID NO 22
<211> LENGTH: 119
<212> TYPE: PRT
<213> ORGANISM: Artificial Sequence
<220> FEATURE:
<223> OTHER INFORMATION: humanized lama

<400> SEQUENCE: 22

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Gln Val Ser Ser
        115

<210> SEQ ID NO 23
<211> LENGTH: 119
<212> TYPE: PRT
<213> ORGANISM: Artificial Sequence
<220> FEATURE:
<223> OTHER INFORMATION: humanized lama

<400> SEQUENCE: 23

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Thr Val Lys Ser
        115

<210> SEQ ID NO 24
```

-continued

```
<211> LENGTH: 119
<212> TYPE: PRT
<213> ORGANISM: Artificial Sequence
<220> FEATURE:
<223> OTHER INFORMATION: humanized lama

<400> SEQUENCE: 24

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser
        115

<210> SEQ ID NO 25
<211> LENGTH: 119
<212> TYPE: PRT
<213> ORGANISM: Artificial Sequence
<220> FEATURE:
<223> OTHER INFORMATION: humanized lama

<400> SEQUENCE: 25

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: humanized lama

<400> SEQUENCE: 26

Glu Val Gln Leu Val Glu Ser Gly Gly Gly Val Val Gln Ala Gly Gly
1               5                   10                  15
```

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Lys Val Ser Ser
            115

<210> SEQ ID NO 27
<211> LENGTH: 119
<212> TYPE: PRT
<213> ORGANISM: Artificial Sequence
<220> FEATURE:
<223> OTHER INFORMATION: humanized lama

<400> SEQUENCE: 27

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Gln Val Ser Ser
            115

<210> SEQ ID NO 28
<211> LENGTH: 119
<212> TYPE: PRT
<213> ORGANISM: Artificial Sequence
<220> FEATURE:
<223> OTHER INFORMATION: humanized lama

<400> SEQUENCE: 28

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

```
Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Lys Ser
        115

<210> SEQ ID NO 29
<211> LENGTH: 119
<212> TYPE: PRT
<213> ORGANISM: Artificial Sequence
<220> FEATURE:
<223> OTHER INFORMATION: humanized lama

<400> SEQUENCE: 29

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser
        115

<210> SEQ ID NO 30
<211> LENGTH: 119
<212> TYPE: PRT
<213> ORGANISM: Artificial Sequence
<220> FEATURE:
<223> OTHER INFORMATION: humanized lama

<400> SEQUENCE: 30

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115
```

```
<210> SEQ ID NO 31
<211> LENGTH: 119
<212> TYPE: PRT
<213> ORGANISM: Artificial Sequence
<220> FEATURE:
<223> OTHER INFORMATION: humanized lama

<400> SEQUENCE: 31
```

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

```
<210> SEQ ID NO 32
<211> LENGTH: 120
<212> TYPE: PRT
<213> ORGANISM: Artificial Sequence
<220> FEATURE:
<223> OTHER INFORMATION: humanized lama

<400> SEQUENCE: 32
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Ala
        115                 120

```
<210> SEQ ID NO 33
<211> LENGTH: 120
<212> TYPE: PRT
<213> ORGANISM: Artificial Sequence
<220> FEATURE:
<223> OTHER INFORMATION: humanized lama

<400> SEQUENCE: 33
```

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Lys Val Ser Ser Ala
            115                 120

<210> SEQ ID NO 34
<211> LENGTH: 120
<212> TYPE: PRT
<213> ORGANISM: Artificial Sequence
<220> FEATURE:
<223> OTHER INFORMATION: humanized lama

<400> SEQUENCE: 34

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Gln Val Ser Ser Ala
            115                 120

<210> SEQ ID NO 35
<211> LENGTH: 120
<212> TYPE: PRT
<213> ORGANISM: Artificial Sequence
<220> FEATURE:
<223> OTHER INFORMATION: humanized lama

<400> SEQUENCE: 35

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr

```
                    65                  70                  75                  80
Leu Gln Met Asn Ser Leu Lys Pro Glu Asp Thr Ala Ile Tyr Tyr Cys
                    85                  90                  95

Ala Gly Asp Lys His Gln Ser Ser Trp Tyr Asp Tyr Trp Gly Gln Gly
            100                 105                 110

Thr Leu Val Thr Val Lys Ser Ala
            115                 120

<210> SEQ ID NO 36
<211> LENGTH: 120
<212> TYPE: PRT
<213> ORGANISM: Artificial Sequence
<220> FEATURE:
<223> OTHER INFORMATION: humanized lama

<400> SEQUENCE: 36

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser Ala
            115                 120

<210> SEQ ID NO 37
<211> LENGTH: 120
<212> TYPE: PRT
<213> ORGANISM: Artificial Sequence
<220> FEATURE:
<223> OTHER INFORMATION: humanized lama

<400> SEQUENCE: 37

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Lys Val Ser Ser Ala
            115                 120
```

<210> SEQ ID NO 38
<211> LENGTH: 120
<212> TYPE: PRT
<213> ORGANISM: Artificial Sequence
<220> FEATURE:
<223> OTHER INFORMATION: humanized lama

<400> SEQUENCE: 38

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Gln Val Ser Ser Ala
        115                 120

<210> SEQ ID NO 39
<211> LENGTH: 120
<212> TYPE: PRT
<213> ORGANISM: Artificial Sequence
<220> FEATURE:
<223> OTHER INFORMATION: humanized lama

<400> SEQUENCE: 39

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Lys Ser Ala
        115                 120

<210> SEQ ID NO 40
<211> LENGTH: 120
<212> TYPE: PRT
<213> ORGANISM: Artificial Sequence
<220> FEATURE:
<223> OTHER INFORMATION: humanized lama

<400> SEQUENCE: 40

Glu Val Gln Leu Val Glu Ser Gly Gly Gly Leu Val Gln Ala Gly Gly

-continued

```
                1               5                  10                  15
Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
            50                  55                  60

Lys Gly Arg Phe Thr Ile Ser Arg Asp Asn Ala Lys Asn Thr Val Tyr
65                      70                  75                  80

Leu Gln Met Asn Ser Leu Lys Pro Glu Asp Thr Ala Leu Tyr Tyr Cys
                    85                  90                  95

Ala Gly Asp Lys His Gln Ser Ser Trp Tyr Asp Tyr Trp Gly Gln Gly
                100                 105                 110

Thr Leu Val Thr Val Gln Ser Ala
            115                 120

<210> SEQ ID NO 41
<211> LENGTH: 120
<212> TYPE: PRT
<213> ORGANISM: Artificial Sequence
<220> FEATURE:
<223> OTHER INFORMATION: humanized lama

<400> SEQUENCE: 41

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
            50                  55                  60

Lys Gly Arg Phe Thr Ile Ser Arg Asp Asn Ala Lys Asn Thr Val Tyr
65                      70                  75                  80

Leu Gln Met Asn Ser Leu Lys Pro Glu Asp Thr Ala Leu Tyr Tyr Cys
                    85                  90                  95

Ala Gly Asp Lys His Gln Ser Ser Trp Tyr Asp Tyr Trp Gly Gln Gly
                100                 105                 110

Thr Leu Val Thr Val Ser Ser Ala
            115                 120

<210> SEQ ID NO 42
<211> LENGTH: 120
<212> TYPE: PRT
<213> ORGANISM: Artificial Sequence
<220> FEATURE:
<223> OTHER INFORMATION: humanized lama

<400> SEQUENCE: 42

Glu Val Gln Leu Val Glu Ser Gly Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
            50                  55                  60
```

```
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Lys Val Ser Ser Ala
        115                 120

<210> SEQ ID NO 43
<211> LENGTH: 120
<212> TYPE: PRT
<213> ORGANISM: Artificial Sequence
<220> FEATURE:
<223> OTHER INFORMATION: humanized lama

<400> SEQUENCE: 43

Glu Val Gln Leu Val Glu Ser Gly Gly Gly Val Val Gln Ala Gly Gly
 1               5                  10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
         35                  40                  45

Ala Val Ile Thr Trp Ser Gly Gly Ile Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Gln Val Ser Ser Ala
        115                 120

<210> SEQ ID NO 44
<211> LENGTH: 120
<212> TYPE: PRT
<213> ORGANISM: Artificial Sequence
<220> FEATURE:
<223> OTHER INFORMATION: humanized lama

<400> SEQUENCE: 44

Glu Val Gln Leu Val Glu Ser Gly Gly Gly Val Val Gln Ala Gly Gly
 1               5                  10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
         35                  40                  45

Ala Val Ile Thr Trp Ser Gly Gly Ile Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Gly Asp Lys His Gln Ser Ser Trp Tyr Asp Tyr Trp Gly Gln Gly
            100                 105                 110

Thr Leu Val Thr Val Lys Ser Ala
        115                 120
```

<210> SEQ ID NO 45
<211> LENGTH: 120
<212> TYPE: PRT
<213> ORGANISM: Artificial Sequence
<220> FEATURE:
<223> OTHER INFORMATION: humanized lama

<400> SEQUENCE: 45

```
Glu Val Gln Leu Val Glu Ser Gly Gly Val Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Gln Ser Ala
        115                 120
```

<210> SEQ ID NO 46
<211> LENGTH: 120
<212> TYPE: PRT
<213> ORGANISM: Artificial Sequence
<220> FEATURE:
<223> OTHER INFORMATION: humanized lama

<400> SEQUENCE: 46

```
Glu Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Ala
        115                 120
```

<210> SEQ ID NO 47
<211> LENGTH: 120
<212> TYPE: PRT
<213> ORGANISM: Artificial Sequence
<220> FEATURE:
<223> OTHER INFORMATION: humanized lama

<400> SEQUENCE: 47

```
Asp Val Gln Leu Val Glu Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Ala
        115                 120
```

<210> SEQ ID NO 48
<211> LENGTH: 119
<212> TYPE: PRT
<213> ORGANISM: Artificial Sequence
<220> FEATURE:
<223> OTHER INFORMATION: humanized lama

<400> SEQUENCE: 48

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Ser Ser
        115
```

<210> SEQ ID NO 49
<211> LENGTH: 119
<212> TYPE: PRT
<213> ORGANISM: Artificial Sequence
<220> FEATURE:
<223> OTHER INFORMATION: humanized lama

<400> SEQUENCE: 49

```
Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60
```

```
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Glu Met Ser Gly Ile Ser Gly Trp Asp Tyr Trp Gly Gln Gly
            100                 105                 110

Thr Gln Val Lys Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: humanized lama

<400> SEQUENCE: 50

Glu Val Gln Leu Val Glu Ser Gly Gly Gly Val Val Gln Ala Gly Gly
 1               5                  10                  15

Ser Leu Arg Leu Ser Cys Ala Ala Ser Gly Gly Thr Phe Ser Phe Tyr
             20                  25                  30

Gly Met Gly Trp Phe Arg Gln Ala Pro Gly Lys Glu Gln Glu Phe Val
         35                  40                  45

Ala Asp Ile Arg Thr Ser Ala Gly Arg Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Glu Met Ser Gly Ile Ser Gly Trp Asp Tyr Trp Gly Gln Gly
            100                 105                 110

Thr Gln Val Gln Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: humanized lama

<400> SEQUENCE: 51

Glu Val Gln Leu Val Glu Ser Gly Gly Gly Val Val Gln Ala Gly Gly
 1               5                  10                  15

Ser Leu Arg Leu Ser Cys Ala Ala Ser Gly Gly Thr Phe Ser Phe Tyr
             20                  25                  30

Gly Met Gly Trp Phe Arg Gln Ala Pro Gly Lys Glu Gln Glu Phe Val
         35                  40                  45

Ala Asp Ile Arg Thr Ser Ala Gly Arg Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Glu Met Ser Gly Ile Ser Gly Trp Asp Tyr Trp Gly Gln Gly
            100                 105                 110

Thr Gln Val Thr Val Lys Ser
```

<210> SEQ ID NO 52
<211> LENGTH: 119
<212> TYPE: PRT
<213> ORGANISM: Artificial Sequence
<220> FEATURE:
<223> OTHER INFORMATION: humanized lama

<400> SEQUENCE: 52

```
Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Gln Ser
        115
```

<210> SEQ ID NO 53
<211> LENGTH: 119
<212> TYPE: PRT
<213> ORGANISM: Artificial Sequence
<220> FEATURE:
<223> OTHER INFORMATION: humanized lama

<400> SEQUENCE: 53

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Lys Val Ser Ser
        115
```

<210> SEQ ID NO 54
<211> LENGTH: 119
<212> TYPE: PRT
<213> ORGANISM: Artificial Sequence
<220> FEATURE:
<223> OTHER INFORMATION: humanized lama

<400> SEQUENCE: 54

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Gln Val Ser Ser
        115
```

<210> SEQ ID NO 55
<211> LENGTH: 119
<212> TYPE: PRT
<213> ORGANISM: Artificial Sequence
<220> FEATURE:
<223> OTHER INFORMATION: humanized lama

<400> SEQUENCE: 55

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Lys Ser
        115
```

<210> SEQ ID NO 56
<211> LENGTH: 119
<212> TYPE: PRT
<213> ORGANISM: Artificial Sequence
<220> FEATURE:
<223> OTHER INFORMATION: humanized lama

<400> SEQUENCE: 56

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
```

```
                50                  55                  60
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110

Thr Gln Val Thr Val Gln Ser
            115

<210> SEQ ID NO 57
<211> LENGTH: 119
<212> TYPE: PRT
<213> ORGANISM: Artificial Sequence
<220> FEATURE:
<223> OTHER INFORMATION: humanized lama

<400> SEQUENCE: 57

Glu Val Gln Leu Val Glu Ser Gly Gly Gly Val Val Gln Ala Gly Gly
 1               5                  10                  15

Ser Leu Arg Leu Ser Cys Ala Ala Ser Gly Gly Thr Phe Ser Phe Tyr
                20                  25                  30

Gly Met Gly Trp Phe Arg Gln Ala Pro Gly Lys Glu Gln Glu Phe Val
             35                  40                  45

Ala Asp Ile Arg Thr Ser Ala Gly Arg Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110

Thr Gln Val Thr Val Ser Ser
            115

<210> SEQ ID NO 58
<211> LENGTH: 119
<212> TYPE: PRT
<213> ORGANISM: Artificial Sequence
<220> FEATURE:
<223> OTHER INFORMATION: humanized lama

<400> SEQUENCE: 58

Glu Val Gln Leu Val Glu Ser Gly Gly Gly Val Val Gln Ala Gly Gly
 1               5                  10                  15

Ser Leu Arg Leu Ser Cys Ala Ala Ser Gly Gly Thr Phe Ser Phe Tyr
                20                  25                  30

Gly Met Gly Trp Phe Arg Gln Ala Pro Gly Lys Glu Gln Glu Phe Val
             35                  40                  45

Ala Asp Ile Arg Thr Ser Ala Gly Arg Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110
```

Thr Gln Val Lys Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: humanized lama

<400> SEQUENCE: 59

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Gln Val Ser Ser
        115

<210> SEQ ID NO 60
<211> LENGTH: 119
<212> TYPE: PRT
<213> ORGANISM: Artificial Sequence
<220> FEATURE:
<223> OTHER INFORMATION: humanized lama

<400> SEQUENCE: 60

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Lys Ser
        115

<210> SEQ ID NO 61
<211> LENGTH: 119
<212> TYPE: PRT
<213> ORGANISM: Artificial Sequence
<220> FEATURE:
<223> OTHER INFORMATION: humanized lama

<400> SEQUENCE: 61

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Gln Ser
        115

<210> SEQ ID NO 62
<211> LENGTH: 119
<212> TYPE: PRT
<213> ORGANISM: Artificial Sequence
<220> FEATURE:
<223> OTHER INFORMATION: humanized lama

<400> SEQUENCE: 62

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: humanized lama

<400> SEQUENCE: 63

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

```
Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Met Ser Gly Ile Ser Gly Trp Asp Tyr Trp Gly Gln Gly
            100                 105                 110

Thr Leu Val Thr Val Ser Ser
            115

<210> SEQ ID NO 64
<211> LENGTH: 119
<212> TYPE: PRT
<213> ORGANISM: Artificial Sequence
<220> FEATURE:
<223> OTHER INFORMATION: humanized lama

<400> SEQUENCE: 64

Asp Val Gln Leu Val Glu Ser Gly Gly Gly Val Val Gln Pro Gly Gly
  1               5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Glu Gln Glu Phe Val
             35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Met Ser Gly Ile Ser Gly Trp Asp Tyr Trp Gly Gln Gly
            100                 105                 110

Thr Leu Val Thr Val Ser Ser
            115

<210> SEQ ID NO 65
<211> LENGTH: 119
<212> TYPE: PRT
<213> ORGANISM: Artificial Sequence
<220> FEATURE:
<223> OTHER INFORMATION: humanized lama

<400> SEQUENCE: 65

Asp Val Gln Leu Val Glu Ser Gly Gly Gly Val Val Gln Pro Gly Gly
  1               5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Glu Arg Glu Phe Val
             35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Met Ser Gly Ile Ser Gly Trp Asp Tyr Trp Gly Gln Gly
            100                 105                 110
```

```
Thr Leu Val Thr Val Ser Ser
        115

<210> SEQ ID NO 66
<211> LENGTH: 120
<212> TYPE: PRT
<213> ORGANISM: Artificial Sequence
<220> FEATURE:
<223> OTHER INFORMATION: humanized lama

<400> SEQUENCE: 66

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Ser Ser Ala
        115                 120

<210> SEQ ID NO 67
<211> LENGTH: 120
<212> TYPE: PRT
<213> ORGANISM: Artificial Sequence
<220> FEATURE:
<223> OTHER INFORMATION: humanized lama

<400> SEQUENCE: 67

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Lys Val Ser Ser Ala
        115                 120

<210> SEQ ID NO 68
<211> LENGTH: 120
<212> TYPE: PRT
<213> ORGANISM: Artificial Sequence
<220> FEATURE:
<223> OTHER INFORMATION: humanized lama
```

<400> SEQUENCE: 68

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Gln Val Ser Ser Ala
        115                 120

<210> SEQ ID NO 69
<211> LENGTH: 120
<212> TYPE: PRT
<213> ORGANISM: Artificial Sequence
<220> FEATURE:
<223> OTHER INFORMATION: humanized lama

<400> SEQUENCE: 69

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Lys Ser Ala
        115                 120

<210> SEQ ID NO 70
<211> LENGTH: 120
<212> TYPE: PRT
<213> ORGANISM: Artificial Sequence
<220> FEATURE:
<223> OTHER INFORMATION: humanized lama

<400> SEQUENCE: 70

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Gln Ser Ala
        115                 120

<210> SEQ ID NO 71
<211> LENGTH: 120
<212> TYPE: PRT
<213> ORGANISM: Artificial Sequence
<220> FEATURE:
<223> OTHER INFORMATION: humanized lama

<400> SEQUENCE: 71

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Lys Val Ser Ser Ala
        115                 120

<210> SEQ ID NO 72
<211> LENGTH: 120
<212> TYPE: PRT
<213> ORGANISM: Artificial Sequence
<220> FEATURE:
<223> OTHER INFORMATION: humanized lama

<400> SEQUENCE: 72

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly 100                 105                 110

Thr Gln Val Gln Val Ser Ser Ala
        115                 120

<210> SEQ ID NO 73
<211> LENGTH: 120
<212> TYPE: PRT
<213> ORGANISM: Artificial Sequence
<220> FEATURE:
<223> OTHER INFORMATION: humanized lama

<400> SEQUENCE: 73

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Lys Ser Ala
        115                 120

<210> SEQ ID NO 74
<211> LENGTH: 120
<212> TYPE: PRT
<213> ORGANISM: Artificial Sequence
<220> FEATURE:
<223> OTHER INFORMATION: humanized lama

<400> SEQUENCE: 74

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Gln Ser Ala
        115                 120

<210> SEQ ID NO 75
<211> LENGTH: 120
<212> TYPE: PRT
<213> ORGANISM: Artificial Sequence
<220> FEATURE:

<223> OTHER INFORMATION: humanized lama

<400> SEQUENCE: 75

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Ser Ser Ala
        115                 120

<210> SEQ ID NO 76
<211> LENGTH: 120
<212> TYPE: PRT
<213> ORGANISM: Artificial Sequence
<220> FEATURE:
<223> OTHER INFORMATION: humanized lama

<400> SEQUENCE: 76

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Lys Val Ser Ser Ala
        115                 120

<210> SEQ ID NO 77
<211> LENGTH: 120
<212> TYPE: PRT
<213> ORGANISM: Artificial Sequence
<220> FEATURE:
<223> OTHER INFORMATION: humanized lama

<400> SEQUENCE: 77

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val

```
                35                  40                  45
Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110

Thr Gln Val Gln Val Ser Ser Ala
        115                 120

<210> SEQ ID NO 78
<211> LENGTH: 120
<212> TYPE: PRT
<213> ORGANISM: Artificial Sequence
<220> FEATURE:
<223> OTHER INFORMATION: humanized lama

<400> SEQUENCE: 78

Glu Val Gln Leu Val Glu Ser Gly Gly Gly Val Val Gln Ala Gly Gly
 1               5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Gln Glu Gln Glu Phe Val
                 35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110

Thr Gln Val Thr Val Lys Ser Ala
        115                 120

<210> SEQ ID NO 79
<211> LENGTH: 120
<212> TYPE: PRT
<213> ORGANISM: Artificial Sequence
<220> FEATURE:
<223> OTHER INFORMATION: humanized lama

<400> SEQUENCE: 79

Glu Val Gln Leu Val Glu Ser Gly Gly Gly Val Val Gln Ala Gly Gly
 1               5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Gln Glu Gln Glu Phe Val
                 35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95
```

Ala Ala Glu Met Ser Gly Ile Ser Gly Trp Asp Tyr Trp Gly Gln Gly
            100                 105                 110

Thr Gln Val Thr Val Gln Ser Ala
        115                 120

<210> SEQ ID NO 80
<211> LENGTH: 120
<212> TYPE: PRT
<213> ORGANISM: Artificial Sequence
<220> FEATURE:
<223> OTHER INFORMATION: humanized lama

<400> SEQUENCE: 80

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Ala
        115                 120

<210> SEQ ID NO 81
<211> LENGTH: 120
<212> TYPE: PRT
<213> ORGANISM: Artificial Sequence
<220> FEATURE:
<223> OTHER INFORMATION: humanized lama

<400> SEQUENCE: 81

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Ala
        115                 120

<210> SEQ ID NO 82
<211> LENGTH: 120
<212> TYPE: PRT
<213> ORGANISM: Artificial Sequence

```
<220> FEATURE:
<223> OTHER INFORMATION: humanized lama

<400> SEQUENCE: 82

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Ala
        115                 120

<210> SEQ ID NO 83
<211> LENGTH: 120
<212> TYPE: PRT
<213> ORGANISM: Artificial Sequence
<220> FEATURE:
<223> OTHER INFORMATION: humanized lama

<400> SEQUENCE: 83

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Ala
        115                 120

<210> SEQ ID NO 84
<211> LENGTH: 115
<212> TYPE: PRT
<213> ORGANISM: Artificial Sequence
<220> FEATURE:
<223> OTHER INFORMATION: humanized lama

<400> SEQUENCE: 84

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30
```

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
                100                 105                 110

Val Ser Ser
        115

<210> SEQ ID NO 85
<211> LENGTH: 115
<212> TYPE: PRT
<213> ORGANISM: Artificial Sequence
<220> FEATURE:
<223> OTHER INFORMATION: humanized lama

<400> SEQUENCE: 85

Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
                100                 105                 110

Val Ser Ser
        115

<210> SEQ ID NO 86
<211> LENGTH: 35
<212> TYPE: PRT
<213> ORGANISM: Artificial Sequence
<220> FEATURE:
<223> OTHER INFORMATION: 35GS linker

<400> SEQUENCE: 86

Gly Gly Gly Gly Ser Gly Gly Gly Ser Gly Gly Gly Gly Ser Gly
 1               5                  10                  15

Gly Gly Gly Ser Gly Gly Gly Ser Gly Gly Gly Gly Ser Gly Gly
                 20                  25                  30

Gly Gly Ser
        35

<210> SEQ ID NO 87
<211> LENGTH: 34
<212> TYPE: PRT
<213> ORGANISM: Artificial Sequence
<220> FEATURE:
<223> OTHER INFORMATION: His6-FLAG3 tag

```
<400> SEQUENCE: 87

His His His His His His Gly Ala Ala Asp Tyr Lys Asp His Asp Gly
1               5                   10                  15

Asp Tyr Lys Asp His Asp Ile Asp Tyr Lys Asp Asp Asp Lys Gly
            20                  25                  30

Ala Ala

<210> SEQ ID NO 88
<211> LENGTH: 5
<212> TYPE: PRT
<213> ORGANISM: Artificial Sequence
<220> FEATURE:
<223> OTHER INFORMATION: C-terminal extender

<400> SEQUENCE: 88

Val Thr Val Lys Ser
1               5

<210> SEQ ID NO 89
<211> LENGTH: 5
<212> TYPE: PRT
<213> ORGANISM: Artificial Sequence
<220> FEATURE:
<223> OTHER INFORMATION: C-terminal extender

<400> SEQUENCE: 89

Val Thr Val Gln Ser
1               5

<210> SEQ ID NO 90
<211> LENGTH: 5
<212> TYPE: PRT
<213> ORGANISM: Artificial Sequence
<220> FEATURE:
<223> OTHER INFORMATION: C-terminal extender

<400> SEQUENCE: 90

Val Lys Val Ser Ser
1               5

<210> SEQ ID NO 91
<211> LENGTH: 5
<212> TYPE: PRT
<213> ORGANISM: Artificial Sequence
<220> FEATURE:
<223> OTHER INFORMATION: C-terminal extender

<400> SEQUENCE: 91

Val Gln Val Ser Ser
1               5

<210> SEQ ID NO 92
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is 1-10 amino acids independently chosen from
      the naturally occurring amino acids

<400> SEQUENCE: 92

Val Thr Val Lys Ser Xaa
1               5
```

```
<210> SEQ ID NO 93
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is 1-10 amino acids independently chosen from
      the naturally occurring amino acids

<400> SEQUENCE: 93

Val Thr Val Gln Ser Xaa
1               5

<210> SEQ ID NO 94
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is 1-10 amino acids independently chosen from
      the naturally occurring amino acids

<400> SEQUENCE: 94

Val Lys Val Ser Ser Xaa
1               5

<210> SEQ ID NO 95
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is 1-10 amino acids independently chosen from
      the naturally occurring amino acids

<400> SEQUENCE: 95

Val Gln Val Ser Ser Xaa
1               5

<210> SEQ ID NO 96
<211> LENGTH: 6
<212> TYPE: PRT
<213> ORGANISM: Artificial Sequence
<220> FEATURE:
<223> OTHER INFORMATION: C-terminal extender

<400> SEQUENCE: 96

Val Thr Val Lys Ser Ala
1               5

<210> SEQ ID NO 97
<211> LENGTH: 6
<212> TYPE: PRT
<213> ORGANISM: Artificial Sequence
<220> FEATURE:
<223> OTHER INFORMATION: C-terminal extender

<400> SEQUENCE: 97

Val Thr Val Gln Ser Ala
```

```
<210> SEQ ID NO 98
<211> LENGTH: 6
<212> TYPE: PRT
<213> ORGANISM: Artificial Sequence
<220> FEATURE:
<223> OTHER INFORMATION: C-terminal extender

<400> SEQUENCE: 98

Val Lys Val Ser Ser Ala
1               5

<210> SEQ ID NO 99
<211> LENGTH: 6
<212> TYPE: PRT
<213> ORGANISM: Artificial Sequence
<220> FEATURE:
<223> OTHER INFORMATION: C-terminal extender

<400> SEQUENCE: 99

Val Gln Val Ser Ser Ala
1               5

<210> SEQ ID NO 100
<211> LENGTH: 5
<212> TYPE: PRT
<213> ORGANISM: Artificial Sequence
<220> FEATURE:
<223> OTHER INFORMATION: C-terminal extender

<400> SEQUENCE: 100

Val Thr Val Ser Ser
1               5

<210> SEQ ID NO 101
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is 1-10 amino acids independently chosen from
      the naturally occurring amino acids

<400> SEQUENCE: 101

Val Thr Val Ser Ser Xaa
1               5

<210> SEQ ID NO 102
<211> LENGTH: 6
<212> TYPE: PRT
<213> ORGANISM: Artificial Sequence
<220> FEATURE:
<223> OTHER INFORMATION: C-terminal extender

<400> SEQUENCE: 102

Val Thr Val Ser Ser Ala
1               5

<210> SEQ ID NO 103
<211> LENGTH: 732
<212> TYPE: PRT
<213> ORGANISM: Artificial Sequence
<220> FEATURE:
<223> OTHER INFORMATION: humanized lama
```

<400> SEQUENCE: 103

```
Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
        195                 200                 205

Gly Gly Ile Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Thr
                325                 330                 335

Phe Ser Tyr Gly Met Gly Trp Phe Arg Gln Ala Pro Gly Lys Glu
            340                 345                 350

Gln Glu Phe Val Ala Asp Ile Arg Thr Ser Ala Gly Arg Thr Tyr Tyr
        355                 360                 365

Ala Asp Ser Val Lys Gly Arg Phe Thr Ile Ser Arg Asp Asn Ser Lys
    370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Met Ser Gly Ile Ser Gly Trp Asp Tyr
```

```
            405                 410                 415
Trp Gly Gln Gly Thr Leu Val Thr Val Ser Ser Gly Gly Gly Ser
            420                 425                 430

Gly Gly Gly Gly Ser Gly Gly Gly Ser Gly Gly Gly Ser Gly
            435                 440                 445

Gly Gly Ser Gly Gly Gly Ser Gly Gly Gly Ser Glu Val
        450             455             460

Gln Leu Val Glu Ser Gly Gly Val Val Gln Pro Gly Gly Ser Leu
465             470                 475                 480

Arg Leu Ser Cys Ala Ala Ser Gly Gly Thr Phe Ser Phe Tyr Gly Met
                485                 490                 495

Gly Trp Phe Arg Gln Ala Pro Gly Lys Glu Gln Glu Phe Val Ala Asp
            500                 505                 510

Ile Arg Thr Ser Ala Gly Arg Thr Tyr Tyr Ala Asp Ser Val Lys Gly
            515                 520                 525

Arg Phe Thr Ile Ser Arg Asp Asn Ser Lys Asn Thr Val Tyr Leu Gln
            530                 535                 540

Met Asn Ser Leu Arg Pro Glu Asp Thr Ala Leu Tyr Tyr Cys Ala Ala
545                 550                 555                 560

Glu Met Ser Gly Ile Ser Gly Trp Asp Tyr Trp Gly Gln Gly Thr Leu
                565                 570                 575

Val Thr Val Ser Ser Gly Gly Gly Gly Ser Gly Gly Gly Gly Ser Gly
            580                 585                 590

Gly Gly Gly Ser Gly Gly Gly Gly Ser Gly Gly Gly Gly Ser Gly Gly
            595                 600                 605

Gly Gly Ser Gly Gly Gly Gly Ser Glu Val Gln Leu Val Glu Ser Gly
        610             615             620

Gly Gly Leu Val Gln Pro Gly Asn Ser Leu Arg Leu Ser Cys Ala Ala
625                 630                 635                 640

Ser Gly Phe Thr Phe Ser Ser Phe Gly Met Ser Trp Val Arg Gln Ala
                645                 650                 655

Pro Gly Lys Gly Leu Glu Trp Val Ser Ser Ile Ser Gly Ser Gly Ser
            660                 665                 670

Asp Thr Leu Tyr Ala Asp Ser Val Lys Gly Arg Phe Thr Ile Ser Arg
            675                 680                 685

Asp Asn Ala Lys Thr Thr Leu Tyr Leu Gln Met Asn Ser Leu Arg Pro
            690                 695                 700

Glu Asp Thr Ala Val Tyr Tyr Cys Thr Ile Gly Gly Ser Leu Ser Arg
705                 710                 715                 720

Ser Ser Gln Gly Thr Leu Val Thr Val Ser Ser Ala
                725                 730

<210> SEQ ID NO 104
<211> LENGTH: 732
<212> TYPE: PRT
<213> ORGANISM: Artificial Sequence
<220> FEATURE:
<223> OTHER INFORMATION: humanized lama

<400> SEQUENCE: 104

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
```

```
                35              40              45
Ala Val Ile Thr Trp Ser Gly Gly Ile Thr Tyr Tyr Ala Asp Ser Val
             50              55              60
Lys Gly Arg Phe Thr Ile Ser Arg Asp Asn Ser Lys Asn Thr Val Tyr
 65              70              75              80
Leu Gln Met Asn Ser Leu Arg Pro Glu Asp Thr Ala Leu Tyr Tyr Cys
                 85              90              95
Ala Gly Asp Lys His Gln Ser Ser Trp Tyr Asp Tyr Trp Gly Gln Gly
            100             105             110
Thr Leu Val Thr Val Ser Ser Gly Gly Gly Ser Gly Gly Gly Gly
            115             120             125
Ser Gly Gly Gly Gly Ser Gly Gly Gly Ser Gly Gly Gly Gly Ser
    130             135             140
Gly Gly Gly Gly Ser Gly Gly Gly Ser Glu Val Gln Leu Val Glu
145             150             155             160
Ser Gly Gly Gly Val Val Gln Pro Gly Gly Ser Leu Arg Leu Ser Cys
                165             170             175
Ala Ala Ser Gly Ser Ile Ala Ser Ile His Ala Met Gly Trp Phe Arg
            180             185             190
Gln Ala Pro Gly Lys Glu Arg Glu Phe Val Ala Val Ile Thr Trp Ser
            195             200             205
Gly Gly Ile Thr Tyr Tyr Ala Asp Ser Val Lys Gly Arg Phe Thr Ile
210             215             220
Ser Arg Asp Asn Ser Lys Asn Thr Val Tyr Leu Gln Met Asn Ser Leu
225             230             235             240
Arg Pro Glu Asp Thr Ala Leu Tyr Tyr Cys Ala Gly Asp Lys His Gln
            245             250             255
Ser Ser Trp Tyr Asp Tyr Trp Gly Gln Gly Thr Leu Val Thr Val Ser
            260             265             270
Ser Gly Gly Gly Gly Ser Gly Gly Gly Gly Ser Gly Gly Gly Gly Ser
            275             280             285
Gly Gly Gly Gly Ser Gly Gly Gly Ser Gly Gly Gly Gly Ser Gly
            290             295             300
Gly Gly Gly Ser Glu Val Gln Leu Val Glu Ser Gly Gly Val Val
305             310             315             320
Gln Pro Gly Gly Ser Leu Arg Leu Ser Cys Ala Ala Ser Gly Gly Thr
            325             330             335
Phe Ser Phe Tyr Gly Met Gly Trp Phe Arg Gln Ala Pro Gly Lys Glu
            340             345             350
Arg Glu Phe Val Ala Asp Ile Arg Thr Ser Ala Gly Arg Thr Tyr Tyr
            355             360             365
Ala Asp Ser Val Lys Gly Arg Phe Thr Ile Ser Arg Asp Asn Ser Lys
            370             375             380
Asn Thr Val Tyr Leu Gln Met Asn Ser Leu Arg Pro Glu Asp Thr Ala
385             390             395             400
Leu Tyr Tyr Cys Ala Ala Glu Met Ser Gly Ile Ser Gly Trp Asp Tyr
                405             410             415
Trp Gly Gln Gly Thr Leu Val Thr Val Ser Ser Gly Gly Gly Ser
            420             425             430
Gly Gly Gly Gly Ser Gly Gly Gly Ser Gly Gly Gly Gly Ser Gly
            435             440             445
Gly Gly Gly Ser Gly Gly Gly Ser Gly Gly Gly Gly Ser Glu Val
            450             455             460
```

```
Gln Leu Val Glu Ser Gly Gly Val Val Gln Pro Gly Gly Ser Leu
465                 470                 475                 480

Arg Leu Ser Cys Ala Ala Ser Gly Gly Thr Phe Ser Phe Tyr Gly Met
                485                 490                 495

Gly Trp Phe Arg Gln Ala Pro Gly Lys Glu Arg Glu Phe Val Ala Asp
                500                 505                 510

Ile Arg Thr Ser Ala Gly Arg Thr Tyr Tyr Ala Asp Ser Val Lys Gly
                515                 520                 525

Arg Phe Thr Ile Ser Arg Asp Asn Ser Lys Asn Thr Val Tyr Leu Gln
                530                 535                 540

Met Asn Ser Leu Arg Pro Glu Asp Thr Ala Leu Tyr Tyr Cys Ala Ala
545                 550                 555                 560

Glu Met Ser Gly Ile Ser Gly Trp Asp Tyr Trp Gly Gln Gly Thr Leu
                565                 570                 575

Val Thr Val Ser Ser Gly Gly Gly Gly Ser Gly Gly Gly Gly Ser Gly
                580                 585                 590

Gly Gly Gly Ser Gly Gly Gly Gly Ser Gly Gly Gly Gly Ser Gly Gly
                595                 600                 605

Gly Gly Ser Gly Gly Gly Gly Ser Glu Val Gln Leu Val Glu Ser Gly
                610                 615                 620

Gly Gly Leu Val Gln Pro Gly Asn Ser Leu Arg Leu Ser Cys Ala Ala
625                 630                 635                 640

Ser Gly Phe Thr Phe Ser Ser Phe Gly Met Ser Trp Val Arg Gln Ala
                645                 650                 655

Pro Gly Lys Gly Leu Glu Trp Val Ser Ser Ile Ser Gly Ser Gly Ser
                660                 665                 670

Asp Thr Leu Tyr Ala Asp Ser Val Lys Gly Arg Phe Thr Ile Ser Arg
                675                 680                 685

Asp Asn Ala Lys Thr Thr Leu Tyr Leu Gln Met Asn Ser Leu Arg Pro
690                 695                 700

Glu Asp Thr Ala Val Tyr Tyr Cys Thr Ile Gly Gly Ser Leu Ser Arg
705                 710                 715                 720

Ser Ser Gln Gly Thr Leu Val Thr Val Ser Ser Ala
                725                 730

<210> SEQ ID NO 105
<211> LENGTH: 732
<212> TYPE: PRT
<213> ORGANISM: Artificial Sequence
<220> FEATURE:
<223> OTHER INFORMATION: humanized lama

<400> SEQUENCE: 105

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
                35                  40                  45

Ala Val Ile Thr Trp Ser Gly Ile Thr Tyr Tyr Ala Asp Ser Val
                50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95
```

```
Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
            130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
            195                 200                 205

Gly Gly Ile Thr Tyr Tyr Ala Asp Ser Val Lys Gly Arg Phe Thr Ile
            210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
            275                 280                 285

Gly Gly Gly Ser Gly Gly Gly Ser Gly Gly Gly Ser Gly
            290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Thr
                325                 330                 335

Phe Ser Phe Tyr Gly Met Gly Trp Phe Arg Gln Ala Pro Gly Lys Glu
            340                 345                 350

Gln Glu Phe Val Ala Asp Ile Arg Thr Ser Ala Gly Arg Thr Tyr Tyr
            355                 360                 365

Ala Asp Ser Val Lys Gly Arg Phe Thr Ile Ser Arg Asp Asn Ser Lys
            370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Met Ser Gly Ile Ser Gly Trp Asp Tyr
                405                 410                 415

Trp Gly Gln Gly Thr Leu Val Thr Val Ser Ser Gly Gly Gly Gly Ser
            420                 425                 430

Gly Gly Gly Gly Ser Gly Gly Gly Gly Ser Gly Gly Gly Gly Ser Gly
            435                 440                 445

Gly Gly Gly Ser Gly Gly Gly Gly Ser Gly Gly Gly Ser Glu Val
            450                 455                 460

Gln Leu Val Glu Ser Gly Gly Val Val Gln Pro Gly Gly Ser Leu
465                 470                 475                 480

Arg Leu Ser Cys Ala Ala Ser Gly Gly Thr Phe Ser Phe Tyr Gly Met
                485                 490                 495

Gly Trp Phe Arg Gln Ala Pro Gly Lys Glu Gln Glu Phe Val Ala Asp
            500                 505                 510
```

```
Ile Arg Thr Ser Ala Gly Arg Thr Tyr Tyr Ala Asp Ser Val Lys Gly
            515                 520                 525

Arg Phe Thr Ile Ser Arg Asp Asn Ser Lys Asn Thr Val Tyr Leu Gln
    530                 535                 540

Met Asn Ser Leu Arg Pro Glu Asp Thr Ala Leu Tyr Tyr Cys Ala Ala
545                 550                 555                 560

Glu Met Ser Gly Ile Ser Gly Trp Asp Tyr Trp Gly Gln Gly Thr Leu
                565                 570                 575

Val Thr Val Ser Ser Gly Gly Gly Ser Gly Gly Gly Ser Gly
            580                 585                 590

Gly Gly Gly Ser Gly Gly Gly Ser Gly Gly Gly Ser Gly Gly
        595                 600                 605

Gly Gly Ser Gly Gly Gly Ser Glu Val Gln Leu Leu Glu Ser Gly
        610                 615                 620

Gly Gly Val Val Gln Pro Gly Gly Ser Leu Arg Leu Ser Cys Ala Ala
625                 630                 635                 640

Ser Gly Phe Thr Phe Arg Ser Phe Gly Met Ser Trp Val Arg Gln Ala
                645                 650                 655

Pro Gly Lys Gly Pro Glu Trp Val Ser Ser Ile Ser Gly Ser Gly Ser
                660                 665                 670

Asp Thr Leu Tyr Ala Asp Ser Val Lys Gly Arg Phe Thr Ile Ser Arg
            675                 680                 685

Asp Asn Ser Lys Asn Thr Leu Tyr Leu Gln Met Asn Ser Leu Arg Pro
    690                 695                 700

Glu Asp Thr Ala Leu Tyr Tyr Cys Thr Ile Gly Gly Ser Leu Ser Arg
705                 710                 715                 720

Ser Ser Gln Gly Thr Leu Val Thr Val Ser Ser Ala
                725                 730

<210> SEQ ID NO 106
<211> LENGTH: 732
<212> TYPE: PRT
<213> ORGANISM: Artificial Sequence
<220> FEATURE:
<223> OTHER INFORMATION: humanized lama

<400> SEQUENCE: 106

Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
        130                 135                 140
```

-continued

```
Gly Gly Gly Gly Ser Gly Gly Gly Ser Glu Val Gln Leu Val Glu
145                 150                 155                 160

Ser Gly Gly Val Val Gln Pro Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
        195                 200                 205

Gly Gly Ile Thr Tyr Tyr Ala Asp Ser Val Lys Gly Arg Phe Thr Ile
        210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Ser Gly Gly Gly Ser
        275                 280                 285

Gly Gly Gly Gly Ser Gly Gly Gly Ser Gly Gly Gly Ser Gly
    290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Thr
            325                 330                 335

Phe Ser Phe Tyr Gly Met Gly Trp Phe Arg Gln Ala Pro Gly Lys Glu
        340                 345                 350

Arg Glu Phe Val Ala Asp Ile Arg Thr Ser Ala Gly Arg Thr Tyr Tyr
                355                 360                 365

Ala Asp Ser Val Lys Gly Arg Phe Thr Ile Ser Arg Asp Asn Ser Lys
            370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Met Ser Gly Ile Ser Gly Trp Asp Tyr
                405                 410                 415

Trp Gly Gln Gly Thr Leu Val Thr Val Ser Ser Gly Gly Gly Gly Ser
            420                 425                 430

Gly Gly Gly Gly Ser Gly Gly Gly Ser Gly Gly Gly Ser Gly
        435                 440                 445

Gly Gly Gly Ser Gly Gly Gly Ser Gly Gly Gly Ser Glu Val
    450                 455                 460

Gln Leu Val Glu Ser Gly Gly Val Val Gln Pro Gly Gly Ser Leu
465                 470                 475                 480

Arg Leu Ser Cys Ala Ala Ser Gly Gly Thr Phe Ser Phe Tyr Gly Met
                485                 490                 495

Gly Trp Phe Arg Gln Ala Pro Gly Lys Glu Arg Glu Phe Val Ala Asp
            500                 505                 510

Ile Arg Thr Ser Ala Gly Arg Thr Tyr Tyr Ala Asp Ser Val Lys Gly
        515                 520                 525

Arg Phe Thr Ile Ser Arg Asp Asn Ser Lys Asn Thr Val Tyr Leu Gln
        530                 535                 540

Met Asn Ser Leu Arg Pro Glu Asp Thr Ala Leu Tyr Tyr Cys Ala Ala
545                 550                 555                 560

Glu Met Ser Gly Ile Ser Gly Trp Asp Tyr Trp Gly Gln Gly Thr Leu
```

```
                    565                 570                 575
Val Thr Val Ser Ser Gly Gly Gly Ser Gly Gly Gly Ser Gly
                580                 585                 590

Gly Gly Gly Ser Gly Gly Gly Ser Gly Gly Gly Ser Gly Gly
            595                 600                 605

Gly Gly Ser Gly Gly Gly Ser Glu Val Gln Leu Leu Glu Ser Gly
        610                 615                 620

Gly Gly Val Val Gln Pro Gly Gly Ser Leu Arg Leu Ser Cys Ala Ala
625                 630                 635                 640

Ser Gly Phe Thr Phe Arg Ser Phe Gly Met Ser Trp Val Arg Gln Ala
                645                 650                 655

Pro Gly Lys Gly Pro Glu Trp Val Ser Ser Ile Ser Gly Ser Gly Ser
                660                 665                 670

Asp Thr Leu Tyr Ala Asp Ser Val Lys Gly Arg Phe Thr Ile Ser Arg
                675                 680                 685

Asp Asn Ser Lys Asn Thr Leu Tyr Leu Gln Met Asn Ser Leu Arg Pro
            690                 695                 700

Glu Asp Thr Ala Leu Tyr Tyr Cys Thr Ile Gly Gly Ser Leu Ser Arg
705                 710                 715                 720

Ser Ser Gln Gly Thr Leu Val Thr Val Ser Ser Ala
                725                 730
```

<210> SEQ ID NO 107
<211> LENGTH: 732
<212> TYPE: PRT
<213> ORGANISM: Artificial Sequence
<220> FEATURE:
<223> OTHER INFORMATION: humanized lama

<400> SEQUENCE: 107

```
Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
                100                 105                 110

Thr Leu Val Thr Val Ser Ser Gly Gly Gly Ser Gly Gly Gly Gly
            115                 120                 125

Ser Gly Gly Gly Gly Ser Gly Gly Gly Ser Gly Gly Gly Ser
        130                 135                 140

Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
                180                 185                 190

Gln Ala Pro Gly Lys Glu Gln Glu Phe Val Ala Asp Ile Arg Thr Ser
```

```
            195                 200                 205
Ala Gly Arg Thr Tyr Tyr Ala Asp Ser Val Lys Gly Arg Phe Thr Ile
210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
                260                 265                 270

Ser Gly Gly Gly Gly Ser Gly Gly Gly Ser Gly Gly Gly Gly Ser
            275                 280                 285

Gly Gly Gly Ser Gly Gly Gly Ser Gly Gly Gly Ser Gly
            290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
                325                 330                 335

Ala Ser Ile His Ala Met Gly Trp Phe Arg Gln Ala Pro Gly Lys Glu
                340                 345                 350

Arg Glu Phe Val Ala Val Ile Thr Trp Ser Gly Gly Ile Thr Tyr Tyr
                355                 360                 365

Ala Asp Ser Val Lys Gly Arg Phe Thr Ile Ser Arg Asp Asn Ser Lys
370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
                405                 410                 415

Trp Gly Gln Gly Thr Leu Val Thr Val Ser Ser Gly Gly Gly Gly Ser
                420                 425                 430

Gly Gly Gly Gly Ser Gly Gly Gly Ser Gly Gly Gly Ser Gly
            435                 440                 445

Gly Gly Gly Ser Gly Gly Gly Ser Gly Gly Gly Ser Glu Val
            450                 455                 460

Gln Leu Val Glu Ser Gly Gly Val Val Gln Pro Gly Gly Ser Leu
465                 470                 475                 480

Arg Leu Ser Cys Ala Ala Ser Gly Ser Ile Ala Ser Ile His Ala Met
                485                 490                 495

Gly Trp Phe Arg Gln Ala Pro Gly Lys Glu Arg Glu Phe Val Ala Val
                500                 505                 510

Ile Thr Trp Ser Gly Gly Ile Thr Tyr Tyr Ala Asp Ser Val Lys Gly
                515                 520                 525

Arg Phe Thr Ile Ser Arg Asp Asn Ser Lys Asn Thr Val Tyr Leu Gln
                530                 535                 540

Met Asn Ser Leu Arg Pro Glu Asp Thr Ala Leu Tyr Tyr Cys Ala Gly
545                 550                 555                 560

Asp Lys His Gln Ser Ser Trp Tyr Asp Tyr Trp Gly Gln Gly Thr Leu
                565                 570                 575

Val Thr Val Ser Ser Gly Gly Gly Gly Ser Gly Gly Gly Gly Ser Gly
                580                 585                 590

Gly Gly Ser Gly Gly Gly Ser Gly Gly Gly Ser Gly Gly
            595                 600                 605

Gly Gly Ser Gly Gly Gly Ser Glu Val Gln Leu Val Glu Ser Gly
            610                 615                 620
```

```
Gly Gly Leu Val Gln Pro Gly Asn Ser Leu Arg Leu Ser Cys Ala Ala
625                 630                 635                 640

Ser Gly Phe Thr Phe Ser Ser Phe Gly Met Ser Trp Val Arg Gln Ala
            645                 650                 655

Pro Gly Lys Gly Leu Glu Trp Val Ser Ser Ile Ser Gly Ser Gly Ser
        660                 665                 670

Asp Thr Leu Tyr Ala Asp Ser Val Lys Gly Arg Phe Thr Ile Ser Arg
        675                 680                 685

Asp Asn Ala Lys Thr Thr Leu Tyr Leu Gln Met Asn Ser Leu Arg Pro
        690                 695                 700

Glu Asp Thr Ala Val Tyr Tyr Cys Thr Ile Gly Gly Ser Leu Ser Arg
705                 710                 715                 720

Ser Ser Gln Gly Thr Leu Val Thr Val Ser Ser Ala
                725                 730
```

<210> SEQ ID NO 108
<211> LENGTH: 732
<212> TYPE: PRT
<213> ORGANISM: Artificial Sequence
<220> FEATURE:
<223> OTHER INFORMATION: humanized lama

<400> SEQUENCE: 108

```
Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Arg Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255
```

Ile Ser Gly Trp Asp Tyr Trp Gly Gln Gly Thr Leu Val Thr Val Ser
                260                 265                 270

Ser Gly Gly Gly Gly Ser Gly Gly Gly Gly Ser Gly Gly Gly Gly Ser
            275                 280                 285

Gly Gly Gly Gly Ser Gly Gly Gly Ser Gly Gly Gly Gly Ser Gly
            290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
                325                 330                 335

Ala Ser Ile His Ala Met Gly Trp Phe Arg Gln Ala Pro Gly Lys Glu
                340                 345                 350

Arg Glu Phe Val Ala Val Ile Thr Trp Ser Gly Gly Ile Thr Tyr Tyr
                355                 360                 365

Ala Asp Ser Val Lys Gly Arg Phe Thr Ile Ser Arg Asp Asn Ser Lys
                370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
                405                 410                 415

Trp Gly Gln Gly Thr Leu Val Thr Val Ser Ser Gly Gly Gly Gly Ser
                420                 425                 430

Gly Gly Gly Gly Ser Gly Gly Gly Gly Ser Gly Gly Gly Gly Ser Gly
                435                 440                 445

Gly Gly Gly Ser Gly Gly Gly Gly Ser Gly Gly Gly Gly Ser Glu Val
                450                 455                 460

Gln Leu Val Glu Ser Gly Gly Gly Val Val Gln Pro Gly Gly Ser Leu
465                 470                 475                 480

Arg Leu Ser Cys Ala Ala Ser Gly Ser Ile Ala Ser Ile His Ala Met
                485                 490                 495

Gly Trp Phe Arg Gln Ala Pro Gly Lys Glu Arg Glu Phe Val Ala Val
                500                 505                 510

Ile Thr Trp Ser Gly Gly Ile Thr Tyr Tyr Ala Asp Ser Val Lys Gly
                515                 520                 525

Arg Phe Thr Ile Ser Arg Asp Asn Ser Lys Asn Thr Val Tyr Leu Gln
                530                 535                 540

Met Asn Ser Leu Arg Pro Glu Asp Thr Ala Leu Tyr Tyr Cys Ala Gly
545                 550                 555                 560

Asp Lys His Gln Ser Ser Trp Tyr Asp Tyr Trp Gly Gln Gly Thr Leu
                565                 570                 575

Val Thr Val Ser Ser Gly Gly Gly Gly Ser Gly Gly Gly Gly Ser Gly
                580                 585                 590

Gly Gly Ser Gly Gly Gly Gly Ser Gly Gly Gly Gly Ser Gly Gly
                595                 600                 605

Gly Gly Ser Gly Gly Gly Gly Ser Glu Val Gln Leu Val Glu Ser Gly
                610                 615                 620

Gly Gly Leu Val Gln Pro Gly Asn Ser Leu Arg Leu Ser Cys Ala Ala
625                 630                 635                 640

Ser Gly Phe Thr Phe Ser Ser Phe Gly Met Ser Trp Val Arg Gln Ala
                645                 650                 655

Pro Gly Lys Gly Leu Glu Trp Val Ser Ser Ile Ser Gly Ser Gly Ser
                660                 665                 670

```
Asp Thr Leu Tyr Ala Asp Ser Val Lys Gly Arg Phe Thr Ile Ser Arg
            675                 680                 685

Asp Asn Ala Lys Thr Thr Leu Tyr Leu Gln Met Asn Ser Leu Arg Pro
        690                 695                 700

Glu Asp Thr Ala Val Tyr Tyr Cys Thr Ile Gly Gly Ser Leu Ser Arg
705                 710                 715                 720

Ser Ser Gln Gly Thr Leu Val Thr Val Ser Ser Ala
                725                 730

<210> SEQ ID NO 109
<211> LENGTH: 732
<212> TYPE: PRT
<213> ORGANISM: Artificial Sequence
<220> FEATURE:
<223> OTHER INFORMATION: humanized lama

<400> SEQUENCE: 109

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Gln Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Gly Ser Gly Gly Gly Gly Ser Gly
    290                 295                 300
```

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
            325                 330                 335

Ala Ser Ile His Ala Met Gly Trp Phe Arg Gln Ala Pro Gly Lys Glu
            340                 345                 350

Arg Glu Phe Val Ala Val Ile Thr Trp Ser Gly Gly Ile Thr Tyr Tyr
            355                 360                 365

Ala Asp Ser Val Lys Gly Arg Phe Thr Ile Ser Arg Asp Asn Ser Lys
370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
            405                 410                 415

Trp Gly Gln Gly Thr Leu Val Thr Val Ser Ser Gly Gly Gly Gly Ser
            420                 425                 430

Gly Gly Gly Gly Ser Gly Gly Gly Ser Gly Gly Gly Gly Ser Gly
            435                 440                 445

Gly Gly Gly Ser Gly Gly Gly Ser Gly Gly Gly Gly Ser Glu Val
            450                 455                 460

Gln Leu Val Glu Ser Gly Gly Val Val Gln Pro Gly Gly Ser Leu
465                 470                 475                 480

Arg Leu Ser Cys Ala Ala Ser Gly Ser Ile Ala Ser Ile His Ala Met
            485                 490                 495

Gly Trp Phe Arg Gln Ala Pro Gly Lys Glu Arg Glu Phe Val Ala Val
            500                 505                 510

Ile Thr Trp Ser Gly Gly Ile Thr Tyr Tyr Ala Asp Ser Val Lys Gly
            515                 520                 525

Arg Phe Thr Ile Ser Arg Asp Asn Ser Lys Asn Thr Val Tyr Leu Gln
            530                 535                 540

Met Asn Ser Leu Arg Pro Glu Asp Thr Ala Leu Tyr Tyr Cys Ala Gly
545                 550                 555                 560

Asp Lys His Gln Ser Ser Trp Tyr Asp Tyr Trp Gly Gln Gly Thr Leu
            565                 570                 575

Val Thr Val Ser Ser Gly Gly Gly Gly Ser Gly Gly Gly Gly Ser Gly
            580                 585                 590

Gly Gly Ser Gly Gly Gly Gly Ser Gly Gly Gly Gly Ser Gly Gly
            595                 600                 605

Gly Gly Ser Gly Gly Gly Gly Ser Glu Val Gln Leu Leu Glu Ser Gly
            610                 615                 620

Gly Gly Val Val Gln Pro Gly Gly Ser Leu Arg Leu Ser Cys Ala Ala
625                 630                 635                 640

Ser Gly Phe Thr Phe Arg Ser Phe Gly Met Ser Trp Val Arg Gln Ala
            645                 650                 655

Pro Gly Lys Gly Pro Glu Trp Val Ser Ser Ile Ser Gly Ser Gly Ser
            660                 665                 670

Asp Thr Leu Tyr Ala Asp Ser Val Lys Gly Arg Phe Thr Ile Ser Arg
            675                 680                 685

Asp Asn Ser Lys Asn Thr Leu Tyr Leu Gln Met Asn Ser Leu Arg Pro
            690                 695                 700

Glu Asp Thr Ala Leu Tyr Tyr Cys Thr Ile Gly Gly Ser Leu Ser Arg
705                 710                 715                 720

Ser Ser Gln Gly Thr Leu Val Thr Val Ser Ser Ala

<210> SEQ ID NO 110
<211> LENGTH: 732
<212> TYPE: PRT
<213> ORGANISM: Artificial Sequence
<220> FEATURE:
<223> OTHER INFORMATION: humanized lama

<400> SEQUENCE: 110

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Ser Gly Gly Gly Gly Ser Gly Gly Gly Gly Ser
130                 135                 140

Gly Gly Gly Gly Ser Gly Gly Gly Ser Glu Val Gln Leu Val Glu
145                 150                 155                 160

Ser Gly Gly Val Val Gln Pro Gly Gly Ser Leu Arg Leu Ser Cys
            165                 170                 175

Ala Ala Ser Gly Gly Thr Phe Ser Phe Tyr Gly Met Gly Trp Phe Arg
            180                 185                 190

Gln Ala Pro Gly Lys Glu Arg Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Ser Gly Gly Gly Gly Ser
            275                 280                 285

Gly Gly Gly Gly Ser Gly Gly Gly Ser Gly Gly Gly Gly Ser Gly
        290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
                325                 330                 335

Ala Ser Ile His Ala Met Gly Trp Phe Arg Gln Ala Pro Gly Lys Glu
            340                 345                 350

Arg Glu Phe Val Ala Val Ile Thr Trp Ser Gly Gly Ile Thr Tyr Tyr

```
                355                 360                 365
Ala Asp Ser Val Lys Gly Arg Phe Thr Ile Ser Arg Asp Asn Ser Lys
    370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
                405                 410                 415

Trp Gly Gln Gly Thr Leu Val Thr Val Ser Ser Gly Gly Gly Gly Ser
            420                 425                 430

Gly Gly Gly Gly Ser Gly Gly Gly Ser Gly Gly Gly Ser Gly
        435                 440                 445

Gly Gly Gly Ser Gly Gly Gly Gly Ser Gly Gly Gly Ser Glu Val
    450                 455                 460

Gln Leu Val Glu Ser Gly Gly Val Val Gln Pro Gly Gly Ser Leu
465                 470                 475                 480

Arg Leu Ser Cys Ala Ala Ser Gly Ser Ile Ala Ser Ile His Ala Met
                485                 490                 495

Gly Trp Phe Arg Gln Ala Pro Gly Lys Glu Arg Glu Phe Val Ala Val
            500                 505                 510

Ile Thr Trp Ser Gly Gly Ile Thr Tyr Tyr Ala Asp Ser Val Lys Gly
        515                 520                 525

Arg Phe Thr Ile Ser Arg Asp Asn Ser Lys Asn Thr Val Tyr Leu Gln
    530                 535                 540

Met Asn Ser Leu Arg Pro Glu Asp Thr Ala Leu Tyr Tyr Cys Ala Gly
545                 550                 555                 560

Asp Lys His Gln Ser Ser Trp Tyr Asp Tyr Trp Gly Gln Gly Thr Leu
                565                 570                 575

Val Thr Val Ser Ser Gly Gly Gly Gly Ser Gly Gly Gly Gly Ser Gly
            580                 585                 590

Gly Gly Ser Gly Gly Gly Gly Ser Gly Gly Gly Gly Ser Gly Gly
        595                 600                 605

Gly Gly Ser Gly Gly Gly Gly Ser Glu Val Gln Leu Leu Glu Ser Gly
    610                 615                 620

Gly Gly Val Val Gln Pro Gly Gly Ser Leu Arg Leu Ser Cys Ala Ala
625                 630                 635                 640

Ser Gly Phe Thr Phe Arg Ser Phe Gly Met Ser Trp Val Arg Gln Ala
                645                 650                 655

Pro Gly Lys Gly Pro Glu Trp Val Ser Ser Ile Ser Gly Ser Gly Ser
            660                 665                 670

Asp Thr Leu Tyr Ala Asp Ser Val Lys Gly Arg Phe Thr Ile Ser Arg
        675                 680                 685

Asp Asn Ser Lys Asn Thr Leu Tyr Leu Gln Met Asn Ser Leu Arg Pro
    690                 695                 700

Glu Asp Thr Ala Leu Tyr Tyr Cys Thr Ile Gly Gly Ser Leu Ser Arg
705                 710                 715                 720

Ser Ser Gln Gly Thr Leu Val Thr Val Ser Ser Ala
                725                 730

<210> SEQ ID NO 111
<211> LENGTH: 424
<212> TYPE: PRT
<213> ORGANISM: Artificial Sequence
<220> FEATURE:
<223> OTHER INFORMATION: humanized lama
```

<400> SEQUENCE: 111

Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Ser Gly Gly Gly Ser Glu Val Gln Leu Val Glu
145                 150                 155                 160

Ser Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Gln Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Gly Ser Gly Gly Gly Gly Ser Gly
    290                 295                 300

Gly Gly Gly Ser Glu Val Gln Leu Val Glu Ser Gly Gly Gly Leu Val
305                 310                 315                 320

Gln Pro Gly Asn Ser Leu Arg Leu Ser Cys Ala Ala Ser Gly Phe Thr
                325                 330                 335

Phe Ser Ser Phe Gly Met Ser Trp Val Arg Gln Ala Pro Gly Lys Gly
            340                 345                 350

Leu Glu Trp Val Ser Ser Ile Ser Gly Ser Gly Ser Asp Thr Leu Tyr
        355                 360                 365

Ala Asp Ser Val Lys Gly Arg Phe Thr Ile Ser Arg Asp Asn Ala Lys
    370                 375                 380

Thr Thr Leu Tyr Leu Gln Met Asn Ser Leu Arg Pro Glu Asp Thr Ala
385                 390                 395                 400

Val Tyr Tyr Cys Thr Ile Gly Gly Ser Leu Ser Arg Ser Ser Gln Gly
                405                 410                 415

Thr Leu Val Thr Val Ser Ser Ala
            420

<210> SEQ ID NO 112
<211> LENGTH: 424
<212> TYPE: PRT
<213> ORGANISM: Artificial Sequence
<220> FEATURE:
<223> OTHER INFORMATION: humanized lama

<400> SEQUENCE: 112

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Arg Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Gly Ser Glu Val Gln Leu Val Glu Ser Gly Gly Gly Leu Val
305                 310                 315                 320

Gln Pro Gly Asn Ser Leu Arg Leu Ser Cys Ala Ala Ser Gly Phe Thr
                325                 330                 335

Phe Ser Ser Phe Gly Met Ser Trp Val Arg Gln Ala Pro Gly Lys Gly
            340                 345                 350

```
Leu Glu Trp Val Ser Ser Ile Ser Gly Ser Gly Ser Asp Thr Leu Tyr
            355                 360                 365

Ala Asp Ser Val Lys Gly Arg Phe Thr Ile Ser Arg Asp Asn Ala Lys
    370                 375                 380

Thr Thr Leu Tyr Leu Gln Met Asn Ser Leu Arg Pro Glu Asp Thr Ala
385                 390                 395                 400

Val Tyr Tyr Cys Thr Ile Gly Gly Ser Leu Ser Arg Ser Ser Gln Gly
                405                 410                 415

Thr Leu Val Thr Val Ser Ser Ala
            420

<210> SEQ ID NO 113
<211> LENGTH: 424
<212> TYPE: PRT
<213> ORGANISM: Artificial Sequence
<220> FEATURE:
<223> OTHER INFORMATION: humanized lama

<400> SEQUENCE: 113

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Gln Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285
```

Gly Gly Gly Gly Ser Gly Gly Gly Ser Gly Gly Gly Ser Gly
            290                 295                 300
Gly Gly Gly Ser Glu Val Gln Leu Leu Glu Ser Gly Gly Val Val
305                 310                 315                 320
Gln Pro Gly Gly Ser Leu Arg Leu Ser Cys Ala Ala Ser Gly Phe Thr
                325                 330                 335
Phe Arg Ser Phe Gly Met Ser Trp Val Arg Gln Ala Pro Gly Lys Gly
                340                 345                 350
Pro Glu Trp Val Ser Ser Ile Ser Gly Ser Gly Ser Asp Thr Leu Tyr
                355                 360                 365
Ala Asp Ser Val Lys Gly Arg Phe Thr Ile Ser Arg Asp Asn Ser Lys
370                 375                 380
Asn Thr Leu Tyr Leu Gln Met Asn Ser Leu Arg Pro Glu Asp Thr Ala
385                 390                 395                 400
Leu Tyr Tyr Cys Thr Ile Gly Gly Ser Leu Ser Arg Ser Ser Gln Gly
                405                 410                 415
Thr Leu Val Thr Val Ser Ser Ala
            420

<210> SEQ ID NO 114
<211> LENGTH: 424
<212> TYPE: PRT
<213> ORGANISM: Artificial Sequence
<220> FEATURE:
<223> OTHER INFORMATION: humanized lama

<400> SEQUENCE: 114

Asp Val Gln Leu Val Glu Ser Gly Gly Gly Val Val Gln Pro Gly Gly
1               5                   10                  15
Ser Leu Arg Leu Ser Cys Ala Ala Ser Gly Ser Ile Ala Ser Ile His
                20                  25                  30
Ala Met Gly Trp Phe Arg Gln Ala Pro Gly Lys Glu Arg Glu Phe Val
            35                  40                  45
Ala Val Ile Thr Trp Ser Gly Gly Ile Thr Tyr Tyr Ala Asp Ser Val
        50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Leu Tyr Tyr Cys
                85                  90                  95
Ala Gly Asp Lys His Gln Ser Ser Trp Tyr Asp Tyr Trp Gly Gln Gly
                100                 105                 110
Thr Leu Val Thr Val Ser Ser Gly Gly Gly Gly Ser Gly Gly Gly Gly
            115                 120                 125
Ser Gly Gly Gly Gly Ser Gly Gly Gly Ser Gly Gly Gly Gly Ser
        130                 135                 140
Gly Gly Gly Gly Ser Gly Gly Gly Ser Glu Val Gln Leu Val Glu
145                 150                 155                 160
Ser Gly Gly Gly Val Val Gln Pro Gly Gly Ser Leu Arg Leu Ser Cys
                165                 170                 175
Ala Ala Ser Gly Gly Thr Phe Ser Phe Tyr Gly Met Gly Trp Phe Arg
                180                 185                 190
Gln Ala Pro Gly Lys Glu Arg Glu Phe Val Ala Asp Ile Arg Thr Ser
            195                 200                 205
Ala Gly Arg Thr Tyr Tyr Ala Asp Ser Val Lys Gly Arg Phe Thr Ile
        210                 215                 220

```
Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
            245                 250                 255

Ile Ser Gly Trp Asp Tyr Trp Gly Gln Gly Thr Leu Val Thr Val Ser
        260                 265                 270

Ser Gly Gly Gly Gly Ser Gly Gly Gly Ser Gly Gly Gly Gly Ser
    275                 280                 285

Gly Gly Gly Gly Ser Gly Gly Gly Ser Gly Gly Gly Ser Gly
    290                 295                 300

Gly Gly Gly Ser Glu Val Gln Leu Leu Glu Ser Gly Gly Val Val
305                 310                 315                 320

Gln Pro Gly Gly Ser Leu Arg Leu Ser Cys Ala Ala Ser Gly Phe Thr
            325                 330                 335

Phe Arg Ser Phe Gly Met Ser Trp Val Arg Gln Ala Pro Gly Lys Gly
            340                 345                 350

Pro Glu Trp Val Ser Ser Ile Ser Gly Ser Gly Ser Asp Thr Leu Tyr
            355                 360                 365

Ala Asp Ser Val Lys Gly Arg Phe Thr Ile Ser Arg Asp Asn Ser Lys
370                 375                 380

Asn Thr Leu Tyr Leu Gln Met Asn Ser Leu Arg Pro Glu Asp Thr Ala
385                 390                 395                 400

Leu Tyr Tyr Cys Thr Ile Gly Gly Ser Leu Ser Arg Ser Ser Gln Gly
                405                 410                 415

Thr Leu Val Thr Val Ser Ser Ala
            420

<210> SEQ ID NO 115
<211> LENGTH: 424
<212> TYPE: PRT
<213> ORGANISM: Artificial Sequence
<220> FEATURE:
<223> OTHER INFORMATION: humanized lama

<400> SEQUENCE: 115

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
50                  55                  60

Lys Gly Arg Phe Thr Ile Ser Arg Asp Asn Lys Asn Thr Val Tyr
65                  70                  75                  80

Leu Gln Met Asn Ser Leu Arg Pro Glu Asp Thr Ala Leu Tyr Tyr Cys
            85                  90                  95

Ala Ala Glu Met Ser Gly Ile Ser Gly Trp Asp Tyr Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Glu Val Gln Leu Val Glu
145                 150                 155                 160
```

Ser Gly Gly Gly Val Val Gln Pro Gly Gly Ser Leu Arg Leu Ser Cys
            165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
            195                 200                 205

Gly Gly Ile Thr Tyr Tyr Ala Asp Ser Val Lys Gly Arg Phe Thr Ile
            210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
            245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Ser Gly Gly Gly Gly Ser
            275                 280                 285

Gly Gly Gly Ser Gly Gly Gly Ser Gly Gly Gly Gly Ser Gly
            290                 295                 300

Gly Gly Ser Glu Val Gln Leu Val Glu Ser Gly Gly Gly Leu Val
305                 310                 315                 320

Gln Pro Gly Asn Ser Leu Arg Leu Ser Cys Ala Ala Ser Gly Phe Thr
            325                 330                 335

Phe Ser Ser Phe Gly Met Ser Trp Val Arg Gln Ala Pro Gly Lys Gly
            340                 345                 350

Leu Glu Trp Val Ser Ser Ile Ser Gly Ser Gly Ser Asp Thr Leu Tyr
            355                 360                 365

Ala Asp Ser Val Lys Gly Arg Phe Thr Ile Ser Arg Asp Asn Ala Lys
            370                 375                 380

Thr Thr Leu Tyr Leu Gln Met Asn Ser Leu Arg Pro Glu Asp Thr Ala
385                 390                 395                 400

Val Tyr Tyr Cys Thr Ile Gly Gly Ser Leu Ser Arg Ser Ser Gln Gly
            405                 410                 415

Thr Leu Val Thr Val Ser Ser Ala
            420

<210> SEQ ID NO 116
<211> LENGTH: 424
<212> TYPE: PRT
<213> ORGANISM: Artificial Sequence
<220> FEATURE:
<223> OTHER INFORMATION: humanized lama

<400> SEQUENCE: 116

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
            35                  40                  45

Ala Asp Ile Arg Thr Ser Ala Gly Arg Thr Tyr Tyr Ala Asp Ser Val
            50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
            85                  90                  95

Ala Ala Glu Met Ser Gly Ile Ser Gly Trp Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Ser Gly Gly Gly Gly Ser Gly Gly Gly Gly Ser
130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
            195                 200                 205

Gly Gly Ile Thr Tyr Tyr Ala Asp Ser Val Lys Gly Arg Phe Thr Ile
            210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
            275                 280                 285

Gly Gly Gly Gly Ser Gly Gly Gly Gly Ser Gly Gly Gly Gly Ser Gly
            290                 295                 300

Gly Gly Ser Glu Val Gln Leu Val Glu Ser Gly Gly Gly Leu Val
305                 310                 315                 320

Gln Pro Gly Asn Ser Leu Arg Leu Ser Cys Ala Ala Ser Gly Phe Thr
                325                 330                 335

Phe Ser Ser Phe Gly Met Ser Trp Val Arg Gln Ala Pro Gly Lys Gly
            340                 345                 350

Leu Glu Trp Val Ser Ser Ile Ser Gly Ser Gly Ser Asp Thr Leu Tyr
            355                 360                 365

Ala Asp Ser Val Lys Gly Arg Phe Thr Ile Ser Arg Asp Asn Ala Lys
            370                 375                 380

Thr Thr Leu Tyr Leu Gln Met Asn Ser Leu Arg Pro Glu Asp Thr Ala
385                 390                 395                 400

Val Tyr Tyr Cys Thr Ile Gly Gly Ser Leu Ser Arg Ser Ser Gln Gly
                405                 410                 415

Thr Leu Val Thr Val Ser Ser Ala
            420

<210> SEQ ID NO 117
<211> LENGTH: 424
<212> TYPE: PRT
<213> ORGANISM: Artificial Sequence
<220> FEATURE:
<223> OTHER INFORMATION: humanized lama

<400> SEQUENCE: 117

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

```
Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Gly Gly Gly Gly Ser Gly Gly Gly Gly Ser
130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
            195                 200                 205

Gly Gly Ile Thr Tyr Tyr Ala Asp Ser Val Lys Gly Arg Phe Thr Ile
            210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
                260                 265                 270

Ser Gly Gly Gly Gly Ser Gly Gly Gly Gly Ser Gly Gly Gly Gly Ser
            275                 280                 285

Gly Gly Gly Gly Ser Gly Gly Gly Ser Gly Gly Gly Gly Ser Gly
290                 295                 300

Gly Gly Gly Ser Glu Val Gln Leu Leu Glu Ser Gly Gly Gly Val Val
305                 310                 315                 320

Gln Pro Gly Gly Ser Leu Arg Leu Ser Cys Ala Ala Ser Gly Phe Thr
            325                 330                 335

Phe Arg Ser Phe Gly Met Ser Trp Val Arg Gln Ala Pro Gly Lys Gly
            340                 345                 350

Pro Glu Trp Val Ser Ser Ile Ser Gly Ser Gly Ser Asp Thr Leu Tyr
            355                 360                 365

Ala Asp Ser Val Lys Gly Arg Phe Thr Ile Ser Arg Asp Asn Ser Lys
370                 375                 380

Asn Thr Leu Tyr Leu Gln Met Asn Ser Leu Arg Pro Glu Asp Thr Ala
385                 390                 395                 400

Leu Tyr Tyr Cys Thr Ile Gly Gly Ser Leu Ser Arg Ser Ser Gln Gly
                405                 410                 415

Thr Leu Val Thr Val Ser Ser Ala
            420

<210> SEQ ID NO 118
<211> LENGTH: 424
```

```
<212> TYPE: PRT
<213> ORGANISM: Artificial Sequence
<220> FEATURE:
<223> OTHER INFORMATION: humanized lama

<400> SEQUENCE: 118
```

| | | | | | | | | | | | | | | |
|---|---|---|---|---|---|---|---|---|---|---|---|---|---|---|
| Asp | Val | Gln | Leu | Val | Glu | Ser | Gly | Gly | Gly | Val | Val | Gln | Pro | Gly | Gly |
| 1 | | | | 5 | | | | | 10 | | | | | 15 |
| Ser | Leu | Arg | Leu | Ser | Cys | Ala | Ala | Ser | Gly | Gly | Thr | Phe | Ser | Phe | Tyr |
| | | | 20 | | | | | 25 | | | | | 30 | |
| Gly | Met | Gly | Trp | Phe | Arg | Gln | Ala | Pro | Gly | Lys | Glu | Arg | Glu | Phe | Val |
| | | | 35 | | | | 40 | | | | | 45 | | |
| Ala | Asp | Ile | Arg | Thr | Ser | Ala | Gly | Arg | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Val | Tyr |
| 65 | | | | | 70 | | | | | 75 | | | | | 80 |
| Leu | Gln | Met | Asn | Ser | Leu | Arg | Pro | Glu | Asp | Thr | Ala | Leu | Tyr | Tyr | Cys |
| | | | | 85 | | | | | 90 | | | | | 95 | |
| Ala | Ala | Glu | Met | Ser | Gly | Ile | Ser | Gly | Trp | Asp | Tyr | Trp | Gly | Gln | Gly |
| | | | 100 | | | | | 105 | | | | | 110 | | |
| Thr | Leu | Val | Thr | Val | Ser | Ser | Gly | Gly | Gly | Ser | Gly | Gly | Gly | Gly |
| | | | 115 | | | | | 120 | | | | | 125 | |
| Ser | Gly | Gly | Gly | Gly | Ser | Gly | Gly | Gly | Gly | Ser | Gly | Gly | Gly | Ser |
| | 130 | | | | | 135 | | | | | 140 | | | | |
| Gly | Gly | Gly | Gly | Ser | Gly | Gly | Gly | Ser | Glu | Val | Gln | Leu | Val | Glu |
| 145 | | | | | 150 | | | | | 155 | | | | | 160 |
| Ser | Gly | Gly | Gly | Val | Val | Gln | Pro | Gly | Gly | Ser | Leu | Arg | Leu | Ser | Cys |
| | | | | 165 | | | | | 170 | | | | | 175 | |
| Ala | Ala | Ser | Gly | Ser | Ile | Ala | Ser | Ile | His | Ala | Met | Gly | Trp | Phe | Arg |
| | | | 180 | | | | | 185 | | | | | 190 | | |
| Gln | Ala | Pro | Gly | Lys | Glu | Arg | Glu | Phe | Val | Ala | Val | Ile | Thr | Trp | Ser |
| | | | 195 | | | | | 200 | | | | | 205 | | |
| Gly | Gly | Ile | Thr | Tyr | Tyr | Ala | Asp | Ser | Val | Lys | Gly | Arg | Phe | Thr | Ile |
| | 210 | | | | | 215 | | | | | 220 | | | | |
| Ser | Arg | Asp | Asn | Ser | Lys | Asn | Thr | Val | Tyr | Leu | Gln | Met | Asn | Ser | Leu |
| 225 | | | | | 230 | | | | | 235 | | | | | 240 |
| Arg | Pro | Glu | Asp | Thr | Ala | Leu | Tyr | Tyr | Cys | Ala | Gly | Asp | Lys | His | Gln |
| | | | | 245 | | | | | 250 | | | | | 255 | |
| Ser | Ser | Trp | Tyr | Asp | Tyr | Trp | Gly | Gln | Gly | Thr | Leu | Val | Thr | Val | Ser |
| | | | 260 | | | | | 265 | | | | | 270 | | |
| Ser | Gly | Gly | Gly | Gly | Ser | Gly | Gly | Gly | Ser | Gly | Gly | Gly | Gly | Ser |
| | | 275 | | | | | 280 | | | | | 285 | | | |
| Gly | Gly | Gly | Gly | Ser | Gly | Gly | Gly | Ser | Gly | Gly | Gly | Ser | Gly |
| | 290 | | | | | 295 | | | | | 300 | | | | |
| Gly | Gly | Gly | Ser | Glu | Val | Gln | Leu | Leu | Glu | Ser | Gly | Gly | Val | Val |
| 305 | | | | | 310 | | | | | 315 | | | | | 320 |
| Gln | Pro | Gly | Gly | Ser | Leu | Arg | Leu | Ser | Cys | Ala | Ala | Ser | Gly | Phe | Thr |
| | | | | 325 | | | | | 330 | | | | | 335 | |
| Phe | Arg | Ser | Phe | Gly | Met | Ser | Trp | Val | Arg | Gln | Ala | Pro | Gly | Lys | Gly |
| | | | 340 | | | | | 345 | | | | | 350 | | |
| Pro | Glu | Trp | Val | Ser | Ser | Ile | Ser | Gly | Ser | Gly | Ser | Asp | Thr | Leu | Tyr |
| | | | 355 | | | | | 360 | | | | | 365 | | |
| Ala | Asp | Ser | Val | Lys | Gly | Arg | Phe | Thr | Ile | Ser | Arg | Asp | Asn | Ser | Lys |
| | 370 | | | | | 375 | | | | | 380 | | | | |

```
Asn Thr Leu Tyr Leu Gln Met Asn Ser Leu Arg Pro Glu Asp Thr Ala
385                 390                 395                 400

Leu Tyr Tyr Cys Thr Ile Gly Gly Ser Leu Ser Arg Ser Ser Gln Gly
            405                 410                 415

Thr Leu Val Thr Val Ser Ser Ala
            420

<210> SEQ ID NO 119
<211> LENGTH: 578
<212> TYPE: PRT
<213> ORGANISM: Artificial Sequence
<220> FEATURE:
<223> OTHER INFORMATION: humanized lama

<400> SEQUENCE: 119

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Gln Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Gly Ser Glu Val Gln Leu Val Glu Ser Gly Gly Gly Val Val
305                 310                 315                 320
```

Gln Pro Gly Gly Ser Leu Arg Leu Ser Cys Ala Ala Ser Gly Gly Thr
                325                 330                 335

Phe Ser Phe Tyr Gly Met Gly Trp Phe Arg Gln Ala Pro Gly Lys Glu
            340                 345                 350

Gln Glu Phe Val Ala Asp Ile Arg Thr Ser Ala Gly Arg Thr Tyr Tyr
        355                 360                 365

Ala Asp Ser Val Lys Gly Arg Phe Thr Ile Ser Arg Asp Asn Ser Lys
370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Met Ser Gly Ile Ser Gly Trp Asp Tyr
            405                 410                 415

Trp Gly Gln Gly Thr Leu Val Thr Val Ser Ser Gly Gly Gly Gly Ser
            420                 425                 430

Gly Gly Gly Gly Ser Gly Gly Gly Ser Gly Gly Gly Gly Ser Gly
            435                 440                 445

Gly Gly Gly Ser Gly Gly Gly Ser Gly Gly Gly Gly Ser Glu Val
        450                 455                 460

Gln Leu Val Glu Ser Gly Gly Gly Leu Val Gln Pro Gly Asn Ser Leu
465                 470                 475                 480

Arg Leu Ser Cys Ala Ala Ser Gly Phe Thr Phe Ser Ser Phe Gly Met
            485                 490                 495

Ser Trp Val Arg Gln Ala Pro Gly Lys Gly Leu Glu Trp Val Ser Ser
            500                 505                 510

Ile Ser Gly Ser Gly Ser Asp Thr Leu Tyr Ala Asp Ser Val Lys Gly
        515                 520                 525

Arg Phe Thr Ile Ser Arg Asp Asn Ala Lys Thr Thr Leu Tyr Leu Gln
    530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Ser Gln Gly Thr Leu Val Thr Val Ser
            565                 570                 575

Ser Ala

<210> SEQ ID NO 120
<211> LENGTH: 578
<212> TYPE: PRT
<213> ORGANISM: Artificial Sequence
<220> FEATURE:
<223> OTHER INFORMATION: humanized lama

<400> SEQUENCE: 120

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
            85                  90                  95

Ala Gly Asp Lys His Gln Ser Ser Trp Tyr Asp Tyr Trp Gly Gln Gly

```
                100             105             110
Thr Leu Val Thr Val Ser Ser Gly Gly Gly Ser Gly Gly Gly
            115             120             125
Ser Gly Gly Gly Gly Ser Gly Gly Gly Ser Gly Gly Gly Ser
130             135             140
Gly Gly Gly Gly Ser Gly Gly Gly Ser Glu Val Gln Leu Val Glu
145             150             155             160
Ser Gly Gly Gly Val Val Gln Pro Gly Gly Ser Leu Arg Leu Ser Cys
                165             170             175
Ala Ala Ser Gly Gly Thr Phe Ser Phe Tyr Gly Met Gly Trp Phe Arg
            180             185             190
Gln Ala Pro Gly Lys Glu Arg Glu Phe Val Ala Asp Ile Arg Thr Ser
            195             200             205
Ala Gly Arg Thr Tyr Tyr Ala Asp Ser Val Lys Gly Arg Phe Thr Ile
            210             215             220
Ser Arg Asp Asn Ser Lys Asn Thr Val Tyr Leu Gln Met Asn Ser Leu
225             230             235             240
Arg Pro Glu Asp Thr Ala Leu Tyr Tyr Cys Ala Ala Glu Met Ser Gly
                245             250             255
Ile Ser Gly Trp Asp Tyr Trp Gly Gln Gly Thr Leu Val Thr Val Ser
                260             265             270
Ser Gly Gly Gly Gly Ser Gly Gly Gly Gly Ser Gly Gly Gly Gly Ser
                275             280             285
Gly Gly Gly Gly Ser Gly Gly Gly Gly Ser Gly Gly Gly Ser Gly
            290             295             300
Gly Gly Gly Ser Glu Val Gln Leu Val Glu Ser Gly Gly Gly Val Val
305             310             315             320
Gln Pro Gly Gly Ser Leu Arg Leu Ser Cys Ala Ala Ser Gly Gly Thr
                325             330             335
Phe Ser Phe Tyr Gly Met Gly Trp Phe Arg Gln Ala Pro Gly Lys Glu
            340             345             350
Arg Glu Phe Val Ala Asp Ile Arg Thr Ser Ala Gly Arg Thr Tyr Tyr
            355             360             365
Ala Asp Ser Val Lys Gly Arg Phe Thr Ile Ser Arg Asp Asn Ser Lys
            370             375             380
Asn Thr Val Tyr Leu Gln Met Asn Ser Leu Arg Pro Glu Asp Thr Ala
385             390             395             400
Leu Tyr Tyr Cys Ala Ala Glu Met Ser Gly Ile Ser Gly Trp Asp Tyr
                405             410             415
Trp Gly Gln Gly Thr Leu Val Thr Val Ser Ser Gly Gly Gly Gly Ser
            420             425             430
Gly Gly Gly Gly Ser Gly Gly Gly Gly Ser Gly Gly Gly Gly Ser Gly
            435             440             445
Gly Gly Gly Ser Gly Gly Gly Gly Ser Gly Gly Gly Gly Ser Glu Val
            450             455             460
Gln Leu Val Glu Ser Gly Gly Leu Val Gln Pro Gly Asn Ser Leu
465             470             475             480
Arg Leu Ser Cys Ala Ala Ser Gly Phe Thr Phe Ser Ser Phe Gly Met
                485             490             495
Ser Trp Val Arg Gln Ala Pro Gly Lys Gly Leu Glu Trp Val Ser Ser
                500             505             510
Ile Ser Gly Ser Gly Ser Asp Thr Leu Tyr Ala Asp Ser Val Lys Gly
            515             520             525
```

```
Arg Phe Thr Ile Ser Arg Asp Asn Ala Lys Thr Thr Leu Tyr Leu Gln
            530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Gln Gly Thr Leu Val Thr Val Ser
            565                 570                 575

Ser Ala

<210> SEQ ID NO 121
<211> LENGTH: 578
<212> TYPE: PRT
<213> ORGANISM: Artificial Sequence
<220> FEATURE:
<223> OTHER INFORMATION: humanized lama

<400> SEQUENCE: 121

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Gln Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
    275                 280                 285

Gly Gly Gly Gly Ser Gly Gly Gly Ser Gly Gly Gly Gly Ser Gly
290                 295                 300
```

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Gly Thr
            325                 330                 335

Phe Ser Phe Tyr Gly Met Gly Trp Phe Arg Gln Ala Pro Gly Lys Glu
            340                 345                 350

Gln Glu Phe Val Ala Asp Ile Arg Thr Ser Ala Gly Arg Thr Tyr Tyr
            355                 360                 365

Ala Asp Ser Val Lys Gly Arg Phe Thr Ile Ser Arg Asp Asn Ser Lys
370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Met Ser Gly Ile Ser Gly Trp Asp Tyr
            405                 410                 415

Trp Gly Gln Gly Thr Leu Val Thr Val Ser Ser Gly Gly Gly Gly Ser
            420                 425                 430

Gly Gly Gly Gly Ser Gly Gly Gly Ser Gly Gly Gly Gly Ser Gly
            435                 440                 445

Gly Gly Gly Ser Gly Gly Gly Ser Gly Gly Gly Gly Ser Glu Val
            450                 455                 460

Gln Leu Leu Glu Ser Gly Gly Val Val Gln Pro Gly Gly Ser Leu
465                 470                 475                 480

Arg Leu Ser Cys Ala Ala Ser Gly Phe Thr Phe Arg Ser Phe Gly Met
            485                 490                 495

Ser Trp Val Arg Gln Ala Pro Gly Lys Gly Pro Glu Trp Val Ser Ser
            500                 505                 510

Ile Ser Gly Ser Gly Ser Asp Thr Leu Tyr Ala Asp Ser Val Lys Gly
            515                 520                 525

Arg Phe Thr Ile Ser Arg Asp Asn Ser Lys Asn Thr Leu Tyr Leu Gln
            530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Ser Gln Gly Thr Leu Val Thr Val Ser
            565                 570                 575

Ser Ala

<210> SEQ ID NO 122
<211> LENGTH: 578
<212> TYPE: PRT
<213> ORGANISM: Artificial Sequence
<220> FEATURE:
<223> OTHER INFORMATION: humanized lama

<400> SEQUENCE: 122

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys

```
                    85                  90                  95
Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Gly Gly Gly Ser Gly Gly Gly Gly Ser
            130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Arg Glu Phe Val Ala Asp Ile Arg Thr Ser
            195                 200                 205

Ala Gly Arg Thr Tyr Tyr Ala Asp Ser Val Lys Gly Arg Phe Thr Ile
            210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Ser Gly Gly Gly Gly Ser
            275                 280                 285

Gly Gly Gly Gly Ser Gly Gly Gly Ser Gly Gly Gly Gly Ser Gly
            290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Gly Thr
                325                 330                 335

Phe Ser Phe Tyr Gly Met Gly Trp Phe Arg Gln Ala Pro Gly Lys Glu
            340                 345                 350

Arg Glu Phe Val Ala Asp Ile Arg Thr Ser Ala Gly Arg Thr Tyr Tyr
            355                 360                 365

Ala Asp Ser Val Lys Gly Arg Phe Thr Ile Ser Arg Asp Asn Ser Lys
            370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Met Ser Gly Ile Ser Gly Trp Asp Tyr
                405                 410                 415

Trp Gly Gln Gly Thr Leu Val Thr Val Ser Ser Gly Gly Gly Gly Ser
            420                 425                 430

Gly Gly Gly Gly Ser Gly Gly Gly Gly Ser Gly Gly Gly Gly Ser Gly
            435                 440                 445

Gly Gly Gly Ser Gly Gly Gly Gly Ser Gly Gly Gly Gly Ser Glu Val
            450                 455                 460

Gln Leu Leu Glu Ser Gly Gly Gly Val Val Gln Pro Gly Gly Ser Leu
465                 470                 475                 480

Arg Leu Ser Cys Ala Ala Ser Gly Phe Thr Phe Arg Ser Phe Gly Met
                485                 490                 495

Ser Trp Val Arg Gln Ala Pro Gly Lys Gly Pro Glu Trp Val Ser Ser
            500                 505                 510
```

```
Ile Ser Gly Ser Gly Ser Asp Thr Leu Tyr Ala Asp Ser Val Lys Gly
        515                 520                 525

Arg Phe Thr Ile Ser Arg Asp Asn Ser Lys Asn Thr Leu Tyr Leu Gln
        530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Ser Gln Gly Thr Leu Val Thr Val Ser
            565                 570                 575

Ser Ala

<210> SEQ ID NO 123
<211> LENGTH: 578
<212> TYPE: PRT
<213> ORGANISM: Artificial Sequence
<220> FEATURE:
<223> OTHER INFORMATION: humanized lama

<400> SEQUENCE: 123

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Gln Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
    275                 280                 285
```

Gly Gly Gly Ser Gly Gly Gly Ser Gly Gly Gly Ser Gly
                290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
                325                 330                 335

Ala Ser Ile His Ala Met Gly Trp Phe Arg Gln Ala Pro Gly Lys Glu
                340                 345                 350

Arg Glu Phe Val Ala Val Ile Thr Trp Ser Gly Ile Thr Tyr Tyr
                355                 360                 365

Ala Asp Ser Val Lys Gly Arg Phe Thr Ile Ser Arg Asp Asn Ser Lys
370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
                405                 410                 415

Trp Gly Gln Gly Thr Leu Val Thr Val Ser Ser Gly Gly Gly Ser
                420                 425                 430

Gly Gly Gly Gly Ser Gly Gly Gly Ser Gly Gly Gly Ser Gly
                435                 440                 445

Gly Gly Gly Ser Gly Gly Gly Gly Ser Gly Gly Gly Ser Glu Val
                450                 455                 460

Gln Leu Val Glu Ser Gly Gly Leu Val Gln Pro Gly Asn Ser Leu
465                 470                 475                 480

Arg Leu Ser Cys Ala Ala Ser Gly Phe Thr Phe Ser Ser Phe Gly Met
                485                 490                 495

Ser Trp Val Arg Gln Ala Pro Gly Lys Gly Leu Glu Trp Val Ser Ser
                500                 505                 510

Ile Ser Gly Ser Gly Ser Asp Thr Leu Tyr Ala Asp Ser Val Lys Gly
                515                 520                 525

Arg Phe Thr Ile Ser Arg Asp Asn Ala Lys Thr Thr Leu Tyr Leu Gln
                530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Ser Gln Gly Thr Leu Val Thr Val Ser
                565                 570                 575

Ser Ala

<210> SEQ ID NO 124
<211> LENGTH: 578
<212> TYPE: PRT
<213> ORGANISM: Artificial Sequence
<220> FEATURE:
<223> OTHER INFORMATION: humanized lama

<400> SEQUENCE: 124

Asp Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
                20                  25                  30

Gly Met Gly Trp Phe Arg Gln Ala Pro Gly Lys Glu Arg Glu Phe Val
                35                  40                  45

Ala Asp Ile Arg Thr Ser Ala Gly Arg Thr Tyr Tyr Ala Asp Ser Val
                50                  55                  60

Lys Gly Arg Phe Thr Ile Ser Arg Asp Asn Ser Lys Asn Thr Val Tyr

```
                65                  70                  75                  80
Leu Gln Met Asn Ser Leu Arg Pro Glu Asp Thr Ala Leu Tyr Tyr Cys
                        85                  90                  95
Ala Ala Glu Met Ser Gly Ile Ser Gly Trp Asp Tyr Trp Gly Gln Gly
                    100                 105                 110
Thr Leu Val Thr Val Ser Ser Gly Gly Gly Ser Gly Gly Gly Gly
                115                 120                 125
Ser Gly Gly Gly Ser Gly Gly Gly Gly Ser Gly Gly Gly Gly Ser
            130                 135                 140
Gly Gly Gly Gly Ser Gly Gly Gly Ser Glu Val Gln Leu Val Glu
145                 150                 155                 160
Ser Gly Gly Gly Val Val Gln Pro Gly Ser Leu Arg Leu Ser Cys
                165                 170                 175
Ala Ala Ser Gly Gly Thr Phe Ser Phe Tyr Gly Met Gly Trp Phe Arg
            180                 185                 190
Gln Ala Pro Gly Lys Glu Arg Glu Phe Val Ala Asp Ile Arg Thr Ser
                195                 200                 205
Ala Gly Arg Thr Tyr Tyr Ala Asp Ser Val Lys Gly Arg Phe Thr Ile
            210                 215                 220
Ser Arg Asp Asn Ser Lys Asn Thr Val Tyr Leu Gln Met Asn Ser Leu
225                 230                 235                 240
Arg Pro Glu Asp Thr Ala Leu Tyr Tyr Cys Ala Ala Glu Met Ser Gly
                245                 250                 255
Ile Ser Gly Trp Asp Tyr Trp Gly Gln Gly Thr Leu Val Thr Val Ser
                260                 265                 270
Ser Gly Gly Gly Gly Ser Gly Gly Gly Gly Ser Gly Gly Gly Gly Ser
            275                 280                 285
Gly Gly Gly Gly Ser Gly Gly Gly Ser Gly Gly Gly Gly Ser Gly
            290                 295                 300
Gly Gly Gly Ser Glu Val Gln Leu Val Glu Ser Gly Gly Val Val
305                 310                 315                 320
Gln Pro Gly Gly Ser Leu Arg Leu Ser Cys Ala Ala Ser Gly Ser Ile
                325                 330                 335
Ala Ser Ile His Ala Met Gly Trp Phe Arg Gln Ala Pro Gly Lys Glu
            340                 345                 350
Arg Glu Phe Val Ala Val Ile Thr Trp Ser Gly Gly Ile Thr Tyr Tyr
            355                 360                 365
Ala Asp Ser Val Lys Gly Arg Phe Thr Ile Ser Arg Asp Asn Ser Lys
            370                 375                 380
Asn Thr Val Tyr Leu Gln Met Asn Ser Leu Arg Pro Glu Asp Thr Ala
385                 390                 395                 400
Leu Tyr Tyr Cys Ala Gly Asp Lys His Gln Ser Ser Trp Tyr Asp Tyr
                405                 410                 415
Trp Gly Gln Gly Thr Leu Val Thr Val Ser Ser Gly Gly Gly Gly Ser
            420                 425                 430
Gly Gly Gly Gly Ser Gly Gly Gly Gly Ser Gly Gly Gly Gly Ser Gly
            435                 440                 445
Gly Gly Gly Ser Gly Gly Gly Ser Gly Gly Gly Gly Ser Glu Val
            450                 455                 460
Gln Leu Val Glu Ser Gly Gly Leu Val Gln Pro Gly Asn Ser Leu
465                 470                 475                 480
Arg Leu Ser Cys Ala Ala Ser Gly Phe Thr Phe Ser Ser Phe Gly Met
                485                 490                 495
```

```
Ser Trp Val Arg Gln Ala Pro Gly Lys Gly Leu Glu Trp Val Ser Ser
                500                 505                 510

Ile Ser Gly Ser Gly Ser Asp Thr Leu Tyr Ala Asp Ser Val Lys Gly
        515                 520                 525

Arg Phe Thr Ile Ser Arg Asp Asn Ala Lys Thr Thr Leu Tyr Leu Gln
    530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Ser Gln Gly Thr Leu Val Thr Val Ser
            565                 570                 575

Ser Ala
```

<210> SEQ ID NO 125
<211> LENGTH: 578
<212> TYPE: PRT
<213> ORGANISM: Artificial Sequence
<220> FEATURE:
<223> OTHER INFORMATION: humanized lama

<400> SEQUENCE: 125

```
Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
            165                 170                 175

Ala Ala Ser Gly Gly Thr Phe Ser Phe Tyr Gly Met Gly Trp Phe Arg
            180                 185                 190

Gln Ala Pro Gly Lys Glu Gln Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
            260                 265                 270
```

-continued

Ser Gly Gly Gly Gly Ser Gly Gly Gly Ser Gly Gly Gly Ser
            275                 280                 285

Gly Gly Gly Gly Ser Gly Gly Gly Ser Gly Gly Gly Ser Gly
            290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
                325                 330                 335

Ala Ser Ile His Ala Met Gly Trp Phe Arg Gln Ala Pro Gly Lys Glu
            340                 345                 350

Arg Glu Phe Val Ala Val Ile Thr Trp Ser Gly Gly Ile Thr Tyr Tyr
            355                 360                 365

Ala Asp Ser Val Lys Gly Arg Phe Thr Ile Ser Arg Asp Asn Ser Lys
        370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
                405                 410                 415

Trp Gly Gln Gly Thr Leu Val Thr Val Ser Ser Gly Gly Gly Gly Ser
            420                 425                 430

Gly Gly Gly Gly Ser Gly Gly Gly Gly Ser Gly Gly Gly Ser Gly
        435                 440                 445

Gly Gly Gly Ser Gly Gly Gly Gly Ser Gly Gly Gly Ser Glu Val
        450                 455                 460

Gln Leu Leu Glu Ser Gly Gly Val Val Gln Pro Gly Gly Ser Leu
465                 470                 475                 480

Arg Leu Ser Cys Ala Ala Ser Gly Phe Thr Phe Arg Ser Phe Gly Met
            485                 490                 495

Ser Trp Val Arg Gln Ala Pro Gly Lys Gly Pro Glu Trp Val Ser Ser
            500                 505                 510

Ile Ser Gly Ser Gly Ser Asp Thr Leu Tyr Ala Asp Ser Val Lys Gly
        515                 520                 525

Arg Phe Thr Ile Ser Arg Asp Asn Ser Lys Asn Thr Leu Tyr Leu Gln
        530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Ser Gln Gly Thr Leu Val Thr Val Ser
                565                 570                 575

Ser Ala

<210> SEQ ID NO 126
<211> LENGTH: 578
<212> TYPE: PRT
<213> ORGANISM: Artificial Sequence
<220> FEATURE:
<223> OTHER INFORMATION: humanized lama

<400> SEQUENCE: 126

Asp Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val

```
                50                  55                  60
Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Gly Gly Gly Gly Ser Gly Gly Gly Ser
                130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
                180                 185                 190

Gln Ala Pro Gly Lys Glu Arg Glu Phe Val Ala Asp Ile Arg Thr Ser
                195                 200                 205

Ala Gly Arg Thr Tyr Tyr Ala Asp Ser Val Lys Gly Arg Phe Thr Ile
                210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Met Ser Gly
                245                 250                 255

Ile Ser Gly Trp Asp Tyr Trp Gly Gln Gly Thr Leu Val Thr Val Ser
                260                 265                 270

Ser Gly Gly Gly Gly Ser Gly Gly Gly Gly Ser Gly Gly Gly Gly Ser
                275                 280                 285

Gly Gly Gly Gly Ser Gly Gly Gly Gly Ser Gly Gly Gly Gly Ser Gly
                290                 295                 300

Gly Gly Gly Ser Glu Val Gln Leu Val Glu Ser Gly Gly Gly Val Val
305                 310                 315                 320

Gln Pro Gly Gly Ser Leu Arg Leu Ser Cys Ala Ala Ser Gly Ser Ile
                325                 330                 335

Ala Ser Ile His Ala Met Gly Trp Phe Arg Gln Ala Pro Gly Lys Glu
                340                 345                 350

Arg Glu Phe Val Ala Val Ile Thr Trp Ser Gly Gly Ile Thr Tyr Tyr
                355                 360                 365

Ala Asp Ser Val Lys Gly Arg Phe Thr Ile Ser Arg Asp Asn Ser Lys
                370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
                405                 410                 415

Trp Gly Gln Gly Thr Leu Val Thr Val Ser Ser Gly Gly Gly Gly Ser
                420                 425                 430

Gly Gly Gly Gly Ser Gly Gly Gly Gly Ser Gly Gly Gly Gly Ser Gly
                435                 440                 445

Gly Gly Ser Gly Gly Gly Gly Ser Gly Gly Gly Gly Ser Glu Val
450                 455                 460

Gln Leu Leu Glu Ser Gly Gly Gly Val Val Gln Pro Gly Gly Ser Leu
465                 470                 475                 480
```

-continued

```
Arg Leu Ser Cys Ala Ala Ser Gly Phe Thr Phe Arg Ser Phe Gly Met
                485                 490                 495
Ser Trp Val Arg Gln Ala Pro Gly Lys Gly Pro Glu Trp Val Ser Ser
            500                 505                 510
Ile Ser Gly Ser Gly Ser Asp Thr Leu Tyr Ala Asp Ser Val Lys Gly
            515                 520                 525
Arg Phe Thr Ile Ser Arg Asp Asn Ser Lys Asn Thr Leu Tyr Leu Gln
        530                 535                 540
Met Asn Ser Leu Arg Pro Glu Asp Thr Ala Leu Tyr Tyr Cys Thr Ile
545                 550                 555                 560
Gly Gly Ser Leu Ser Arg Ser Ser Gln Gly Thr Leu Val Thr Val Ser
                565                 570                 575
Ser Ala

<210> SEQ ID NO 127
<211> LENGTH: 578
<212> TYPE: PRT
<213> ORGANISM: Artificial Sequence
<220> FEATURE:
<223> OTHER INFORMATION: humanized lama

<400> SEQUENCE: 127

Asp Val Gln Leu Val Glu Ser Gly Gly Val Val Gln Pro Gly Gly
1               5                   10                  15
Ser Leu Arg Leu Ser Cys Ala Ala Ser Gly Ser Ile Ala Ser Ile His
            20                  25                  30
Ala Met Gly Trp Phe Arg Gln Ala Pro Gly Lys Glu Arg Glu Phe Val
        35                  40                  45
Ala Val Ile Thr Trp Ser Gly Gly Ile Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Leu Tyr Tyr Cys
                85                  90                  95
Ala Gly Asp Lys His Gln Ser Ser Trp Tyr Asp Tyr Trp Gly Gln Gly
            100                 105                 110
Thr Leu Val Thr Val Ser Ser Gly Gly Gly Gly Ser Gly Gly Gly Gly
        115                 120                 125
Ser Gly Gly Gly Gly Ser Gly Gly Gly Gly Ser Gly Gly Gly Gly Ser
    130                 135                 140
Gly Gly Gly Gly Ser Gly Gly Gly Gly Ser Glu Val Gln Leu Val Glu
145                 150                 155                 160
Ser Gly Gly Gly Val Val Gln Pro Gly Gly Ser Leu Arg Leu Ser Cys
                165                 170                 175
Ala Ala Ser Gly Ser Ile Ala Ser Ile His Ala Met Gly Trp Phe Arg
            180                 185                 190
Gln Ala Pro Gly Lys Glu Arg Glu Phe Val Ala Val Ile Thr Trp Ser
        195                 200                 205
Gly Gly Ile Thr Tyr Tyr Ala Asp Ser Val Lys Gly Arg Phe Thr Ile
    210                 215                 220
Ser Arg Asp Asn Ser Lys Asn Thr Val Tyr Leu Gln Met Asn Ser Leu
225                 230                 235                 240
Arg Pro Glu Asp Thr Ala Leu Tyr Tyr Cys Ala Gly Asp Lys His Gln
                245                 250                 255
```

```
Ser Ser Trp Tyr Asp Tyr Trp Gly Gln Gly Thr Leu Val Thr Val Ser
            260                 265                 270

Ser Gly Gly Gly Ser Gly Gly Gly Ser Gly Gly Gly Ser
        275                 280                 285

Gly Gly Gly Gly Ser Gly Gly Gly Ser Gly Gly Gly Ser Gly
        290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Gly Thr
                325                 330                 335

Phe Ser Phe Tyr Gly Met Gly Trp Phe Arg Gln Ala Pro Gly Lys Glu
            340                 345                 350

Arg Glu Phe Val Ala Asp Ile Arg Thr Ser Ala Gly Arg Thr Tyr Tyr
            355                 360                 365

Ala Asp Ser Val Lys Gly Arg Phe Thr Ile Ser Arg Asp Asn Ser Lys
        370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Met Ser Gly Ile Ser Gly Trp Asp Tyr
            405                 410                 415

Trp Gly Gln Gly Thr Leu Val Thr Val Ser Gly Gly Gly Gly Ser
            420                 425                 430

Gly Gly Gly Ser Gly Gly Gly Ser Gly Gly Gly Ser Gly
        435                 440                 445

Gly Gly Gly Ser Gly Gly Gly Ser Gly Gly Gly Ser Glu Val
        450                 455                 460

Gln Leu Val Glu Ser Gly Gly Leu Val Gln Pro Gly Asn Ser Leu
465                 470                 475                 480

Arg Leu Ser Cys Ala Ala Ser Gly Phe Thr Phe Ser Phe Gly Met
            485                 490                 495

Ser Trp Val Arg Gln Ala Pro Gly Lys Gly Leu Glu Trp Val Ser Ser
            500                 505                 510

Ile Ser Gly Ser Gly Ser Asp Thr Leu Tyr Ala Asp Ser Val Lys Gly
        515                 520                 525

Arg Phe Thr Ile Ser Arg Asp Asn Ala Lys Thr Thr Leu Tyr Leu Gln
        530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Gln Gly Thr Leu Val Thr Val Ser
            565                 570                 575

Ser Ala

<210> SEQ ID NO 128
<211> LENGTH: 578
<212> TYPE: PRT
<213> ORGANISM: Artificial Sequence
<220> FEATURE:
<223> OTHER INFORMATION: humanized lama

<400> SEQUENCE: 128

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
```

-continued

```
            35                  40                  45
Ala Val Ile Thr Trp Ser Gly Gly Ile Thr Tyr Tyr Ala Asp Ser Val
 50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Pro Glu Asp Thr Ala Leu Tyr Tyr Cys
                 85                  90                  95
Ala Gly Asp Lys His Gln Ser Ser Trp Tyr Asp Tyr Trp Gly Gln Gly
                100                 105                 110
Thr Leu Val Thr Val Ser Ser Gly Gly Gly Ser Gly Gly Gly Gly
                115                 120                 125
Ser Gly Gly Gly Gly Ser Gly Gly Gly Ser Gly Gly Gly Gly Ser
    130                 135                 140
Gly Gly Gly Gly Ser Gly Gly Gly Ser Glu Val Gln Leu Val Glu
145                 150                 155                 160
Ser Gly Gly Gly Val Val Gln Pro Gly Gly Ser Leu Arg Leu Ser Cys
                165                 170                 175
Ala Ala Ser Gly Ser Ile Ala Ser Ile His Ala Met Gly Trp Phe Arg
                180                 185                 190
Gln Ala Pro Gly Lys Glu Arg Glu Phe Val Ala Val Ile Thr Trp Ser
                195                 200                 205
Gly Gly Ile Thr Tyr Tyr Ala Asp Ser Val Lys Gly Arg Phe Thr Ile
    210                 215                 220
Ser Arg Asp Asn Ser Lys Asn Thr Val Tyr Leu Gln Met Asn Ser Leu
225                 230                 235                 240
Arg Pro Glu Asp Thr Ala Leu Tyr Tyr Cys Ala Gly Asp Lys His Gln
                245                 250                 255
Ser Ser Trp Tyr Asp Tyr Trp Gly Gln Gly Thr Leu Val Thr Val Ser
                260                 265                 270
Ser Gly Gly Gly Gly Ser Gly Gly Gly Gly Ser Gly Gly Gly Gly Ser
    275                 280                 285
Gly Gly Gly Gly Ser Gly Gly Gly Ser Gly Gly Gly Gly Ser Gly
    290                 295                 300
Gly Gly Gly Ser Glu Val Gln Leu Val Glu Ser Gly Gly Val Val
305                 310                 315                 320
Gln Pro Gly Gly Ser Leu Arg Leu Ser Cys Ala Ala Ser Gly Gly Thr
                325                 330                 335
Phe Ser Phe Tyr Gly Met Gly Trp Phe Arg Gln Ala Pro Gly Lys Glu
                340                 345                 350
Gln Glu Phe Val Ala Asp Ile Arg Thr Ser Ala Gly Arg Thr Tyr Tyr
                355                 360                 365
Ala Asp Ser Val Lys Gly Arg Phe Thr Ile Ser Arg Asp Asn Ser Lys
                370                 375                 380
Asn Thr Val Tyr Leu Gln Met Asn Ser Leu Arg Pro Glu Asp Thr Ala
385                 390                 395                 400
Leu Tyr Tyr Cys Ala Ala Glu Met Ser Gly Ile Ser Gly Trp Asp Tyr
                405                 410                 415
Trp Gly Gln Gly Thr Leu Val Thr Val Ser Ser Gly Gly Gly Gly Ser
                420                 425                 430
Gly Gly Gly Gly Ser Gly Gly Gly Gly Ser Gly Gly Gly Ser Gly
    435                 440                 445
Gly Gly Gly Ser Gly Gly Gly Ser Gly Gly Gly Gly Ser Glu Val
    450                 455                 460
```

```
Gln Leu Val Glu Ser Gly Gly Leu Val Gln Pro Gly Asn Ser Leu
465                 470                 475                 480

Arg Leu Ser Cys Ala Ala Ser Gly Phe Thr Phe Ser Ser Phe Gly Met
            485                 490                 495

Ser Trp Val Arg Gln Ala Pro Gly Lys Gly Leu Glu Trp Val Ser Ser
            500                 505                 510

Ile Ser Gly Ser Gly Ser Asp Thr Leu Tyr Ala Asp Ser Val Lys Gly
            515                 520                 525

Arg Phe Thr Ile Ser Arg Asp Asn Ala Lys Thr Thr Leu Tyr Leu Gln
            530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Ser Gln Gly Thr Leu Val Thr Val Ser
            565                 570                 575

Ser Ala

<210> SEQ ID NO 129
<211> LENGTH: 578
<212> TYPE: PRT
<213> ORGANISM: Artificial Sequence
<220> FEATURE:
<223> OTHER INFORMATION: humanized lama

<400> SEQUENCE: 129

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Gly Gly Gly Ser Gly Gly Gly Gly Ser
        130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
            195                 200                 205

Gly Gly Ile Thr Tyr Tyr Ala Asp Ser Val Lys Gly Arg Phe Thr Ile
        210                 215                 220

Ser Arg Asp Asn Ser Lys Asn Thr Val Tyr Leu Gln Met Asn Ser Leu
225                 230                 235                 240
```

```
Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Ser Gly Gly Gly Gly Ser
        275                 280                 285

Gly Gly Gly Gly Ser Gly Gly Gly Ser Gly Gly Gly Ser Gly
        290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Gly Thr
                325                 330                 335

Phe Ser Phe Tyr Gly Met Gly Trp Phe Arg Gln Ala Pro Gly Lys Glu
                340                 345                 350

Arg Glu Phe Val Ala Asp Ile Arg Thr Ser Ala Gly Arg Thr Tyr Tyr
                355                 360                 365

Ala Asp Ser Val Lys Gly Arg Phe Thr Ile Ser Arg Asp Asn Ser Lys
            370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Met Ser Gly Ile Ser Gly Trp Asp Tyr
                405                 410                 415

Trp Gly Gln Gly Thr Leu Val Thr Val Ser Ser Gly Gly Gly Gly Ser
            420                 425                 430

Gly Gly Gly Gly Ser Gly Gly Gly Ser Gly Gly Gly Gly Ser Gly
            435                 440                 445

Gly Gly Gly Ser Gly Gly Gly Ser Gly Gly Gly Gly Ser Glu Val
            450                 455                 460

Gln Leu Leu Glu Ser Gly Gly Val Val Gln Pro Gly Gly Ser Leu
465                 470                 475                 480

Arg Leu Ser Cys Ala Ala Ser Gly Phe Thr Phe Arg Ser Phe Gly Met
                485                 490                 495

Ser Trp Val Arg Gln Ala Pro Gly Lys Gly Pro Glu Trp Val Ser Ser
                500                 505                 510

Ile Ser Gly Ser Gly Ser Asp Thr Leu Tyr Ala Asp Ser Val Lys Gly
            515                 520                 525

Arg Phe Thr Ile Ser Arg Asp Asn Ser Lys Asn Thr Leu Tyr Leu Gln
            530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Ser Gln Gly Thr Leu Val Thr Val Ser
                565                 570                 575

Ser Ala

<210> SEQ ID NO 130
<211> LENGTH: 578
<212> TYPE: PRT
<213> ORGANISM: Artificial Sequence
<220> FEATURE:
<223> OTHER INFORMATION: humanized lama

<400> SEQUENCE: 130

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
```

```
            20                  25                  30
Ala Met Gly Trp Phe Arg Gln Ala Pro Gly Lys Glu Arg Glu Phe Val
            35                  40                  45
Ala Val Ile Thr Trp Ser Gly Gly Ile Thr Tyr Tyr Ala Asp Ser Val
            50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Leu Tyr Tyr Cys
                85                  90                  95
Ala Gly Asp Lys His Gln Ser Ser Trp Tyr Asp Tyr Trp Gly Gln Gly
            100                 105                 110
Thr Leu Val Thr Val Ser Ser Gly Gly Gly Ser Gly Gly Gly Gly
            115                 120                 125
Ser Gly Gly Gly Ser Gly Gly Gly Ser Gly Gly Gly Ser
            130                 135                 140
Gly Gly Gly Ser Gly Gly Gly Ser Glu Val Gln Leu Val Glu
145                 150                 155                 160
Ser Gly Gly Gly Val Val Gln Pro Gly Gly Ser Leu Arg Leu Ser Cys
                165                 170                 175
Ala Ala Ser Gly Ser Ile Ala Ser Ile His Ala Met Gly Trp Phe Arg
            180                 185                 190
Gln Ala Pro Gly Lys Glu Arg Glu Phe Val Ala Val Ile Thr Trp Ser
            195                 200                 205
Gly Gly Ile Thr Tyr Tyr Ala Asp Ser Val Lys Gly Arg Phe Thr Ile
            210                 215                 220
Ser Arg Asp Asn Ser Lys Asn Thr Val Tyr Leu Gln Met Asn Ser Leu
225                 230                 235                 240
Arg Pro Glu Asp Thr Ala Leu Tyr Tyr Cys Ala Gly Asp Lys His Gln
                245                 250                 255
Ser Ser Trp Tyr Asp Tyr Trp Gly Gln Gly Thr Leu Val Thr Val Ser
            260                 265                 270
Ser Gly Gly Gly Ser Gly Gly Gly Ser Gly Gly Gly Ser
            275                 280                 285
Gly Gly Gly Ser Gly Gly Gly Ser Gly Gly Gly Ser Gly
            290                 295                 300
Gly Gly Ser Glu Val Gln Leu Val Glu Ser Gly Gly Val Val
305                 310                 315                 320
Gln Pro Gly Gly Ser Leu Arg Leu Ser Cys Ala Ala Ser Gly Thr
            325                 330                 335
Phe Ser Phe Tyr Gly Met Gly Trp Phe Arg Gln Ala Pro Gly Lys Glu
            340                 345                 350
Gln Glu Phe Val Ala Asp Ile Arg Thr Ser Ala Gly Arg Thr Tyr Tyr
            355                 360                 365
Ala Asp Ser Val Lys Gly Arg Phe Thr Ile Ser Arg Asp Asn Ser Lys
            370                 375                 380
Asn Thr Val Tyr Leu Gln Met Asn Ser Leu Arg Pro Glu Asp Thr Ala
385                 390                 395                 400
Leu Tyr Tyr Cys Ala Ala Glu Met Ser Gly Ile Ser Gly Trp Asp Tyr
                405                 410                 415
Trp Gly Gln Gly Thr Leu Val Thr Val Ser Ser Gly Gly Gly Ser
            420                 425                 430
Gly Gly Gly Gly Ser Gly Gly Gly Ser Gly Gly Gly Ser Gly
            435                 440                 445
```

```
Gly Gly Gly Ser Gly Gly Gly Ser Gly Gly Gly Ser Glu Val
    450                 455                 460

Gln Leu Leu Glu Ser Gly Gly Val Val Gln Pro Gly Gly Ser Leu
465                 470                 475                 480

Arg Leu Ser Cys Ala Ala Ser Gly Phe Thr Phe Arg Ser Phe Gly Met
                485                 490                 495

Ser Trp Val Arg Gln Ala Pro Gly Lys Gly Pro Glu Trp Val Ser Ser
            500                 505                 510

Ile Ser Gly Ser Gly Ser Asp Thr Leu Tyr Ala Asp Ser Val Lys Gly
        515                 520                 525

Arg Phe Thr Ile Ser Arg Asp Asn Ser Lys Asn Thr Leu Tyr Leu Gln
    530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Ser Gln Gly Thr Leu Val Thr Val Ser
                565                 570                 575

Ser Ala

<210> SEQ ID NO 131
<211> LENGTH: 578
<212> TYPE: PRT
<213> ORGANISM: Artificial Sequence
<220> FEATURE:
<223> OTHER INFORMATION: humanized lama

<400> SEQUENCE: 131

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
        195                 200                 205

Gly Gly Ile Thr Tyr Tyr Ala Asp Ser Val Lys Gly Arg Phe Thr Ile
    210                 215                 220
```

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
            245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Ser Gly Gly Gly Gly Ser
        275                 280                 285

Gly Gly Gly Gly Ser Gly Gly Gly Ser Gly Gly Gly Gly Ser Gly
        290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
            325                 330                 335

Ala Ser Ile His Ala Met Gly Trp Phe Arg Gln Ala Pro Gly Lys Glu
            340                 345                 350

Arg Glu Phe Val Ala Val Ile Thr Trp Ser Gly Ile Thr Tyr Tyr
        355                 360                 365

Ala Asp Ser Val Lys Gly Arg Phe Thr Ile Ser Arg Asp Asn Ser Lys
370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
            405                 410                 415

Trp Gly Gln Gly Thr Leu Val Thr Val Ser Ser Gly Gly Gly Gly Ser
            420                 425                 430

Gly Gly Gly Gly Ser Gly Gly Gly Ser Gly Gly Gly Gly Ser Gly
        435                 440                 445

Gly Gly Gly Ser Gly Gly Gly Ser Gly Gly Gly Gly Ser Glu Val
        450                 455                 460

Gln Leu Val Glu Ser Gly Gly Gly Leu Val Gln Pro Gly Asn Ser Leu
465                 470                 475                 480

Arg Leu Ser Cys Ala Ala Ser Gly Phe Thr Phe Ser Ser Phe Gly Met
            485                 490                 495

Ser Trp Val Arg Gln Ala Pro Gly Lys Gly Leu Glu Trp Val Ser Ser
            500                 505                 510

Ile Ser Gly Ser Gly Ser Asp Thr Leu Tyr Ala Asp Ser Val Lys Gly
            515                 520                 525

Arg Phe Thr Ile Ser Arg Asp Asn Ala Lys Thr Thr Leu Tyr Leu Gln
            530                 535                 540

Met Asn Ser Leu Arg Pro Glu Asp Thr Ala Val Tyr Tyr Cys Thr Ile
545                 550                 555                 560

Gly Gly Ser Leu Ser Arg Ser Ser Gln Gly Thr Leu Val Thr Val Ser
            565                 570                 575

Ser Ala

<210> SEQ ID NO 132
<211> LENGTH: 578
<212> TYPE: PRT
<213> ORGANISM: Artificial Sequence
<220> FEATURE:
<223> OTHER INFORMATION: humanized lama

<400> SEQUENCE: 132

Asp Val Gln Leu Val Glu Ser Gly Gly Gly Val Val Gln Pro Gly Gly

-continued

```
1               5                   10                  15
Ser Leu Arg Leu Ser Cys Ala Ala Ser Gly Gly Thr Phe Ser Phe Tyr
            20                  25                  30
Gly Met Gly Trp Phe Arg Gln Ala Pro Gly Lys Glu Arg Glu Phe Val
            35                  40                  45
Ala Asp Ile Arg Thr Ser Ala Gly Arg Thr Tyr Tyr Ala Asp Ser Val
            50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Pro Glu Asp Thr Ala Leu Tyr Tyr Cys
                85                  90                  95
Ala Ala Glu Met Ser Gly Ile Ser Gly Trp Asp Tyr Trp Gly Gln Gly
            100                 105                 110
Thr Leu Val Thr Val Ser Ser Gly Gly Gly Ser Gly Gly Gly Gly
            115                 120                 125
Ser Gly Gly Gly Gly Ser Gly Gly Gly Gly Ser Gly Gly Gly Gly Ser
    130                 135                 140
Gly Gly Gly Ser Gly Gly Gly Ser Glu Val Gln Leu Val Glu
145                 150                 155                 160
Ser Gly Gly Gly Val Val Gln Pro Gly Gly Ser Leu Arg Leu Ser Cys
                165                 170                 175
Ala Ala Ser Gly Ser Ile Ala Ser Ile His Ala Met Gly Trp Phe Arg
            180                 185                 190
Gln Ala Pro Gly Lys Glu Arg Glu Phe Val Ala Val Ile Thr Trp Ser
            195                 200                 205
Gly Gly Ile Thr Tyr Tyr Ala Asp Ser Val Lys Gly Arg Phe Thr Ile
            210                 215                 220
Ser Arg Asp Asn Ser Lys Asn Thr Val Tyr Leu Gln Met Asn Ser Leu
225                 230                 235                 240
Arg Pro Glu Asp Thr Ala Leu Tyr Tyr Cys Ala Gly Asp Lys His Gln
                245                 250                 255
Ser Ser Trp Tyr Asp Tyr Trp Gly Gln Gly Thr Leu Val Thr Val Ser
            260                 265                 270
Ser Gly Gly Gly Gly Ser Gly Gly Gly Gly Ser Gly Gly Gly Gly Ser
            275                 280                 285
Gly Gly Gly Gly Ser Gly Gly Gly Ser Gly Gly Gly Ser Gly
            290                 295                 300
Gly Gly Gly Ser Glu Val Gln Leu Val Glu Ser Gly Gly Gly Val Val
305                 310                 315                 320
Gln Pro Gly Gly Ser Leu Arg Leu Ser Cys Ala Ala Ser Gly Ser Ile
            325                 330                 335
Ala Ser Ile His Ala Met Gly Trp Phe Arg Gln Ala Pro Gly Lys Glu
            340                 345                 350
Arg Glu Phe Val Ala Val Ile Thr Trp Ser Gly Gly Ile Thr Tyr Tyr
            355                 360                 365
Ala Asp Ser Val Lys Gly Arg Phe Thr Ile Ser Arg Asp Asn Ser Lys
            370                 375                 380
Asn Thr Val Tyr Leu Gln Met Asn Ser Leu Arg Pro Glu Asp Thr Ala
385                 390                 395                 400
Leu Tyr Tyr Cys Ala Gly Asp Lys His Gln Ser Ser Trp Tyr Asp Tyr
                405                 410                 415
Trp Gly Gln Gly Thr Leu Val Thr Val Ser Ser Gly Gly Gly Gly Ser
            420                 425                 430
```

```
Gly Gly Gly Gly Ser Gly Gly Gly Ser Gly Gly Gly Ser Gly
        435                 440                 445
Gly Gly Gly Ser Gly Gly Gly Ser Gly Gly Gly Ser Glu Val
    450                 455                 460
Gln Leu Val Glu Ser Gly Gly Leu Val Gln Pro Gly Asn Ser Leu
465                 470                 475                 480
Arg Leu Ser Cys Ala Ala Ser Gly Phe Thr Phe Ser Ser Phe Gly Met
                485                 490                 495
Ser Trp Val Arg Gln Ala Pro Gly Lys Gly Leu Glu Trp Val Ser Ser
            500                 505                 510
Ile Ser Gly Ser Gly Ser Asp Thr Leu Tyr Ala Asp Ser Val Lys Gly
            515                 520                 525
Arg Phe Thr Ile Ser Arg Asp Asn Ala Lys Thr Thr Leu Tyr Leu Gln
        530                 535                 540
Met Asn Ser Leu Arg Pro Glu Asp Thr Ala Val Tyr Tyr Cys Thr Ile
545                 550                 555                 560
Gly Gly Ser Leu Ser Arg Ser Ser Gln Gly Thr Leu Val Thr Val Ser
                565                 570                 575
Ser Ala
```

<210> SEQ ID NO 133
<211> LENGTH: 578
<212> TYPE: PRT
<213> ORGANISM: Artificial Sequence
<220> FEATURE:
<223> OTHER INFORMATION: humanized lama

<400> SEQUENCE: 133

```
Asp Val Gln Leu Val Glu Ser Gly Gly Val Val Gln Pro Gly Gly
1               5                   10                  15
Ser Leu Arg Leu Ser Cys Ala Ala Ser Gly Gly Thr Phe Ser Phe Tyr
            20                  25                  30
Gly Met Gly Trp Phe Arg Gln Ala Pro Gly Lys Glu Gln Glu Phe Val
        35                  40                  45
Ala Asp Ile Arg Thr Ser Ala Gly Arg Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Leu Tyr Tyr Cys
                85                  90                  95
Ala Ala Glu Met Ser Gly Ile Ser Gly Trp Asp Tyr Trp Gly Gln Gly
            100                 105                 110
Thr Leu Val Thr Val Ser Ser Gly Gly Gly Gly Ser Gly Gly Gly Gly
        115                 120                 125
Ser Gly Gly Gly Gly Ser Gly Gly Gly Gly Ser Gly Gly Gly Gly Ser
    130                 135                 140
Gly Gly Gly Gly Ser Gly Gly Gly Gly Ser Glu Val Gln Leu Val Glu
145                 150                 155                 160
Ser Gly Gly Gly Val Val Gln Pro Gly Gly Ser Leu Arg Leu Ser Cys
                165                 170                 175
Ala Ala Ser Gly Ser Ile Ala Ser Ile His Ala Met Gly Trp Phe Arg
            180                 185                 190
Gln Ala Pro Gly Lys Glu Arg Glu Phe Val Ala Val Ile Thr Trp Ser
        195                 200                 205
```

-continued

Gly Gly Ile Thr Tyr Tyr Ala Asp Ser Val Lys Gly Arg Phe Thr Ile
        210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
                260                 265                 270

Ser Gly Gly Gly Gly Ser Gly Gly Gly Ser Gly Gly Gly Gly Ser
        275                 280                 285

Gly Gly Gly Gly Ser Gly Gly Gly Ser Gly Gly Gly Gly Ser Gly
        290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
                325                 330                 335

Ala Ser Ile His Ala Met Gly Trp Phe Arg Gln Ala Pro Gly Lys Glu
                340                 345                 350

Arg Glu Phe Val Ala Val Ile Thr Trp Ser Gly Gly Ile Thr Tyr Tyr
                355                 360                 365

Ala Asp Ser Val Lys Gly Arg Phe Thr Ile Ser Arg Asp Asn Ser Lys
370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
                405                 410                 415

Trp Gly Gln Gly Thr Leu Val Thr Val Ser Ser Gly Gly Gly Gly Ser
                420                 425                 430

Gly Gly Gly Gly Ser Gly Gly Gly Ser Gly Gly Gly Gly Ser Gly
        435                 440                 445

Gly Gly Gly Ser Gly Gly Gly Ser Gly Gly Gly Gly Ser Glu Val
        450                 455                 460

Gln Leu Leu Glu Ser Gly Gly Val Val Gln Pro Gly Gly Ser Leu
465                 470                 475                 480

Arg Leu Ser Cys Ala Ala Ser Gly Phe Thr Phe Arg Ser Phe Gly Met
                485                 490                 495

Ser Trp Val Arg Gln Ala Pro Gly Lys Gly Pro Glu Trp Val Ser Ser
                500                 505                 510

Ile Ser Gly Ser Gly Ser Asp Thr Leu Tyr Ala Asp Ser Val Lys Gly
                515                 520                 525

Arg Phe Thr Ile Ser Arg Asp Asn Ser Lys Asn Thr Leu Tyr Leu Gln
                530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Ser Gln Gly Thr Leu Val Thr Val Ser
                565                 570                 575

Ser Ala

<210> SEQ ID NO 134
<211> LENGTH: 578
<212> TYPE: PRT
<213> ORGANISM: Artificial Sequence
<220> FEATURE:
<223> OTHER INFORMATION: humanized lama

```
<400> SEQUENCE: 134

Asp Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
                35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
                100                 105                 110

Thr Leu Val Thr Val Ser Ser Gly Gly Gly Ser Gly Gly Gly Gly
            115                 120                 125

Ser Gly Gly Gly Gly Ser Gly Gly Gly Ser Gly Gly Gly Gly Ser
    130                 135                 140

Gly Gly Gly Ser Gly Gly Gly Ser Glu Val Gln Leu Val Glu
145                 150                 155                 160

Ser Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
                195                 200                 205

Gly Gly Ile Thr Tyr Tyr Ala Asp Ser Val Lys Gly Arg Phe Thr Ile
            210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
            275                 280                 285

Gly Gly Gly Gly Ser Gly Gly Gly Gly Ser Gly Gly Gly Gly Ser Gly
        290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Ser Ile
                325                 330                 335

Ala Ser Ile His Ala Met Gly Trp Phe Arg Gln Ala Pro Gly Lys Glu
            340                 345                 350

Arg Glu Phe Val Ala Val Ile Thr Trp Ser Gly Gly Ile Thr Tyr Tyr
            355                 360                 365

Ala Asp Ser Val Lys Gly Arg Phe Thr Ile Ser Arg Asp Asn Ser Lys
    370                 375                 380

Asn Thr Val Tyr Leu Gln Met Asn Ser Leu Arg Pro Glu Asp Thr Ala
385                 390                 395                 400

Leu Tyr Tyr Cys Ala Gly Asp Lys His Gln Ser Ser Trp Tyr Asp Tyr
                405                 410                 415
```

```
Trp Gly Gln Gly Thr Leu Val Thr Val Ser Ser Gly Gly Gly Ser
                420                 425                 430

Gly Gly Gly Gly Ser Gly Gly Gly Ser Gly Gly Gly Ser Gly
            435                 440                 445

Gly Gly Gly Ser Gly Gly Gly Ser Gly Gly Gly Ser Glu Val
    450                 455                 460

Gln Leu Leu Glu Ser Gly Gly Val Val Gln Pro Gly Gly Ser Leu
465                 470                 475                 480

Arg Leu Ser Cys Ala Ala Ser Gly Phe Thr Phe Arg Ser Phe Gly Met
                485                 490                 495

Ser Trp Val Arg Gln Ala Pro Gly Lys Gly Pro Glu Trp Val Ser Ser
                500                 505                 510

Ile Ser Gly Ser Gly Ser Asp Thr Leu Tyr Ala Asp Ser Val Lys Gly
                515                 520                 525

Arg Phe Thr Ile Ser Arg Asp Asn Ser Lys Asn Thr Leu Tyr Leu Gln
                530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Gln Gly Thr Leu Val Thr Val Ser
                565                 570                 575

Ser Ala

<210> SEQ ID NO 135
<211> LENGTH: 119
<212> TYPE: PRT
<213> ORGANISM: Artificial Sequence
<220> FEATURE:
<223> OTHER INFORMATION: humanized lama

<400> SEQUENCE: 135

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
        115

<210> SEQ ID NO 136
<211> LENGTH: 119
<212> TYPE: PRT
<213> ORGANISM: Artificial Sequence
<220> FEATURE:
<223> OTHER INFORMATION: humanized lama

<400> SEQUENCE: 136

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
            115

<210> SEQ ID NO 137
<211> LENGTH: 119
<212> TYPE: PRT
<213> ORGANISM: Artificial Sequence
<220> FEATURE:
<223> OTHER INFORMATION: humanized lama

<400> SEQUENCE: 137

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser
            115

<210> SEQ ID NO 138
<211> LENGTH: 270
<212> TYPE: PRT
<213> ORGANISM: Artificial Sequence
<220> FEATURE:
<223> OTHER INFORMATION: humanized lama

<400> SEQUENCE: 138

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr

```
            65                  70                  75                  80
Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Gly Gly Gly Gly Ser Gly Gly Gly Ser
            130                 135                 140

Gly Gly Gly Gly Ser Gly Gly Gly Ser Glu Val Gln Leu Val Glu
145                 150                 155                 160

Ser Gly Gly Gly Val Val Gln Pro Gly Asn Ser Leu Arg Leu Ser Cys
                165                 170                 175

Ala Ala Ser Gly Phe Thr Phe Ser Ser Phe Gly Met Ser Trp Val Arg
                180                 185                 190

Gln Ala Pro Gly Lys Gly Leu Glu Trp Val Ser Ser Ile Ser Gly Ser
                195                 200                 205

Gly Ser Asp Thr Leu Tyr Ala Asp Ser Val Lys Gly Arg Phe Thr Ile
                210                 215                 220

Ser Arg Asp Asn Ala Lys Thr Thr Leu Tyr Leu Gln Met Asn Ser Leu
225                 230                 235                 240

Arg Pro Glu Asp Thr Ala Leu Tyr Tyr Cys Thr Ile Gly Gly Ser Leu
                245                 250                 255

Ser Arg Ser Ser Gln Gly Thr Leu Val Thr Val Ser Ser Ala
                260                 265                 270

<210> SEQ ID NO 139
<211> LENGTH: 424
<212> TYPE: PRT
<213> ORGANISM: Artificial Sequence
<220> FEATURE:
<223> OTHER INFORMATION: humanized lama

<400> SEQUENCE: 139

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
                20                  25                  30

Ala Met Gly Trp Phe Arg Gln Ala Pro Gly Lys Glu Arg Glu Phe Val
                35                  40                  45

Ala Val Ile Thr Trp Ser Gly Gly Ile Thr Tyr Tyr Ala Asp Ser Val
            50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Gly Gly Gly Gly Ser Gly Gly Gly Ser
            130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
```

```
                165                 170                 175
Ala Ala Ser Gly Ser Ile Ala Ser Ile His Ala Met Gly Trp Phe Arg
            180                 185                 190
Gln Ala Pro Gly Lys Glu Arg Glu Phe Val Ala Val Ile Thr Trp Ser
            195                 200                 205
Gly Gly Ile Thr Tyr Tyr Ala Asp Ser Val Lys Gly Arg Phe Thr Ile
            210                 215                 220
Ser Arg Asp Asn Ser Lys Asn Thr Val Tyr Leu Gln Met Asn Ser Leu
225                 230                 235                 240
Arg Pro Glu Asp Thr Ala Leu Tyr Tyr Cys Ala Gly Asp Lys His Gln
            245                 250                 255
Ser Ser Trp Tyr Asp Tyr Trp Gly Gln Gly Thr Leu Val Thr Val Ser
            260                 265                 270
Ser Gly Gly Gly Ser Gly Gly Gly Ser Gly Gly Gly Ser
            275                 280                 285
Gly Gly Gly Ser Gly Gly Gly Ser Gly Gly Gly Ser Gly
            290                 295                 300
Gly Gly Ser Glu Val Gln Leu Val Glu Ser Gly Gly Val Val
305                 310                 315                 320
Gln Pro Gly Asn Ser Leu Arg Leu Ser Cys Ala Ala Ser Gly Phe Thr
            325                 330                 335
Phe Ser Ser Phe Gly Met Ser Trp Val Arg Gln Ala Pro Gly Lys Gly
            340                 345                 350
Leu Glu Trp Val Ser Ser Ile Ser Gly Ser Gly Ser Asp Thr Leu Tyr
            355                 360                 365
Ala Asp Ser Val Lys Gly Arg Phe Thr Ile Ser Arg Asp Asn Ala Lys
            370                 375                 380
Thr Thr Leu Tyr Leu Gln Met Asn Ser Leu Arg Pro Glu Asp Thr Ala
385                 390                 395                 400
Leu Tyr Tyr Cys Thr Ile Gly Gly Ser Leu Ser Arg Ser Ser Gln Gly
            405                 410                 415
Thr Leu Val Thr Val Ser Ser Ala
            420

<210> SEQ ID NO 140
<211> LENGTH: 119
<212> TYPE: PRT
<213> ORGANISM: Artificial Sequence
<220> FEATURE:
<223> OTHER INFORMATION: humanized lama

<400> SEQUENCE: 140

Asp Val Gln Leu Val Glu Ser Gly Gly Gly Val Val Gln Pro Gly Gly
1               5                   10                  15
Ser Leu Arg Leu Ser Cys Ala Ala Ser Gly Ser Ile Ala Ser Ile His
            20                  25                  30
Ala Met Gly Trp Phe Arg Gln Ala Pro Gly Lys Glu Arg Glu Phe Val
            35                  40                  45
Ala Val Ile Thr Val Ser Gly Gly Ile Thr Tyr Tyr Ala Asp Ser Val
            50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Leu Tyr Tyr Cys
            85                  90                  95
Ala Gly Asp Lys His Gln Ser Ser Phe Tyr Asp Tyr Trp Gly Gln Gly
```

Thr Leu Val Thr Val Ser Ser
        115

<210> SEQ ID NO 141
<211> LENGTH: 119
<212> TYPE: PRT
<213> ORGANISM: Artificial Sequence
<220> FEATURE:
<223> OTHER INFORMATION: humanized lama

<400> SEQUENCE: 141

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Gln Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser
        115

<210> SEQ ID NO 142
<211> LENGTH: 119
<212> TYPE: PRT
<213> ORGANISM: Artificial Sequence
<220> FEATURE:
<223> OTHER INFORMATION: humanized lama

<400> SEQUENCE: 142

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Val Ser Gly Gly Ile Thr Tyr Tyr Ala Asp Ser Val
    50                  55                  60

Lys Gly Arg Phe Thr Ile Ser Arg Asp Pro Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Phe Tyr Asp Tyr Trp Gly Gln Gly
            100                 105                 110

Thr Leu Val Thr Val Ser Ser
        115

<210> SEQ ID NO 143
<211> LENGTH: 119
<212> TYPE: PRT
<213> ORGANISM: Artificial Sequence
<220> FEATURE:

<223> OTHER INFORMATION: humanized lama

<400> SEQUENCE: 143

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser
            115

<210> SEQ ID NO 144
<211> LENGTH: 110
<212> TYPE: PRT
<213> ORGANISM: Artificial Sequence
<220> FEATURE:
<223> OTHER INFORMATION: humanized lama
<220> FEATURE:
<221> NAME/KEY: MISC_FEATURE
<222> LOCATION: (11)..(11)
<223> OTHER INFORMATION: X is L or V
<220> FEATURE:
<221> NAME/KEY: MISC_FEATURE
<222> LOCATION: (93)..(93)
<223> OTHER INFORMATION: X is L or V

<400> SEQUENCE: 144

Glu Val Gln Leu Val Glu Ser Gly Gly Gly Xaa Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Xaa Tyr Tyr Cys
                85                  90                  95

Thr Ile Gly Gly Ser Leu Ser Arg Ser Ser Gln Gly Thr Leu
            100                 105                 110

<210> SEQ ID NO 145
<211> LENGTH: 1272
<212> TYPE: DNA
<213> ORGANISM: Artificial Sequence
<220> FEATURE:
<223> OTHER INFORMATION: humanized lama

<400> SEQUENCE: 145
gacgtgcaat tggtggagtc tggtggcgga gttgtccagc ctggcggcag tctgcggtta    60

| | |
|---|---|
| tcttgcgccg cttctggcag cattgccagt attcacgcta tgggttggtt caggcaggct | 120 |
| cctggtaaag aacgtgagtt tgtggctgtg attacttggt ccgtggtat tacttactac | 180 |
| gctgatagcg ttaagggccg gtttacaatt tcccgtgata atagcaaaaa taccgtctat | 240 |
| ctgcaaatga acagtctgcg cccggaagat accgccctgt attactgtgc gggcgataaa | 300 |
| catcagtcct catggtatga ctactggggg caagggaccc tggtcacggt ctcctccgga | 360 |
| ggcggtgggt caggtggcgg aggcagcggt ggaggaggta gtggcggtgg cggtagtggg | 420 |
| ggtggaggca gcggaggcgg aggcagtggg ggcggtggat ccgaggtgca gttggtggag | 480 |
| tctgggggag gagtggtgca gccggggggc tctctgagac tctcctgtgc agcctctggt | 540 |
| ggcaccttca gtttctatgg catgggctgg ttccgccagg ctccagggaa ggagcgcgag | 600 |
| tttgtagcag atattagaac cagtgctggt aggacatact atgcagactc cgtgaagggc | 660 |
| cgattcacca tctccagaga caacagcaag aacacggtgt atctgcaaat gaacagcctg | 720 |
| cgccctgagg acacggccct gtattactgt gcagcagagc caagtggaat aagtggttgg | 780 |
| gactactggg gccaggggac cctggtcacg gtctcgagcg gaggcggtgg gtcaggtggc | 840 |
| ggaggcagcg gtggaggagg tagtggcggt ggcggtagtg ggggtggagg cagcggaggc | 900 |
| ggaggcagtg ggggcggtgg ctcagaggta aactagtgg agtctggagg tggcgttgtg | 960 |
| caaccgggta acagtctgcg ccttagctgc gcagcgtctg gctttacctt cagctccttt | 1020 |
| ggcatgagct gggttcgcca ggctccggga aaaggactgg aatgggtttc gtctattagc | 1080 |
| ggcagtggta gcgatacgct ctacgcggac tccgtgaagg gccgtttcac catctcccgc | 1140 |
| gataacgcca aaactacact gtatctgcaa atgaatagcc tgcgtcctga agatacggcc | 1200 |
| ctgtattact gtactattgg tggctcgtta agccgttctt cacagggtac cctggtcacc | 1260 |
| gtctcctcag cg | 1272 |

<210> SEQ ID NO 146
<211> LENGTH: 424
<212> TYPE: PRT
<213> ORGANISM: Artificial Sequence
<220> FEATURE:
<223> OTHER INFORMATION: humanized lama

<400> SEQUENCE: 146

```
Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140
```

```
Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Arg Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Pro Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Ser Gly Gly Gly Ser Gly
    290                 295                 300

Gly Gly Gly Ser Glu Val Gln Leu Val Glu Ser Gly Gly Val Val
305                 310                 315                 320

Gln Pro Gly Asn Ser Leu Arg Leu Ser Cys Ala Ala Ser Gly Phe Thr
                325                 330                 335

Phe Ser Ser Phe Gly Met Ser Trp Val Arg Gln Ala Pro Gly Lys Gly
            340                 345                 350

Leu Glu Trp Val Ser Ser Ile Ser Gly Ser Gly Ser Asp Thr Leu Tyr
        355                 360                 365

Ala Asp Ser Val Lys Gly Arg Phe Thr Ile Ser Arg Asp Asn Ala Lys
    370                 375                 380

Thr Thr Leu Tyr Leu Gln Met Asn Ser Leu Arg Pro Glu Asp Thr Ala
385                 390                 395                 400

Leu Tyr Tyr Cys Thr Ile Gly Gly Ser Leu Ser Arg Ser Ser Gln Gly
                405                 410                 415

Thr Leu Val Thr Val Ser Ser Ala
            420

<210> SEQ ID NO 147
<211> LENGTH: 85
<212> TYPE: PRT
<213> ORGANISM: Artificial Sequence
<220> FEATURE:
<223> OTHER INFORMATION: humanized lama

<400> SEQUENCE: 147

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80
```

Ser Leu Glu Lys Arg
            85

<210> SEQ ID NO 148
<211> LENGTH: 1734
<212> TYPE: DNA
<213> ORGANISM: Artificial Sequence
<220> FEATURE:
<223> OTHER INFORMATION: humanized lama

<400> SEQUENCE: 148

| | | | | | |
|---|---|---|---|---|---|
| gacgtgcaat | tggtggagtc | tggtggcgga | gttgtccagc | ctggcggcag | tctgcggtta | 60 |
| tcttgcgccg | cttctggcag | cattgccagt | attcacgcta | tgggttggtt | caggcaggct | 120 |
| cctggtaaag | aacgtgagtt | tgtggctgtg | attacttggt | ccggtggtat | tacttactac | 180 |
| gctgatagcg | ttaagggccg | gtttacaatt | tcccgtgata | atagcaaaaa | taccgtctat | 240 |
| ctgcaaatga | acagtctgcg | cccggaagat | accgccctgt | attactgtgc | gggcgataaa | 300 |
| catcagtcct | catggtatga | ctactggggg | caagggaccc | tggtcacggt | ctcctccgga | 360 |
| ggcggtgggt | caggtggcgg | aggcagcggt | ggaggaggta | gtgcggtgg | cggtagtggg | 420 |
| ggtggaggca | gcggaggcgg | aggcagtggg | ggcggtggat | cagaggtgca | gttggtggag | 480 |
| tctggtggcg | gagttgtcca | gcctggcggc | agtctgcggt | tatcttgcgc | cgcttctggc | 540 |
| agcattgcca | gtattcacgc | tatgggttgg | ttcaggcagg | ctcctggtaa | agaacgtgag | 600 |
| tttgtggctg | tgattacttg | gtccggtggt | attacttact | acgctgatag | cgttaagggc | 660 |
| cggtttacaa | tttcccgtga | taatagcaaa | aataccgtct | atctgcaaat | gaacagtctg | 720 |
| cgcccggaag | ataccgccct | gtattactgt | gcgggcgata | aacatcagtc | ctcatggtat | 780 |
| gactactggg | ggcaagggac | cctggtcacg | gtctcctcag | gaggcggtgg | gtcaggtggc | 840 |
| ggaggcagcg | gtggaggagg | tagtgcggt | ggcggtagtg | gggtggagg | cagcggaggc | 900 |
| ggaggcagtg | gggcggtgg | atccgaggtg | cagttggtgg | agtctggggg | aggagtggtg | 960 |
| cagccggggg | gctctctgag | actctcctgt | gcagcctctg | gtggcacctt | cagtttctat | 1020 |
| ggcatgggct | ggttccgcca | ggctccaggg | aaggagcgcg | agtttgtagc | agatattaga | 1080 |
| accagtgctg | taggacata | ctatgcagac | tccgtgaagg | gccgattcac | catctccaga | 1140 |
| gacaacagca | agaacacggt | gtatctgcaa | atgaacagcc | tgcgccctga | ggacacggcc | 1200 |
| ctgtattact | gtgcagcaga | gccaagtgga | ataagtggtt | gggactactg | ggccaggggg | 1260 |
| accctggtca | cggtctcgag | cggaggcggt | gggtcaggtg | gcggaggcag | cggtggagga | 1320 |
| ggtagtggcg | gtggcggtag | tggggtgga | ggcagcggag | gcggaggcag | tggggcggt | 1380 |
| ggctcagagg | tacaactagt | ggagtctgga | ggtggcgttg | tgcaaccggg | taacagtctg | 1440 |
| cgccttagct | gcgcagcgtc | tggctttacc | ttcagctcct | ttggcatgag | ctgggttcgc | 1500 |
| caggctccgg | gaaaaggact | ggaatggttt | cgtctatta | gcggcagtgg | tagcgatacg | 1560 |
| ctctacgcgg | actccgtgaa | gggccgtttc | accatctccc | gcgataacgc | caaaactaca | 1620 |
| ctgtatctgc | aaatgaatag | cctgcgtcct | gaagatacgg | ccctgtatta | ctgtactatt | 1680 |
| ggtggctcgt | taagccgttc | ttcacagggt | accctggtca | ccgtctcctc | agcg | 1734 |

<210> SEQ ID NO 149
<211> LENGTH: 578
<212> TYPE: PRT
<213> ORGANISM: Artificial Sequence
<220> FEATURE:
<223> OTHER INFORMATION: humanized lama

```
<400> SEQUENCE: 149

Asp Val Gln Leu Val Glu Ser Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Ser Gly Gly Gly Ser Glu Val Gln Leu Val Glu
145                 150                 155                 160

Ser Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
        195                 200                 205

Gly Gly Ile Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Gly Asp Lys His Gln
                245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Gly Ser Gly Gly Gly Gly Ser Gly
    290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Gly Thr
                325                 330                 335

Phe Ser Phe Tyr Gly Met Gly Trp Phe Arg Gln Ala Pro Gly Lys Glu
            340                 345                 350

Arg Glu Phe Val Ala Asp Ile Arg Thr Ser Ala Gly Arg Thr Tyr Tyr
        355                 360                 365

Ala Asp Ser Val Lys Gly Arg Phe Thr Ile Ser Arg Asp Asn Ser Lys
    370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Pro Ser Gly Ile Ser Gly Trp Asp Tyr
                405                 410                 415
```

Trp Gly Gln Gly Thr Leu Val Thr Val Ser Ser Gly Gly Gly Ser
            420                 425                 430

Gly Gly Gly Gly Ser Gly Gly Gly Ser Gly Gly Gly Ser Gly
            435                 440                 445

Gly Gly Gly Ser Gly Gly Gly Ser Gly Gly Gly Ser Glu Val
450                 455                 460

Gln Leu Val Glu Ser Gly Gly Val Val Gln Pro Gly Asn Ser Leu
465                 470                 475                 480

Arg Leu Ser Cys Ala Ala Ser Gly Phe Thr Phe Ser Ser Phe Gly Met
            485                 490                 495

Ser Trp Val Arg Gln Ala Pro Gly Lys Gly Leu Glu Trp Val Ser Ser
            500                 505                 510

Ile Ser Gly Ser Gly Ser Asp Thr Leu Tyr Ala Asp Ser Val Lys Gly
            515                 520                 525

Arg Phe Thr Ile Ser Arg Asp Asn Ala Lys Thr Thr Leu Tyr Leu Gln
            530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Ser Gln Gly Thr Leu Val Thr Val Ser
            565                 570                 575

Ser Ala

<210> SEQ ID NO 150
<211> LENGTH: 1734
<212> TYPE: PRT
<213> ORGANISM: Artificial Sequence
<220> FEATURE:
<223> OTHER INFORMATION: humanized lama

<400> SEQUENCE: 150

Gly Ala Cys Gly Thr Gly Cys Ala Ala Thr Gly Gly Thr Gly Gly
1               5                   10                  15

Ala Gly Thr Cys Thr Gly Gly Thr Gly Gly Cys Gly Gly Ala Gly Thr
            20                  25                  30

Thr Gly Thr Cys Thr Gly Cys Ala Gly Cys Cys Thr Gly Gly Cys Gly
            35                  40                  45

Ala Gly Thr Cys Thr Gly Cys Gly Gly Thr Thr Ala Thr Cys Thr Thr
            50                  55                  60

Gly Cys Gly Cys Cys Gly Cys Thr Cys Thr Gly Gly Cys Ala Gly
65                  70                  75                  80

Cys Ala Thr Thr Gly Cys Cys Ala Gly Thr Ala Thr Cys Ala Cys
                85                  90                  95

Gly Cys Thr Ala Thr Gly Gly Thr Thr Gly Gly Thr Thr Cys Ala
            100                 105                 110

Gly Gly Cys Ala Gly Gly Cys Thr Cys Cys Thr Gly Gly Thr Ala Ala
            115                 120                 125

Ala Gly Ala Ala Cys Gly Thr Gly Ala Gly Thr Thr Gly Thr Gly
            130                 135                 140

Gly Cys Thr Gly Thr Gly Ala Thr Thr Ala Cys Thr Gly Gly Thr
145                 150                 155                 160

Cys Cys Gly Gly Thr Gly Gly Thr Ala Thr Ala Cys Thr Ala
                165                 170                 175

Cys Thr Ala Cys Gly Cys Thr Gly Ala Thr Ala Gly Cys Gly Thr Thr
                180                 185                 190

-continued

```
Ala Ala Gly Gly Gly Cys Cys Gly Gly Thr Thr Ala Cys Ala Ala
            195                 200                 205
Thr Thr Thr Cys Cys Cys Gly Thr Gly Ala Thr Ala Ala Thr Ala Gly
        210                 215                 220
Cys Ala Ala Ala Ala Thr Ala Cys Cys Gly Thr Cys Thr Ala Thr
225                 230                 235                 240
Cys Thr Gly Cys Ala Ala Thr Gly Ala Ala Cys Ala Gly Thr Cys
            245                 250                 255
Thr Gly Cys Gly Cys Cys Cys Gly Ala Ala Gly Ala Thr Ala Cys
            260                 265                 270
Cys Gly Cys Cys Cys Thr Gly Thr Ala Thr Ala Cys Thr Gly Thr
            275                 280                 285
Gly Cys Gly Gly Gly Cys Gly Ala Thr Ala Ala Ala Cys Ala Thr Cys
        290                 295                 300
Ala Gly Thr Cys Cys Thr Cys Ala Thr Gly Gly Thr Ala Thr Gly Ala
305                 310                 315                 320
Cys Thr Ala Cys Thr Gly Gly Gly Gly Cys Ala Ala Gly Gly Gly
            325                 330                 335
Ala Cys Cys Cys Thr Gly Gly Thr Cys Ala Cys Gly Gly Thr Cys Thr
        340                 345                 350
Cys Cys Thr Cys Ala Gly Gly Cys Gly Gly Thr Gly Gly
        355                 360                 365
Gly Thr Cys Ala Gly Gly Thr Gly Gly Cys Gly Gly Ala Gly Gly Cys
        370                 375                 380
Ala Gly Cys Gly Gly Thr Gly Gly Ala Gly Gly Ala Gly Gly Thr Ala
385                 390                 395                 400
Gly Thr Gly Gly Cys Gly Gly Thr Gly Gly Cys Gly Gly Thr Ala Gly
            405                 410                 415
Thr Gly Gly Gly Gly Thr Gly Gly Ala Gly Gly Cys Ala Gly Cys
        420                 425                 430
Gly Gly Ala Gly Gly Cys Gly Gly Ala Gly Gly Cys Ala Gly Thr Gly
            435                 440                 445
Gly Gly Gly Gly Cys Gly Gly Thr Gly Gly Ala Thr Cys Cys Gly Ala
        450                 455                 460
Gly Gly Thr Gly Cys Ala Gly Thr Thr Gly Thr Gly Gly Ala Gly
465                 470                 475                 480
Thr Cys Thr Gly Gly Gly Gly Gly Ala Gly Gly Cys Thr Thr Gly Gly
            485                 490                 495
Thr Gly Cys Ala Gly Cys Cys Gly Gly Gly Gly Gly Cys Thr Cys
            500                 505                 510
Thr Cys Thr Gly Ala Gly Ala Cys Thr Cys Thr Cys Cys Thr Gly Thr
        515                 520                 525
Gly Cys Ala Gly Cys Cys Thr Cys Thr Gly Gly Thr Gly Gly Cys Ala
        530                 535                 540
Cys Cys Thr Thr Cys Ala Gly Thr Thr Cys Thr Ala Thr Gly Gly
545                 550                 555                 560
Cys Ala Thr Gly Gly Gly Cys Thr Gly Gly Thr Thr Cys Cys Gly Cys
            565                 570                 575
Cys Ala Gly Gly Cys Thr Cys Cys Ala Gly Gly Gly Ala Ala Gly Gly
            580                 585                 590
Ala Gly Cys Gly Cys Gly Ala Gly Thr Thr Thr Gly Thr Ala Gly Cys
            595                 600                 605
Ala Gly Ala Thr Ala Thr Thr Ala Gly Ala Ala Cys Cys Ala Gly Thr
```

-continued

```
            610                 615                 620

Gly Cys Thr Gly Gly Thr Ala Gly Gly Cys Ala Thr Ala Cys Thr
625                 630                 635                 640

Ala Thr Gly Cys Ala Gly Ala Cys Thr Cys Gly Thr Gly Ala Ala
            645                 650                 655

Gly Gly Gly Cys Cys Gly Ala Thr Thr Cys Ala Cys Cys Ala Thr Cys
            660                 665                 670

Thr Cys Cys Ala Gly Ala Gly Ala Cys Ala Ala Cys Ala Gly Cys Ala
            675                 680                 685

Ala Gly Ala Ala Cys Ala Cys Gly Gly Thr Gly Thr Ala Thr Cys Thr
690                 695                 700

Gly Cys Ala Ala Ala Thr Gly Ala Ala Cys Ala Gly Cys Cys Thr Gly
705                 710                 715                 720

Cys Gly Cys Cys Cys Thr Gly Ala Gly Gly Ala Cys Ala Cys Gly Gly
            725                 730                 735

Cys Cys Cys Thr Gly Thr Ala Thr Thr Ala Cys Thr Gly Thr Gly Cys
            740                 745                 750

Ala Gly Cys Ala Gly Ala Gly Cys Cys Ala Ala Gly Thr Gly Gly Ala
            755                 760                 765

Ala Thr Ala Ala Gly Thr Gly Gly Thr Thr Gly Gly Gly Ala Cys Thr
770                 775                 780

Ala Cys Thr Gly Gly Gly Gly Cys Cys Ala Gly Gly Gly Ala Cys Cys
785                 790                 795                 800

Cys Cys Thr Gly Gly Thr Cys Ala Cys Gly Gly Thr Cys Thr Cys Gly
            805                 810                 815

Ala Gly Cys Gly Gly Ala Gly Cys Gly Gly Thr Gly Gly Thr
            820                 825                 830

Cys Ala Gly Gly Thr Gly Gly Cys Gly Gly Cys Ala Gly Gly
            835                 840                 845

Cys Gly Gly Thr Gly Gly Ala Gly Gly Ala Gly Gly Thr Ala Gly Thr
850                 855                 860

Gly Gly Cys Gly Gly Thr Gly Gly Cys Gly Gly Thr Ala Gly Thr Gly
865                 870                 875                 880

Gly Gly Gly Gly Thr Gly Gly Ala Gly Gly Cys Ala Gly Cys Gly Gly
            885                 890                 895

Ala Gly Gly Cys Gly Gly Ala Gly Gly Cys Ala Gly Thr Gly Gly Gly
            900                 905                 910

Gly Gly Cys Gly Gly Thr Gly Gly Ala Thr Cys Ala Gly Ala Gly Gly
            915                 920                 925

Thr Gly Cys Ala Gly Thr Thr Gly Gly Thr Gly Gly Ala Gly Thr Cys
930                 935                 940

Thr Gly Gly Gly Gly Gly Ala Gly Gly Ala Thr Gly Gly Thr Gly
945                 950                 955                 960

Cys Ala Gly Cys Cys Gly Gly Gly Gly Gly Cys Thr Cys Thr
            965                 970                 975

Thr Gly Ala Gly Ala Cys Thr Cys Thr Cys Thr Gly Thr Gly Cys
            980                 985                 990

Ala Gly Cys Cys Thr Cys Thr Gly  Thr Gly Gly Cys  Ala Cys Cys
            995                 1000                1005

Thr Thr  Cys Ala Gly Thr Thr  Cys Thr Ala Thr  Gly Gly Cys
            1010                1015                1020

Ala Thr  Gly Gly Gly Cys Thr  Gly Gly Thr Thr Cys  Cys Gly Cys
            1025                1030                1035
```

```
Cys Ala Gly Gly Cys Thr Cys Cys Ala Gly Gly Ala Ala Gly
    1040                1045                1050

Gly Ala Gly Cys Gly Cys Gly Ala Gly Thr Thr Thr Gly Thr Ala
    1055                1060                1065

Gly Cys Ala Gly Ala Thr Ala Thr Thr Ala Gly Ala Ala Cys Cys
    1070                1075                1080

Ala Gly Thr Gly Cys Thr Gly Gly Thr Ala Gly Gly Ala Cys Ala
    1085                1090                1095

Thr Ala Cys Thr Ala Thr Gly Cys Ala Gly Ala Cys Thr Cys Cys
    1100                1105                1110

Gly Thr Gly Ala Ala Gly Gly Gly Cys Cys Gly Ala Thr Thr Cys
    1115                1120                1125

Ala Cys Cys Ala Thr Cys Thr Cys Cys Ala Gly Ala Gly Ala Cys
    1130                1135                1140

Ala Ala Cys Ala Gly Cys Ala Ala Gly Ala Ala Cys Ala Cys Gly
    1145                1150                1155

Gly Thr Gly Thr Ala Thr Cys Thr Gly Cys Ala Ala Ala Thr Gly
    1160                1165                1170

Ala Ala Cys Ala Gly Cys Cys Thr Gly Cys Gly Cys Cys Cys Thr
    1175                1180                1185

Gly Ala Gly Gly Ala Cys Ala Cys Gly Gly Cys Cys Cys Thr Gly
    1190                1195                1200

Thr Ala Thr Thr Ala Cys Thr Gly Thr Gly Cys Ala Gly Cys Ala
    1205                1210                1215

Gly Ala Gly Cys Cys Ala Ala Gly Thr Gly Gly Ala Ala Thr Ala
    1220                1225                1230

Ala Gly Thr Gly Gly Thr Thr Gly Gly Gly Ala Cys Thr Ala Cys
    1235                1240                1245

Thr Gly Gly Gly Gly Cys Cys Ala Gly Gly Gly Ala Cys Cys
    1250                1255                1260

Cys Thr Gly Gly Thr Cys Ala Cys Gly Gly Thr Cys Thr Cys Cys
    1265                1270                1275

Thr Cys Ala Gly Gly Ala Gly Gly Cys Gly Gly Thr Gly Gly Gly
    1280                1285                1290

Thr Cys Ala Gly Gly Thr Gly Gly Cys Gly Gly Ala Gly Gly Cys
    1295                1300                1305

Ala Gly Cys Gly Gly Thr Gly Ala Gly Gly Ala Gly Gly Thr
    1310                1315                1320

Ala Gly Thr Gly Gly Cys Gly Gly Thr Gly Gly Cys Gly Gly Thr
    1325                1330                1335

Ala Gly Thr Gly Gly Gly Gly Gly Thr Gly Gly Ala Gly Gly Cys
    1340                1345                1350

Ala Gly Cys Gly Gly Ala Gly Gly Cys Gly Gly Ala Gly Gly Cys
    1355                1360                1365

Ala Gly Thr Gly Gly Gly Gly Gly Cys Gly Gly Thr Gly Gly Ala
    1370                1375                1380

Thr Cys Ala Gly Ala Gly Gly Thr Gly Cys Ala Ala Cys Thr Ala
    1385                1390                1395

Gly Thr Gly Gly Ala Gly Thr Cys Thr Gly Gly Ala Gly Gly Thr
    1400                1405                1410

Gly Gly Cys Gly Thr Thr Gly Thr Gly Cys Ala Ala Cys Cys Gly
    1415                1420                1425
```

Gly Gly Thr Ala Ala Cys Ala Gly Thr Cys Thr Gly Cys Gly Cys
        1430               1435               1440

Cys Thr Thr Ala Gly Cys Thr Gly Cys Gly Cys Ala Gly Cys Gly
        1445               1450               1455

Thr Cys Thr Gly Gly Cys Thr Thr Ala Cys Cys Thr Thr Cys
        1460               1465               1470

Ala Gly Cys Thr Cys Cys Thr Thr Gly Gly Cys Ala Thr Gly
        1475               1480               1485

Ala Gly Cys Thr Gly Gly Thr Thr Cys Gly Cys Cys Ala Gly
        1490               1495               1500

Gly Cys Thr Cys Cys Gly Gly Ala Ala Ala Gly Gly Ala
        1505               1510               1515

Cys Thr Gly Gly Ala Ala Thr Gly Gly Thr Thr Cys Gly
        1520               1525               1530

Thr Cys Thr Ala Thr Thr Ala Gly Cys Gly Gly Cys Ala Gly Thr
        1535               1540               1545

Gly Gly Thr Ala Gly Cys Gly Ala Thr Ala Cys Gly Cys Thr Cys
        1550               1555               1560

Thr Ala Cys Gly Cys Gly Gly Ala Cys Thr Cys Cys Gly Thr Gly
        1565               1570               1575

Ala Ala Gly Gly Gly Cys Cys Gly Thr Thr Cys Ala Cys Cys
        1580               1585               1590

Ala Thr Cys Thr Cys Cys Cys Gly Cys Gly Ala Thr Ala Ala Cys
        1595               1600               1605

Gly Cys Cys Ala Ala Ala Cys Thr Ala Cys Ala Cys Thr Gly
        1610               1615               1620

Thr Ala Thr Cys Thr Gly Cys Ala Ala Ala Thr Gly Ala Ala Thr
        1625               1630               1635

Ala Gly Cys Cys Thr Gly Cys Gly Thr Cys Cys Thr Gly Ala Ala
        1640               1645               1650

Gly Ala Thr Ala Cys Gly Gly Cys Cys Cys Thr Gly Thr Ala Thr
        1655               1660               1665

Thr Ala Cys Thr Gly Thr Ala Cys Thr Ala Thr Gly Gly Thr
        1670               1675               1680

Gly Gly Cys Thr Cys Gly Thr Ala Ala Gly Cys Cys Gly Thr
        1685               1690               1695

Thr Cys Thr Thr Cys Ala Cys Ala Gly Gly Gly Thr Ala Cys Cys
        1700               1705               1710

Cys Thr Gly Gly Thr Cys Ala Cys Cys Gly Thr Cys Thr Cys Cys
        1715               1720               1725

Thr Cys Ala Gly Cys Gly
        1730

<210> SEQ ID NO 151
<211> LENGTH: 578
<212> TYPE: PRT
<213> ORGANISM: Artificial Sequence
<220> FEATURE:
<223> OTHER INFORMATION: humanized lama

<400> SEQUENCE: 151

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
            35                  40                  45

Ala Val Ile Thr Trp Ser Gly Gly Ile Thr Tyr Tyr Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Ser Gly Gly Gly Gly Gly Ser
            130                 135                 140

Gly Gly Gly Gly Ser Gly Gly Gly Ser Glu Val Gln Leu Val Glu
 145                 150                 155                 160

Ser Gly Gly Gly Val Val Gln Pro Gly Gly Ser Leu Arg Leu Ser Cys
            165                 170                 175

Ala Ala Ser Gly Gly Thr Phe Ser Phe Tyr Gly Met Gly Trp Phe Arg
            180                 185                 190

Gln Ala Pro Gly Lys Glu Arg Glu Phe Val Ala Asp Ile Arg Thr Ser
            195                 200                 205

Ala Gly Arg Thr Tyr Tyr Ala Asp Ser Val Lys Gly Arg Phe Thr Ile
            210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Pro Ser Gly
            245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
            275                 280                 285

Gly Gly Gly Gly Ser Gly Gly Gly Ser Gly Gly Gly Gly Ser Gly
            290                 295                 300

Gly Gly Gly Ser Glu Val Gln Leu Val Glu Ser Gly Gly Val Val
305                 310                 315                 320

Gln Pro Gly Gly Ser Leu Arg Leu Ser Cys Ala Ala Ser Gly Gly Thr
            325                 330                 335

Phe Ser Phe Tyr Gly Met Gly Trp Phe Arg Gln Ala Pro Gly Lys Glu
            340                 345                 350

Arg Glu Phe Val Ala Asp Ile Arg Thr Ser Ala Gly Arg Thr Tyr Tyr
            355                 360                 365

Ala Asp Ser Val Lys Gly Arg Phe Thr Ile Ser Arg Asp Asn Ser Lys
            370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Pro Ser Gly Ile Ser Gly Trp Asp Tyr
            405                 410                 415

Trp Gly Gln Gly Thr Leu Val Thr Val Ser Ser Gly Gly Gly Gly Ser
            420                 425                 430

Gly Gly Gly Gly Ser Gly Gly Gly Ser Gly Gly Gly Gly Ser Gly
            435                 440                 445

Gly Gly Gly Ser Gly Gly Gly Gly Ser Gly Gly Gly Gly Ser Glu Val

```
                  450                 455                 460
Gln Leu Val Glu Ser Gly Gly Val Val Gln Pro Gly Asn Ser Leu
465                 470                 475                 480

Arg Leu Ser Cys Ala Ala Ser Gly Phe Thr Phe Ser Ser Phe Gly Met
                485                 490                 495

Ser Trp Val Arg Gln Ala Pro Gly Lys Gly Leu Glu Trp Val Ser Ser
                500                 505                 510

Ile Ser Gly Ser Gly Ser Asp Thr Leu Tyr Ala Asp Ser Val Lys Gly
            515                 520                 525

Arg Phe Thr Ile Ser Arg Asp Asn Ala Lys Thr Thr Leu Tyr Leu Gln
            530                 535                 540

Met Asn Ser Leu Arg Pro Glu Asp Thr Ala Leu Tyr Tyr Cys Thr Ile
545                 550                 555                 560

Gly Gly Ser Leu Ser Arg Ser Ser Gln Gly Thr Leu Val Thr Val Ser
                565                 570                 575

Ser Ala

<210> SEQ ID NO 152
<211> LENGTH: 2196
<212> TYPE: DNA
<213> ORGANISM: Artificial Sequence
<220> FEATURE:
<223> OTHER INFORMATION: humanized lama

<400> SEQUENCE: 152
gacgtgcaat tggtggagtc tggtggcgga gttgtccagc ctggcggcag tctgcggtta      60
tcttgcgccg cttctggcag cattgccagt attcacgcta tgggttggtt caggcaggct     120
cctggtaaag aacgtgagtt tgtggctgtg attacttggt ccgtggtat tacttactac     180
gctgatagcg ttaagggccg gtttacaatt tcccgtgata atagcaaaaa taccgtctat     240
ctgcaaatga acagtctgcg cccggaagat accgccctgt attactgtgc gggcgataaa     300
catcagtcct catggtatga ctactggggg caagggaccc tggtcacggt ctcctccgga     360
ggcggtgggt caggtggcgg aggcagcggt ggaggaggta gtggcggtgg cggtagtggg     420
ggtggaggca gcggaggcgg aggcagtggg ggcggtggat cagaggtgca gttggtggag     480
tctggtggcg gagttgtcca gcctggcggc agtctgcggt tatcttgcgc cgcttctggc     540
agcattgcca gtattcacgc tatgggttgg ttcaggcagg ctcctggtaa agaacgtgag     600
tttgtggctg tgattacttg gtccggtggt attacttact acgctgatag cgttaagggc     660
cggtttacaa tttcccgtga taatagcaaa ataccgtctc atctgcaaat gaacagtctg     720
cgcccggaag ataccgccct gtattactgt gcgggcgata acatcagtc ctcatggtat     780
gactactggg gcaagggac cctggtcacg gtctcctcag gaggcggtgg gtcaggtggc     840
ggaggcagcg gtggaggagg tagtggcggt ggcggtagtg gggtggagg cagcggaggc     900
ggaggcagtg ggggcggtgg atccgaggtg cagttggtgg agtctggggg aggagtggtg     960
cagccggggg gctctctgag actctcctgt gcagcctctg gtggcacctt cagtttctat    1020
ggcatgggct ggttccgcca ggctccaggg aaggagcgcg agtttgtagc agatattaga    1080
accagtgctg gtaggacata ctatgcagac tccgtgaagg gccgattcac catctcccaga   1140
gacaacagca agaacacggt gtatctgcaa atgaacagcc tgcgccctga ggacacggcc    1200
ctgtattact gtgcagcaga gccaagtgga ataagtggtt gggactactg gggccagggg    1260
accctggtca cggtctcgag cggaggcggt gggtcaggtg gcggaggcag cggtggagga    1320
```

```
ggtagtggcg gtggcggtag tgggggtgga ggcagcggag gcggaggcag tgggggcggt    1380
ggatcagagg tgcagttggt ggagtctggg ggaggagtgg tgcagccggg gggctctctg    1440
agactctcct gtgcagcctc tggtggcacc ttcagtttct atggcatggg ctggttccgc    1500
caggctccag gaaggagcg cgagtttgta gcagatatta gaaccagtgc tggtaggaca    1560
tactatgcag actccgtgaa gggccgattc accatctcca gagacaacag caagaacacg    1620
gtgtatctgc aaatgaacag cctgcgccct gaggacacgg ccctgtatta ctgtgcagca    1680
gagccaagtg aataagtgg ttgggactac tggggccagg ggaccctggt cacggtctcc    1740
tcaggaggcg gtgggtcagg tggcggaggc agcggtggag gaggtagtgg cggtggcggt    1800
agtgggggtg gaggcagcgg aggcggaggc agtgggggcg gtggatcaga ggtgcaacta    1860
gtggagtctg gaggtggcgt tgtgcaaccg ggtaacagtc tgcgccttag ctgcgcagcg    1920 tctggctttta ccttcagctc ctttggcatg agctgggttc gccaggctcc gggaaaagga    1980
ctggaatggg tttcgtctat tagcggcagt ggtagcgata cgctctacgc ggactccgtg    2040
aagggccgtt tcaccatctc ccgcgataac gccaaaacta cactgtatct gcaaatgaat    2100
agcctgcgtc ctgaagatac ggccctgtat tactgtacta ttggtggctc gttaagccgt    2160
tcttcacagg gtaccctggt caccgtctcc tcagcg                              2196
```

<210> SEQ ID NO 153
<211> LENGTH: 732
<212> TYPE: PRT
<213> ORGANISM: Artificial Sequence
<220> FEATURE:
<223> OTHER INFORMATION: humanized lama

<400> SEQUENCE: 153

Asp Val Gln Leu Val Glu Ser Gly Gly Gly Val Val Gln Pro Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Gly Asp Lys His Gln Ser Ser Trp Tyr Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Ser Ile Ala Ser Ile His Ala Met Gly Trp Phe Arg
            180                 185                 190

Gln Ala Pro Gly Lys Glu Arg Glu Phe Val Ala Val Ile Thr Trp Ser
        195                 200                 205

```
Gly Gly Ile Thr Tyr Tyr Ala Asp Ser Val Lys Gly Arg Phe Thr Ile
    210             215                 220

Ser Arg Asp Asn Ser Lys Asn Thr Val Tyr Leu Gln Met Asn Ser Leu
225             230                 235                 240

Arg Pro Glu Asp Thr Ala Leu Tyr Tyr Cys Ala Gly Asp Lys His Gln
            245                 250                 255

Ser Ser Trp Tyr Asp Tyr Trp Gly Gln Gly Thr Leu Val Thr Val Ser
            260                 265                 270

Ser Gly Gly Gly Gly Ser Gly Gly Gly Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Gly Ser Glu Val Gln Leu Val Glu Ser Gly Gly Val Val
305             310                 315                 320

Gln Pro Gly Gly Ser Leu Arg Leu Ser Cys Ala Ala Ser Gly Thr
                325                 330                 335

Phe Ser Phe Tyr Gly Met Gly Trp Phe Arg Gln Ala Pro Gly Lys Glu
            340                 345                 350

Arg Glu Phe Val Ala Asp Ile Arg Thr Ser Ala Gly Arg Thr Tyr Tyr
            355                 360                 365

Ala Asp Ser Val Lys Gly Arg Phe Thr Ile Ser Arg Asp Asn Ser Lys
370                 375                 380

Asn Thr Val Tyr Leu Gln Met Asn Ser Leu Arg Pro Glu Asp Thr Ala
385                 390                 395                 400

Leu Tyr Tyr Cys Ala Ala Glu Pro Ser Gly Ile Ser Gly Trp Asp Tyr
                405                 410                 415

Trp Gly Gln Gly Thr Leu Val Thr Val Ser Ser Gly Gly Gly Gly Ser
        420                 425                 430

Gly Gly Gly Gly Ser Gly Gly Gly Ser Gly Gly Gly Gly Ser Gly
            435                 440                 445

Gly Gly Gly Ser Gly Gly Gly Ser Gly Gly Gly Gly Ser Glu Val
    450                 455                 460

Gln Leu Val Glu Ser Gly Gly Val Val Gln Pro Gly Gly Ser Leu
465                 470                 475                 480

Arg Leu Ser Cys Ala Ala Ser Gly Gly Thr Phe Ser Phe Tyr Gly Met
            485                 490                 495

Gly Trp Phe Arg Gln Ala Pro Gly Lys Glu Arg Glu Phe Val Ala Asp
            500                 505                 510

Ile Arg Thr Ser Ala Gly Arg Thr Tyr Tyr Ala Asp Ser Val Lys Gly
            515                 520                 525

Arg Phe Thr Ile Ser Arg Asp Asn Ser Lys Asn Thr Val Tyr Leu Gln
530                 535                 540

Met Asn Ser Leu Arg Pro Glu Asp Thr Ala Leu Tyr Tyr Cys Ala Ala
545             550                 555                 560

Glu Pro Ser Gly Ile Ser Gly Trp Asp Tyr Trp Gly Gln Gly Thr Leu
            565                 570                 575

Val Thr Val Ser Ser Gly Gly Gly Gly Ser Gly Gly Gly Gly Ser Gly
            580                 585                 590

Gly Gly Ser Gly Gly Gly Gly Ser Gly Gly Gly Ser Gly Gly
        595                 600                 605

Gly Gly Ser Gly Gly Gly Ser Glu Val Gln Leu Val Glu Ser Gly
    610                 615                 620

Gly Val Val Gln Pro Gly Asn Ser Leu Arg Leu Ser Cys Ala Ala
```

```
                625                 630                 635                 640
Ser Gly Phe Thr Phe Ser Ser Phe Gly Met Ser Trp Val Arg Gln Ala
                    645                 650                 655

Pro Gly Lys Gly Leu Glu Trp Val Ser Ser Ile Ser Gly Ser Gly Ser
                660                 665                 670

Asp Thr Leu Tyr Ala Asp Ser Val Lys Gly Arg Phe Thr Ile Ser Arg
            675                 680                 685

Asp Asn Ala Lys Thr Thr Leu Tyr Leu Gln Met Asn Ser Leu Arg Pro
        690                 695                 700

Glu Asp Thr Ala Leu Tyr Tyr Cys Thr Ile Gly Gly Ser Leu Ser Arg
705                 710                 715                 720

Ser Ser Gln Gly Thr Leu Val Thr Val Ser Ser Ala
                    725                 730
```

<210> SEQ ID NO 154
<211> LENGTH: 11
<212> TYPE: PRT
<213> ORGANISM: Rattus

<400> SEQUENCE: 154

```
Lys Thr Ser Gln Asn Ile Phe Glu Asn Leu Ala
1               5                   10
```

<210> SEQ ID NO 155
<211> LENGTH: 7
<212> TYPE: PRT
<213> ORGANISM: Rattus

<400> SEQUENCE: 155

```
Asn Ala Ser Pro Leu Gln Ala
1               5
```

<210> SEQ ID NO 156
<211> LENGTH: 8
<212> TYPE: PRT
<213> ORGANISM: Rattus

<400> SEQUENCE: 156

```
His Gln Tyr Tyr Ser Gly Tyr Thr
1               5
```

<210> SEQ ID NO 157
<211> LENGTH: 10
<212> TYPE: PRT
<213> ORGANISM: Rattus

<400> SEQUENCE: 157

```
Gly Phe Thr Phe Ser Asp Tyr His Met Ala
1               5                   10
```

<210> SEQ ID NO 158
<211> LENGTH: 17
<212> TYPE: PRT
<213> ORGANISM: Rattus

<400> SEQUENCE: 158

```
Ser Ile Thr Leu Asp Ala Thr Tyr Thr Tyr Tyr Arg Asp Ser Val Arg
1               5                   10                  15

Gly
```

<210> SEQ ID NO 159

```
<211> LENGTH: 10
<212> TYPE: PRT
<213> ORGANISM: Rattus

<400> SEQUENCE: 159

His Arg Gly Phe Ser Val Trp Leu Asp Tyr
1               5                   10

<210> SEQ ID NO 160
<211> LENGTH: 10
<212> TYPE: PRT
<213> ORGANISM: Rattus

<400> SEQUENCE: 160

Gly Tyr Ile Phe Thr Asp Tyr Ala Met His
1               5                   10

<210> SEQ ID NO 161
<211> LENGTH: 16
<212> TYPE: PRT
<213> ORGANISM: Rattus

<400> SEQUENCE: 161

Thr Phe Ile Pro Leu Leu Asp Thr Ser Asp Tyr Asn Gln Asn Phe Lys
1               5                   10                  15

<210> SEQ ID NO 162
<211> LENGTH: 11
<212> TYPE: PRT
<213> ORGANISM: Rattus

<400> SEQUENCE: 162

Met Gly Val Thr His Ser Tyr Val Met Asp Ala
1               5                   10

<210> SEQ ID NO 163
<211> LENGTH: 11
<212> TYPE: PRT
<213> ORGANISM: Rattus

<400> SEQUENCE: 163

Arg Ala Ser Gln Pro Ile Ser Ile Ser Val His
1               5                   10

<210> SEQ ID NO 164
<211> LENGTH: 7
<212> TYPE: PRT
<213> ORGANISM: Rattus

<400> SEQUENCE: 164

Phe Ala Ser Gln Ser Ile Ser
1               5

<210> SEQ ID NO 165
<211> LENGTH: 9
<212> TYPE: PRT
<213> ORGANISM: Rattus

<400> SEQUENCE: 165

Gln Gln Thr Phe Ser Leu Pro Tyr Thr
1               5

<210> SEQ ID NO 166
<211> LENGTH: 10
<212> TYPE: PRT
```

<213> ORGANISM: Mus

<400> SEQUENCE: 166

Gly Phe Ile Ile Lys Ala Thr Tyr Met His
1               5                   10

<210> SEQ ID NO 167
<211> LENGTH: 17
<212> TYPE: PRT
<213> ORGANISM: Mus

<400> SEQUENCE: 167

Arg Ile Asp Pro Ala Asn Gly Glu Thr Lys Tyr Asp Pro Lys Phe Gln
1               5                   10                  15
Val

<210> SEQ ID NO 168
<211> LENGTH: 7
<212> TYPE: PRT
<213> ORGANISM: Mus

<400> SEQUENCE: 168

Tyr Ala Trp Tyr Phe Asp Val
1               5

<210> SEQ ID NO 169
<211> LENGTH: 11
<212> TYPE: PRT
<213> ORGANISM: Mus

<400> SEQUENCE: 169

Arg Ala Ser Glu Asn Ile Tyr Ser Phe Leu Ala
1               5                   10

<210> SEQ ID NO 170
<211> LENGTH: 7
<212> TYPE: PRT
<213> ORGANISM: Mus

<400> SEQUENCE: 170

His Ala Lys Thr Leu Ala Glu
1               5

<210> SEQ ID NO 171
<211> LENGTH: 9
<212> TYPE: PRT
<213> ORGANISM: Mus

<400> SEQUENCE: 171

Gln His Tyr Tyr Gly Ser Pro Leu Thr
1               5

<210> SEQ ID NO 172
<211> LENGTH: 447
<212> TYPE: PRT
<213> ORGANISM: Artificial Sequence
<220> FEATURE:
<223> OTHER INFORMATION: humanized mouse

<400> SEQUENCE: 172

Gln Val Gln Leu Val Gln Ser Gly Val Glu Val Lys Lys Pro Gly Ala
1               5                   10                  15
Ser Val Lys Val Ser Cys Lys Ala Ser Gly Tyr Thr Phe Thr Asn Tyr
            20                  25                  30

-continued

Tyr Met Tyr Trp Val Arg Gln Ala Pro Gly Gln Gly Leu Glu Trp Met
         35                  40                  45

Gly Gly Ile Asn Pro Ser Asn Gly Gly Thr Asn Phe Asn Glu Lys Phe
 50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Thr Ala Val Tyr Tyr Cys
                 85                  90                  95

Ala Arg Arg Asp Tyr Arg Phe Asp Met Gly Phe Asp Tyr Trp Gly Gln
             100                 105                 110

Gly Thr Thr Val Thr Val Ser Ser Ala Ser Thr Lys Gly Pro Ser Val
         115                 120                 125

Phe Pro Leu Ala Pro Cys Ser Arg Ser Thr Ser Glu Ser Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Lys Thr Tyr Thr Cys Asn Val Asp His Lys
         195                 200                 205

Pro Ser Asn Thr Lys Val Asp Lys Arg Val Glu Ser Lys Tyr Gly Pro
     210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser Gln Glu Asp Pro Glu
             260                 265                 270

Val Gln Phe Asn Trp Tyr Val Asp Gly Val Glu Val His Asn Ala Lys
         275                 280                 285

Thr Lys Pro Arg Glu Glu Gln Phe Asn Ser Thr Tyr Arg Val Val Ser
     290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                 325                 330                 335

Ser Lys Ala Lys Gly Gln Pro Arg Glu Pro Gln Val Tyr Thr Leu Pro
             340                 345                 350

Pro Ser Gln Glu Glu Met Thr Lys Asn Gln Val Ser Leu Thr Cys Leu
         355                 360                 365

Val Lys Gly Phe Tyr Pro Ser Asp Ile Ala Val Glu Trp Glu Ser Asn
     370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                 405                 410                 415

Trp Gln Glu Gly Asn Val Phe Ser Cys Ser Val Met His Glu Ala Leu
             420                 425                 430

His Asn His Tyr Thr Gln Lys Ser Leu Ser Leu Ser Leu Gly Lys
         435                 440                 445

```
<210> SEQ ID NO 173
<211> LENGTH: 218
<212> TYPE: PRT
<213> ORGANISM: Artificial Sequence
<220> FEATURE:
<223> OTHER INFORMATION: humanized mouse

<400> SEQUENCE: 173

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 174
<211> LENGTH: 440
<212> TYPE: PRT
<213> ORGANISM: Homo sapiens

<400> SEQUENCE: 174

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
```

```
                100             105             110
Ser Ala Ser Thr Lys Gly Pro Ser Val Phe Pro Leu Ala Pro Cys Ser
            115             120             125
Arg Ser Thr Ser Glu Ser Thr Ala Ala Leu Gly Cys Leu Val Lys Asp
            130             135             140
Tyr Phe Pro Glu Pro Val Thr Val Ser Trp Asn Ser Gly Ala Leu Thr
145             150             155             160
Ser Gly Val His Thr Phe Pro Ala Val Leu Gln Ser Ser Gly Leu Tyr
                165             170             175
Ser Leu Ser Ser Val Val Thr Val Pro Ser Ser Ser Leu Gly Thr Lys
            180             185             190
Thr Tyr Thr Cys Asn Val Asp His Lys Pro Ser Asn Thr Lys Val Asp
            195             200             205
Lys Arg Val Glu Ser Lys Tyr Gly Pro Pro Cys Pro Pro Cys Pro Ala
210             215             220
Pro Glu Phe Leu Gly Gly Pro Ser Val Phe Leu Phe Pro Pro Lys Pro
225             230             235             240
Lys Asp Thr Leu Met Ile Ser Arg Thr Pro Glu Val Thr Cys Val Val
            245             250             255
Val Asp Val Ser Gln Glu Asp Pro Glu Val Gln Phe Asn Trp Tyr Val
            260             265             270
Asp Gly Val Glu Val His Asn Ala Lys Thr Lys Pro Arg Glu Glu Gln
            275             280             285
Phe Asn Ser Thr Tyr Arg Val Val Ser Val Leu Thr Val Leu His Gln
290             295             300
Asp Trp Leu Asn Gly Lys Glu Tyr Lys Cys Lys Val Ser Asn Lys Gly
305             310             315             320
Leu Pro Ser Ser Ile Glu Lys Thr Ile Ser Lys Ala Lys Gly Gln Pro
            325             330             335
Arg Glu Pro Gln Val Tyr Thr Leu Pro Pro Ser Gln Glu Glu Met Thr
            340             345             350
Lys Asn Gln Val Ser Leu Thr Cys Leu Val Lys Gly Phe Tyr Pro Ser
            355             360             365
Asp Ile Ala Val Glu Trp Glu Ser Asn Gly Gln Pro Glu Asn Asn Tyr
            370             375             380
Lys Thr Thr Pro Pro Val Leu Asp Ser Asp Gly Ser Phe Phe Leu Tyr
385             390             395             400
Ser Arg Leu Thr Val Asp Lys Ser Arg Trp Gln Glu Gly Asn Val Phe
            405             410             415
Ser Cys Ser Val Met His Glu Ala Leu His Asn His Tyr Thr Gln Lys
            420             425             430
Ser Leu Ser Leu Ser Leu Gly Lys
            435             440

<210> SEQ ID NO 175
<211> LENGTH: 214
<212> TYPE: PRT
<213> ORGANISM: Homo sapiens

<400> SEQUENCE: 175

Glu Ile Val Leu Thr Gln Ser Pro Ala Thr Leu Ser Leu Ser Pro Gly
1               5               10              15
Glu Arg Ala Thr Leu Ser Cys Arg Ala Ser Gln Ser Val Ser Ser Tyr
            20              25              30
```

Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 176
<211> LENGTH: 153
<212> TYPE: PRT
<213> ORGANISM: Artificial Sequence
<220> FEATURE:
<223> OTHER INFORMATION: Humanized Lama

<400> SEQUENCE: 176

Glu Val Gln Leu Val Glu Ser Gly Gly Gly Val Val Gln Pro Gly Gly
 1               5                  10                  15

Ser Leu Arg Leu Ser Cys Ala Ala Ser Gly Gly Thr Phe Ser Phe Tyr
                20                  25                  30

Gly Met Gly Trp Phe Arg Gln Ala Pro Gly Lys Glu Arg Glu Phe Val
                35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Lys Asn Thr Val Tyr
 65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
                100                 105                 110

Thr Leu Val Thr Val Ser Ser Ala Ala Ala Asp Tyr Lys Asp His Asp
                115                 120                 125

Gly Asp Tyr Lys Asp His Asp Ile Asp Tyr Lys Asp Asp Asp Asp Lys
                130                 135                 140

Gly Ala Ala His His His His His His
145                 150

<210> SEQ ID NO 177
<211> LENGTH: 153

```
<212> TYPE: PRT
<213> ORGANISM: Artificial Sequence
<220> FEATURE:
<223> OTHER INFORMATION: Humanized Lama

<400> SEQUENCE: 177
```

| Glu | Val | Gln | Leu | Val | Glu | Ser | Gly | Gly | Gly | Val | Val | Gln | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Ser Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

```
<210> SEQ ID NO 178
<211> LENGTH: 153
<212> TYPE: PRT
<213> ORGANISM: Artificial Sequence
<220> FEATURE:
<223> OTHER INFORMATION: Humanized Lama

<400> SEQUENCE: 178
```

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Val Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

```
<210> SEQ ID NO 179
```

<211> LENGTH: 153
<212> TYPE: PRT
<213> ORGANISM: Artificial Sequence
<220> FEATURE:
<223> OTHER INFORMATION: Humanized Lama

<400> SEQUENCE: 179

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Gly Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 180
<211> LENGTH: 153
<212> TYPE: PRT
<213> ORGANISM: Artificial Sequence
<220> FEATURE:
<223> OTHER INFORMATION: Humanized Lama

<400> SEQUENCE: 180

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Arg Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

```
<210> SEQ ID NO 181
<211> LENGTH: 153
<212> TYPE: PRT
<213> ORGANISM: Artificial Sequence
<220> FEATURE:
<223> OTHER INFORMATION: Humanized Lama

<400> SEQUENCE: 181

Glu Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Gln Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 182
<211> LENGTH: 153
<212> TYPE: PRT
<213> ORGANISM: Artificial Sequence
<220> FEATURE:
<223> OTHER INFORMATION: Humanized Lama

<400> SEQUENCE: 182

Glu Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Met Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150
```

```
<210> SEQ ID NO 183
<211> LENGTH: 153
<212> TYPE: PRT
<213> ORGANISM: Artificial Sequence
<220> FEATURE:
<223> OTHER INFORMATION: Humanized Lama

<400> SEQUENCE: 183

Glu Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp His Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 184
<211> LENGTH: 153
<212> TYPE: PRT
<213> ORGANISM: Artificial Sequence
<220> FEATURE:
<223> OTHER INFORMATION: Humanized Lama

<400> SEQUENCE: 184

Glu Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Thr Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150
```

<210> SEQ ID NO 185
<211> LENGTH: 153
<212> TYPE: PRT
<213> ORGANISM: Artificial Sequence
<220> FEATURE:
<223> OTHER INFORMATION: Humanized Lama

<400> SEQUENCE: 185

```
Glu Val Gln Leu Val Glu Ser Gly Gly Val Val Gln Pro Gly Gly
1               5                  10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asp Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150
```

<210> SEQ ID NO 186
<211> LENGTH: 153
<212> TYPE: PRT
<213> ORGANISM: Artificial Sequence
<220> FEATURE:
<223> OTHER INFORMATION: Humanized Lama

<400> SEQUENCE: 186

```
Glu Val Gln Leu Val Glu Ser Gly Gly Gly Val Val Gln Pro Gly Gly
1               5                  10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Glu Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
```

<210> SEQ ID NO 187
<211> LENGTH: 153
<212> TYPE: PRT
<213> ORGANISM: Artificial Sequence
<220> FEATURE:
<223> OTHER INFORMATION: Humanized Lama

<400> SEQUENCE: 187

```
Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Trp Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150
```

<210> SEQ ID NO 188
<211> LENGTH: 153
<212> TYPE: PRT
<213> ORGANISM: Artificial Sequence
<220> FEATURE:
<223> OTHER INFORMATION: Humanized Lama

<400> SEQUENCE: 188

```
Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Phe Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140
```

Gly Ala Ala His His His His His His
145                 150

<210> SEQ ID NO 189
<211> LENGTH: 153
<212> TYPE: PRT
<213> ORGANISM: Artificial Sequence
<220> FEATURE:
<223> OTHER INFORMATION: Humanized Lama

<400> SEQUENCE: 189

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Lys Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 190
<211> LENGTH: 153
<212> TYPE: PRT
<213> ORGANISM: Artificial Sequence
<220> FEATURE:
<223> OTHER INFORMATION: Humanized Lama

<400> SEQUENCE: 190

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Ala Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His
145                 150

<210> SEQ ID NO 191
<211> LENGTH: 153
<212> TYPE: PRT
<213> ORGANISM: Artificial Sequence
<220> FEATURE:
<223> OTHER INFORMATION: Humanized Lama

<400> SEQUENCE: 191

Glu Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Tyr Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His
145                 150

<210> SEQ ID NO 192
<211> LENGTH: 153
<212> TYPE: PRT
<213> ORGANISM: Artificial Sequence
<220> FEATURE:
<223> OTHER INFORMATION: Humanized Lama

<400> SEQUENCE: 192

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Pro Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys

```
                130                 135                 140
Gly Ala Ala His His His His His
145                 150
```

<210> SEQ ID NO 193
<211> LENGTH: 424
<212> TYPE: PRT
<213> ORGANISM: Artificial Sequence
<220> FEATURE:
<223> OTHER INFORMATION: Humanized Lama

<400> SEQUENCE: 193

```
Asp Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Arg Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Pro Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Ser Gly Gly Gly Ser Gly
    290                 295                 300

Gly Gly Gly Ser Glu Val Gln Leu Val Glu Ser Gly Gly Val Val
305                 310                 315                 320

Gln Pro Gly Asn Ser Leu Arg Leu Ser Cys Ala Ala Ser Gly Phe Thr
                325                 330                 335

Phe Ser Ser Phe Gly Met Ser Trp Val Arg Gln Ala Pro Gly Lys Gly
```

```
                 340                 345                 350
Leu Glu Trp Val Ser Ser Ile Ser Gly Ser Gly Ser Asp Thr Leu Tyr
            355                 360                 365

Ala Asp Ser Val Lys Gly Arg Phe Thr Ile Ser Arg Asp Asn Ala Lys
        370                 375                 380

Thr Thr Leu Tyr Leu Gln Met Asn Ser Leu Arg Pro Glu Asp Thr Ala
385                 390                 395                 400

Leu Tyr Tyr Cys Thr Ile Gly Gly Ser Leu Ser Arg Ser Ser Gln Gly
                405                 410                 415

Thr Leu Val Thr Val Ser Ser Ala
            420

<210> SEQ ID NO 194
<211> LENGTH: 270
<212> TYPE: PRT
<213> ORGANISM: Artificial Sequence
<220> FEATURE:
<223> OTHER INFORMATION: Humanized Lama

<400> SEQUENCE: 194

Asp Val Gln Leu Val Glu Ser Gly Gly Val Val Gln Pro Gly Gly
1               5                  10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Asn Ser Leu Arg Leu Ser Cys
                165                 170                 175

Ala Ala Ser Gly Phe Thr Phe Ser Ser Phe Gly Met Ser Trp Val Arg
            180                 185                 190

Gln Ala Pro Gly Lys Gly Leu Glu Trp Val Ser Ser Ile Ser Gly Ser
        195                 200                 205

Gly Ser Asp Thr Leu Tyr Ala Asp Ser Val Lys Gly Arg Phe Thr Ile
    210                 215                 220

Ser Arg Asp Asn Ala Lys Thr Thr Leu Tyr Leu Gln Met Asn Ser Leu
225                 230                 235                 240

Arg Pro Glu Asp Thr Ala Leu Tyr Tyr Cys Thr Ile Gly Gly Ser Leu
                245                 250                 255

Ser Arg Ser Ser Gln Gly Thr Leu Val Thr Val Ser Ser Ala
            260                 265                 270
```

```
<210> SEQ ID NO 195
<211> LENGTH: 138
<212> TYPE: PRT
<213> ORGANISM: Homo sapiens

<400> SEQUENCE: 195

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
            35                  40                  45

Cys Ala Ala Thr Tyr Met Met Gly Asn Glu Leu Thr Phe Leu Asp Asp
50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
                100                 105                 110

Ile Tyr Val Ile Asp Pro Glu Pro Cys Pro Asp Ser Asp Phe His His
            115                 120                 125

His His His His His His Gly Gly Gln
    130                 135

<210> SEQ ID NO 196
<211> LENGTH: 119
<212> TYPE: PRT
<213> ORGANISM: Artificial Sequence
<220> FEATURE:
<223> OTHER INFORMATION: Humanized Lama
<220> FEATURE:
<221> NAME/KEY: MISC_FEATURE
<222> LOCATION: (1)..(1)
<223> OTHER INFORMATION: X is E or D
<220> FEATURE:
<221> NAME/KEY: MISC_FEATURE
<222> LOCATION: (74)..(74)
<223> OTHER INFORMATION: X is S, V, G, R, Q, M, H, T, D, E, W, F, K, A,
      Y or P

<400> SEQUENCE: 196

Xaa Val Gln Leu Val Glu Ser Gly Gly Gly Val Gln Pro Gly Gly
1               5                   10                  15

Ser Leu Arg Leu Ser Cys Ala Ala Ser Gly Gly Thr Phe Ser Phe Tyr
                20                  25                  30

Gly Met Gly Trp Phe Arg Gln Ala Pro Gly Lys Glu Arg Glu Phe Val
            35                  40                  45

Ala Asp Ile Arg Thr Ser Ala Gly Arg Thr Tyr Tyr Ala Asp Ser Val
50                  55                  60

Lys Gly Arg Phe Thr Ile Ser Arg Asp Xaa Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
                100                 105                 110

Thr Leu Val Thr Val Ser Ser
            115
```

-continued

```
<210> SEQ ID NO 197
<211> LENGTH: 223
<212> TYPE: PRT
<213> ORGANISM: Homo sapiens
<220> FEATURE:
<221> NAME/KEY: mat_peptide
<222> LOCATION: (36)..(223)

<400> SEQUENCE: 197

Met Ala Cys Leu Gly Phe Gln Arg His Lys Ala Gln Leu Asn Leu Ala
-35                 -30                 -25                 -20

Thr Arg Thr Trp Pro Cys Thr Leu Leu Phe Phe Leu Leu Phe Ile Pro
            -15                 -10                  -5

Val Phe Cys Lys Ala Met His Val Ala Gln Pro Ala Val Val Leu Ala
             -1  1               5                  10

Ser Ser Arg Gly Ile Ala Ser Phe Val Cys Glu Tyr Ala Ser Pro Gly
         15                  20                  25

Lys Ala Thr Glu Val Arg Val Thr Val Leu Arg Gln Ala Asp Ser Gln
 30                  35                  40                  45

Val Thr Glu Val Cys Ala Ala Thr Tyr Met Met Gly Asn Glu Leu Thr
                 50                  55                  60

Phe Leu Asp Asp Ser Ile Cys Thr Gly Thr Ser Ser Gly Asn Gln Val
             65                  70                  75

Asn Leu Thr Ile Gln Gly Leu Arg Ala Met Asp Thr Gly Leu Tyr Ile
         80                  85                  90

Cys Lys Val Glu Leu Met Tyr Pro Pro Pro Tyr Tyr Leu Gly Ile Gly
     95                 100                 105

Asn Gly Thr Gln Ile Tyr Val Ile Asp Pro Glu Pro Cys Pro Asp Ser
110                 115                 120                 125

Asp Phe Leu Leu Trp Ile Leu Ala Ala Val Ser Ser Gly Leu Phe Phe
                130                 135                 140

Tyr Ser Phe Leu Leu Thr Ala Val Ser Leu Ser Lys Met Leu Lys Lys
                145                 150                 155

Arg Ser Pro Leu Thr Thr Gly Val Tyr Val Lys Met Pro Pro Thr Glu
                160                 165                 170

Pro Glu Cys Glu Lys Gln Phe Gln Pro Tyr Phe Ile Pro Ile Asn
                175                 180                 185

<210> SEQ ID NO 198
<211> LENGTH: 288
<212> TYPE: PRT
<213> ORGANISM: Homo sapiens
<220> FEATURE:
<221> NAME/KEY: mat_peptide
<222> LOCATION: (21)..(288)

<400> SEQUENCE: 198

Met Gln Ile Pro Gln Ala Pro Trp Pro Val Val Trp Ala Val Leu Gln
-20                 -15                 -10                  -5

Leu Gly Trp Arg Pro Gly Trp Phe Leu Asp Ser Pro Asp Arg Pro Trp
             -1  1                   5                  10

Asn Pro Pro Thr Phe Ser Pro Ala Leu Leu Val Val Thr Glu Gly Asp
         15                  20                  25

Asn Ala Thr Phe Thr Cys Ser Phe Ser Asn Thr Ser Glu Ser Phe Val
 30                  35                  40

Leu Asn Trp Tyr Arg Met Ser Pro Ser Asn Gln Thr Asp Lys Leu Ala
 45                  50                  55                  60
```

```
Ala Phe Pro Glu Asp Arg Ser Gln Pro Gly Gln Asp Cys Arg Phe Arg
                65                  70                  75

Val Thr Gln Leu Pro Asn Gly Arg Asp Phe His Met Ser Val Val Arg
            80                  85                  90

Ala Arg Arg Asn Asp Ser Gly Thr Tyr Leu Cys Gly Ala Ile Ser Leu
        95                 100                 105

Ala Pro Lys Ala Gln Ile Lys Glu Ser Leu Arg Ala Glu Leu Arg Val
   110                 115                 120

Thr Glu Arg Arg Ala Glu Val Pro Thr Ala His Pro Ser Pro Ser Pro
125                 130                 135                 140

Arg Pro Ala Gly Gln Phe Gln Thr Leu Val Val Gly Val Val Gly Gly
                145                 150                 155

Leu Leu Gly Ser Leu Val Leu Leu Val Trp Val Leu Ala Val Ile Cys
            160                 165                 170

Ser Arg Ala Ala Arg Gly Thr Ile Gly Ala Arg Arg Thr Gly Gln Pro
        175                 180                 185

Leu Lys Glu Asp Pro Ser Ala Val Pro Val Phe Ser Val Asp Tyr Gly
    190                 195                 200

Glu Leu Asp Phe Gln Trp Arg Glu Lys Thr Pro Glu Pro Pro Val Pro
205                 210                 215                 220

Cys Val Pro Glu Gln Thr Glu Tyr Ala Thr Ile Val Phe Pro Ser Gly
                225                 230                 235

Met Gly Thr Ser Ser Pro Ala Arg Arg Gly Ser Ala Asp Gly Pro Arg
            240                 245                 250

Ser Ala Gln Pro Leu Arg Pro Glu Asp Gly His Cys Ser Trp Pro Leu
        255                 260                 265
```

<210> SEQ ID NO 199
<211> LENGTH: 10
<212> TYPE: PRT
<213> ORGANISM: Artificial Sequence
<220> FEATURE:
<223> OTHER INFORMATION: Lama Sp.

<400> SEQUENCE: 199

```
Gly Phe Thr Phe Ser Ser Phe Gly Met Ser
1               5                   10
```

<210> SEQ ID NO 200
<211> LENGTH: 17
<212> TYPE: PRT
<213> ORGANISM: Artificial Sequence
<220> FEATURE:
<223> OTHER INFORMATION: Lama Sp.

<400> SEQUENCE: 200

```
Ser Ile Ser Gly Ser Gly Ser Asp Thr Leu Tyr Ala Asp Ser Val Lys
1               5                   10                  15

Gly
```

<210> SEQ ID NO 201
<211> LENGTH: 6
<212> TYPE: PRT
<213> ORGANISM: Artificial Sequence
<220> FEATURE:
<223> OTHER INFORMATION: Lama Sp.

```
<400> SEQUENCE: 201

Gly Gly Ser Leu Ser Arg
1               5
```